United States Patent [19]
Donlon

[11] Patent Number: 6,110,187
[45] Date of Patent: *Aug. 29, 2000

[54] DEVICE AND METHOD FOR MINIMIZING HEART DISPLACEMENTS DURING A BEATING HEART SURGICAL PROCEDURE

[75] Inventor: Brian S. Donlon, Los Altos Hills, Calif.

[73] Assignee: Heartport, Inc., Redwood City, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/710,231

[22] Filed: Sep. 13, 1996

Related U.S. Application Data

[60] Division of application No. 08/680,889, Jul. 16, 1996, which is a continuation-in-part of application No. 08/394,333, Feb. 24, 1995.

[51] Int. Cl.$^7$ .................................................. A61B 17/00
[52] U.S. Cl. ......................... 606/151; 600/210; 600/215; 600/219; 600/235; 128/898
[58] Field of Search ..................................... 606/151, 212, 606/213, 215, 216, 218; 600/201, 204, 210, 213, 215, 219, 226, 227, 235; 128/898, 95.1, 172.1

[56] References Cited

U.S. PATENT DOCUMENTS

| | | |
|---|---|---|
| 3,254,650 | 6/1966 | Collito . |
| 3,254,651 | 6/1966 | Collito . |
| 3,519,187 | 7/1970 | Kapitanov et al. . |

(List continued on next page.)

FOREIGN PATENT DOCUMENTS

WO 97/10753  3/1997  WIPO .

OTHER PUBLICATIONS

Guyton et al. "A Mechanical Device for Sutureless Aorta–Saphenous Vein Anastomosis" *Ann Thorac Surg*28:342–345 (1979).

Androsov, P.I. "New Method of Surgical Treatment of Blood Vessel Lesions", *Arch Surg*.73:902–910 (1956).

Vogelfanger et al., "A Concept of Automation in Vascular Surgery: A Preliminary Report on a Mechanical Instrument for Arterial Anastomosis" *Can. J. of Surg*1:262–265 (1958).

Gottlob et al. "Anastomoses of small arteries and veins by means of bushings and adhesive" *J. Cardiac Surg*9:337–341 (1968).

Cooper et al. "Development of the Surgical Stapler with Emphasis on Vascular Anastomosis" *Transactions –The New York Academy of Sciences*, 23:365–377 (1963).

Goetz et al. "Internal Mammary–Coronary Artery Anastomosis –A Nonsuture Method Employing Tantalum Rings" *Thorac Cardiac Surg*41:378–386 (1961).

Rohman et al. Chapter IX –Cardiovascular Technique "Double Coronary Artery–Internal Mammary Artery Anastomoses, Tantalum Ring Technique" *Surg. Forum*11:236 (1960).

Holt et al. "A New Technique for End–To–End Anastomosis of Small Arteries" *Surg. Forum*11:242 (1960).

Inokuchi, K. "A New Type of Vessel–Suturing Apparatus" *Arch Surg*.77:954–957 (1958).

Berggren et al. "Clinical Experience with the Unilink/3M Precise Microvascular Anastomotic Device" *Scand J Plast Reconstr Hand Surg*27:35–39 (1993).

(List continued on next page.)

*Primary Examiner*—Jeffrey A. Schmidt
*Attorney, Agent, or Firm*—Jens E. Hoekendijk; Jeffry J. Grainger

[57] ABSTRACT

A device for minimizing displacements of the heart when performing a beating heart surgical procedure including two heart engaging members. The heart engaging members are slidably coupled to a retractor. The heart engaging members may be rotated and extended as necessary to reach the target site on the patient's heart. The heart engaging members have curved distal ends which are configured to engage a coronary shunt positioned in the coronary artery. A suture extends around the coronary and is coupled to the heart engaging members.

21 Claims, 76 Drawing Sheets

U.S. PATENT DOCUMENTS

| | | |
|---|---|---|
| 3,774,615 | 11/1973 | Lim et al. . |
| 4,350,160 | 9/1982 | Kolesov et al. . |
| 4,352,358 | 10/1982 | Angelchik . |
| 4,366,819 | 1/1983 | Kaster . |
| 4,368,736 | 1/1983 | Kaster . |
| 4,523,592 | 6/1985 | Daniel . |
| 4,553,542 | 11/1985 | Schenck et al. . |
| 4,593,693 | 6/1986 | Schenck . |
| 4,607,637 | 8/1986 | Berggren et al. . |
| 4,624,255 | 11/1986 | Schenck et al. . |
| 4,624,257 | 11/1986 | Berggren et al. . |
| 4,657,019 | 4/1987 | Walsh et al. . |
| 4,665,906 | 5/1987 | Jervis . |
| 4,726,356 | 2/1988 | Santilli et al. . |
| 4,747,407 | 5/1988 | Liu et al. . |
| 4,907,591 | 3/1990 | Vasconcellos et al. . |
| 4,917,087 | 4/1990 | Walsh et al. . |
| 4,917,090 | 4/1990 | Berggren et al. . |
| 4,917,091 | 4/1990 | Berggren et al. . |
| 4,950,283 | 8/1990 | Dzubow et al. ................. 600/215 |
| 5,119,983 | 6/1992 | Green et al. . |
| 5,167,223 | 12/1992 | Koros et al. . |
| 5,324,447 | 6/1994 | Kaster et al. . |
| 5,336,233 | 8/1994 | Chen . |
| 5,366,462 | 11/1994 | Kaster et al. . |
| 5,478,354 | 12/1995 | Tovey et al. . |
| 5,509,890 | 4/1996 | Kazama ............................. 600/201 |
| 5,522,834 | 6/1996 | Fonger et al. . |
| 5,727,569 | 3/1998 | Benetti et al. . |

OTHER PUBLICATIONS

Ragnarsson et al. "Microvenous End–To–Side Anastomosis: An Experimental Study Comparing the Unilink System and Sutures" *J Reconstr Microsurg*5(3):217–224 (1989).

Narter et al. "An Experimental Method for Nonsuture Anastomosis of the Aorta" *Surg. Gyn. Obstet*119:362–364 (1964).

Inokuchi, K. "Stapling Device for End–to–Side Anastomosis of Blood Vessel" *Arch. Surg.*82:337–341 (1961).

Nakayama et al. A simple new apparatus for small vessel anastomosis (free autograft of the sigmoid included) *Surgery*52(6):918–931 (1962).

Ragnarsson et al. "Arterial End–to–Side Anastomosis with the Unilink System" *Ann Plastic Surg*22(5):405–415 (1989).

Li et al. "End–To–Side Anastomosis in the Dog Using the 3M Precise Microvascular Anastomotic System: A Comparative Study" *J. Reconstr Microsurg*7(4):345–350 (1991).

Gentili et al. A Technique for Rapid Non–Suture Vascular Anastomosis *Can J Neurol Sci*14:92–95 (1987).

Lanzetta et al. "Long–term Results of 1 millimeter Arterial Anastomisis Using the 3M Precise Microvascular Anastomotic System" *Microsurg*13:313–320 (1992).

Miller, T.R. "The Russian Stapling Device" *Transactions –The New York Academy of Sciences*25:378–381 (1963).

Olearchyk, A.S. "Vasilii I. Kolesov –A pioneer of coronary revascularization by internal mammary–coronary artery grafting" *J. Thorac Cardiovasc Surg*96:13–18 (1988).

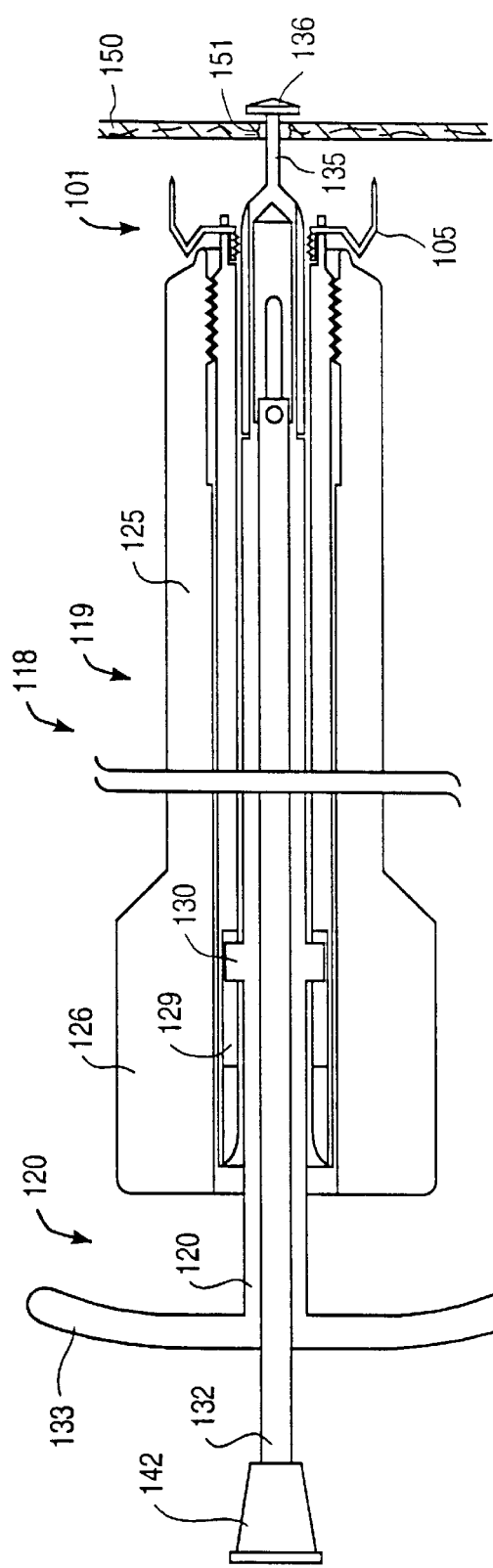
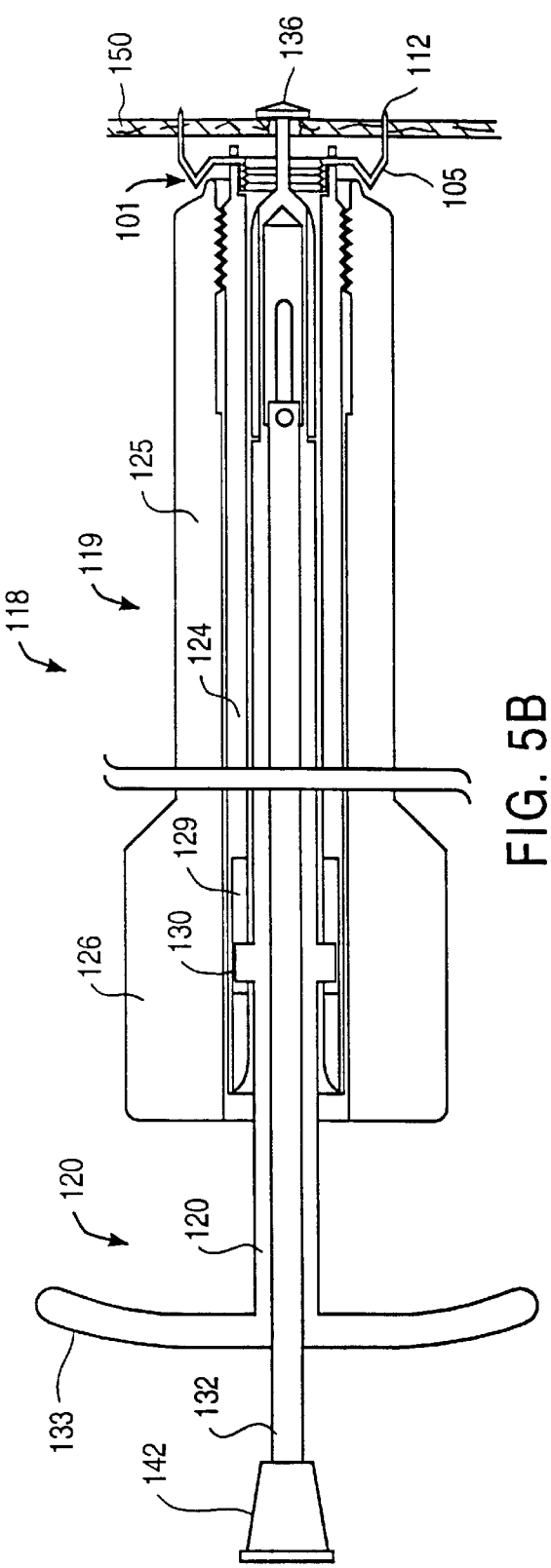
FIG. 5A
FIG. 5B

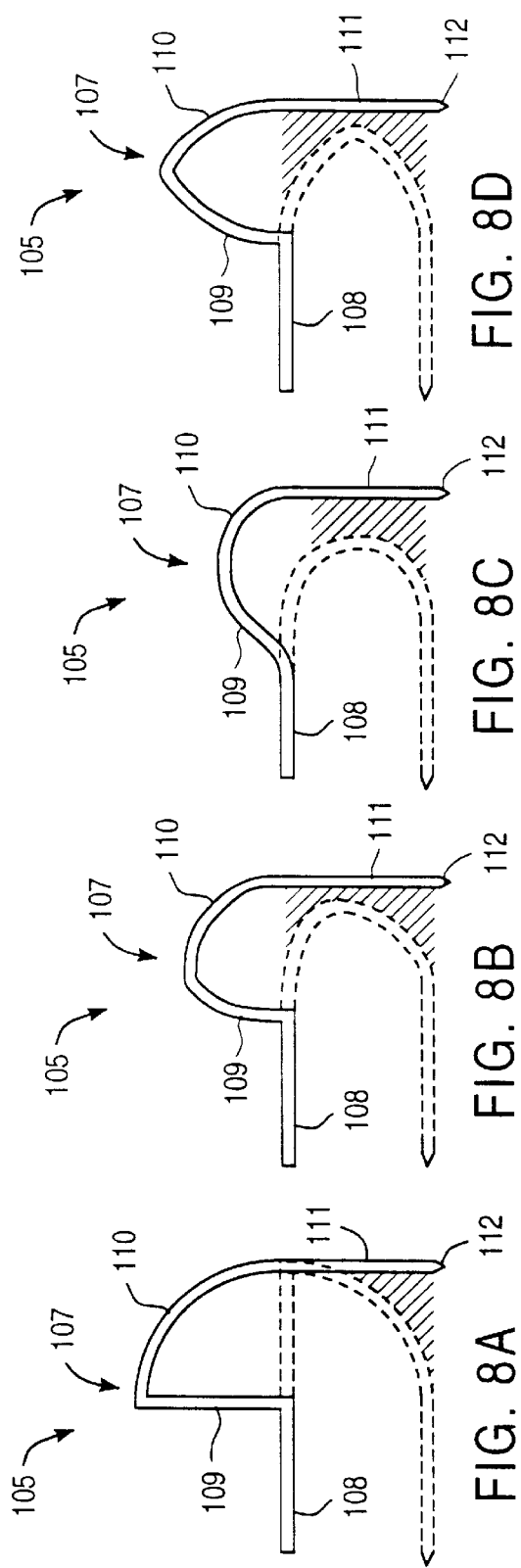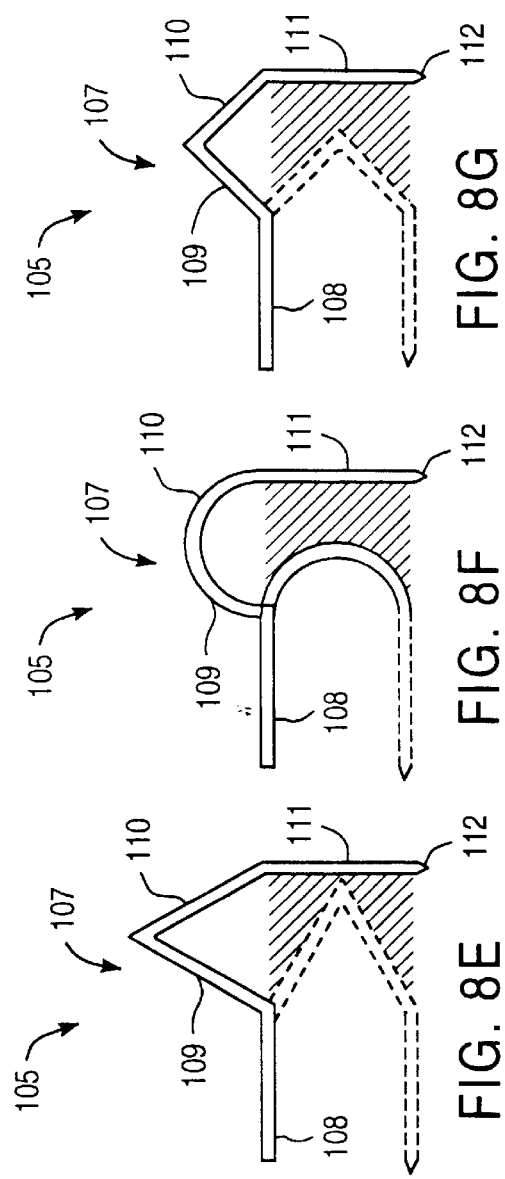

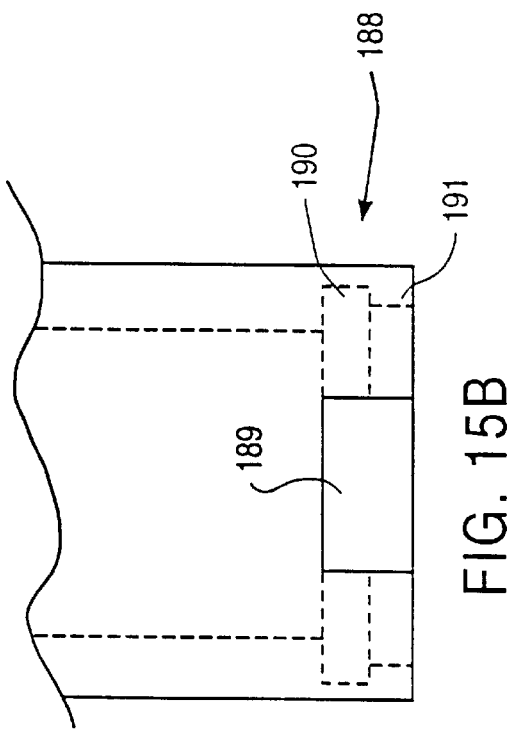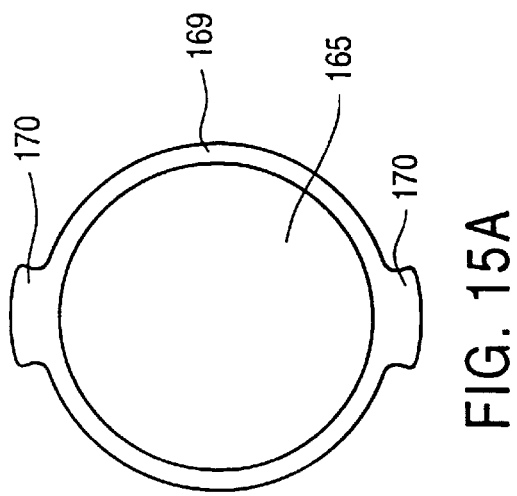

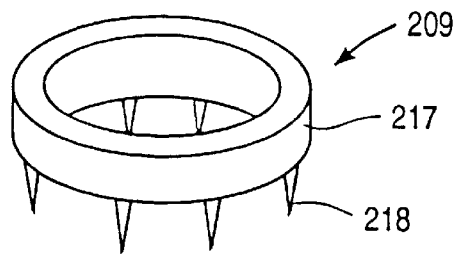
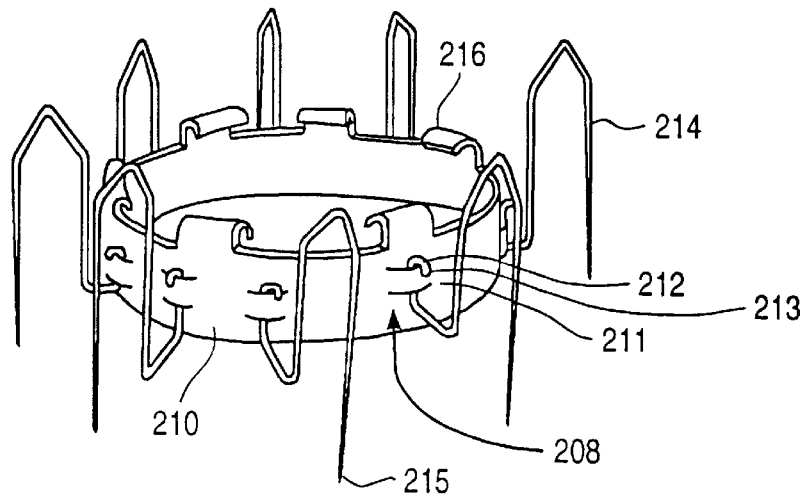
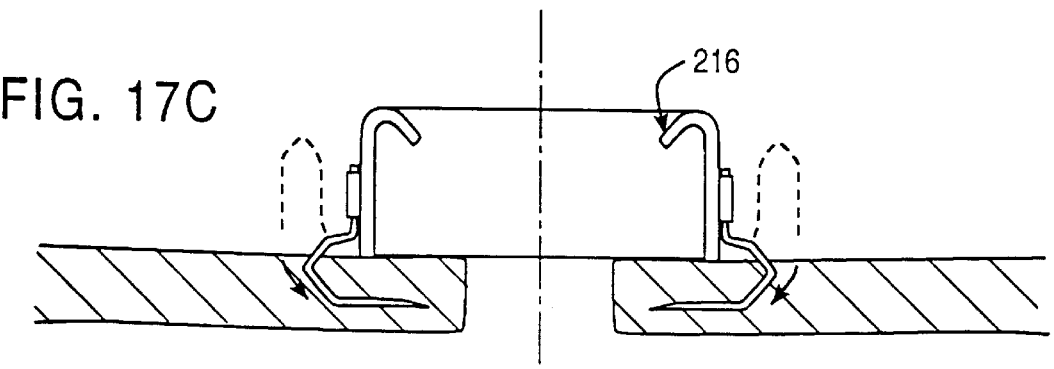
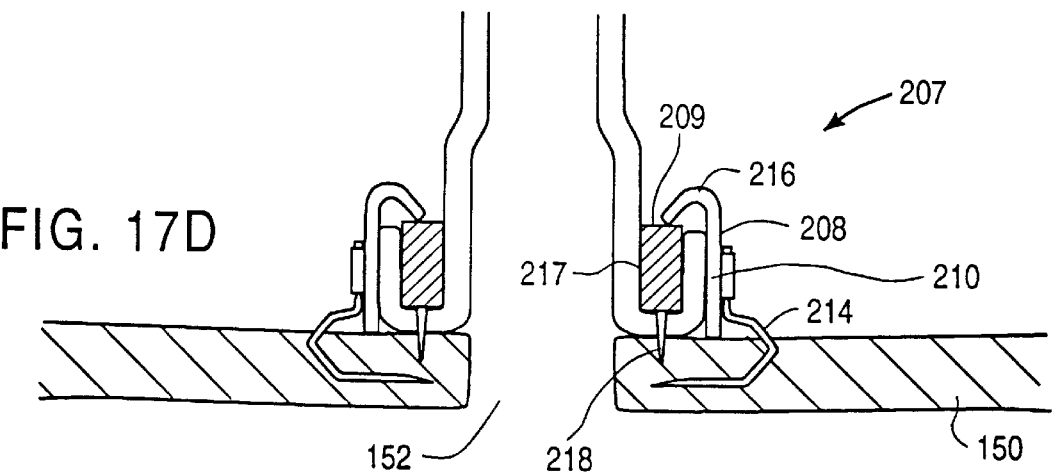

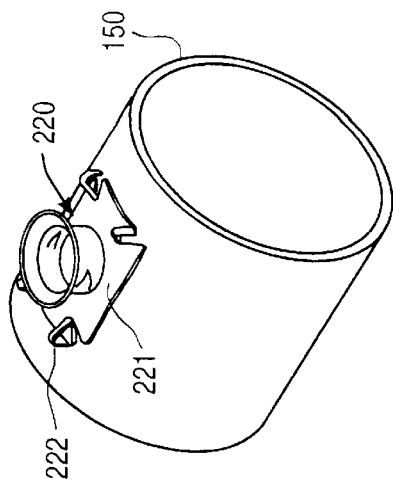
FIG. 18A
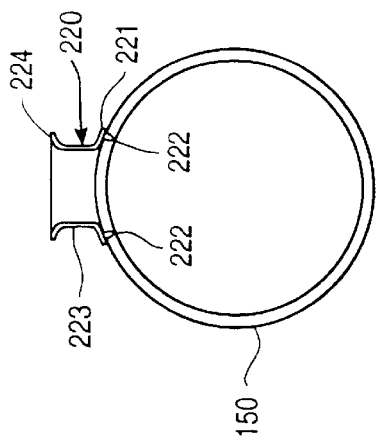
FIG. 18B
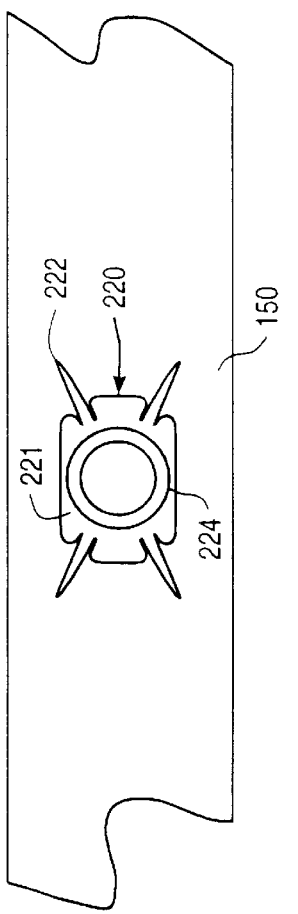
FIG. 18C
FIG. 18D
FIG. 18E
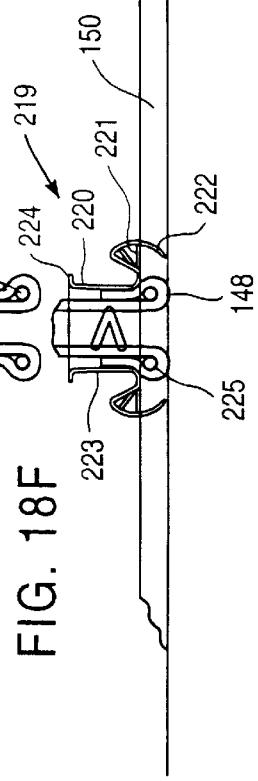
FIG. 18F

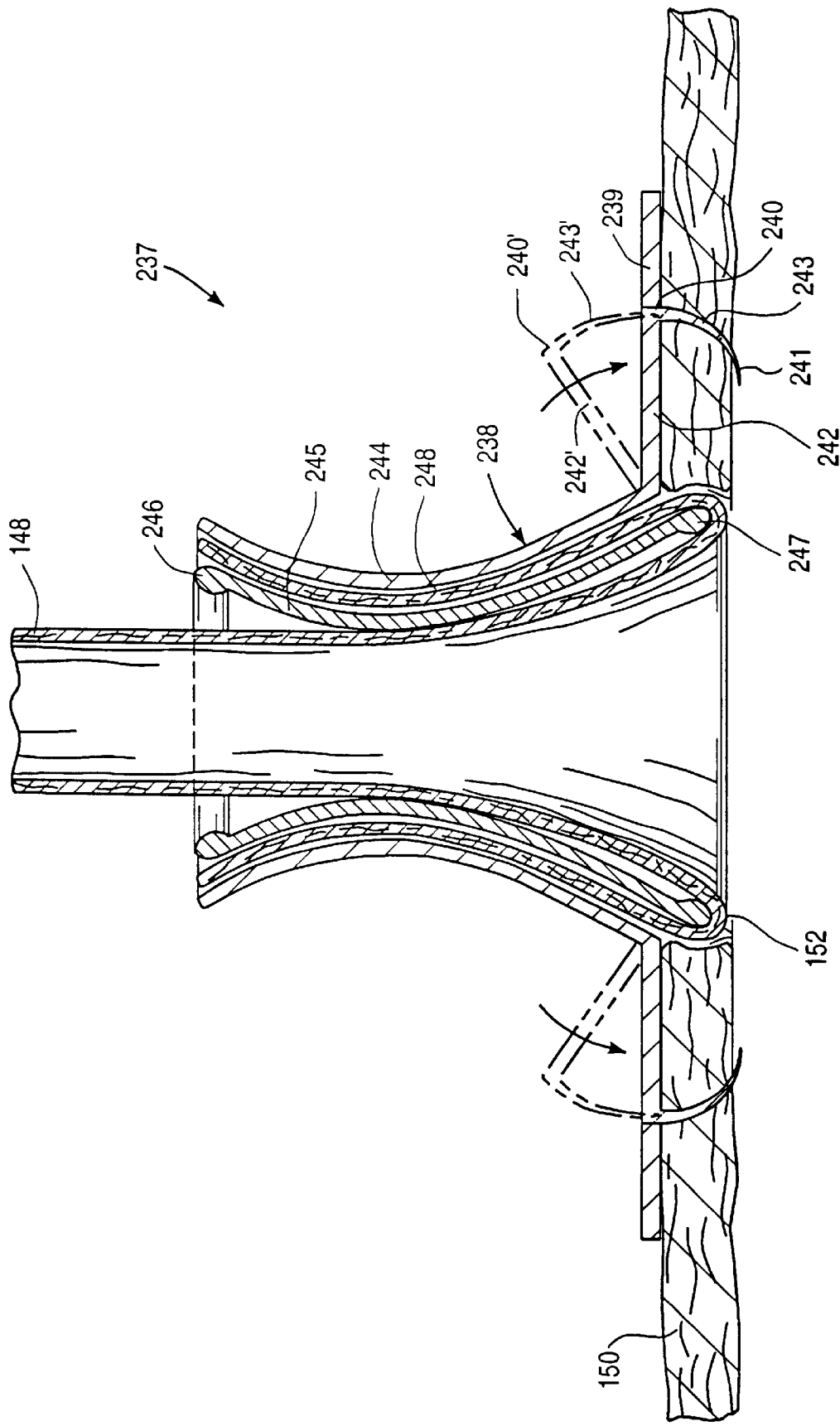

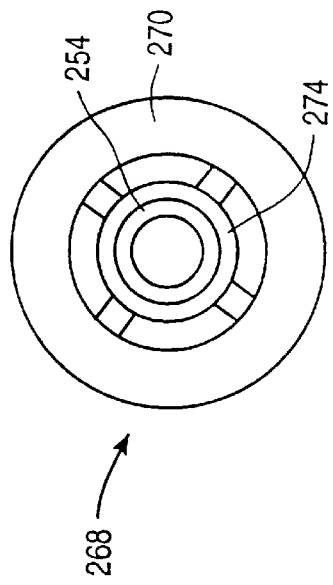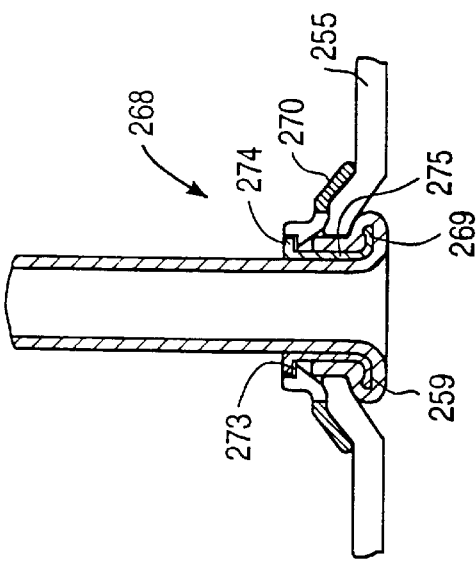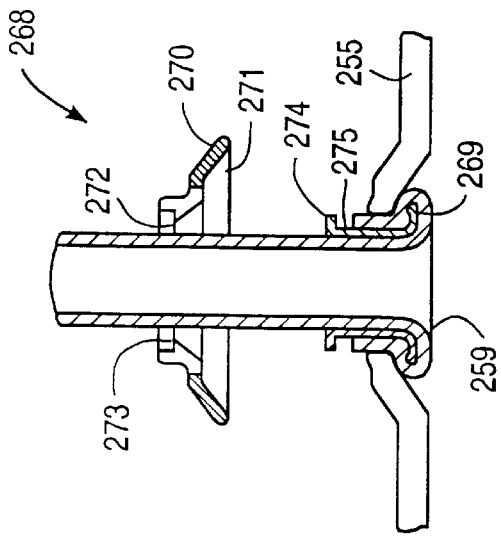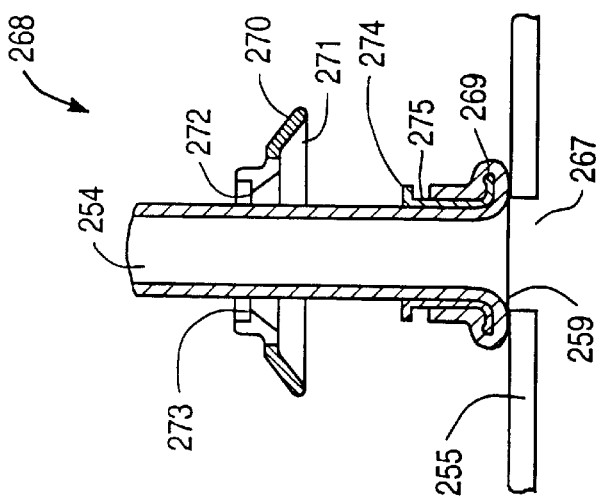

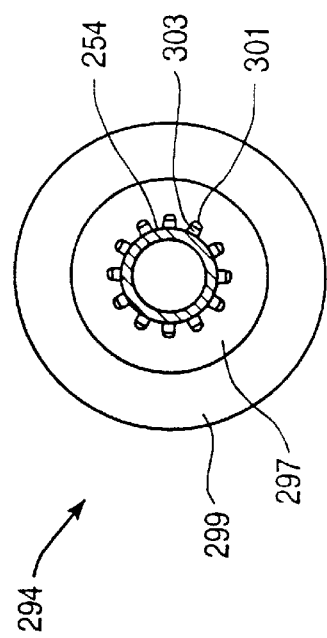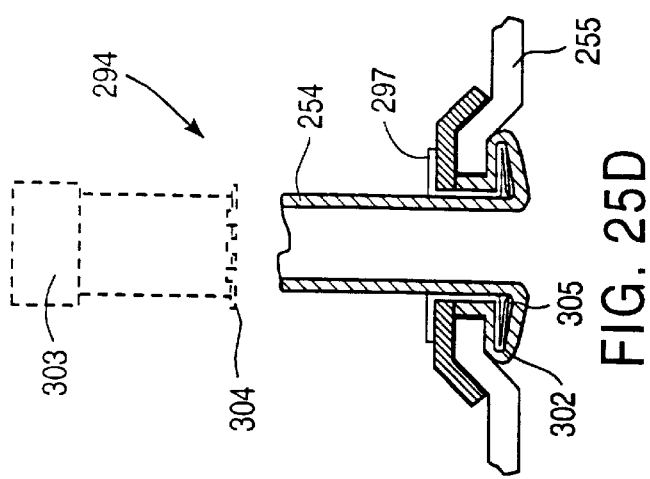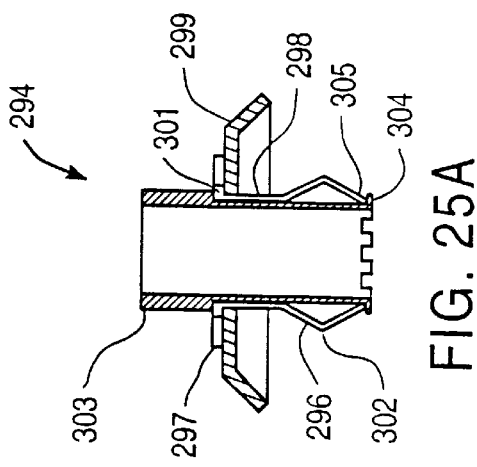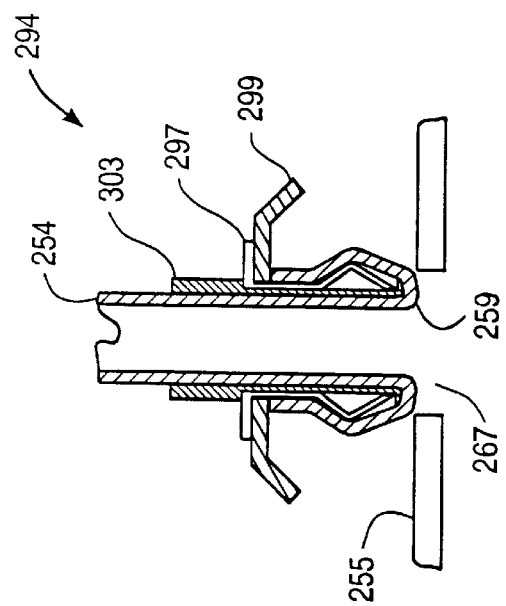

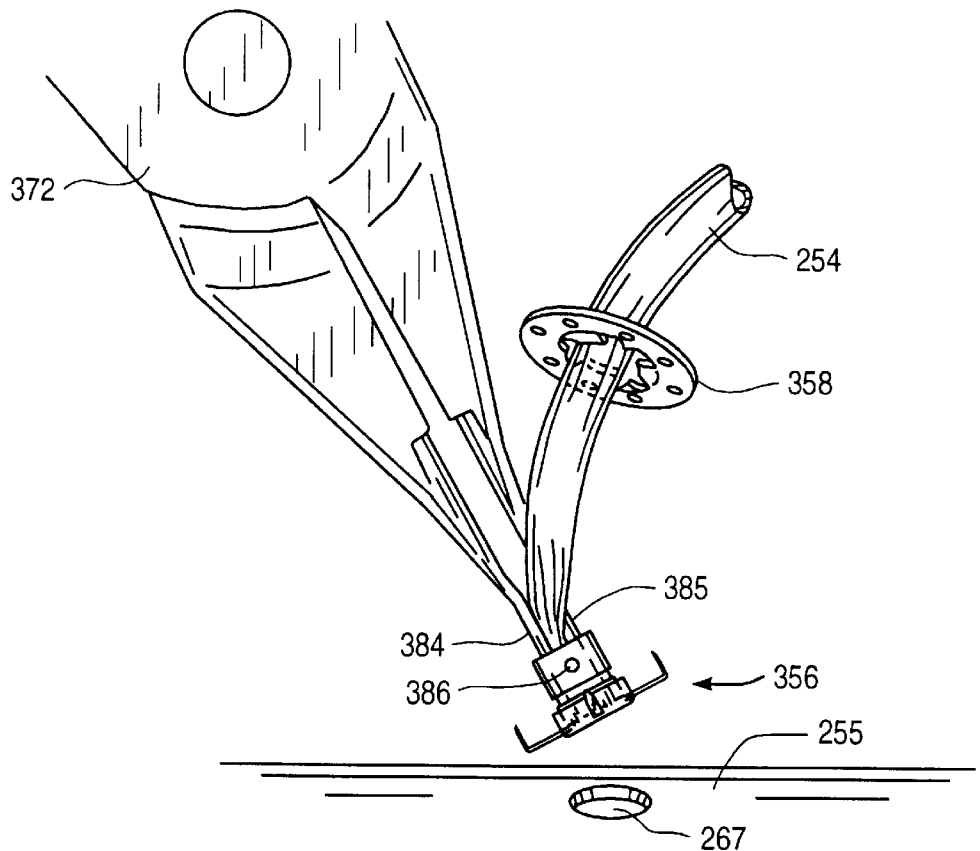
FIG. 30I
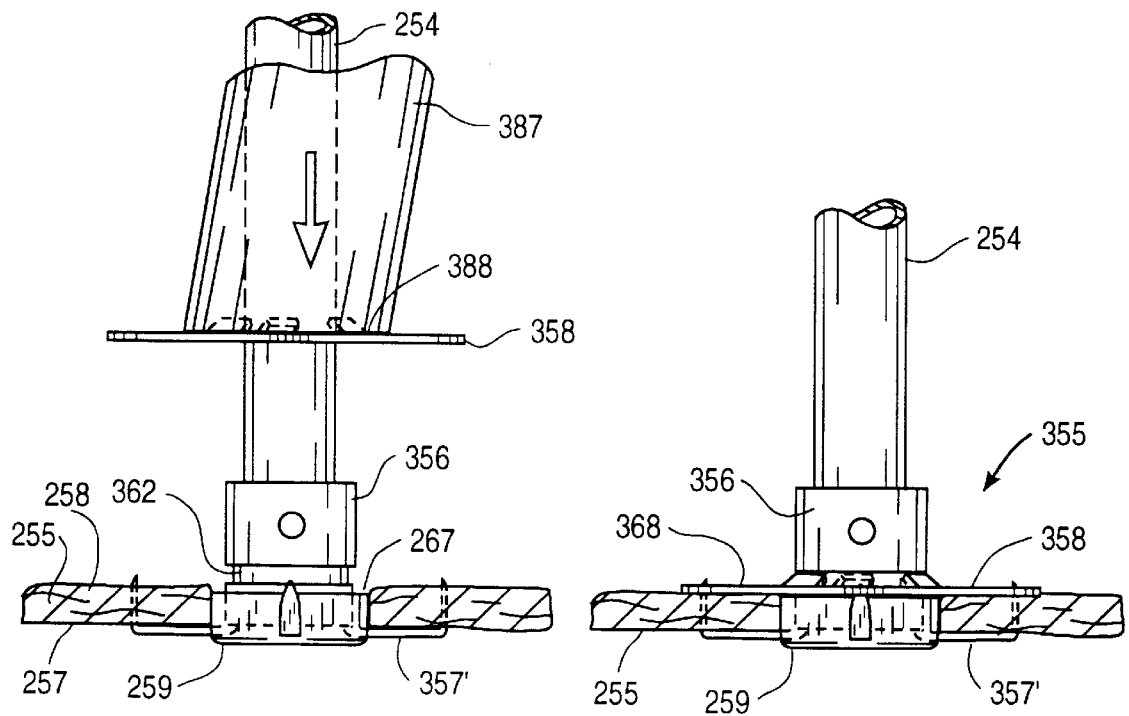
FIG. 30J
FIG. 30K

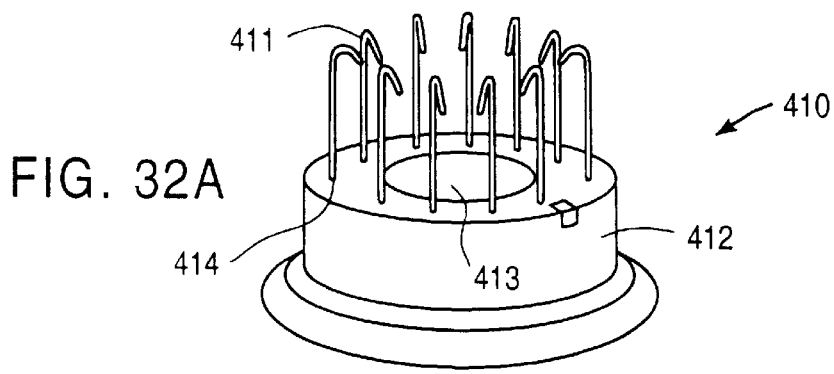
FIG. 32A
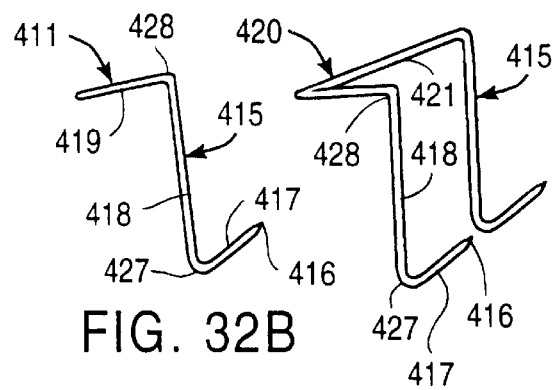
FIG. 32C
FIG. 32B
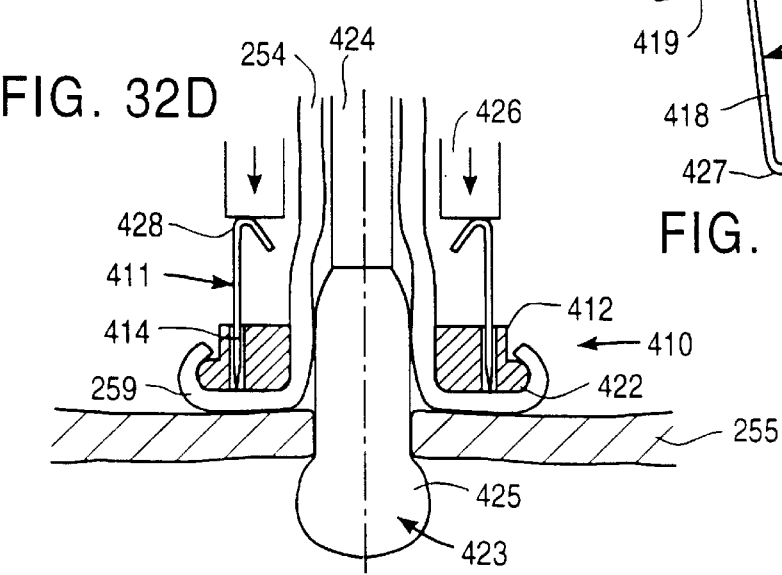
FIG. 32D
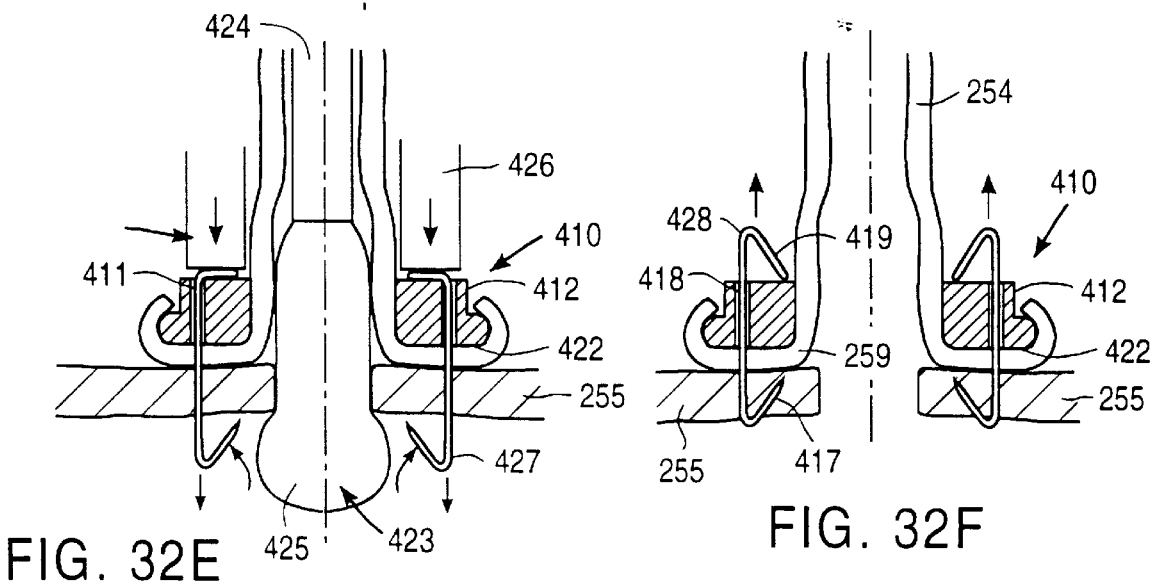
FIG. 32E
FIG. 32F

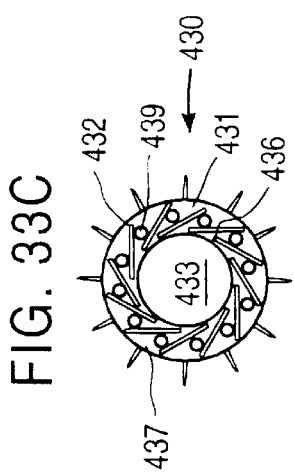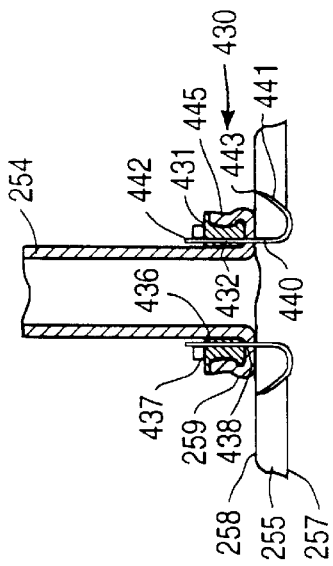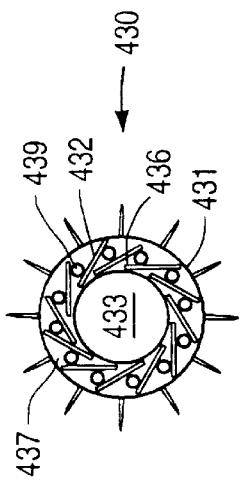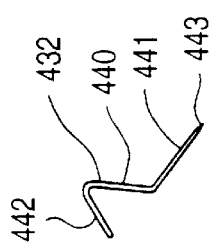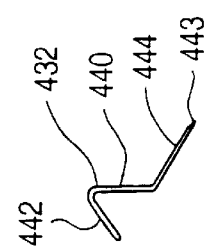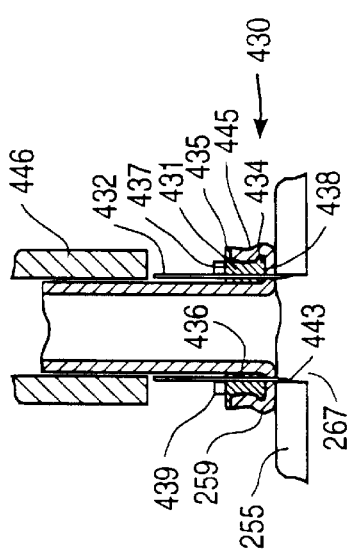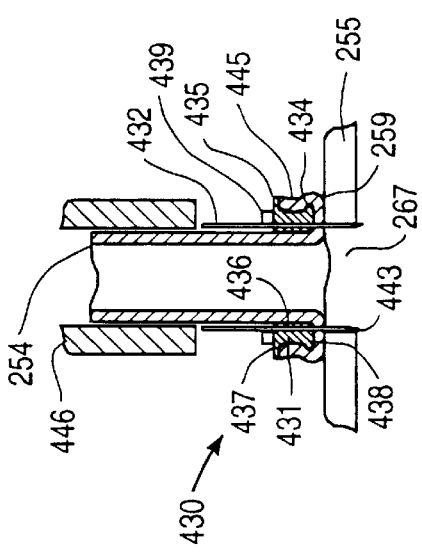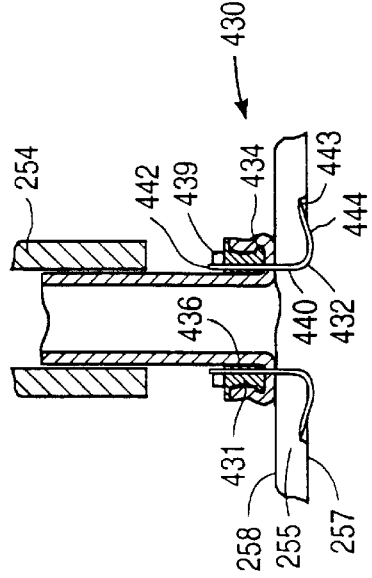

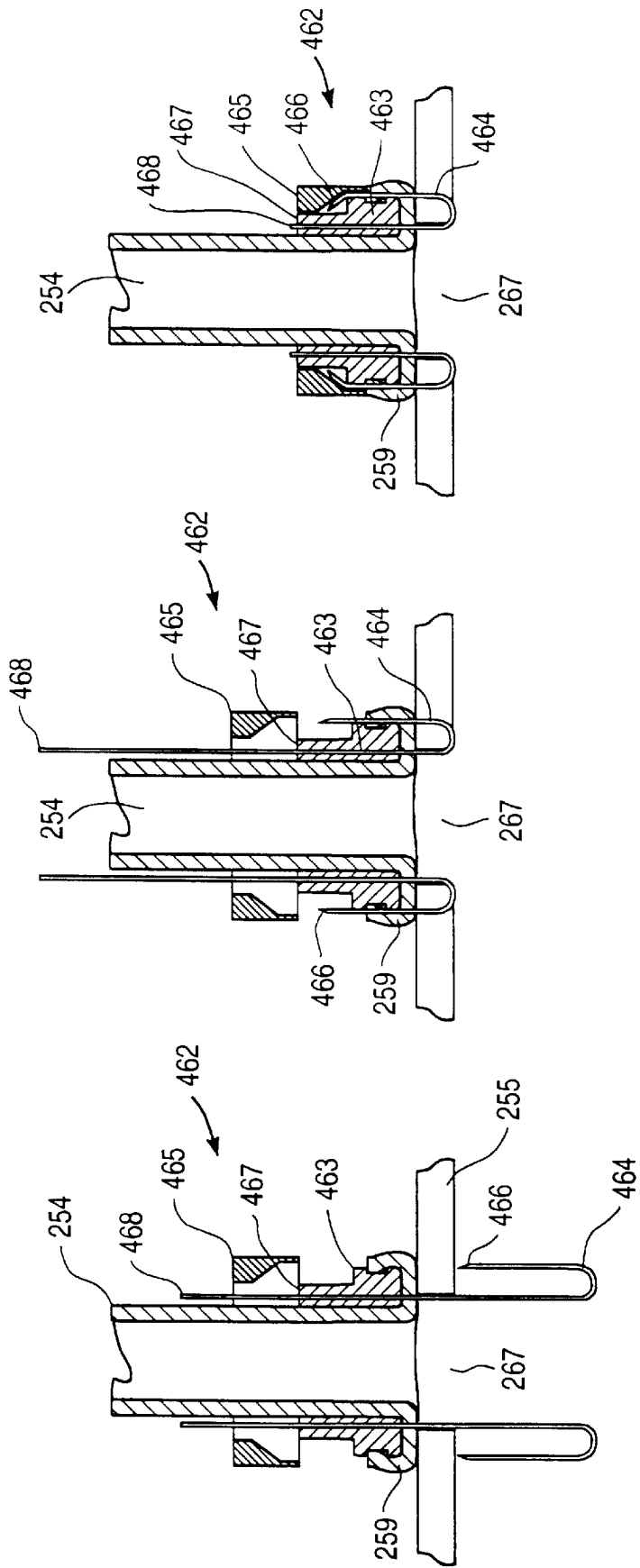

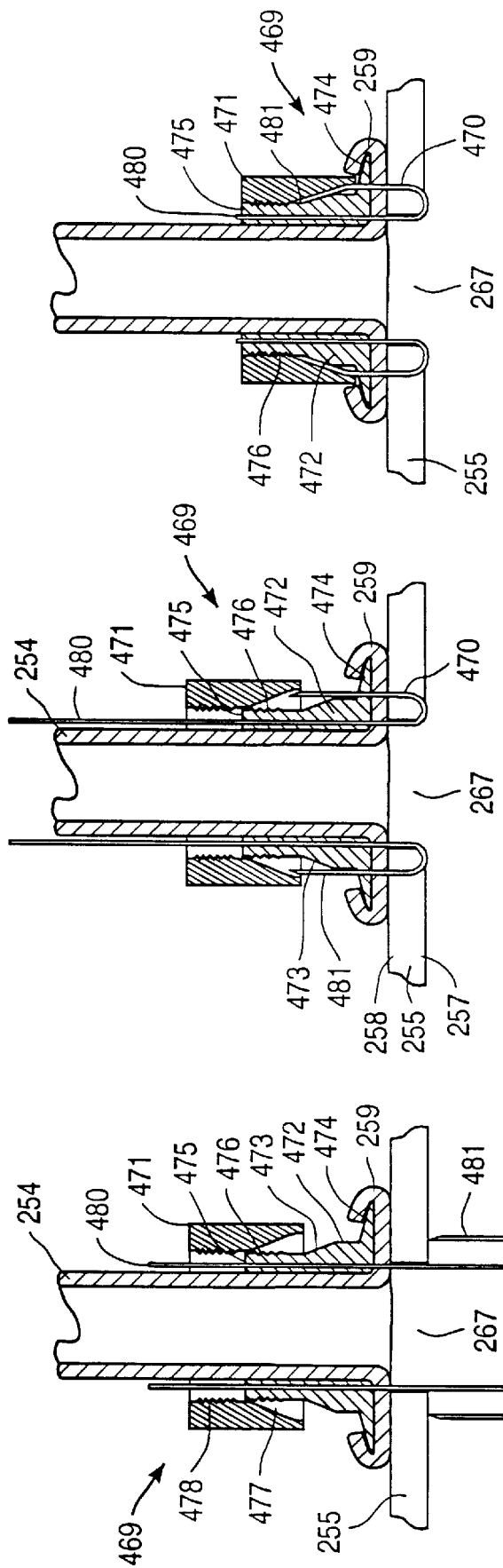

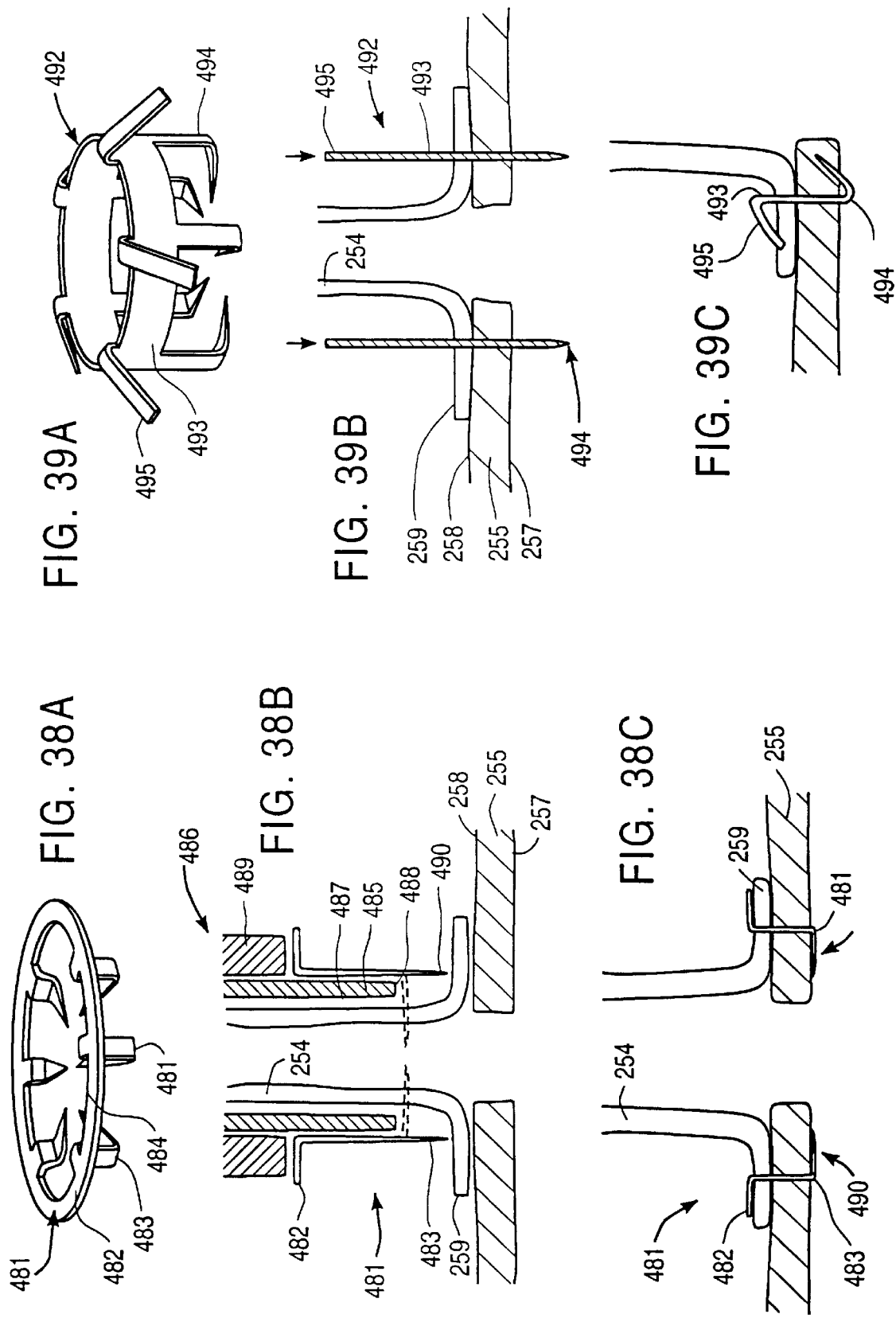

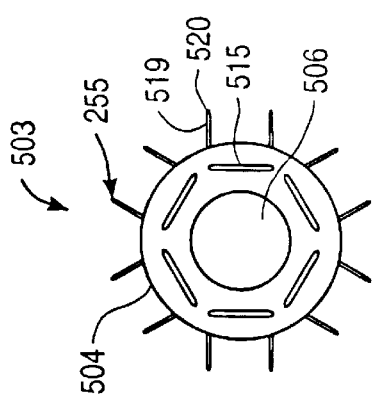
FIG. 41E
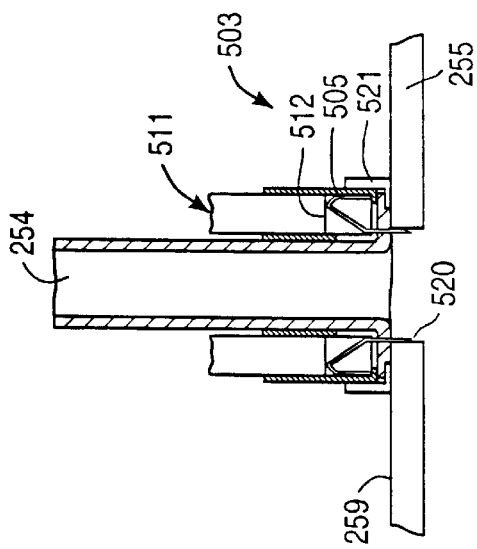
FIG. 41B
FIG. 41D
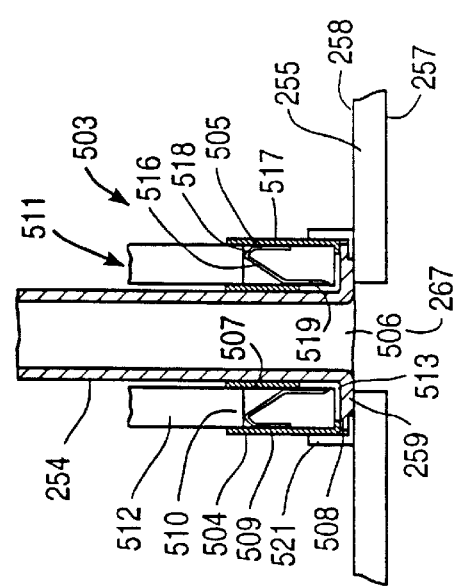
FIG. 41A
FIG. 41C

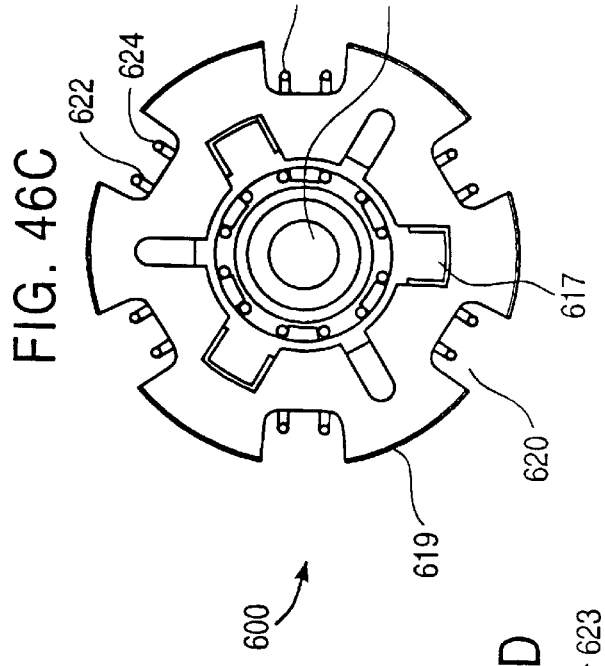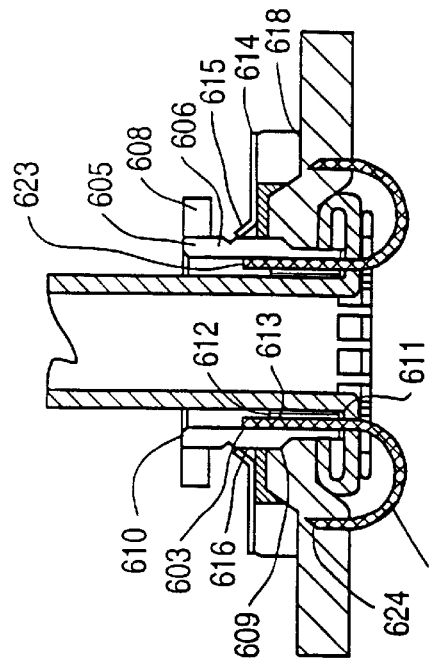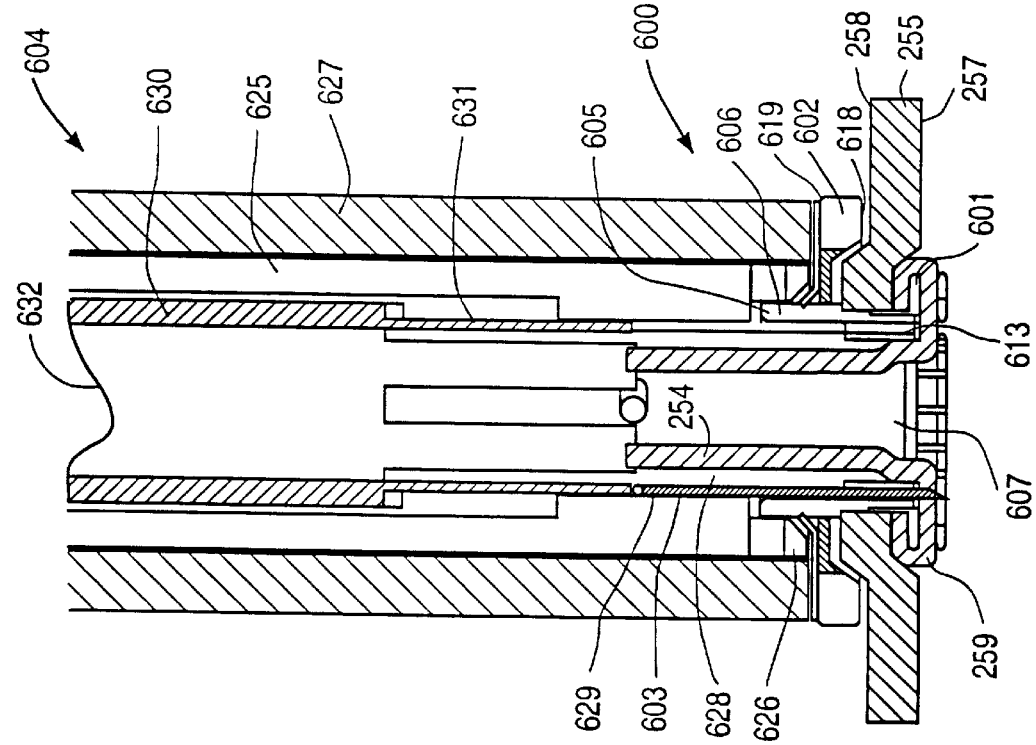

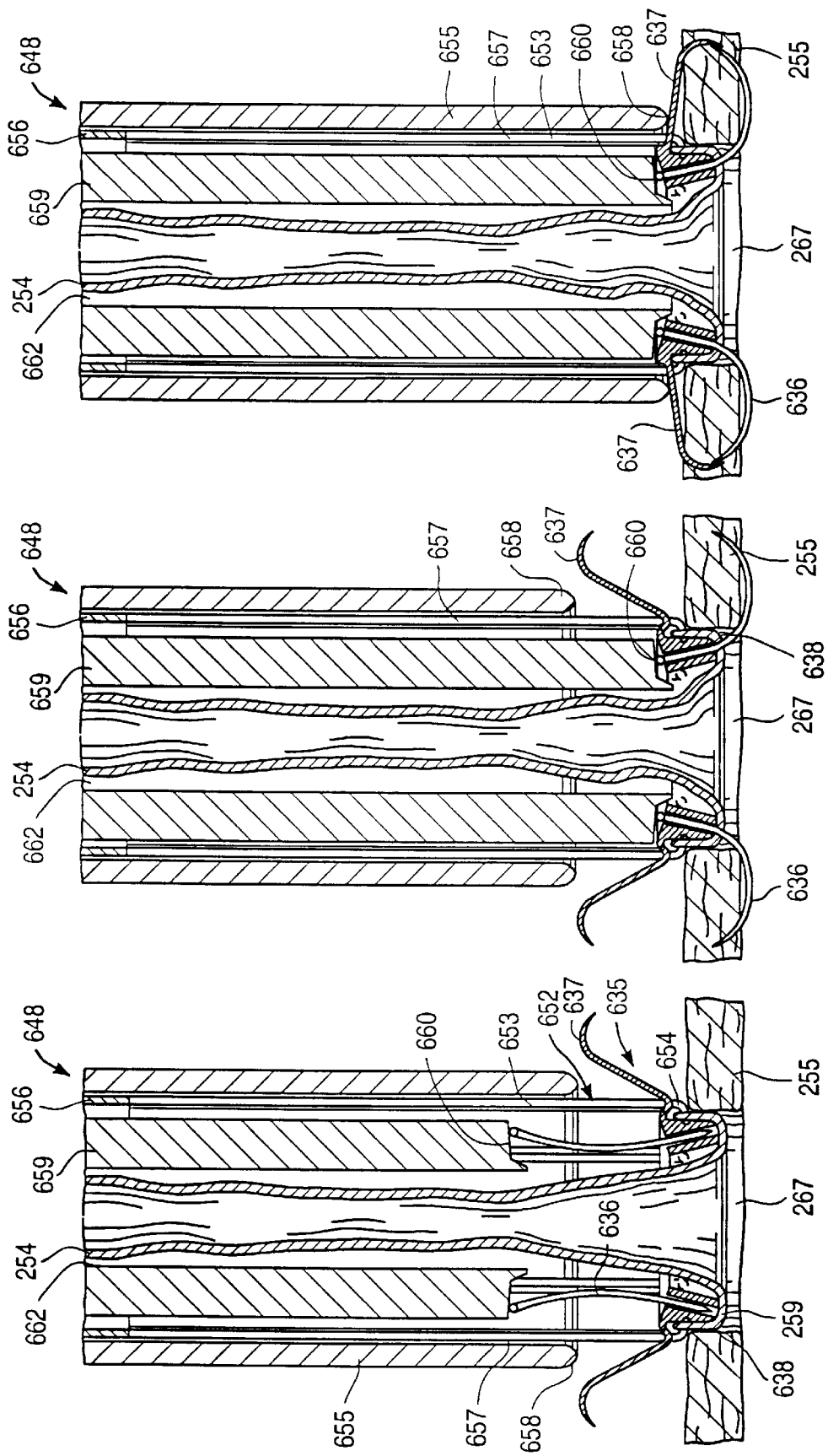

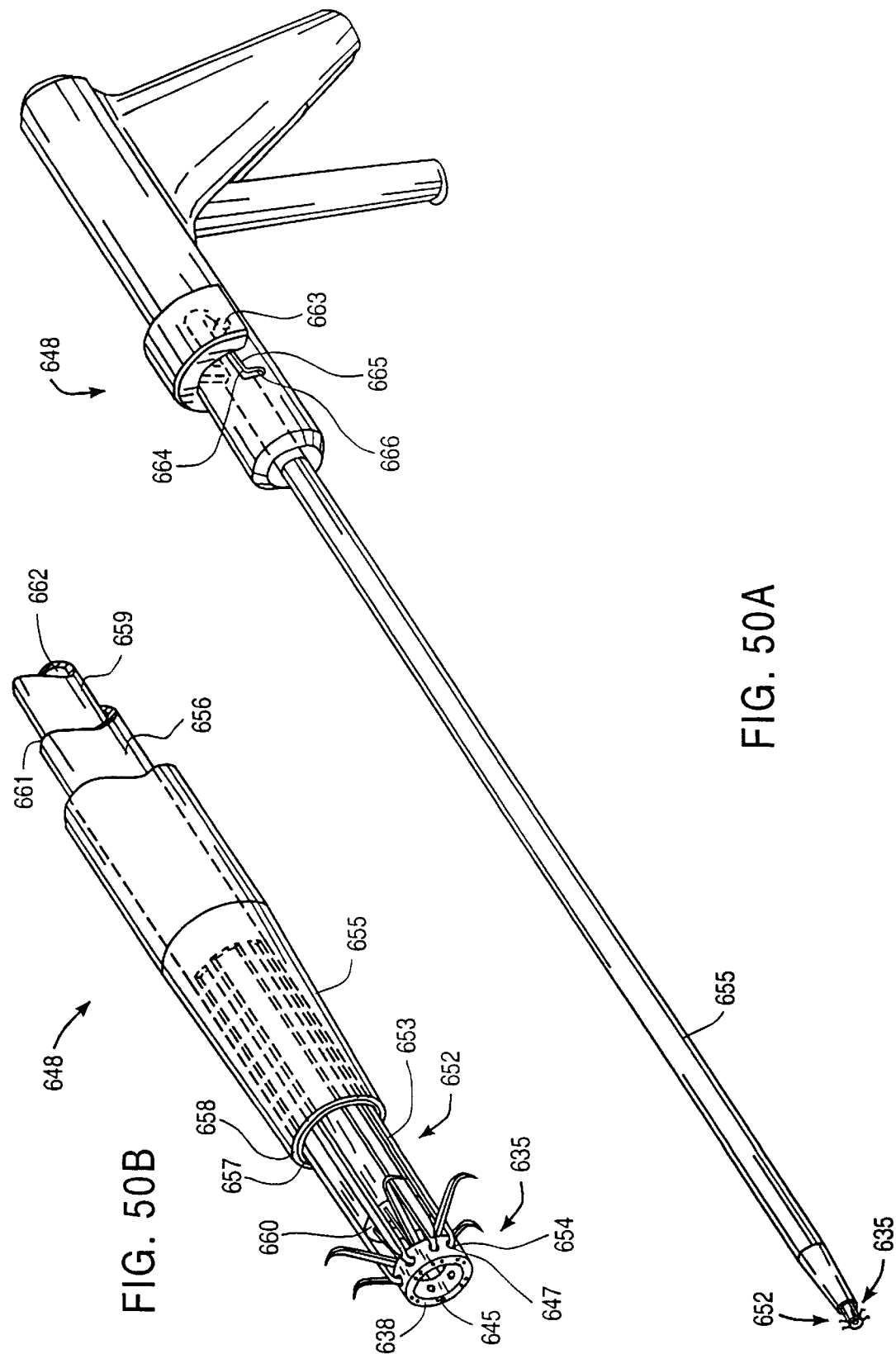

FIG. 53
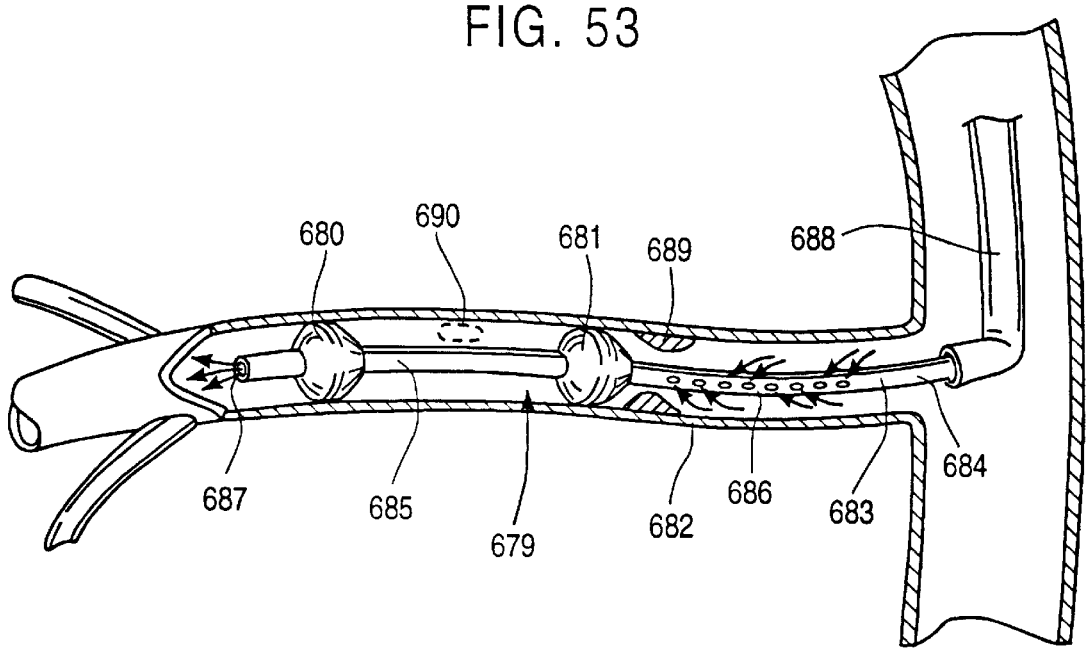
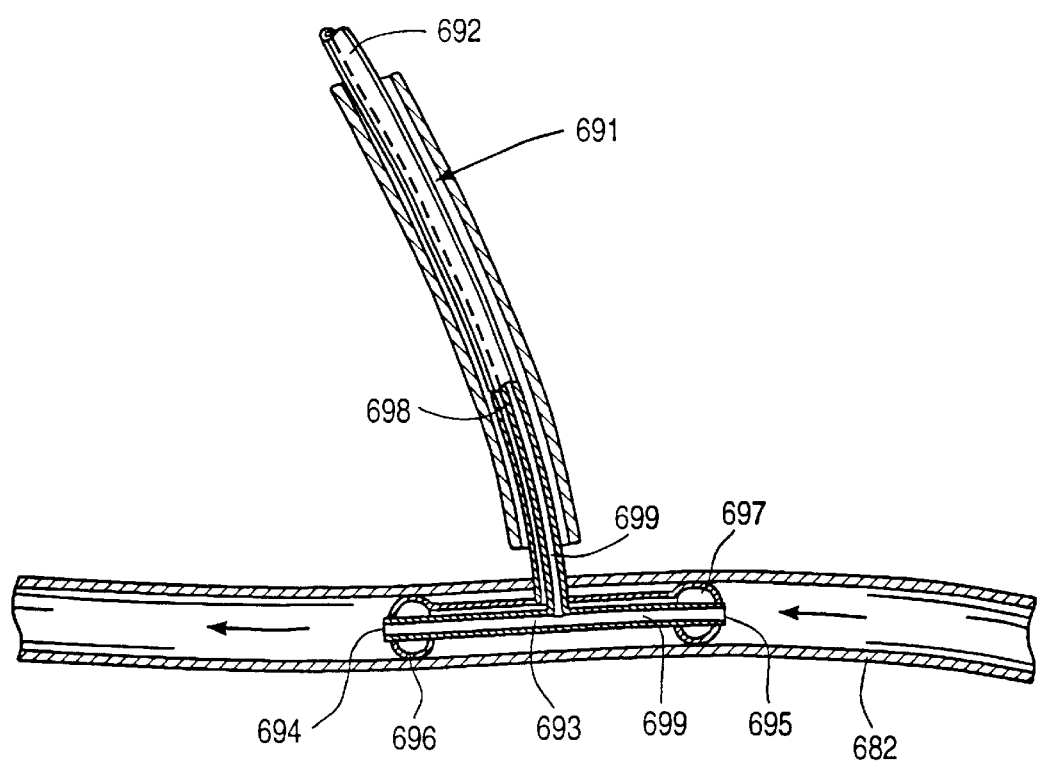
FIG. 54

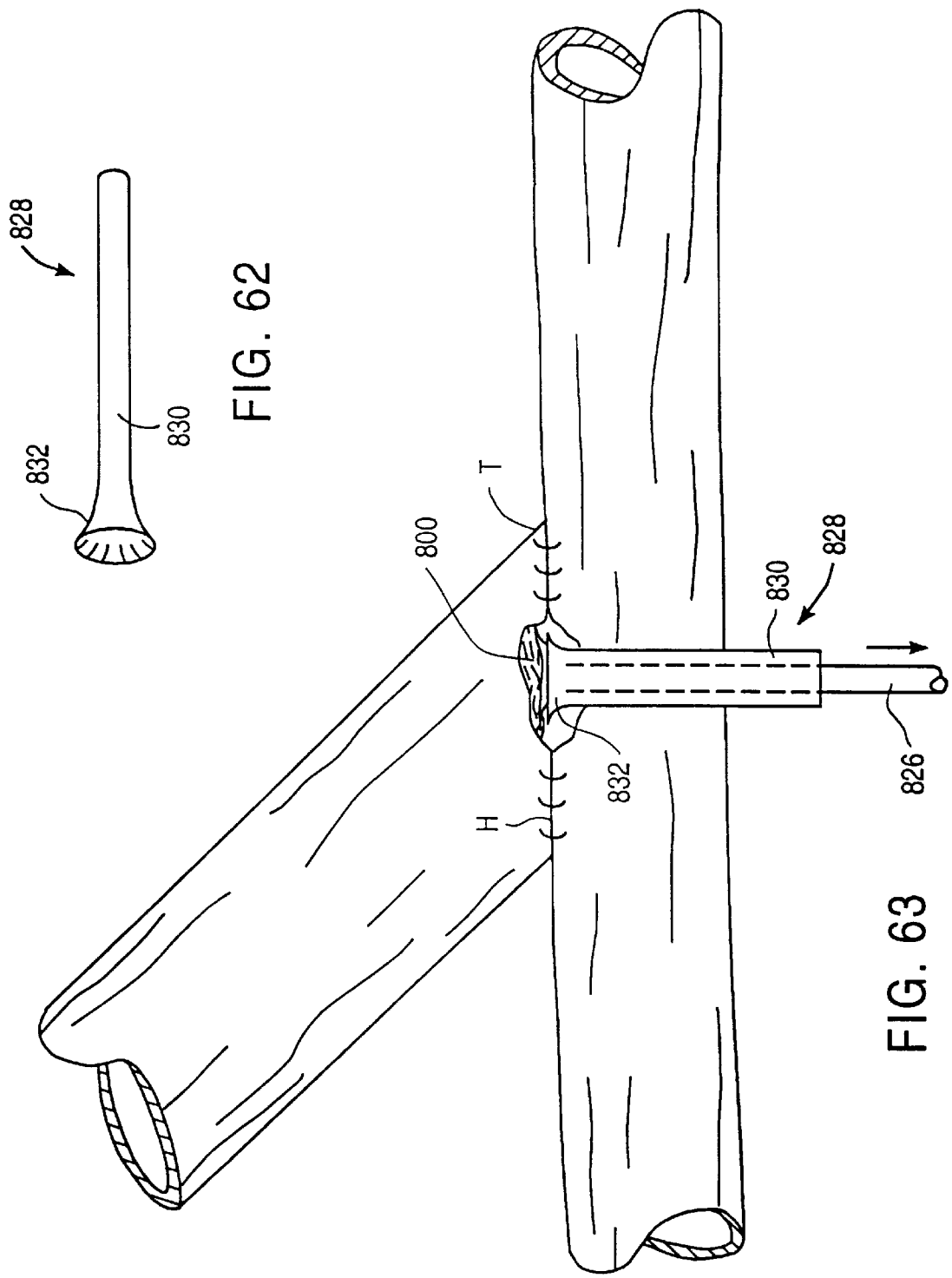

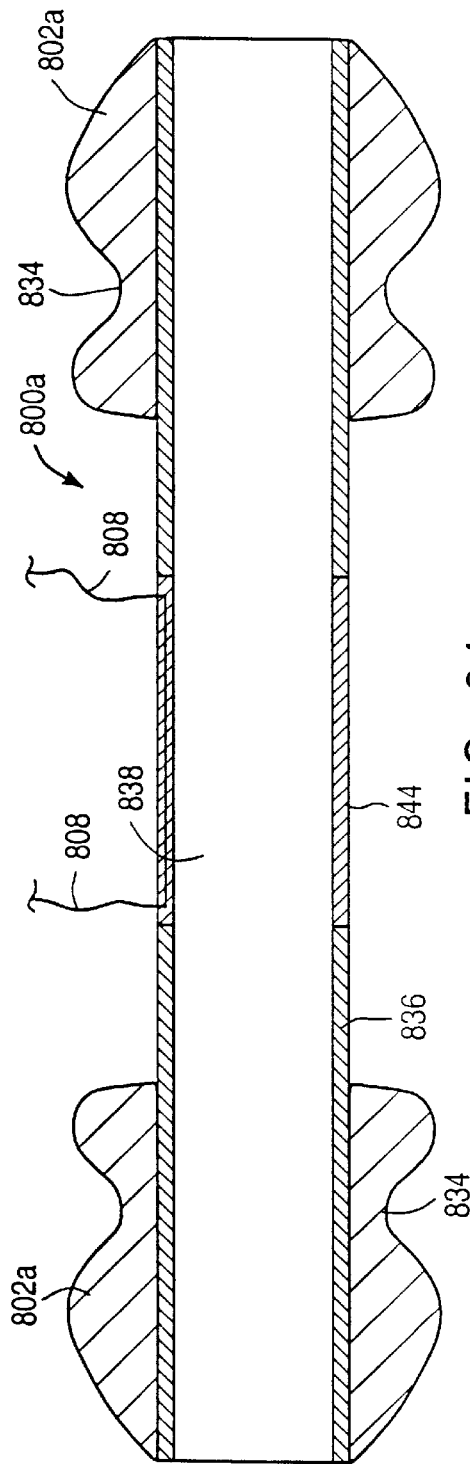
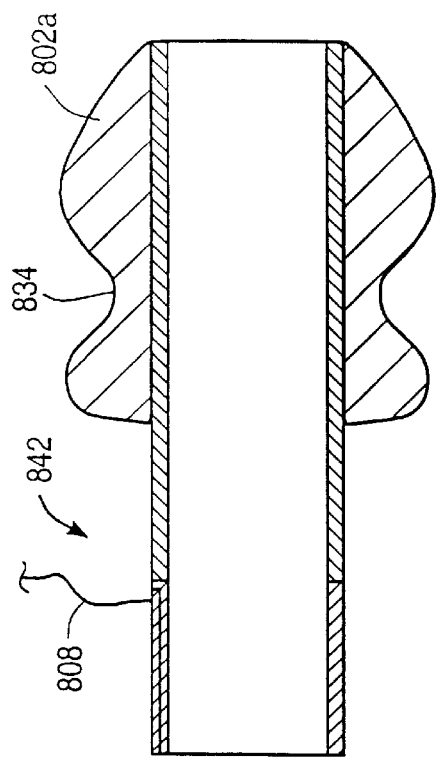
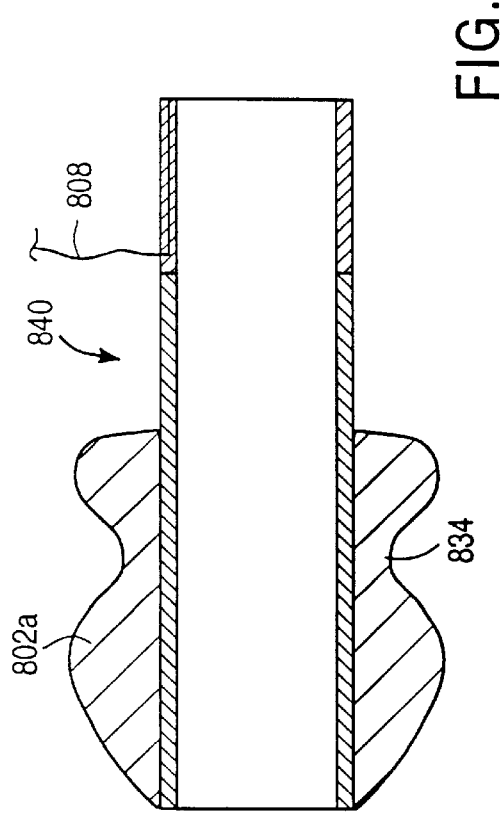
FIG. 64
FIG. 65

DEVICE AND METHOD FOR MINIMIZING HEART DISPLACEMENTS DURING A BEATING HEART SURGICAL PROCEDURE

CROSS-REFERENCE TO RELATED APPLICATIONS

This is a Division of application Ser. No. 08/680,889, filed Jul. 16, 1996 which is a c-i-p of Ser. No. 08/396,333 filed Feb. 24, 1995.

FIELD OF INVENTION

The present invention relates to devices and methods for coronary artery bypass grafting.

BACKGROUND OF THE INVENTION

Anastomosis is the surgical joining of biological tissues, especially the joining of tubular organs to create an intercommunication between them. Vascular surgery often involves creating an anastomosis between blood vessels or between a blood vessel and a vascular graft to create or restore a blood flow path to essential tissues. Coronary artery bypass graft surgery (CABG) is a surgical procedure to restore blood flow to ischemic heart muscle whose blood supply has been compromised by occlusion or stenosis of one or more of the coronary arteries. One method for performing CABG surgery involves harvesting a saphenous vein or other venous or arterial conduit from elsewhere in the body, or using an artificial conduit, such as one made of Dacron or Goretex tubing, and connecting this conduit as a bypass graft from a viable artery, such as the aorta, to the coronary artery downstream of the blockage or narrowing. A graft with both the proximal and distal ends of the graft detached is known as a "free graft". A second method involves rerouting a less essential artery, such as the internal mammary artery, from its native location so that it may be connected to the coronary artery downstream of the blockage. The proximal end of the graft vessel remains attached in its native position. This type of graft is known as a "pedicled graft". In the first case, the bypass graft must be attached to the native arteries by an end-to-side anastomosis at both the proximal and distal ends of the graft. In the second technique at least one end-to-side anastomosis must be made at the distal end of the artery used for the bypass. In the description below we will refer to the anastomoses on a free graft as the proximal anastomosis and the distal anastomosis. A proximal anastomosis is an anastomosis on the end of the graft vessel connected to a source of blood (e.g. the aorta) and a distal anastomosis is an anastomosis on the end of the graft vessel connected to the destination of the blood flowing through it (e.g. a coronary artery). The anastomoses will also sometimes be called the first anastomosis or second anastomosis, which refers to the order in which the anastomoses are performed regardless of whether the anastomosis is on the proximal or distal end of the graft.

At present, essentially all vascular anastomoses are performed by conventional hand suturing. Suturing the anastomoses is a time-consuming and difficult task, requiring much skill and practice on the part of the surgeon. It is important that each anastomosis provide a smooth, open flow path for the blood and that the attachment be completely free of leaks. A completely leak-free seal is not always achieved on the very first try. Consequently, there is a frequent need for resuturing of the anastomosis to close any leaks that are detected.

The time consuming nature of hand sutured anastomoses is of special concern in CABG surgery for several reasons. Firstly, the patient is required to be supported on cardiopulmonary bypass (CPB) for most of the surgical procedure, the heart must be isolated from the systemic circulation (i.e. "cross-clamped"), and the heart must usually be stopped, typically by infusion of cold cardioplegia solution, so that the anastomosis site on the heart is still and blood-free during the suturing of the anastomosis. CPB, circulatory isolation and cardiac arrest are inherently very traumatic, and it has been found that the frequency of certain postsurgical complications varies directly with the duration for which the heart is under cardioplegic arrest (frequently referred to as the "crossclamp time"). Secondly, because of the high cost of cardiac operating room time, any prolongation of the surgical procedure can significantly increase the cost of the bypass operation to the hospital and to the patient. Thus, it is desirable to reduce the duration of the crossclamp time and of the entire surgery by expediting the anastomosis procedure without reducing the quality or effectiveness of the anastomoses.

The already high degree of manual skill required for conventional manually sutured anastomoses is even more elevated for closed-chest or port-access thoracoscopic bypass surgery, a newly developed surgical procedure designed to reduce the morbidity of CABG surgery as compared to the standard open-chest CABG procedure. This procedure is more fully described in commonly-assigned, co-pending patent applications 08/023,778, filed Feb. 22, 1993, and 08/281,981, filed Jul. 28, 1994, the complete disclosures of which are hereby incorporated by reference. In the closed-chest procedure, surgical access to the heart is made through narrow access ports made in the intercostal spaces of the patient's chest, and the procedure is performed under thoracoscopic observation. Because the patient's chest is not opened, the suturing of the anastomoses must be performed at some distance, using elongated instruments positioned through the access ports for approximating the tissues and for holding and manipulating the needles and sutures used to make the anastomoses. This requires even greater manual skill than the already difficult procedure of suturing anastomoses during open-chest CABG surgery.

In order to reduce the difficulty of creating the vascular anastomoses during either open or closed-chest CABG surgery, it would be desirable to provide a rapid means for making a reliable end-to-side anastomosis between a bypass graft or artery and the aorta or the native vessels of the heart. A first approach to expediting and improving anastomosis procedures has been through stapling technology. Stapling technology has been successfully employed in many different areas of surgery for making tissue attachments faster and more reliably. The greatest progress in stapling technology has been in the area of gastrointestinal surgery. Various surgical stapling instruments have been developed for end-to-end, side-to-side, and end-to-side anastomoses of hollow or tubular organs, such as the bowel. These instruments, unfortunately, are not easily adaptable for use in creating vascular anastomoses. This is partially due to the difficulty in miniaturizing the instruments to make them suitable for smaller organs such as blood vessels. Possibly even more important is the necessity of providing a smooth, open flow path for the blood. Known gastrointestinal stapling instruments for end-to-side or end-to-end anastomosis of tubular organs are designed to create an inverted anastomosis, that is, one where the tissue folds inward into the lumen of the organ that is being attached. This is acceptable in gastrointestinal surgery, where it is most important to approximate the outer layers of the intestinal tract (the serosa). This is the tissue which grows together to form a strong, permanent connection. However, in vascular surgery this geometry is unacceptable for several reasons. Firstly, the inverted vessel walls would cause a disruption in the blood flow. This could cause decreased flow and ischemia downstream of the disruption, or, worse yet, the flow disruption or eddies created could become a locus for thrombosis which could shed emboli or occlude the vessel at the anastomosis site. Secondly, unlike the intestinal tract, the outer surfaces of the blood vessels (the adventitia) will not grow together when approximated. The sutures, staples, or other joining device may therefore be needed permanently to maintain the structural integrity of the vascular anastomosis. Thirdly, to establish a permanent, nonthrombogenic vessel, the innermost layer (the endothelium) should grow together for a continuous, uninterrupted lining of the entire vessel. Thus, it would be preferable to have a stapling instrument that would create vascular anastomoses that are everted, that is folded outward, or which create direct edge-to-edge coaptation without inversion.

At least one stapling instrument has been applied to performing vascular anastomoses during CABG surgery. This device, first adapted for use in CABG surgery by Dr. Vasilii I. Kolesov and later refined by Dr. Evgenii V. Kolesov (U.S. Pat. No. 4,350,160), was used to create an end-to-end anastomosis between the internal mammary artery (IMA) or a vein graft and one of the coronary arteries, primarily the left anterior descending coronary artery (LAD). Because the device could only perform end-to-end anastomoses, the coronary artery first had to be severed and dissected from the surrounding myocardium, and the exposed end everted for attachment. This technique limited the indications of the device to cases where the coronary artery was totally occluded, and therefore there was no loss of blood flow by completely severing the coronary artery downstream of the blockage to make the anastomosis. Consequently, this device is not applicable where the coronary artery is only partially occluded and is not at all applicable to making the proximal side-to-end anastomosis between a bypass graft and the aorta.

One attempt to provide a vascular stapling device for end-to-side vascular anastomoses is described in U.S. Pat. No. 5,234,447, granted to Kaster et al. for a Side-to-end Vascular Anastomotic Staple Apparatus. Kaster et al. provide a ring-shaped staple with staple legs extending from the proximal and distal ends of the ring to join two blood vessels together in an end-to-side anastomosis. However, this device falls short of fulfilling the desired objectives of the present invention. Specifically, Kaster does not provide a complete system for quickly and automatically performing an anastomosis. The method of applying the anastomosis staple disclosed by Kaster involves a great deal of manual manipulation of the staple, using hand operated tools to individually deform the distal tines of the staple after the graft has been attached and before it is inserted into the opening made in the aortic wall. One of the more difficult maneuvers in applying the Kaster staple involves carefully everting the graft vessel over the sharpened ends of the staple legs, then piercing the everted edge of the vessel with the staple legs. Experimental attempts to apply this technique have proven to be very problematic because of difficulty in manipulating the graft vessel and the potential for damage to the graft vessel wall. For speed, reliability and convenience, it is preferable to avoid the need for complex maneuvers while performing the anastomosis. Further bending operations must then be performed on the staple legs. Once the distal tines of the staple have been deformed, it may be difficult to insert the staple through the aortotomy opening. Another disadvantage of the Kaster device is that the distal tines of the staple pierce the wall of the graft vessel at the point where it is everted over the staple. Piercing the wall of the graft vessel potentially invites leaking of the anastomosis and may compromise the structural integrity of the graft vessel wall, serving as a locus for a dissection or even a tear which could lead to catastrophic failure. Because the Kaster staple legs only apply pressure to the anastomosis at selected points, there is a potential for leaks between the staple legs. The distal tines of the staple are also exposed to the blood flow path at the anastomosis site where it is most critical to avoid the potential for thrombosis. There is also the potential that exposure of the medial layers of the graft vessel where the staple pierces the wall could be a site for the onset of intimal hyperplasia, which would compromise the long-term patency of the graft. Because of these potential drawbacks, it is desirable to make the attachment to the graft vessel as atraumatic to the vessel wall as possible and to eliminate as much as possible the exposure of any foreign materials or any vessel layers other than a smooth uninterrupted intimal layer within the anastomosis site or within the graft vessel lumen.

A second approach to expediting and improving anastomosis procedures is through the use of anastomotic fittings for joining blood vessels together. One attempt to provide a vascular anastomotic fitting device for end-to-side vascular anastomoses is described in U.S. Pat. No. 4,366,819, granted to Kaster for an Anastomotic Fitting. This device is a four-part anastomotic fitting having a tubular member over which the graft vessel is everted, a ring flange which engages the aortic wall from within the aortic lumen, and a fixation ring and a locking ring which engage the exterior of the aortic wall. Another similar Anastomotic Fitting is described in U.S. Pat. No. 4,368,736, also granted to Kaster. This device is a tubular fitting with a flanged distal end that fastens to the aortic wall with an attachment ring, and a proximal end with a graft fixation collar for attaching to the graft vessel. These devices have a number of drawbacks that the present invention seeks to overcome. Firstly, the anastomotic fittings described expose the foreign material of the anastomotic device to the blood flow path within the arteries. This is undesirable because foreign materials within the blood flow path can have a tendency to cause hemolysis, platelet deposition and thrombosis. Immune responses to foreign material, such as rejection of the foreign material or auto-immune responses triggered by the presence of foreign material, tend to be stronger when the material is exposed to the bloodstream. As such, it is preferable that as much as possible of the interior surfaces of an anastomotic fitting that will be exposed to the blood flow path be covered with vascular tissue, either from the target vessel or from the graft vessel, so that a smooth, continuous, hemocompatible endothelial layer will be presented to the bloodstream. The anastomotic fitting described by Kaster in the '819 patent also has the potential drawback that the spikes that hold the graft vessel onto the anastomotic fitting are very close to the blood flow path, potentially causing trauma to the blood vessel that could lead to leaks in the anastomosis or compromise of the mechanical integrity of the vessels. Consequently, it is desirable to provide an anastomosis fitting that is as atraumatic to the graft vessel as possible. Any sharp features such as attachment spikes should be placed as far away from the blood flow path and the anastomosis site as possible so that there is no compromise of the anastomosis seal or the structural integrity of the vessels.

Another device, the 3M-Unilink device for end-to-end anastomosis (U.S. Pat. Nos. 4,624,257; 4,917,090; 4,917, 091) is designed for use in microsurgery, such as for reattaching vessels severed in accidents. This device provides an anastomosis clamp that has two eversion rings which are locked together by a series of impaling spikes on their opposing faces. However, this device is awkward for use in end-to-side anastomosis and tends to deform the target vessel; therefore it is not currently used in CABG surgery. Due to the delicate process needed to insert the vessels into the device, it would also be unsuitable for port-access surgery. In order to solve these and other problems, it is desirable to provide an anastomosis device which performs an end-to-side anastomosis between blood vessels or other hollow organs and vessels. It is also desirable to provide an anastomosis device which minimizes the trauma to the blood vessels while performing the anastomosis, which minimizes the amount of foreign materials exposed to the blood flow path within the blood vessels and which avoids leakage problems, and which promotes rapid endothelialization and healing. Further, it would be desirable to provide such a device which could be used in port-access CABG surgery. Whether it is used with open-chest or closed-chest surgical techniques, it is also desirable that the invention provide a complete system for quickly and automatically performing an anastomosis with a minimal amount of manual manipulation.

In another aspect of coronary artery bypass grafting, the coronary artery is occluded on both sides of the opening in the coronary artery to provide a clear surgical site. Typically, the coronary artery is occluded with tourniquets. A problem with conventional tourniquets is that the downstream side of the coronary artery does not receive oxygenated blood and ischemia may result.

Another method of providing a clear surgical site when performing an anastomosis is to use a shunt having a blood flow lumen therethrough. The blood flow lumen permits blood flow across the anastomosis to prevent ischemia on the downstream side of the coronary artery. The shunt is simply a tube which may have occluding members for occluding the coronary artery or tourniquets may be used around the tube to occlude the coronary artery around the shunt.

A problem with known coronary shunts is that they are difficult to remove. A method of removing the coronary shunt is to use a tourniquet extending around the middle of the shunt. The tourniquet extends through the graft and is pulled through the graft when the anastomosis is complete. A problem with this method of removing the shunt is that the graft may be damaged by the shunt when the shunt is pulled through the graft. Another problem with this method is that it cannot be used when the internal mammary artery is used since the proximal end of the graft is not cut open for removing the shunt.

Another method of removing the shunt is to simply pull the shunt through an opening between the graft and the coronary artery before the anastomosis is complete. A problem with this method of removing the shunt is that the shunt may rip the anastomosis when removed.

SUMMARY OF THE INVENTION

In keeping with the foregoing discussion, the present invention provides an anastomosis s stem for quickly and reliably performing an end-to-side vascular anastomosis. The anastomosis system includes an anastomosis device, an application instrument and methods for their use in performing an end-to-side vascular anastomosis. The system is especially useful for performing an anastomosis between a vascular graft and the wall of the ascending aorta in CABG surgery, particularly in port-access CABG surgery. One desirable attribute of the anastomosis system is that the system should be as atraumatic as possible to the graft vessel in creating the anastomosis. Another desirable attribute of the anastomosis system is that the anastomosis device should minimize the amount of foreign material exposed to the blood flow path in the completed anastomosis. The anastomosis device of the system has a generally tubular or ring-shaped body having a proximal end and a distal end. An orifice or internal lumen in the body allows the graft vessel to pass through the device from the proximal end to the distal end. The body of the device has an attachment means at the distal end for attachment to the graft vessel, generally by everting the graft vessel over the attachment means. Means are provided for attaching the device and the graft vessel to the wall of the target vessel. Different embodiments of the anastomosis device are presented which vary in the form of the means used for attaching to the graft vessel and the target vessel.

A first aspect of the present invention takes the form of a vascular anastomosis staple device which may be used as part of an overall anastomosis stapling system and method designed to efficiently and reliably perform an end-to-side anastomosis between a graft vessel and the wall of a target vessel. The anastomosis staple device forms an atraumatic attachment to the end of the graft vessel so that only a smooth uninterrupted layer of intimal cells is exposed at the anastomosis site or within the graft vessel lumen. The anastomosis staple device creates a firm, reliable attachment between the graft vessel and the target vessel wall, with a tailored amount of tissue compression applied at the anastomosis site to form a leak-proof joint between the graft vessel and the target vessel wall. The anastomosis stapling system is designed to combine the various functions of graft vessel preparation, target vessel preparation, vessel approximation and anastomosis stapling into an integrated system of instruments so that the anastomosis can be performed efficiently with a minimum of manual manipulation of the vessels or the instruments involved. Different embodiments of the anastomosis stapling system are provided to meet the needs of performing either a first anastomosis or a second anastomosis of a bypass procedure. The anastomosis stapling system is configured to be adaptable for closed-chest or port-access CABG surgery or for more conventional open-chest CABG surgery.

In one preferred configuration of the invention, the anastomosis staple device consists of two parts: an anchor member and a coupling member. The anchor member forms the attachment with the target vessel wall. The coupling member separately forms the attachment with the bypass graft vessel. The complete anastomosis is created when the coupling member, with the graft vessel attached, is inserted into the anchor member. In a second preferred configuration of the invention, the anastomosis staple device combines the functions of the anchor member and the coupling member into a single member. A one-piece anastomosis staple device attaches to both the target vessel wall and the graft vessel to form a complete end-to-side anastomosis. In all embodiments of the anastomosis staple device, certain desirable aspects are maintained, specifically the atraumatic attachment of the device to the graft vessel and the rapid, reliable formation of the anastomosis, as well as the adaptability of the staple device to port-access CABG surgery.

A second aspect of the present invention takes the form of an anastomotic fitting for attaching the end of a graft vessel to an opening formed in the side wall of a target vessel. The anastomotic fitting has an inner flange which provides an atraumatic attachment for the everted end of a graft vessel. The inner flange is configured so that, wherever possible, a smooth, continuous, uninterrupted layer of intimal tissue lines the graft vessel, the target vessel and the anastomotic site, with as little foreign material as possible exposed to the blood flow path. The outer flange contacts the exterior surface of the target vessel. A locking means, which may be part of the outer flange, locks the outer flange in a fixed position relative to the inner flange. The inner flange, in combination with the outer flange, provides a firm attachment to the target vessel wall. A tailored amount of compression applied by the inner and outer flanges grips the target vessel wall and creates a leak-proof seal between the graft vessel and the target vessel. Optionally, attachment spikes on the surfaces of either the inner or the outer flange provide additional grip on the graft vessel and/or the target vessel. The attachment spikes are isolated from the blood flow lumens of the graft vessel and the target vessel so that they do not compromise the anastomotic seal or the structural integrity of the anastomotic attachment.

In a first representative embodiment, the anastomotic fitting is made up of two coacting parts: a) a tubular inner sleeve, which has an internal lumen of sufficient size to accommodate the external diameter of the graft vessel and an inner flange which is attached at the distal end of the inner sleeve, and b) an outer flange which has a central orifice that is sized to fit over the exterior of the inner sleeve. An adjustable locking mechanism holds the outer flange on the inner sleeve at a selected position to create a tailored degree of tissue compression at the anastomotic site.

The anastomosis procedure is performed by passing the end of the graft vessel through the inner lumen of the inner sleeve until the end of the vessel extends a short distance from the distal end of the sleeve. The end of the graft vessel is then everted over the inner flange of the fitting to form an atraumatic attachment. A loop of suture or spikes on the outside of the inner sleeve or flange may be added to help retain the graft vessel in its everted position. The inner flange and the everted end of the graft vessel are then passed through an opening that has previously been made in the wall of the target vessel with an instrument such as an aortic punch. The opening must stretch slightly to allow the inner flange to pass through. The elastic recovery of the target vessel wall around the opening helps to create an anastomotic seal by contracting around the inner sleeve and the everted graft vessel wall. The outer flange is then slid onto the proximal end of the inner sleeve. If the anastomosis being performed is the first anastomosis on a free graft, such as a saphenous vein graft, then the outer flange can be slid over the graft vessel from the free end. If the other end of the graft vessel is not free, such as when performing the second anastomosis of a free graft or a distal anastomosis on a pedicled graft like the IMA, then the outer flange should be back loaded onto the graft vessel or preloaded onto the proximal end of the inner sleeve before the end of the graft vessel is attached to the inner flange of the fitting. The outer flange is slid down the inner sleeve until it contacts the exterior wall of the target vessel. A tailored amount of compression is applied to the anastomosis and the locking mechanism is engaged to complete the anastomosis.

A second representative embodiment of the anastomotic fitting has an expanding inner flange which facilitates the atraumatic attachment of the graft vessel to the fitting and makes it easier to pass the inner flange and the everted graft vessel through the opening in the target vessel wall. The graft vessel is passed through an internal lumen of an inner sleeve which has the expandable inner flange attached at its distal end. The end of the graft vessel is everted over the unexpanded inner flange. The inner flange and the everted end of the graft vessel are passed through the opening in the target vessel wall. Once the inner flange of the fitting is in the lumen of the target vessel, it is expanded to a diameter which is significantly larger than the opening in the target vessel wall. Then an outer flange is applied and locked into a selected position on the inner sleeve as described above to complete the anastomosis.

Different mechanisms are disclosed to accomplish the expansion of the inner flange. In a first variant of the expanding inner flange, the flange and a portion of the inner sleeve are slotted to create multiple fingers which are initially collapsed inward toward the center of the sleeve. A second inner sleeve is slidably received within the slotted inner sleeve. The graft vessel is inserted through the internal lumen of both sleeves and everted over the collapsed fingers of the flange. The collapsed flange is inserted through the opening in the target vessel. Then, the second inner sleeve is slid distally within the slotted inner sleeve. The second inner sleeve forces the fingers outward, expanding the flange within the target vessel. The anastomosis is completed by applying the outer flange to the fitting as described above.

A second variant of the expanding inner flange has a slotted inner sleeve with multiple fingers that are oriented essentially longitudinally to the inner sleeve. Each of the fingers has a bend in it to predispose it to bend outward at the middle when under longitudinal compression. A tubular forming tool slidably received within the slotted sleeve is crenellated with multiple radially extending tabs. The radially extending tabs engage the distal ends of the fingers of the slotted inner sleeve. The anastomosis is performed by passing the graft vessel through the internal lumen of the fitting and everting it over the fingers. If desired, a loop of suture can be used to hold the everted vessel in place. The fingers of the fitting and the everted end of the graft vessel are inserted through an opening in the target vessel wall. When the tubular forming tool is slid proximally with respect to the slotted inner sleeve, the radially extending tabs bear against the distal ends of the fingers, compressing them longitudinally. The fingers bow outward, folding at the bend to expand and create an inner flange which engages the inner surface of the target vessel wall. In a preferred embodiment of this variation, the slotted inner sleeve has a proximal collar which captures the outer flange of the fitting so that the outer flange is applied simultaneously with the expansion of the inner flange. After the inner flange has been expanded, the tubular forming tool can be removed by rotating it with respect to the slotted inner sleeve so that the tabs align with the slots allowing it to be withdrawn from the fitting. This reduces the mass of foreign material that is left as an implant at the anastomotic site.

A third representative embodiment is a one-piece anastomotic fitting with an inner sleeve that is integrally attached to a fixed inner flange and to a deformable outer flange. The anastomosis is performed by passing the graft vessel through the internal lumen of the inner sleeve and everting it over the inner flange. The inner flange and the everted end of the graft vessel are inserted through an opening in the wall of the target vessel. Then, the outer flange is deformed against the exterior surface of the target vessel wall with a tailored degree of tissue compression to complete the anastomosis. Two variants of the deformable outer flange are disclosed. The first variant has an outer flange that is divided into flange segments. The flange segments are attached to the inner sleeve by deformable hinges. The second variant has an outer flange in the form of a deformable hollow body. The hollow body is deformed against the exterior surface of the target vessel to complete the anastomosis.

The vascular anastomotic fitting is also part of a complete anastomosis system which includes instruments for applying the anastomosis fitting in a rapid, efficient and reliable manner to expedite the anastomosis process and to reduce the amount of manual manipulation necessary to perform the anastomosis. The application instrument has an elongated body with means at the distal end for grasping the anastomosis fitting and inserting the fitting into the chest cavity of a patient through an access port. The instrument includes an actuating means for deploying the inner and/or outer flange of the fitting to create the anastomosis. Variants of the instrument are specially adapted for each different embodiment and subvariation of the anastomosis fitting.

A third approach to expediting and improving anastomosis procedures used by the present invention combines the advantages of surgical stapling technology with other advantages of anastomotic fittings. Surgical stapling technology has the potential to improve anastomosis procedures over hand suturing techniques by decreasing the difficulty and complexity of the manipulations necessary and by increasing the speed and reliability of creating the anastomosis. The Kaster vascular staple in U.S. Pat. No. 5,234,447 overcomes one of the major limitations of the previous Kolesov stapling device by allowing a stapled end-to-side anastomosis. This device, however, requires many delicate manual manipulations of the graft vessel and the staple while performing the anastomosis. This device therefore does not take full advantage of the time saving potential usually associated with stapling techniques.

The present invention attempts to marry the advantages of stapling approaches and anastomotic fitting approaches while carefully avoiding their potential drawbacks. As such, the present invention takes full advantage of the speed and reliability of stapling techniques, avoiding inasmuch as possible the need for complex manual manipulations. The invention also profits from the advantages of anastomotic fittings by providing a ring or flange that exerts even pressure around the anastomotic interface to eliminate potential leaks between the stapled attachments. The ring or flange also serves as a stent or support for the anastomosis site to prevent acute or long-term closure of the anastomosis. Inasmuch as possible the bulk of the fitting is kept on the exterior of the anastomosis so as to eliminate exposed foreign material in the bloodstream of the graft vessel or the target vessel. In most cases, only the narrow staple legs penetrate the anastomosis site, so that an absolute minimum of foreign material is exposed to the blood flow path, on the same order as the mass of suture exposed in a standard sutured anastomosis. The attachment technique for the anastomosis device eliminates the need to evert the graft vessel over a complex, irregular or sharp object such as the sharpened ends of the staple legs. Instead, a smooth ring or flange surface is provided for everting the graft vessel without damage or undue complication. The staple legs are separate or recessed within the flange to avoid potential damage to the graft vessel while attaching it to the device.

In a third aspect, the present invention takes the form of an anastomosis device which has a ring or flange to which the graft vessel attaches, typically by everting the graft vessel over the distal end of the ring. The ring or flange resides on the exterior of the graft vessel so that it does not contact the blood flow path. A plurality of staple-like members attach the ring and the everted end of the graft vessel to the wall of the target vessel, which may be the aorta, a coronary artery or other vessel. An opening is created in the target vessel wall with an aortic punch or similar instrument to allow the target vessel lumen to communicate with the graft vessel lumen. The opening in the target vessel wall can be made before or after the device has been attached, depending on the application technique employed. In most of the examples disclosed, the staple members pierce the everted wall of the graft vessel and the wall of the target vessel to hold the two vessels together. Alternatively, the staple members may enter the lumen of the target vessel through the opening in the wall and then pierce the wall of the target vessel in the reverse direction. This variation pins together the vascular layers in the target vessel at the cut edge, potentially reducing the incidence of hemodynamically generated dissections in the wall of the target vessel.

Various configurations of the invention are disclosed which all exhibit the unifying characteristics of a cooperating ring or flange and a plurality of staple members. A first exemplary embodiment includes a ring-like fastening flange with deformable staple members for attaching the flange. A specially adapted staple applying device which operates through the lumen of the graft vessel is used to deform the staples to complete the anastomosis. A second embodiment includes a ring-like fastening flange with preformed, spring-like staple members. The elastic memory of the spring-like staple members holds the anastomosis tightly together. A family of embodiments includes a tubular fastening flange with U-shaped staple members and a locking means for fastening the staple members to complete the anastomosis. Another family of embodiments includes one or more ring-shaped fastening flanges with integrally formed staple members. Another family of embodiments includes a ring-like fastening flange with self-deploying staple members made of a superelastic metal alloy or a thermally activated shape-memory alloy. A specially adapted staple applying device deploys the superelastic staple members. The specially adapted staple applying device together with the anastomosis device itself forms a total anastomosis system that is adaptable for either conventional open-chest CABG surgery or port-access CABG surgery.

Catheter devices are described which can be used as part of the total anastomosis system for isolating a portion of the target artery to facilitate performing the anastomosis procedure. One catheter device is configured to isolate a portion of the ascending aorta wall without occluding blood flow through the lumen of the aorta. A second catheter device is configured to be delivered by a transluminal approach for isolating a portion of a coronary artery during the anastomosis procedure. A third catheter device is configured to be delivered through the lumen of the graft vessel for isolating a portion of a coronary artery during the anastomosis procedure.

In yet another aspect of the present invention, a coronary shunt is disclosed which is movable from a first shape to a second shape. The first shape is generally larger than the second shape and is used to occlude the coronary artery and provide a blood flow path across the anastomosis. When the coronary shunt is removed, the coronary shunt is moved to the second, smaller shape which facilitates removing the shunt.

In a preferred embodiment, the shunt is inflatable so that the shunt is simply deflated when removed. The inflatable shunt preferably also includes inflatable occluding members for occluding the coronary artery. In another preferred embodiment, the shunt is separable into first and second parts which are each easier to remove than the entire coronary shunt. In yet another preferred embodiment, the shunt is collapsible to change the overall length of the shunt. In still another preferred embodiment, the shunt is made of an elongate member which can be unwrapped while the shunt is in the coronary artery to reduce the size of the shunt.

BRIEF DESCRIPTION OF THE DRAWINGS

FIGS. 5A–5G are side cross section view showing the sequence of operations for creating an end-to-side anastomosis with the two-piece anastomosis staple device of FIG. 1.

FIGS. 8A–8G are side views of various configurations of the attachment legs of the anchor member of FIG. 1 which allow for tailored amounts of tissue compression at the anastomosis site.

FIG. 15A is a detail drawing of the female bayonet connector on the distal end of the anastomosis staple applying tool of FIG. 13.

FIG. 15B is an end view of the male bayonet connector on the proximal end of the one-piece anastomosis staple device of FIG. 9.

FIG. 17A–17B are a perspective views of a first alternate construction of the two-piece anastomosis staple device of FIG. 1.

FIG. 17C is a cross section view of the anchor member of the anastomosis staple device of FIG. 17A attached to the wall of a target vessel.

FIG. 17D is a cross section view of a completed anastomosis using the device of FIG. 17A–17B.

FIGS. 18A–18F show a second alternate construction of the two-piece anastomosis staple device of FIG. 1.

FIG. 20 is a side cross section view of a fourth alternate construction of the two-piece anastomosis staple device of FIG. 1.

FIGS. 22A–22C are side cross section views of an anastomosis fitting which is a variation of the embodiment of FIGS. 21A–21C.

FIG. 22D is a proximal end view of the anastomosis fitting of FIG. 22C.

FIGS. 25A–25H show a second variant of the anastomotic fitting with an expanding inner flange is shown in FIGS. 24A–24D.

FIGS. 30A–30K show an embodiment of the anastomotic fitting combining deformable inner staple members and an outer flange.

FIGS. 32A–32F show an anastomosis device using preformed spring-like fastening staple members.

FIGS. 33A–33D show an anastomosis device using S-shaped staple members that pierce the interior wall of the target vessel.

FIGS. 34A–34D show an anastomosis device using S-shaped staple members that do not pierce the interior wall of the target vessel.

FIGS. 36A–36C show an anastomosis device using U-shaped staple members and a locking collar.

FIGS. 37A–37C show a second anastomosis device using U-shaped staple members and a locking collar.

FIGS. 38A–38C show a one-piece anastomosis device with integral staple members.

FIGS. 39A–39C show a second one-piece anastomosis device with integral staple members.

FIGS. 41A–41E show an anastomosis device having a fastening flange and a plurality of individual staple members.

FIGS. 46A–46D illustrate a second embodiment of the anastomosis system using an anastomosis device with an inner fastening flange, an outer flange and staple members made of a superelastic alloy.

FIGS. 49A–49C show the sequence of operations for deploying the anastomosis staple device of FIGS. 47A–47B.

FIGS. 50A–50B show a staple application instrument for applying the anastomosis staple devices of FIGS. 47A–47B.

FIG. 53 shows a dual-balloon coronary isolation and perfusion catheter for use in performing a distal anastomosis in CABG surgery.

FIG. 54 shows a T-shaped dual-balloon coronary isolation and perfusion catheter for use in performing a distal anastomosis in CABG surgery.

FIG. 62 shows a removal device.

FIG. 63 illustrates use of the removal device of FIG. 62.

FIG. 64 is a cross-sectional view of a second coronary shunt.

FIG. 65 is a cross-sectional view of the second coronary shunt separated into first and second parts.

DETAILED DESCRIPTION OF THE INVENTION

The invention will be now be described in detail with reference to the accompanying drawings. The detailed description describes the invention in relation to a proximal anastomosis during CABG surgery for joining the proximal end of the bypass graft to the aortic wall. This example is given by way of illustration only and is in no way meant to be limiting. Those skilled in the art will recognize that the anastomosis staple device and anastomosis stapling system of the present invention are readily adaptable for end-to-side connections of distal anastomoses (i.e. graft to coronary artery anastomoses) during CABG surgery, as well as for use on other blood vessels and other tubular organs within the body. For consistency and convenience, throughout the description the two ends of the anastomosis staple are referred to as the proximal and distal ends of the staple, the distal end of the staple being the end which is closest to the inner lumen of the target vessel and the proximal end being the free end which is farthest from the inner lumen of the target vessel.

Figure 1:
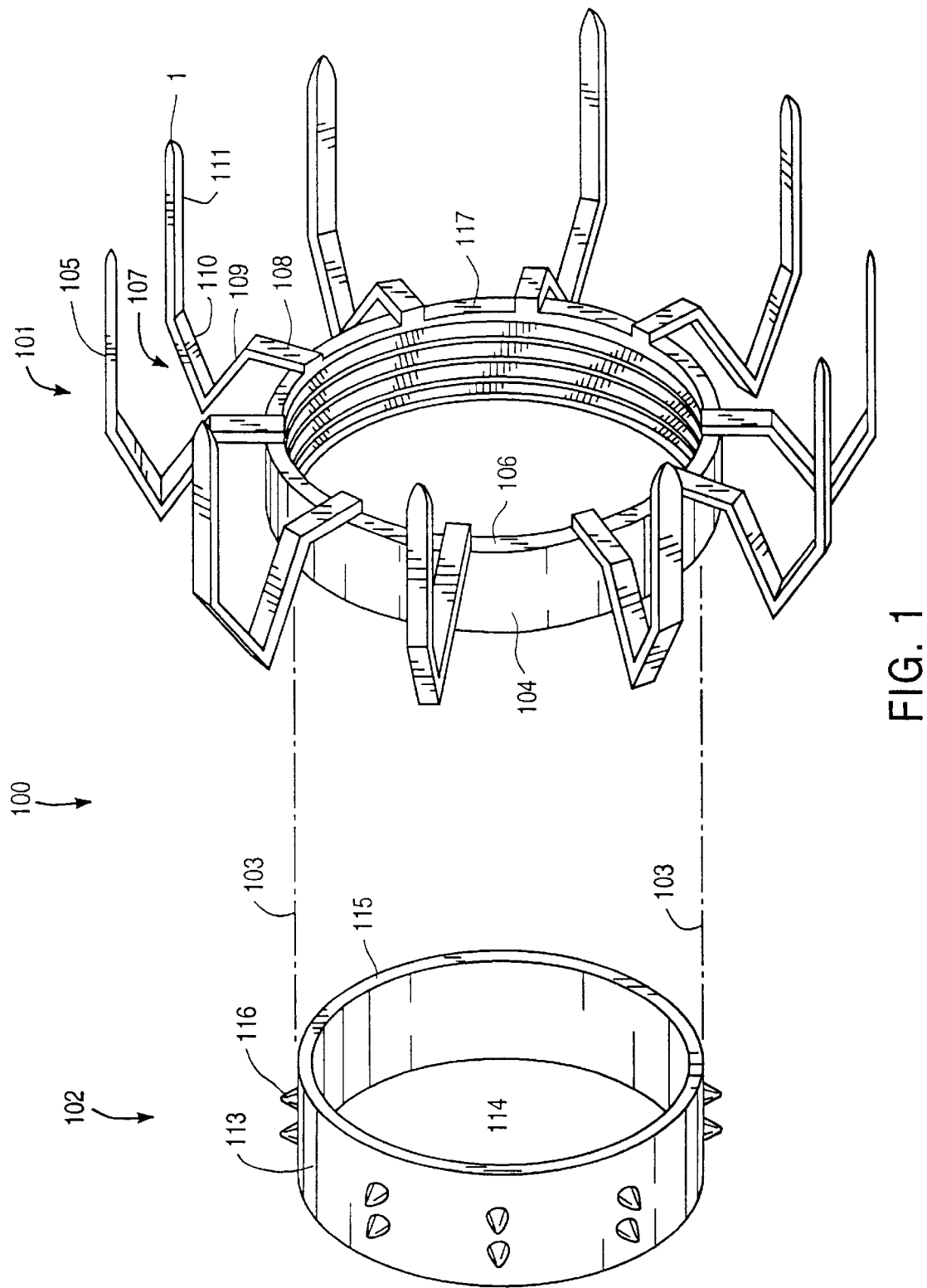
FIG. 1 is a perspective view of the anchor member and the coupling member of a two-piece embodiment of the anastomosis staple device of the present invention.

FIG. 1 is a perspective drawing of a first embodiment of the anastomosis staple device of a first aspect of the present invention. The anastomosis staple device 100 consists of two parts: an anchor member 101, and a coupling member 102. The anchor member 101 forms the attachment to the exterior surface of the wall of a target vessel such as the aorta. The coupling member 102 forms the attachment to the bypass graft vessel. When the coupling member is joined to the anchor member, as shown by the dotted lines 103, it forms a complete anastomosis.

The anchor member 101 has a ring-shaped frame 104 which is configured to encircle an opening in the wall of a target vessel, such as the aorta. The ring-shaped frame 104 has a plurality of attachment legs 105, preferably six to twelve, circumferentially spaced around the frame 104 and projecting from the distal end 106 of the ring. The anchor member 101 is preferably made of stainless steel or a titanium alloy for strength, biocompatibility and absence of MRI interference. The ring-shaped frame 104 and the attachment legs 105 preferably have a wall thickness of approximately 0.2 to 0.6 mm. The width of each of the attachment legs 105 is preferably between 0.5 and 2.0 mm. The attachment legs 105 could also be made with a round cross section to eliminate sharp edges which might propagate tears. The precise dimensions of the attachment legs 105 would be a compromise between making the legs rigid enough to pierce the wall of the target vessel without undue deformation, yet flexible enough to permit the stapling mechanism to deform the attachment legs after they have pierced the target vessel wall to hold the anchor member in place. These dimensions may vary depending on which vessel is chosen as the target vessel for the anastomosis.

The attachment legs 105 extend first radially outward from the ring 104, then there is a transition curve 107, after which the legs 105 extend axially away from the ring 104 in the distal direction. The transition curve 107 in each attachment leg 105 is shaped so that the anchor member 101 can be placed precisely on the target vessel wall, then affixed firmly in place with minimal displacement of the anchor member 101 or distortion of the target vessel wall. This attachment process will be described more fully in the operational description below.

The points of attachment between the attachment legs 105 and the ring-shaped frame 104 in this illustrative embodiment are all shown as being coplanar with one another. In other preferred embodiments, the distal extremity 106 of the anchor member 101 may be contoured to match the curvature of the exterior surface of the target vessel. Thus, the points of attachment between the attachment legs 105 and the ring shaped frame 104 will be arranged on a cylindrically curved surface which intersects the ring 104 of the anchor member 101 rather than a plane. This would be especially important when there is closer parity between the diameter of the graft vessel and the diameter of the target vessel, such as when performing a distal anastomosis between a venous or arterial graft and a coronary artery, because a planar arrangement of the attachment legs 105 would not approximate the curvature of the target vessel wall as well as for a larger target vessel such as the aorta. In other alternate embodiments, the distal end of the anchor member 106 and the attachment legs 105 may be angled with respect to the ring-shaped frame 104 to permit an angled takeoff of the graft vessel from the target vessel.

One preferred configuration for the transition curve 107 in the attachment legs 105 is illustrated in FIG. 1. The first segment 108 of each attachment leg extends radially from the ring-shaped frame for a short distance. The second segment 109 of each leg angles proximally from the first segment at approximately 60° for a short distance. Then, the third segment 110 angles approximately 60° in the distal direction from the second segment 109. The fourth segment 111 extends in the distal direction from the third segment 110 so that the fourth segment 111 extends axially away from the ring-shaped frame 104 parallel to the central axis of the ring 104. The second 109 and the third 110 segments should be approximately equal in length to one another. The actual length of the second 109 and third 110 segments will be determined by the wall thickness of the target vessel. A typical length of 1.5–5 mm would be used for attachment to the wall of the aorta. The distal ends 112 of the attachment legs 105 are sharpened to easily penetrate the aortic wall.

This illustrates just one preferred transition curve 107 for the attachment legs 105. Alternate transition curves 107 for the attachment legs 105 may include arc-shaped segments in place of some of the straight segments or may include a greater number of straight segments to approximate a smoother curve. When choosing alternate curves, it is important to preserve the axially extending final segment 111 of the attachment legs in order to penetrate the target vessel wall. In addition, it is important to control the amount of distortion of the target vessel wall when the anchor member 101 is attached. This is in contrast to many standard wound closure staples which deliberately bunch up the tissue when they are applied to create a closer approximation of the tissues being joined. This type of distortion may be counterproductive in attaching a graft vessel to the aortic wall because the wall may be too stiff to distort in this manner and the distortion might cause problems in creating a leak proof seal at the anastomosis. The anvil geometry of the stapling mechanism will also be important in determining the optimum geometry of the attachment legs.

The amount of radial compression of the target vessel wall around the anastomosis can be tailored by the choice of the transition curve 107 in the attachment legs 105 of the anchor member 101. Radial compression of the target vessel wall around the anastomosis helps to create and maintain an anastomotic seal between the target vessel and the graft vessel in the completed anastomosis. This is especially important when blood pressure is restored in the target vessel which will tend to stretch the target vessel wall and pull it away from the anastomosis. The radial compression by the attachment legs counteracts this expansion and maintains the anastomotic seal under pressure. FIG. 8A–8G show various other possible geometries for the attachment legs 105 of the anchor member 101 arranged according to the degree of tissue compression applied to the target vessel wall. FIG. 8A shows a staple attachment leg 105 where the transition curve 107 consists of a straight second segment which extends upward at ninety degrees from the first radially extending segment. The third segment 110 describes a 90° arc with a center of rotation at the transition point between the first 108 and second 109 segments. The fourth segment 111 extends straight in an axial direction from the third segment 110. This embodiment of the attachment legs 105 creates very little tissue compression when applied. The amount of tissue compression is indicated by the shaded region between the straight insertion path of the fourth segment 111 and the final position of the actuated staple shown in phantom lines 105. FIG. 8B shows a transition curve 107 with an elliptically shaped second segment 109 which smoothly evolves into an arc-shaped third segment 110 with a center of rotation at the transition point between the first 108 and second 109 segments. This embodiment creates a slightly greater degree of tissue compression. FIG. 8C shows an attachment leg geometry which is formed entirely of smooth curves so as to avoid any sharp bends in the attachment legs 105, but which produces approximately the same tissue compression as the attachment leg of FIG. 8B. FIG. 8D shows a transition curve 107 with a 30° arc-shaped second segment 109 connecting to a 30° arc-shaped third segment 110 with a center of rotation at the transition point between the first 108 and second 109 segments. FIG. 8E shows a side view of the embodiment illustrated and described above in FIG. 1. The second segment 109 angles 60° upward from the first segment 108, and the third segment 110 angles downward at 60° from the second segment 109. This produces a selected degree of tissue compression when the attachment legs 105 are actuated. FIG. 8F shows an attachment leg geometry which produces slightly greater tissue compression in the target vessel. The second 109 and third 110 segments of the transition 107 are smoothly blended together in a continuous semicircular arc. FIG. 8G shows an attachment leg geometry which produces even more tissue compression. The second segment 109 angles upward at 45° from the first segment 108 and the third segment 110 angles downward from the second 109 at a 90° angle. Many other attachment leg geometries may be tailored to produce the desired degree of tissue compression in the target vessel.

The coupling member 102, as seen in FIG. 1, has a tubular body 113 with a passage 114 through it. The distal end of the coupling 102 has an atraumatic edge 115 over which the graft vessel will be everted in forming the anastomosis. The atraumatic edge 115 is important to avoid piercing or damaging the vessel wall in the vicinity of the anastomosis which occurs with some prior art devices. Atraumatic attachment of the graft vessel to the coupling member helps to assure a reliable anastomotic seal between the graft vessel and the target vessel and reduces the likelihood of mechanical failure of the graft vessel wall due to punctures or tears in the wall. The exterior of the coupling member 102 is sized to fit into the interior of the ring-shaped frame 104 of the anchor member with enough space between them to accommodate one wall thickness of the bypass graft. The coupling member 102 is preferably made of stainless steel, a titanium alloy or plastic with a wall thickness of approximately 0.1 to 0.6 mm. The exterior of the coupling member 102 has exterior surface features 116 which serve a dual purpose. The exterior surface features 116 serve to hold the everted end of the bypass graft onto the coupling member 102, as well as to interlock the coupling member 102 with the anchor member 101 to complete the anastomosis. Likewise, the interior of the anchor member 101 is made with interior surface features 117 which interact with the exterior surface features 116 to create the interlock. The exterior surface features 116 of the coupling member 102 could be in the form of bumps, pins, points, barbs, ridges, threads, holes or a combination of these features. The interior surface features 117 of the anchor member 101 would then be in the form of corresponding bumps, pins, points, barbs, ridges, threads or holes to lock the two parts together. It should be noted that, if pins, points, barbs or other piercing members are used as the interior 117 or exterior 116 surface features of the anastomosis staple device 100, these potentially traumatic features are located away from the everted edge of the graft vessel and outside of the lumens of the graft vessel and target vessel that will serve as the conduit of the bypass so as not to compromise the integrity of the anastomosis.

In the embodiment illustrated, the coupling member 102 is shown with bump-shaped exterior surface features 117 that hold the everted graft vessel onto the coupling member 102 and interlock with a series of circumferential ridges 116 within the anchor member 101. The interior ridges 116 of the anchor member 101 permit a variable degree of engagement between the coupling member 102 and the anchor member 101 to allow for different wall thicknesses of the target vessel and the graft vessel used in the anastomosis. The axial position of the coupling member 102 with respect to the anchor member 101 can be varied to create the desired degree of axial tissue compression to assure an anastomotic seal despite variations in the vessel wall thicknesses.

Figure 2:
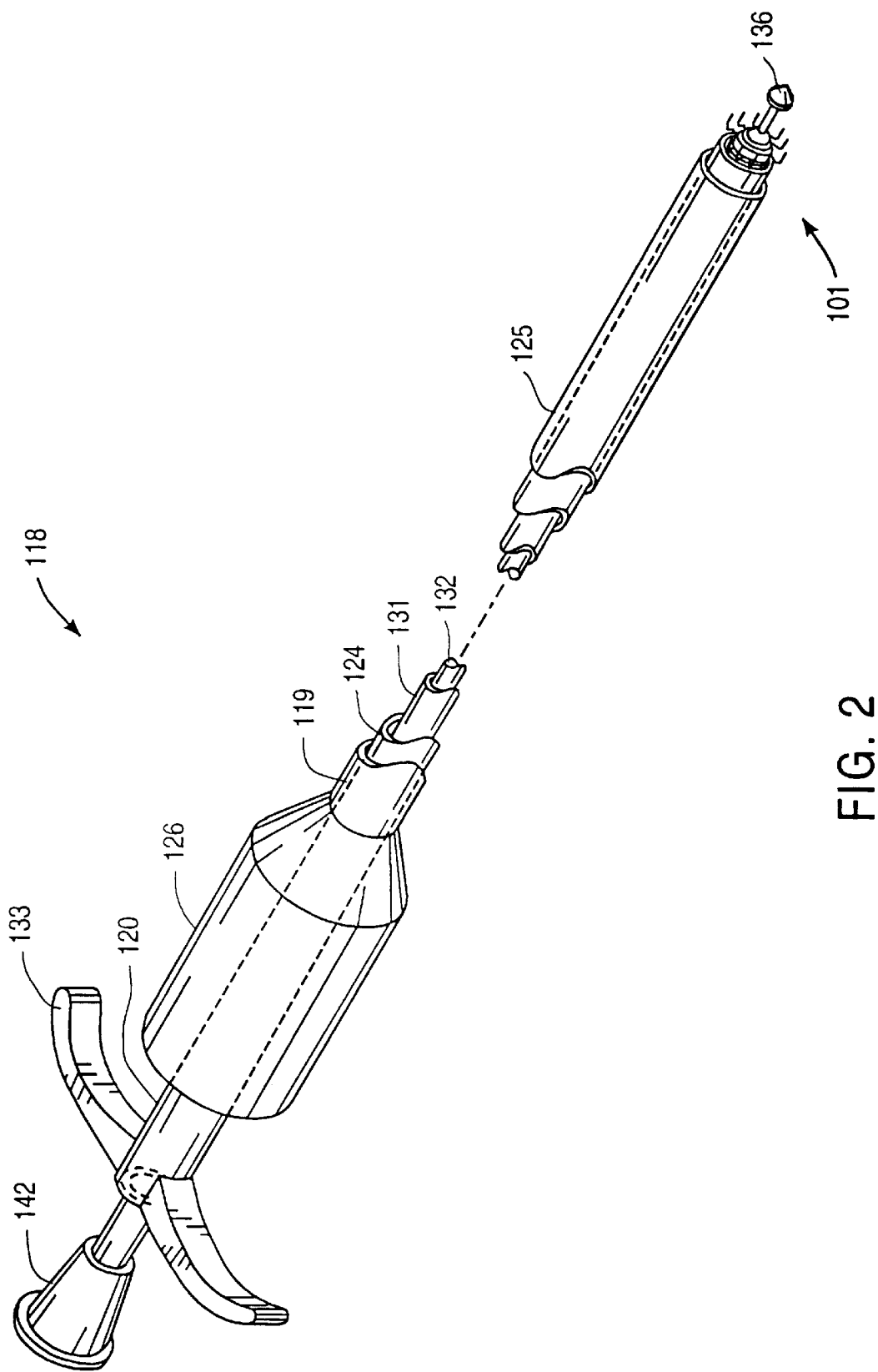
FIG. 2 is a perspective view of a staple applier system for applying the anastomosis staple device of FIG. 1.

The complete anastomosis stapling system includes the anastomosis staple device 100 and an instrument 118 for applying the anastomosis staple 100. The instrument 118 for applying the two-part anastomosis staple 100 consists of three separate, but interacting, mechanisms: a stapling mechanism 119, a vessel punch mechanism 120, and a graft insertion tool 121, 122. Together with the anchor member 101 and the coupling member 102, they comprise a complete system for performing an anastomosis. In FIG. 2, we can see two of these mechanisms, the stapling mechanism 119 and the vessel punch mechanism 120, assembled together with the anchor member 101 of the anastomosis staple 100, prepared for the first stage of the anastomosis procedure. The third mechanism, the graft insertion tool, is shown in two different embodiments 121, 122 in FIGS. 6A–6C and FIGS. 7A–7C, respectively.

Figure 4:
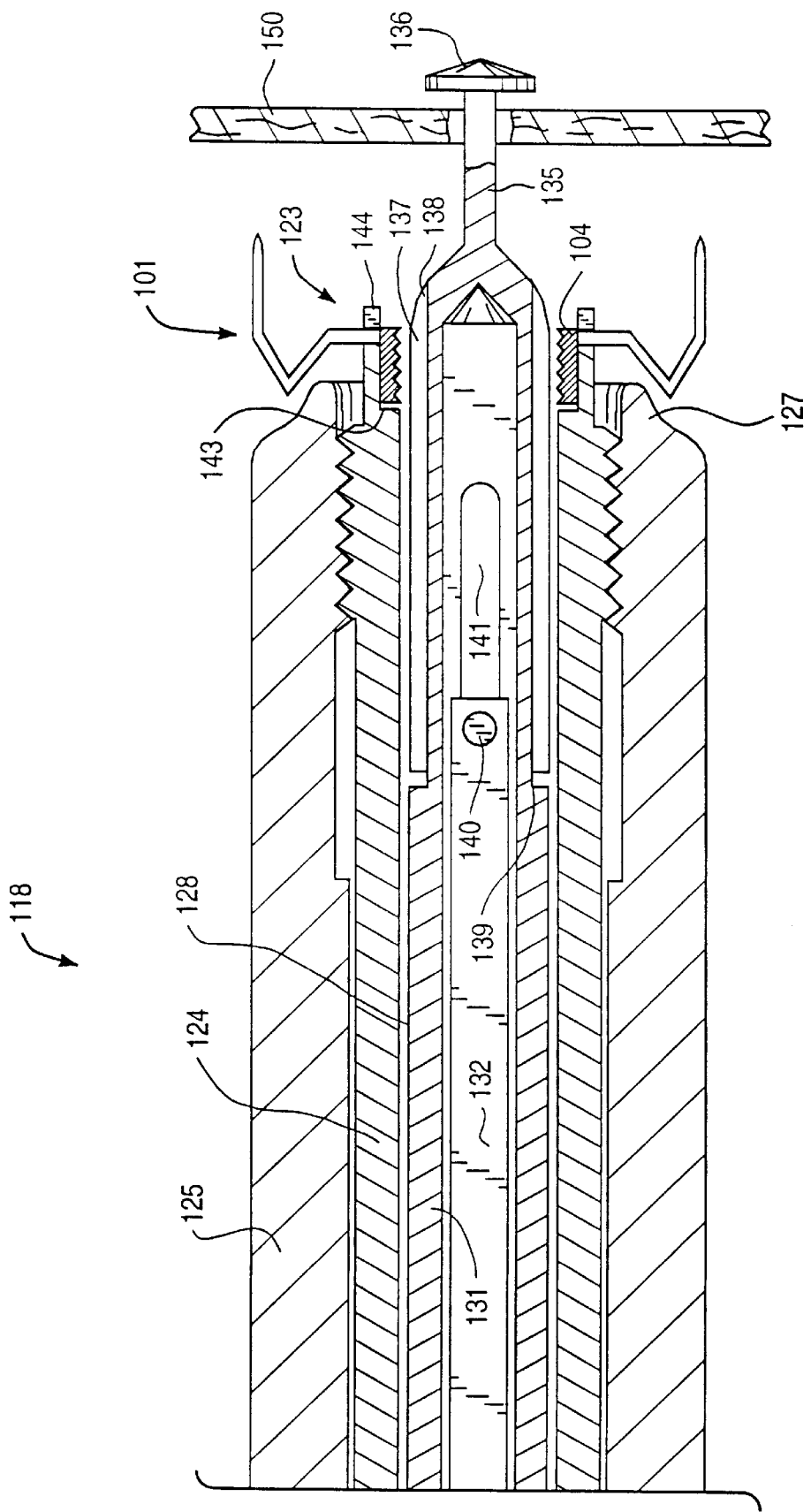
FIG. 4 is a cross sectional view of the distal ends of the stapling mechanism and the vessel punch mechanism of the staple applier system of FIG. 2 along with the anchor member of the two-piece anastomosis staple device of FIG. 1.

The stapling mechanism 119 and the vessel punch 120 are shown assembled together in a perspective view in FIG. 2. The anchor member 101 of the anastomosis staple 100 is held by the staple retainer 123 on the distal end of the stapling mechanism. This same assembly can be seen in cross section in the operational drawings 5A–5C. The distal end of this assembly is shown in greater detail in cross section in FIG. 4. The stapling mechanism 119 has an inner tube 124 and an outer tube 125 which are threaded together at their distal ends. The outer tube 125 has a handle 126 at the proximal end and an annular staple driver 127 at the distal end of the tube. The inner tube 124 has a staple retainer 123 for holding the anchor member 101 of the anastomosis staple 100 on the distal end of the tube. The inner tube 124 has an internal lumen 128 of sufficient size to accommodate the vessel punch mechanism 120 and the graft insertion tool 121, alternately. The proximal end of the inner tube 124 has a pair of opposing slots 129 on the inner surface that act as splines for engagement with a corresponding pair of lugs 130, 134 on the exterior of the vessel punch mechanism 120 and on the graft insertion tool 121.

The vessel punch mechanism 120 is sized to fit through the internal lumen 128 of the inner tube 124 of the stapling mechanism 119. The vessel punch mechanism 120 has an outer tube 131 and an inner drive member 132 slidably received within the outer tube. The proximal end of the outer tube 131 is attached to a T-shaped handle 133. The outer tube 131 has a pair of lugs 130 near the proximal end which extend radially from the exterior of the tube 131 to engage the opposing slots 129 in the inner tube 124 of the stapling mechanism 119. The distal end of the outer tube 131 tapers to form a neck 135 which attaches to a cutter anvil 136. The vessel punch cutter 137 is a tubular member which slides telescopically on the distal end of the outer tube 131 of the vessel punch 120. The distal edge 138 of the tubular cutter 137 is sharpened with an approximately conical bevel 138. The outer tube 131 of the vessel punch mechanism 120 may include a step 139 against which the cutter is located in the retracted position as in FIGS. 5A and 5B. The tubular cutter 137 is attached to the drive member by a transverse pin 140 which extends through a pair of opposing slots 141 in the distal end of the outer tube 131. The proximal end of the drive member 132 is attached to an actuating plunger 142 which extends proximally of the T-shaped handle 133.

Figure 5C:
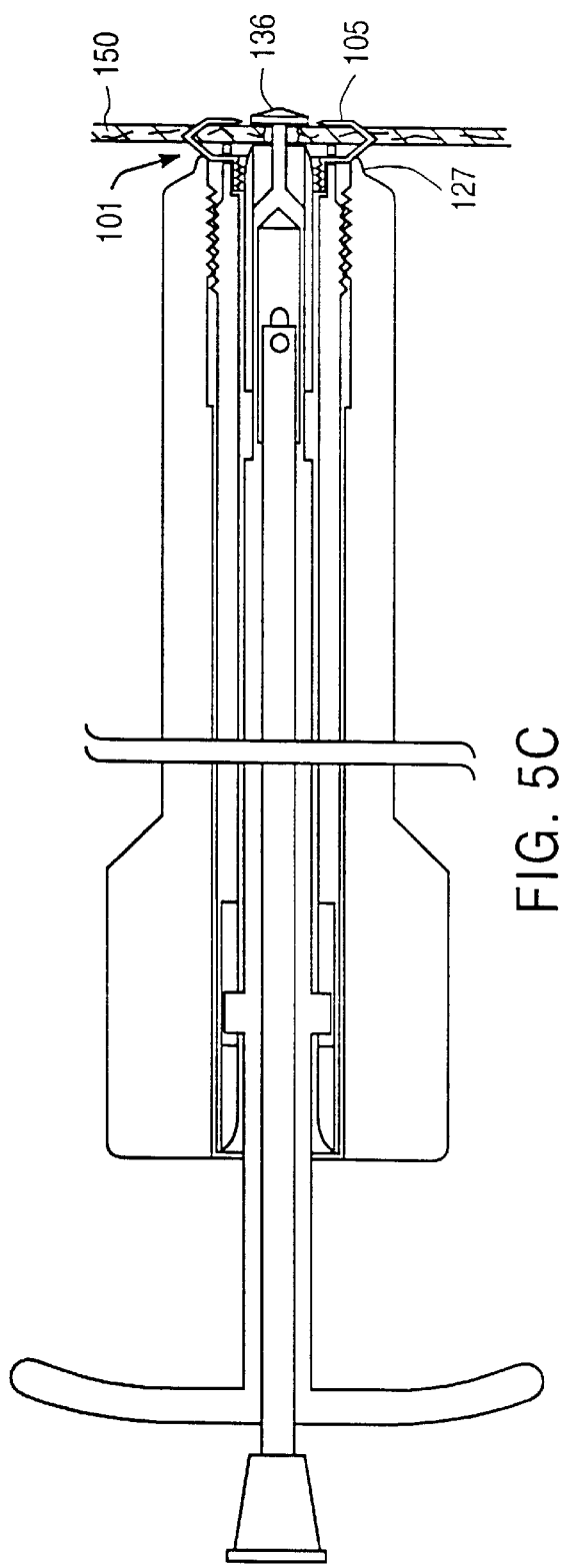

The vessel punch mechanism 120 is actuated by pressing on the actuating plunger 142 to move it with respect to the T-shaped handle 133. This linear motion is transferred to the inner drive member 132 and then, in turn, to the tubular cutter 137 by way of the transverse pin 140. The tubular cutter 137 slides forward until the inner lumen of the cutter 137 slides over the anvil 136 in a shearing action. There is a very tight clearance between the inner lumen of the cutter 137 and the outer diameter of the anvil 136. This tight clearance assures a cleanly cut hole through the vessel wall without ragged or torn edges. In FIG. 5C, the vessel punch mechanism 120 is shown actuated to cut a hole through the aortic wall tissue.

Figure 3:
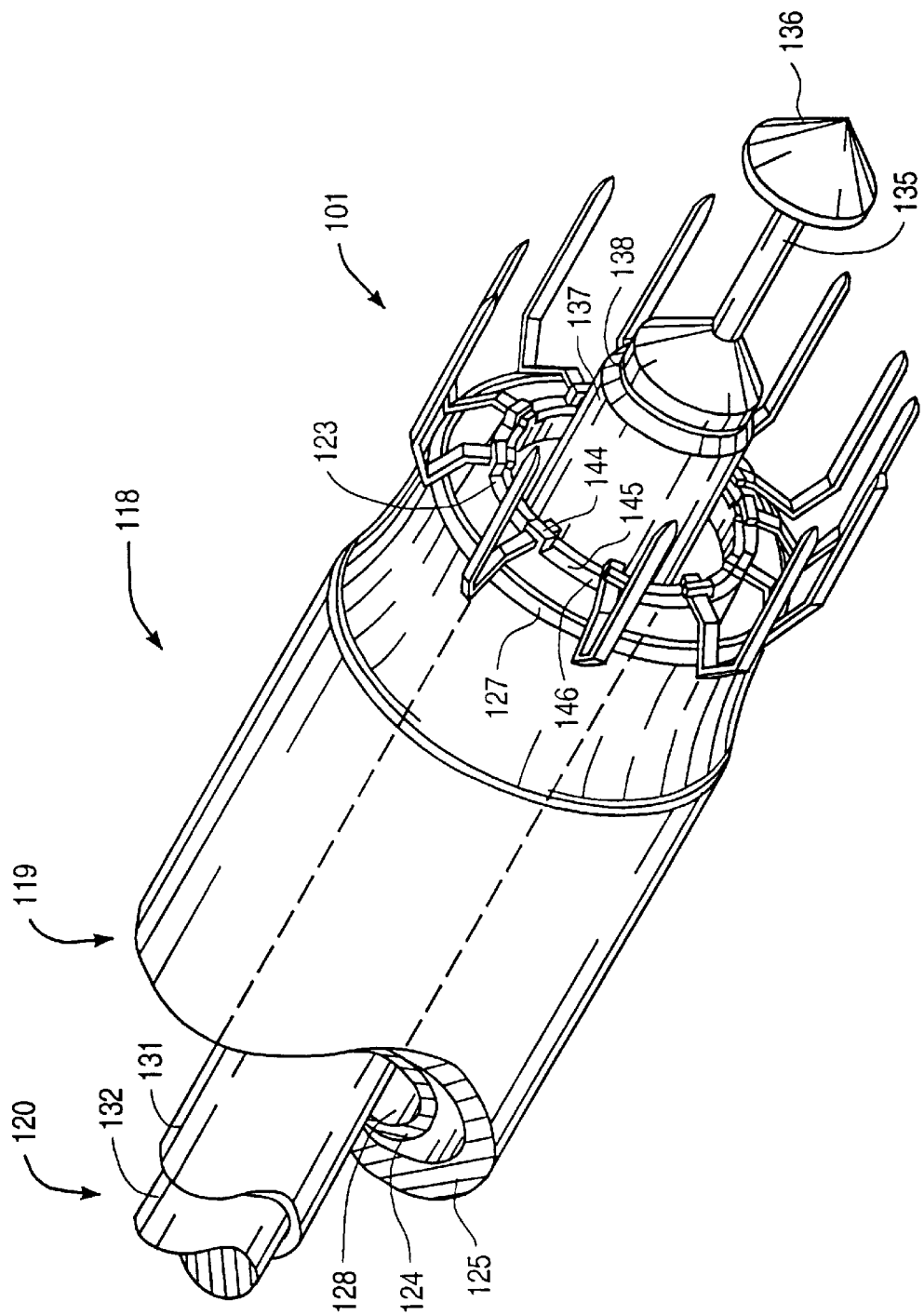
FIG. 3 is a perspective view of the distal end of the staple applier system of FIG. 2 showing the stapling mechanism and the vessel punch mechanism along with the anchor member of the two-piece anastomosis staple device of FIG. 1.

FIG. 3 is a large scale perspective detail drawing of the distal end of the vessel punch mechanism 120 assembled with the stapling mechanism 119. The anchor member 101 of the anastomosis staple 100 is held by the staple retainer 123 on the distal end of the inner tube 124 of the stapling mechanism 119. The ring-shaped frame 104 of the anchor member 101 fits inside of a counterbore 143 on the distal end of the inner tube, as can be seen in FIGS. 4 and 5A–5E. The attachment legs 105 of the anchor member 101 are captured and held by the L-shaped gripping fingers 144 which extend from the distal end of the inner tube 124. There are an equal number of gripping fingers 144 on the inner tube 124 as there are attachment legs 105 on the anchor member 101. Each gripping finger 144 has an axial slot 145 alongside of it which is at least as wide as the attachment legs 105. The axial slot 145 connects with a transverse slot 146 in the side of each gripping finger 144. The anchor member 101 of the anastomosis staple 100 is loaded onto the staple retainer 123 by aligning the attachment legs 105 with the ends of the axial slots 145, pushing the attachment legs 105 to the bottom of the axial slots 145, then turning the anchor member 101 counterclockwise until the attachment legs 105 enter the transverse slots 146 in the side of the gripping fingers 144. The anchor member 101 can be secured in this position by rotating the outer tube 124 of the stapling mechanism to advance it distally until the staple driver 127 contacts the attachment legs 105 with enough force to hold the anchor member 101 in place without deforming the legs. Alternatively, the inner tube 124 of the stapling mechanism 119 could be adapted to grip the ring-shaped element 104 of the anchor member 101 directly.

The T-shaped handle 133 of the vessel punch mechanism 120 also serves as the handle for the inner tube 124 of the stapling mechanism 119 at this stage of the procedure because the lugs 130 on the exterior of the vessel punch outer tube 131 engage the slots 129 in the interior of the stapler inner tube 124. Likewise, in the latter stages of the procedure, the T-shaped handle 133 of the graft insertion tool 121 can also serve as a handle for the inner tube 124 of the stapling mechanism 119 because the lugs 134 of the graft insertion tool 121 engage the inner slots 129 of the stapler inner tube 124 in a similar fashion. Alternatively, the inner tube 124 of the stapling mechanism may be supplied with a separate handle or knob of its own so the inner 124 and outer 125 tubes of the stapling mechanism can be rotated with respect to one another to operate the stapling mechanism when neither the aortic punch mechanism 120 nor the graft insertion tool 121 is inserted into the stapling mechanism 119.

Figure 6B:
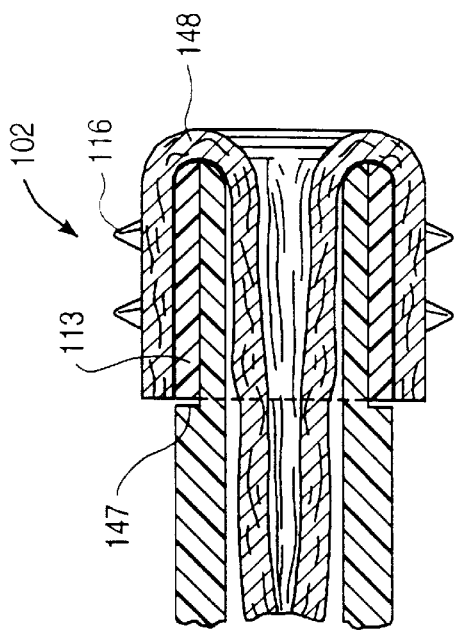
FIGS. 6B–6C are side cross section and perspective views, respectively, of the distal end of the graft insertion tool of FIG. 6A.
Figure 6A:
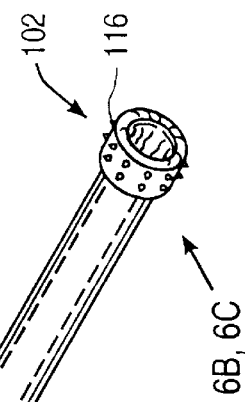
FIGS. 6A is a perspective view of the graft insertion tool of the anastomosis staple applier system of FIG. 2 prepared for insertion of the bypass graft with the coupling member of the two-piece anastomosis staple device.
Figure 6C:
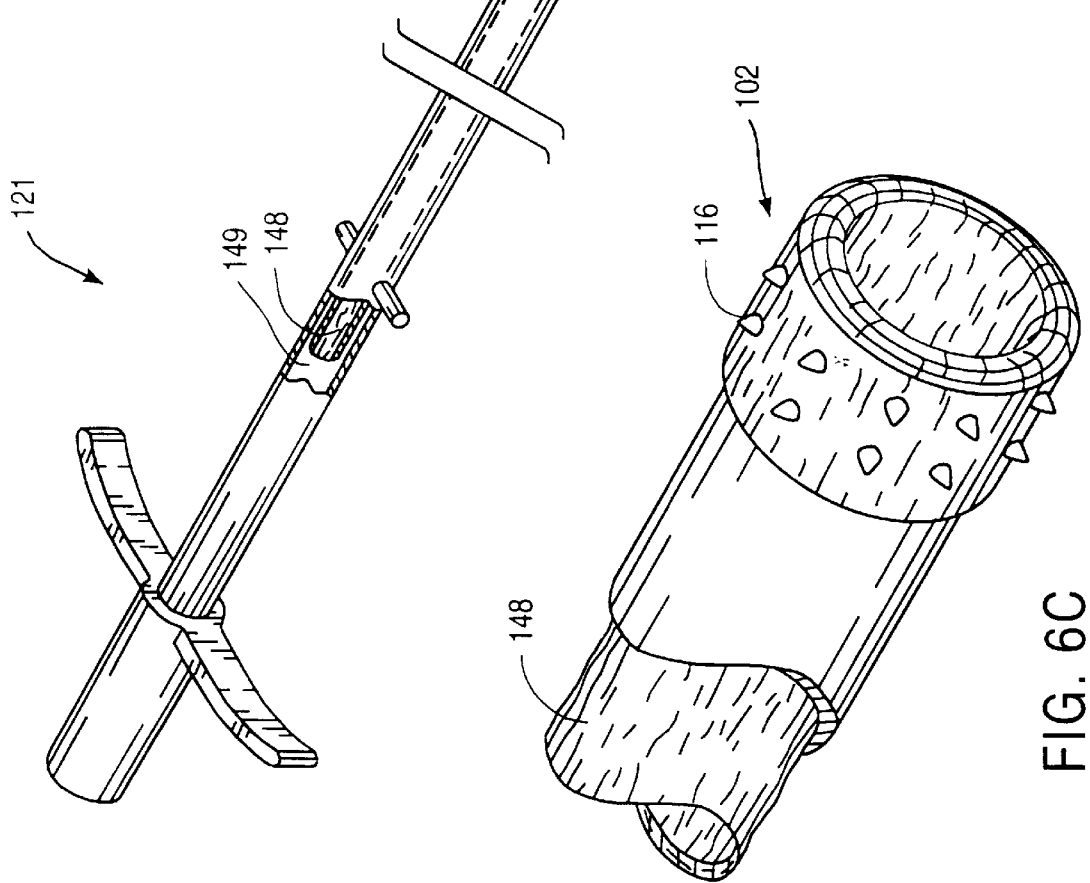

A first embodiment of the graft insertion tool 121 and its relationship to the coupling member 102 of the anastomosis staple 100 are shown in detail in FIGS. 6A–6C. This embodiment of the graft insertion tool 121 may be used when the anastomosis staple 100 is used to form the first anastomosis of the bypass procedure no matter whether the first anastomosis is the proximal or the distal anastomosis of the graft. To prepare the bypass graft for creating the anastomosis, the coupling member 102 is first loaded onto the distal end of the graft insertion tool 121. A shoulder 147 on the graft insertion tool 121 holds the coupling member 102 in the correct position, and a tight interference fit or a spring action prevents it from inadvertently falling off. The graft vessel 148 is then loaded into the internal lumen 149 of the graft insertion tool 121. This can be done by tying a suture around the graft vessel on the end opposite to the end that will be anastomosed, passing the suture through the internal lumen 149 of the graft insertion tool 121, then drawing the graft vessel 148 into the lumen until the end 192 of the graft vessel 148 to be anastomosed extends a short distance from the distal end of the graft insertion tool 121. Alternatively, a special tool, such as a narrow pair of endoscopic forceps or a nerve hook, may be used for grasping the graft vessel 148 and drawing it through the graft insertion tool 121. At this point, the end 192 of the graft vessel 148 to be anastomosed is everted over the end of the graft insertion tool 121 and the coupling member 102, as shown in FIGS. 6A–6C. The external surface features 116 of the coupling member 102 serve to hold the graft vessel onto the exterior of the coupling member 102 in the everted position. The external surface features 116 of the coupling member may at least partially penetrate the wall of the graft vessel 148 to provide greater holding force.

Figure 5D:
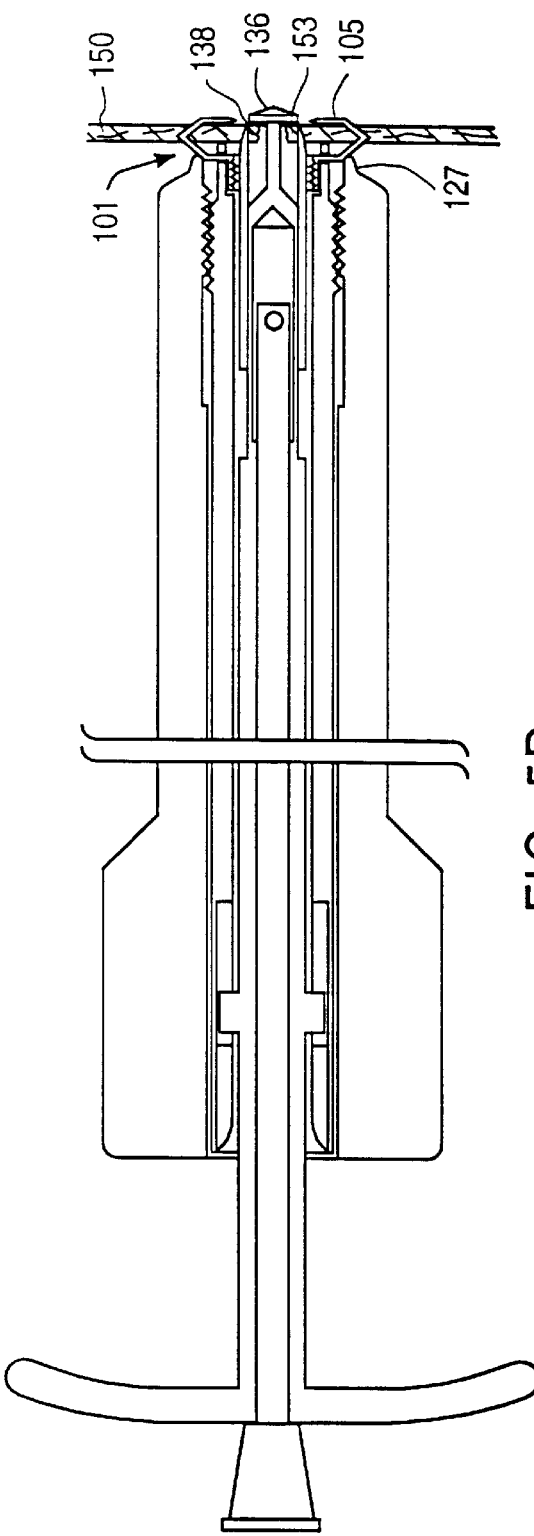
Figure 5E:
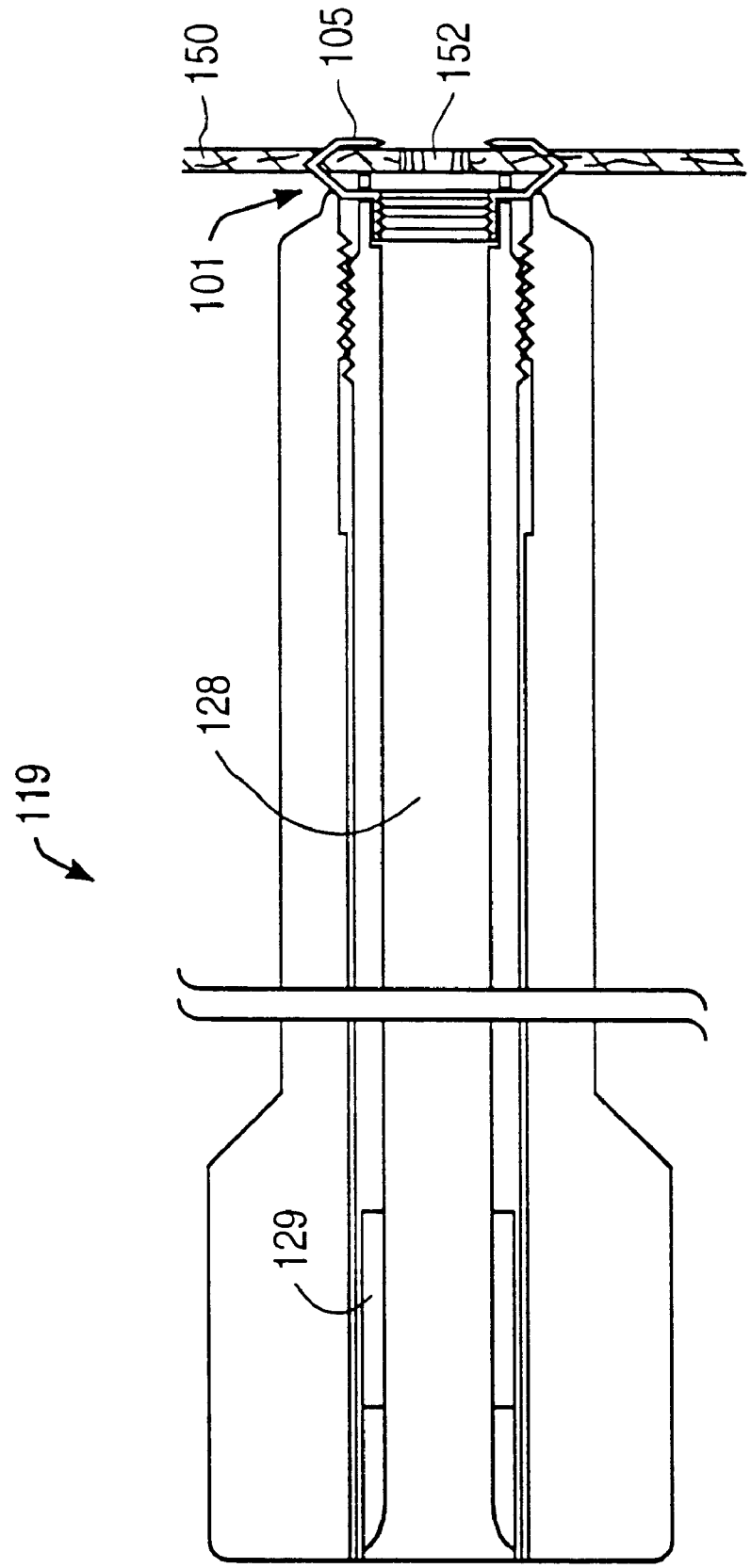

With the anchor member 101 loaded onto the stapling mechanism 119 and the graft vessel 148 prepared by everting and attaching it to the coupling member 102 as described above, the device is ready to perform the end-to-side anastomosis, as illustrated in FIGS. 5A–5G. Referring now to FIG. 5A, the stapling mechanism 119 and the vessel punch mechanism 120 are shown assembled together. A slit 150 is made in the target vessel wall 150 with a scalpel or other sharp instrument, and the anvil 136 of the vessel punch 120 is inserted through the slit 151 into the lumen of the target vessel 150. The anvil 136 serves to center the stapling mechanism 119 and the anchor member 101 around the chosen attachment point on the target vessel 150 where the slit 151 is made. The stapling mechanism 119 is advanced over the vessel punch mechanism 120 toward the wall of the target vessel 150, as shown in FIG. 5B. A slight tension is maintained on the T-handle 133 of the vessel punch mechanism 120 so that the anvil 136 supports the wall of the target vessel 150 as the attachment legs 105 of the anchor member 101 contact and penetrate the target vessel wall 150. The fourth segments 111 of the attachment legs 105 penetrate the target vessel wall 150 in a linear path. Once the fourth segments 111 of the attachment legs 105 have traversed the target vessel wall 150, the attachment legs 105 are actuated, as shown in FIG. 5C. The outer tube 125 of the stapling mechanism 119 is advanced over the inner tube 124 by rotating the handle 126 of the outer tube 125 with respect to the T-handle 133 of the vessel punch mechanism 120. This advances the staple driver 127 against the attachment legs 105, deforming them into the position shown in FIG. 5C. After the attachment legs 105 have been actuated, the tubular cutter 137 of the vessel punch mechanism 120 is advanced with respect to the anvil 136, as shown in FIG. 5D, by pressing on the actuating plunger 142 at the proximal end of the drive member 132. The punch mechanism 120 creates an opening 152 through the target vessel wall 150. The vessel punch mechanism 120 with the tissue 153 that was excised by the punch can now be withdrawn from the inner lumen 128 of the stapling mechanism 119, as shown in FIG. 5E, leaving the anchor member 101 attached to the target vessel wall 150 in alignment with the opening 152 punched therein.

Figure 5F:
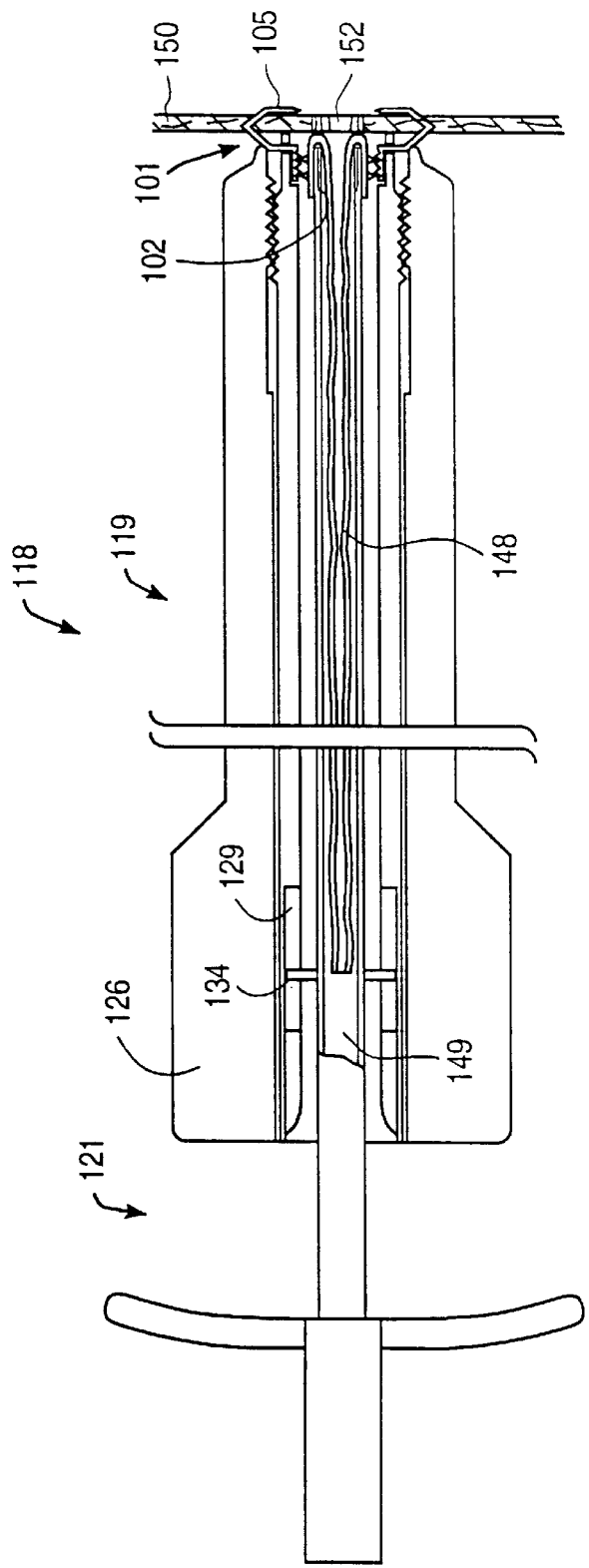
Figure 5G:
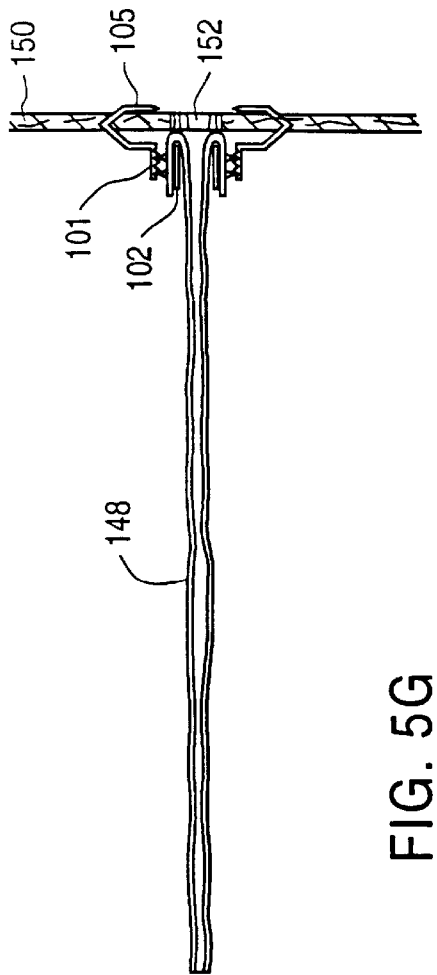

The graft vessel insertion tool 121 with the prepared graft vessel 148 and coupling member 102 in place is inserted into the inner lumen 128 of the stapling mechanism 119 as shown in FIG. 5F. The coupling member 102 is pressed into the ring-shaped frame 104 of the anchor member 101 and the exterior features 116 on the coupling member 102 engage the interior features 117 of the ring-shaped frame 104 to hold the coupling member 102 and the anchor member 101 together. The staple retainer 123 of the stapling mechanism 119 still has a firm grasp on the anchor member 101 to provide support as the coupling member 102 is pressed into the ring-shaped frame 101. The coupling member 102 should be pressed into the ring-shaped frame 104 until the everted end of the graft vessel 148 bears against the exterior surface of the target vessel wall 150, creating a fluid tight seal at the anastomosis site. Alternatively, the coupling member 102, with the everted end of the graft vessel 148 attached, can be made to extend into the opening 152 in the target vessel wall 150 with the target vessel wall 150 creating a radial compression around the graft vessel 148 and the coupling member 102. The stapling mechanism 119 can now be disengaged from the from the anchor member 101 by turning the handle 126 of the outer tube 125 with respect to the T-handle 133 of the graft insertion tool 121 until the staple driver is withdrawn from the attachment legs 105. Then the inner tube 124 of the stapling device can be turned counterclockwise by turning the T-shaped handle 133 of the graft insertion tool 121 to disengage the gripping fingers 144 of the staple retainer 123 from the attachment legs 105 of the anchor member 101. A complete end-to-side anastomosis, as shown in FIG. 5G, is left at the anastomosis site.

It should be noted that the order of the steps of the anastomosis procedure 127 could be altered. For instance, the opening could be first punched in the target vessel with an aortic punch or similar instrument, and then the anchor member of the staple could be attached. In this instance, the graft vessel could be attached to the anchor member either before or after the anchor member is attached to the target vessel. Other variations in the order of the steps are also possible.

Figures 7A, 7B:
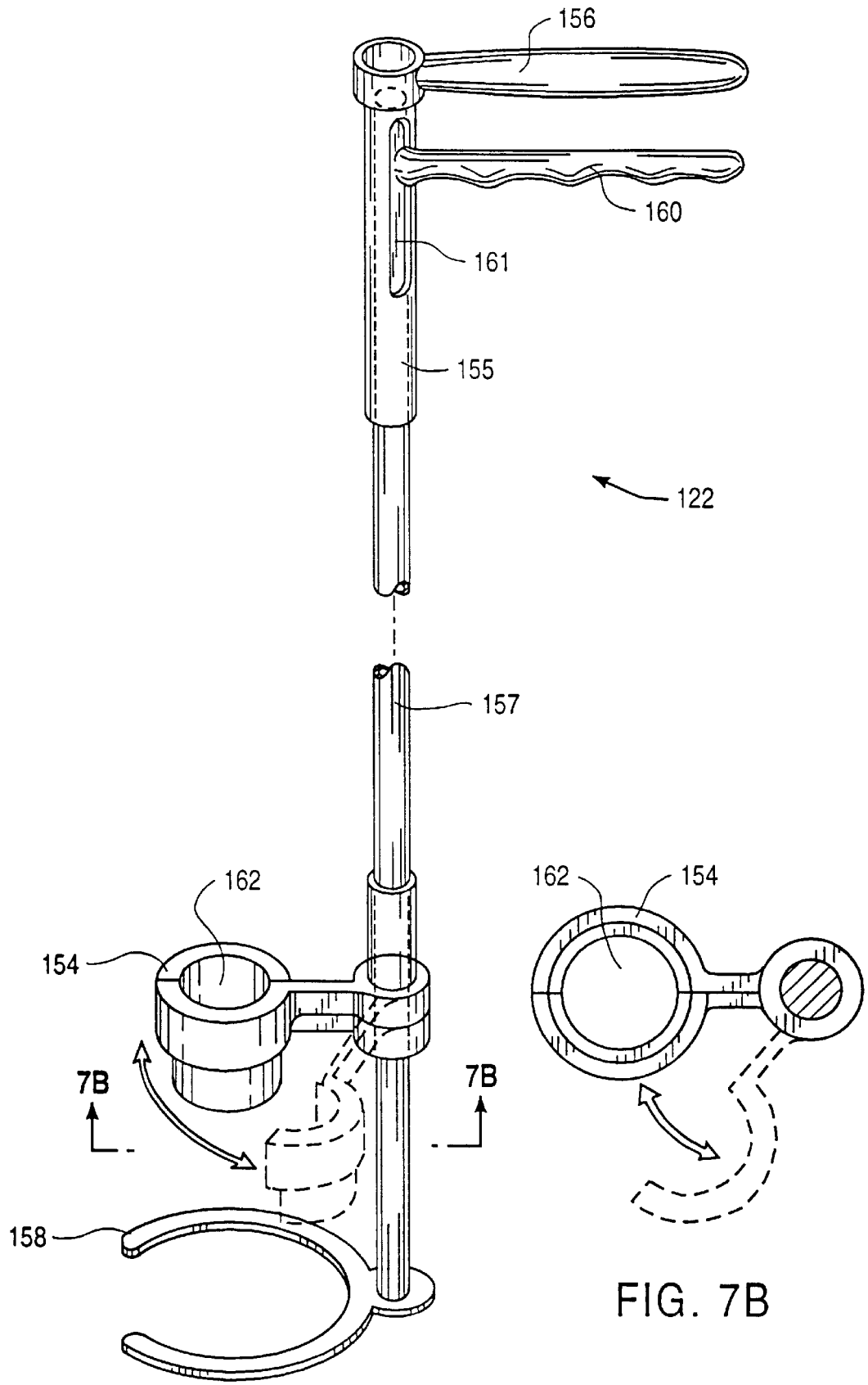
FIGS. 7A–7C are perspective, bottom end, and side cross section views, respectively, showing a variation of the graft insertion tool prepared for creating a second anastomosis of the bypass graft using the two-piece anastomosis staple device of FIG. 1.

FIG. 7A shows a perspective drawing of a second embodiment of the graft insertion tool 122 for use in performing the second anastomosis on a graft vessel, one end of which has already been anastomosed, or for other situations when both ends of the graft vessel are not available, such as when making the distal anastomosis on an internal mammary artery bypass graft. This embodiment of the graft insertion tool 122 is made with a two-part, hinged holder 154 for the coupling member of the anastomosis staple device so that the holder 154 can be removed from around the graft vessel 148 after both ends of the graft have been anastomosed. The holder 154 is attached to the distal end of a tubular member 155 which is attached on its proximal end to a handle grip 156. A shaft 157 is slidably received within the tubular member 156. The distal end of the shaft 157 is attached to a U-shaped yoke 158 which is configured to grip a flange 159 or a pair of lugs on the proximal end of the anchor member 101. The handle grip 156 has a coacting trigger member 160 which is attached to the proximal end of the shaft 157 through a slot 161 in the side of the tubular member 155. The holder 154 is spring biased toward the open position 154'. The force of the spring action helps the holder 154 to grip the coupling member 102 so that it does not slip off of the holder 154 prematurely. A distal end view of the holder 154 is shown in FIG. 7B, with the holder 154 shown in both the closed position and the open position (phantom lines 154').

Figure 7C:
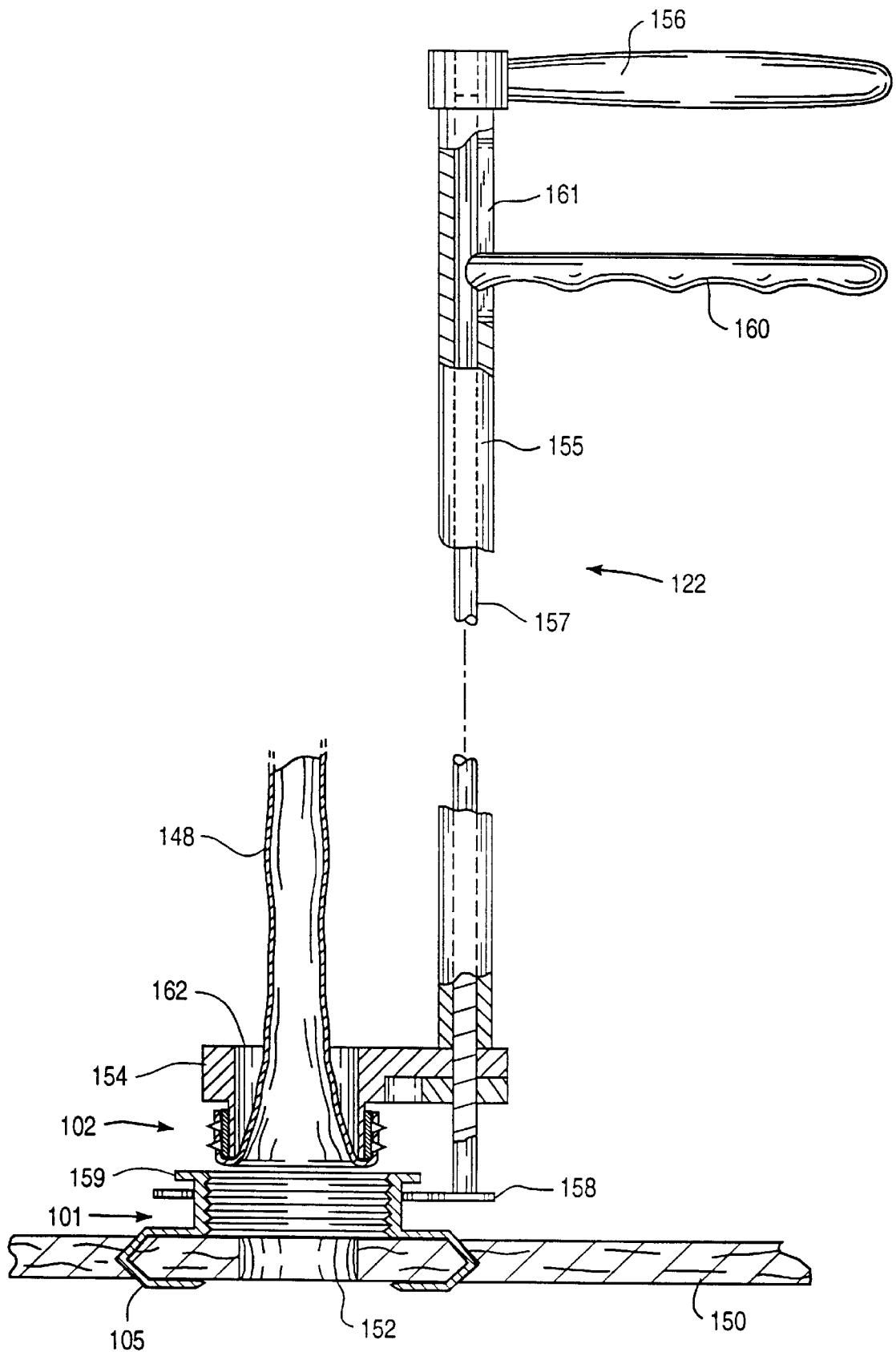

To prepare the graft vessel 148 for the anastomosis, the coupling member 102 is first placed onto the holder 154 and the end of the graft vessel 148 to be anastomosed is passed through the lumen 162 of the holder 154 and the coupling member 102 from the proximal to the distal end. The end of the graft vessel 148 is then everted back over the coupling member 102, as shown in FIG. 7C. The external surface features 116 on the coupling member 102 will hold the everted vessel in place on the coupling member. In FIG. 7C, the anchor member 101 of the anastomosis staple device 100 has been fastened to the target vessel 150, as described above in relation to FIGS. 5A–5E, and the stapling mechanism 119 has been removed by turning the handle 126 of the stapling mechanism 119 counterclockwise relative to the handle 126 on the vessel punch mechanism 120 until the anchor member 101 is released. The graft insertion tool 122 with the prepared graft vessel 148 is now positioned at the anastomosis site and the U-shaped yoke 158 is used to grip the anchor member 101, retained by the flange 159 on its proximal end. With the graft vessel 148 and the coupling member 102 aligned with the anchor member 101 as shown, the handle grip 156 and the trigger 160 are squeezed together to press the coupling member 102 into the anchor member 101 until the everted end of the graft vessel 148 is pressed against the outer surface of the target vessel 150 creating a leak-proof anastomosis. The holder 154 is then retracted from the coupling member 102 by moving the trigger 160 away from the handle grip 154. The hinged holder 154 opens when it is withdrawn from the coupling member 102, releasing the graft vessel 148 from the lumen 162 of the holder 154. The U-shaped yoke 158 can now be slid sideways off of the anchor member and the anastomosis is complete.

A one-piece version of the anastomosis staple device of the present invention along with a specially adapted staple applying tool will now be described in detail. In the one-piece embodiments which follow, a tubular member, analogous to the coupling member of the previously described embodiment, is permanently attached to a circular staple member, which is analogous to the anchor member 101 of the previously described embodiment.

Figure 9:
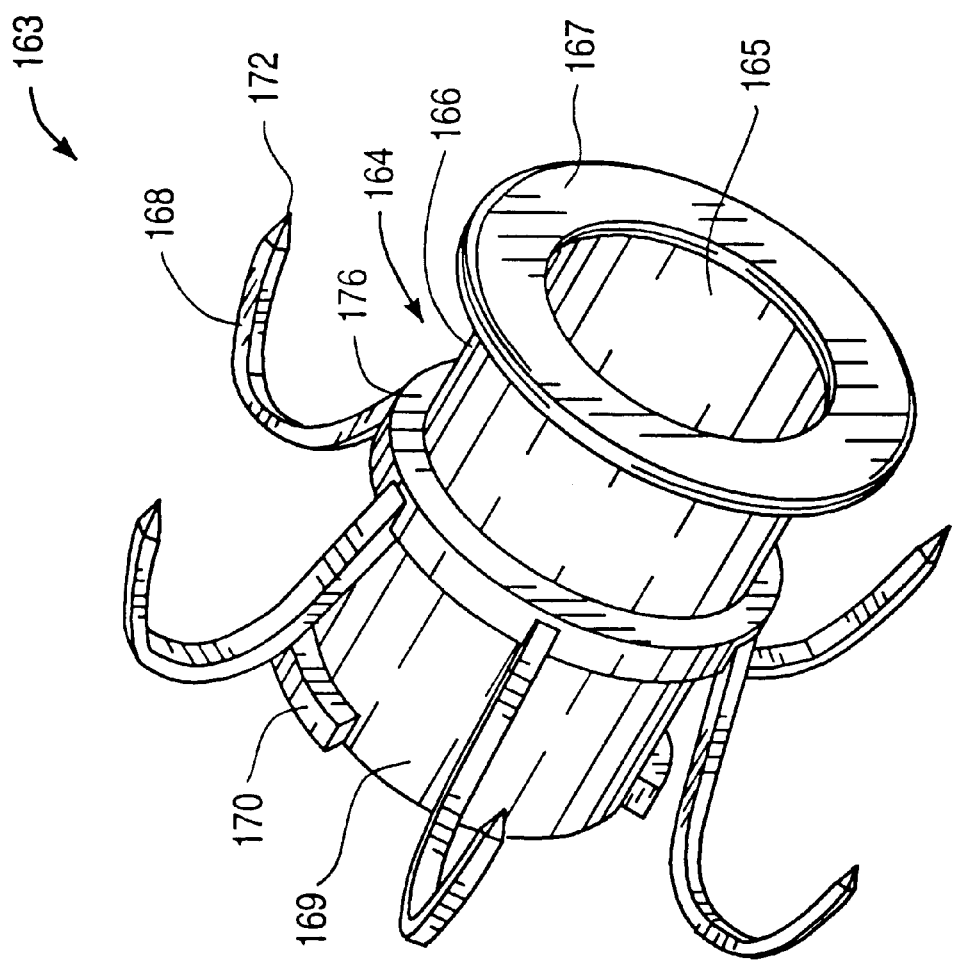
FIG. 9 is a perspective view of a one-piece embodiment of the anastomosis staple device of the present invention.

FIG. 9 shows a perspective view of a first embodiment of the one-piece anastomosis staple device 163 of the present invention. This same embodiment is shown in cross section in FIGS. 11 and 13. The anastomosis staple 163 has a tubular body member 164 which has an inner lumen 165 sized to accommodate the exterior diameter of the graft vessel 148. Means for attaching the graft vessel 148 are provided at the distal end of the tubular body member 164 or on the outside of the tubular member 164. In the preferred embodiment, the means for attaching the graft vessel 148 to the anastomosis staple 163 is a tubular distal extension 166 of the tubular body over which the graft vessel 148 is everted. The tubular extension 166 may include a flange 167 to secure the attachment of the everted graft vessel 148 to the tubular extension 166. This flange 167 may also engage the inner surface of the target vessel 150 to help retain the graft 148 in place.

The anastomosis staple device 163 has a multiplicity of staple legs 168 extending from the tubular body member 164 proximal to the tubular distal extension 166. Optionally, the tubular body member 164 may extend proximally 169 from the staple legs 168 as shown, or the tubular body member can be truncated at or near the level of the staple legs to decrease the overall profile of the staple. The optional proximal extension 169 of the tubular body member 164 may include lugs or tabs 170 or a flange or other features that can be used for gripping the staple 163 by a staple applying tool.

The anastomosis staple 163 typically has five to twelve staple legs 168 for attaching to the target vessel wall 150. The presently preferred embodiment of the staple 163 has six staple legs 168 as illustrated in FIG. 9. The staple legs 168 are distributed circumferentially around the exterior of the tubular body member 164. The staple legs 168 can be formed integrally with the tubular body member 164, or they can be manufactured separately and attached to the tubular body member 164. Optionally, the exterior of the tubular body member 164 may include a circumferential ledge 171 to which the staple legs 168 are attached. In the pre-actuated position, the legs 168 angle proximally from where they attach to the tubular body member 164 so that the sharpened tips 172 of the staple legs are proximal to the point of attachment with the body. The staple legs 168 have a first segment 173 which extends approximately straight from the tubular body member; then there is a transitional segment 174 and a curved end segment 175. The curved end segment 175 of each staple leg has a sharpened tip 172 for easily piercing the wall of the target vessel 150. The curve of the end segment 175 is a circular arc whose center of rotation coincides approximately with the point of attachment 176 between the staple leg and the tubular body member. The point of attachment 176 serves as a pivot point for the staple leg 168 when it is actuated, so that the end segment 175 of the staple legs 168 describes an arc-shaped path through the tissue of the target vessel wall that follows the curvature of the arc-shaped end segment 175.

Figure 10:
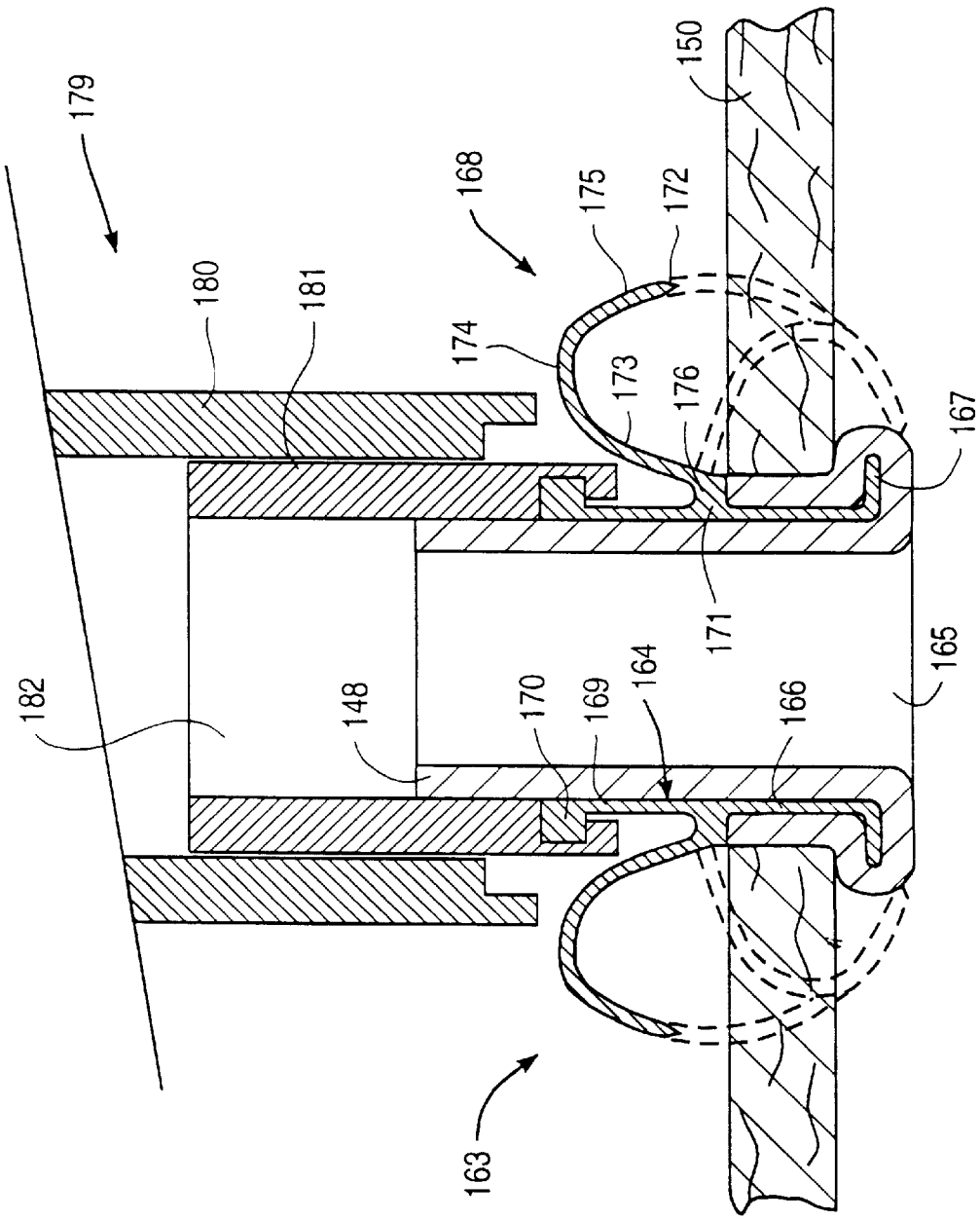
FIG. 10 is a cross sectional view of the one-piece anastomosis staple device of FIG. 9 being actuated to form an end-to-side anastomosis.
Figure 11:
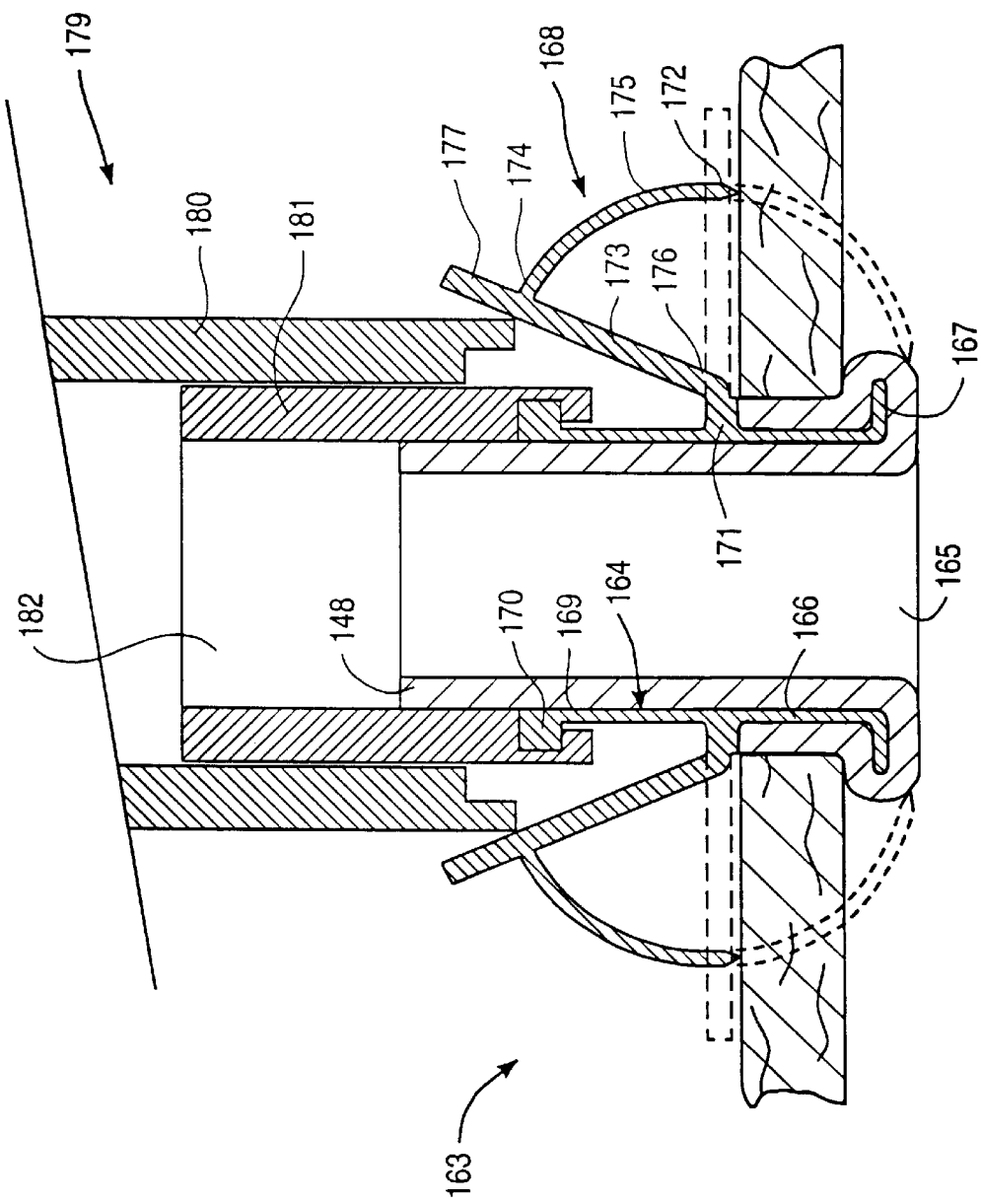
FIG. 11 is a cross sectional view of a one-piece anastomosis staple device with extended first segments on the staple legs.

The transition segment 174 of the staple legs 168 can take on one of several forms depending on the effect desired in the actuated staple. If the transition segment 174 is largely a right-angle bend, so that only the end segment 175 penetrates the tissue, then the staple legs 168 will cause very little radial compression of the target vessel wall tissue 150 as the staple 163 is actuated. If, on the other hand, the transition segment 174 has a curve of smaller radius than that of the curved end segment 175, the tissue will be compressed and pulled toward the tubular body member 164 as the transition segment 174 enters and travels through the target vessel wall 150, as illustrated in FIG. 10. The degree of radial tissue compression can be regulated to the appropriate amount by proper design of the curve in the transition segment 174 of the staple legs 168. In addition, the shape of the first segment 173 may help to define the surface shape of the target vessel 150 after the staple 163 is applied. It may be desirable to keep it as flat as possible, or it may be desirable to "tent up" the target vessel somewhat in the area of the anastomosis. Optionally, the first segment may be given greater effect on the target vessel surface shape by extending the first segment 173 beyond the transition point with the second segment 174, as shown in FIG. 11. The straight extension 177 of the first segment 173 beyond the attachment point of the transition curve 174 will tend to flatten out the tissue of the target vessel wall 150 at the anastomosis site so that undue deformation of the vessel wall does not compromise the integrity of the anastomosis.

Figure 12:
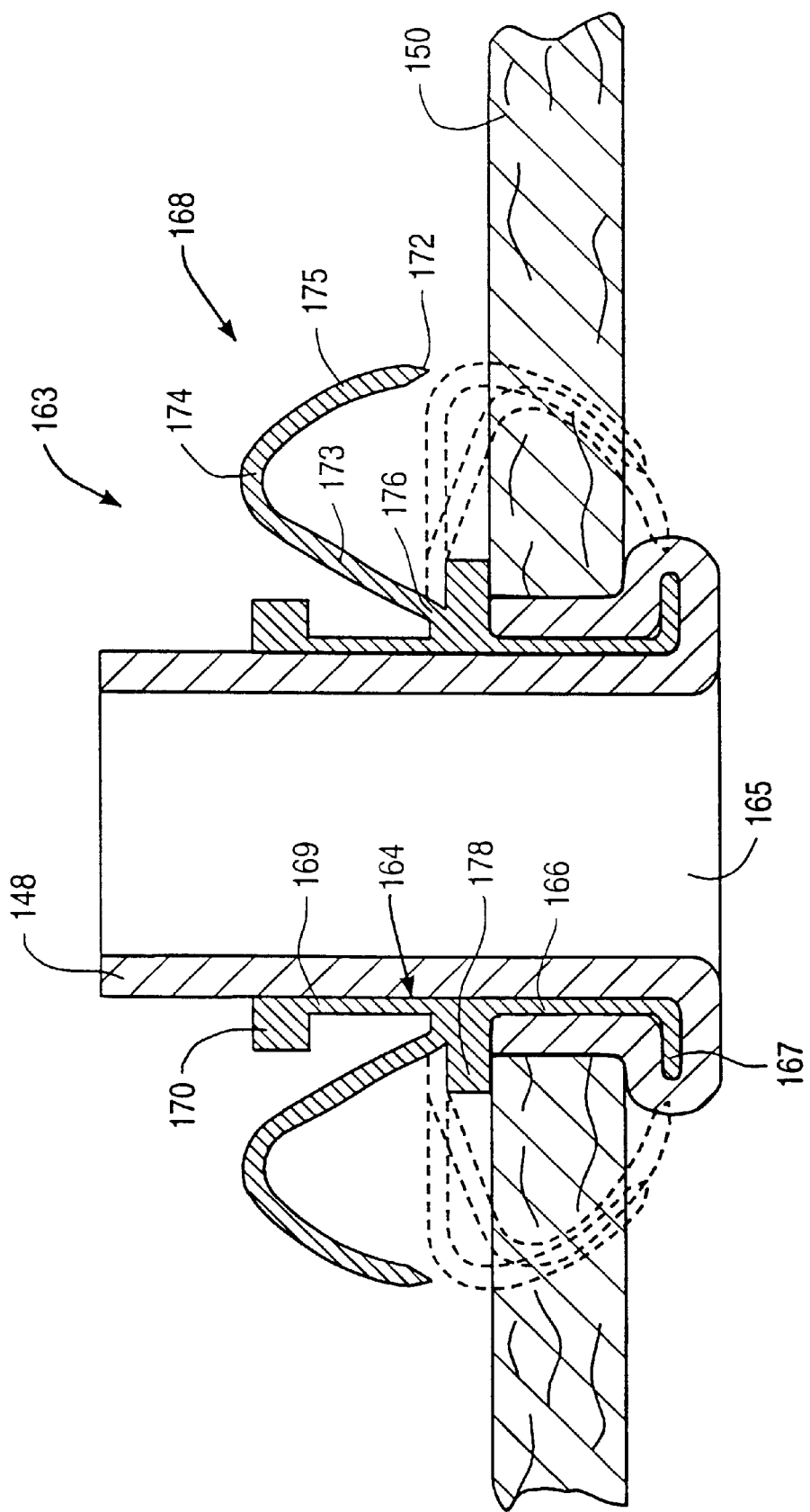
FIG. 12 is a cross sectional view of a one-piece anastomosis staple device with secondary pivot points on the staple legs to create radial tissue compression.

FIG. 12 shows another means for accomplishing the tissue compression performed by the transition segment 174 of the staple legs 168 in the embodiment of FIGS. 9 and 10. In this embodiment, the transition segment 174 of the staple legs 168 is essentially a right angle bend with very little radiusing, so the staple legs 168 cause very little tissue compression as they pierce the target vessel wall 150 and travel through the tissue. However, before the staple legs 168 have reached the end of their travel, the first segment 173 comes into contact with a circumferential ledge 178 that extends outward from the tubular body member 164 just below the attachment point 176 of the staple legs 168. When the staple legs 168 contact the ledge 178, the first segments 173 of the legs bend where they contact the outer edge of the ledge 178. This moves the center of rotation outward and shortens the radius of rotation of the curved end segment 175 so that the staple legs will pull the tissue of the target vessel wall 150 toward the tubular body member 164, compressing the tissue.

The staple legs 168 are preferably dimensioned so that the staple legs travel all the way through the target vessel wall 150 when the staple is actuated. In the embodiment of FIG. 10, after actuation, the ends 172 of the staple legs 168 rest just distal to the flange 167 on the distal end 166 of the tubular body member 164. In the embodiment of FIG. 12, the staple legs 168 are configured to pierce the wall of the graft vessel 148 just proximal to the flange 167 on the distal end 166 of the tubular body member 164, adding to the security of the attachment. In both embodiments the flange 167 supports the tissue of the target vessel wall 150 as the ends 172 of the staple legs 168 emerge, helping to insure that the staple legs 168 will pierce cleanly through the target vessel wall 150 without separating the lamina, which could lead to dissection. In both cases, the staple legs 168 are configured so that the curved end segments 175 of the staple legs 168 are driven all the way through the target vessel wall 150 before there is significant compression of the tissues. The tubular body member 164 isolates the cut edge at the opening 152 in the target vessel wall 150 from the blood flow path so that blood pressure will not cause delamination of the target vessel wall 150. The staple legs 168, the tubular body member 164 and the flange 167 form a closed loop, similar to a sutured attachment. These factors also help to minimize the danger of dissection of the target vessel wall 150.

Figure 13:
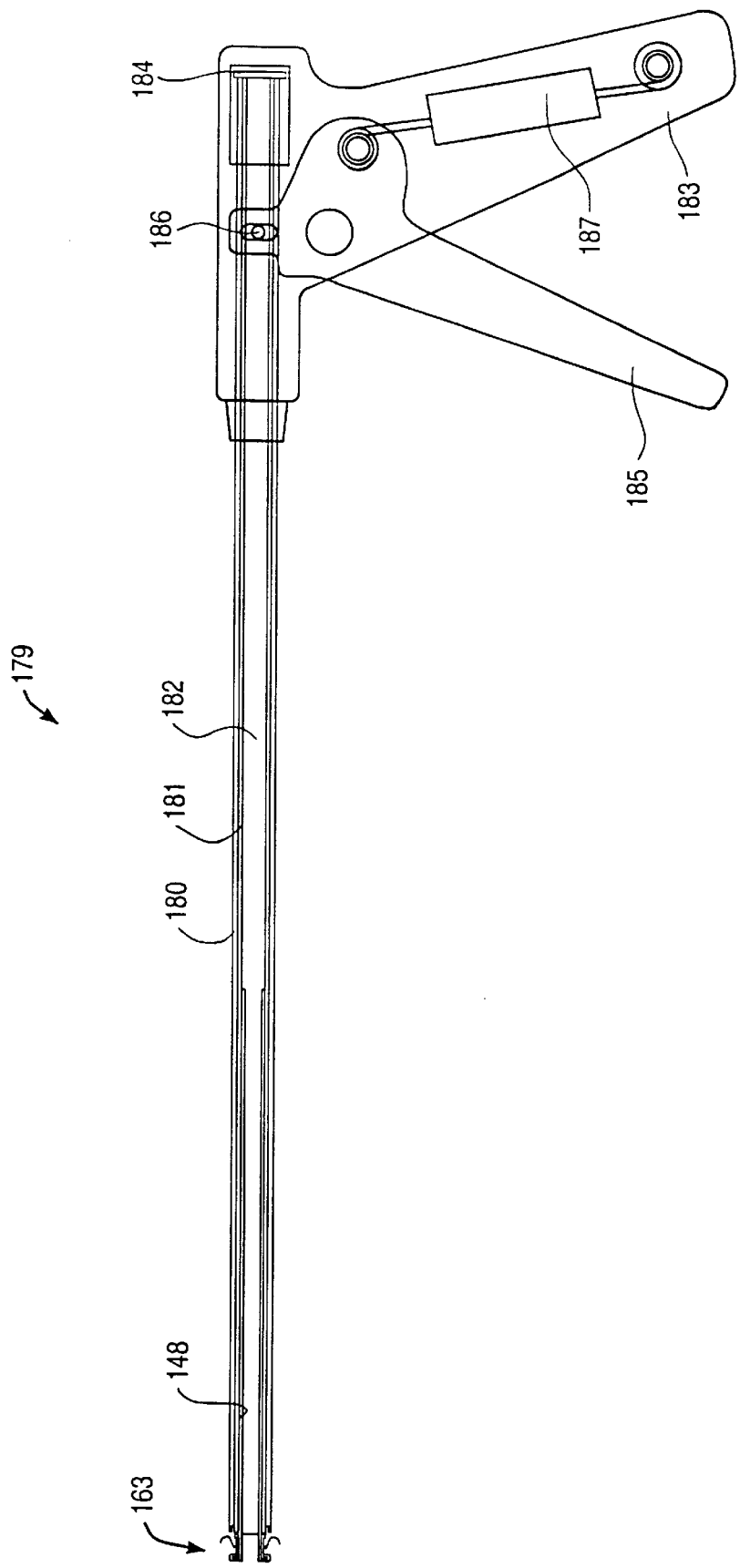
FIG. 13 is a side cross sectional view of a staple applying tool for creating an end-to-side anastomosis using the one-piece anastomosis staple device of FIG. 9.

FIG. 13 shows one preferred embodiment of the one-piece anastomosis staple 163 mounted on the distal end of a specially adapted staple applying tool 179. The staple applying tool 179 has an outer tube 180 and an inner tube 181 slidably received within the outer tube 180. The inner tube 181 has an inner lumen 182 of sufficient diameter to accommodate the outer diameter of the graft vessel 148 that will be used for the anastomosis. The staple applying tool 179 has a main body 183 which is shaped in the form of a pistol grip. The proximal end of the inner tube 181 is anchored with respect to the main body 183 by a flange 184 or other attachment on the proximal end. The outer tube 180 is slidable with respect to the inner tube 181 by actuating the lever 185 of the staple applying tool 179 which engages a pair of pins 186 attached to the exterior of the outer tube. Pulling the lever 185 advances the outer tube 180 distally over the inner tube 181. A return spring 187 attached to the lever 185 returns the lever 185 and the outer tube 180 to their unactuated positions.

Figure 14:
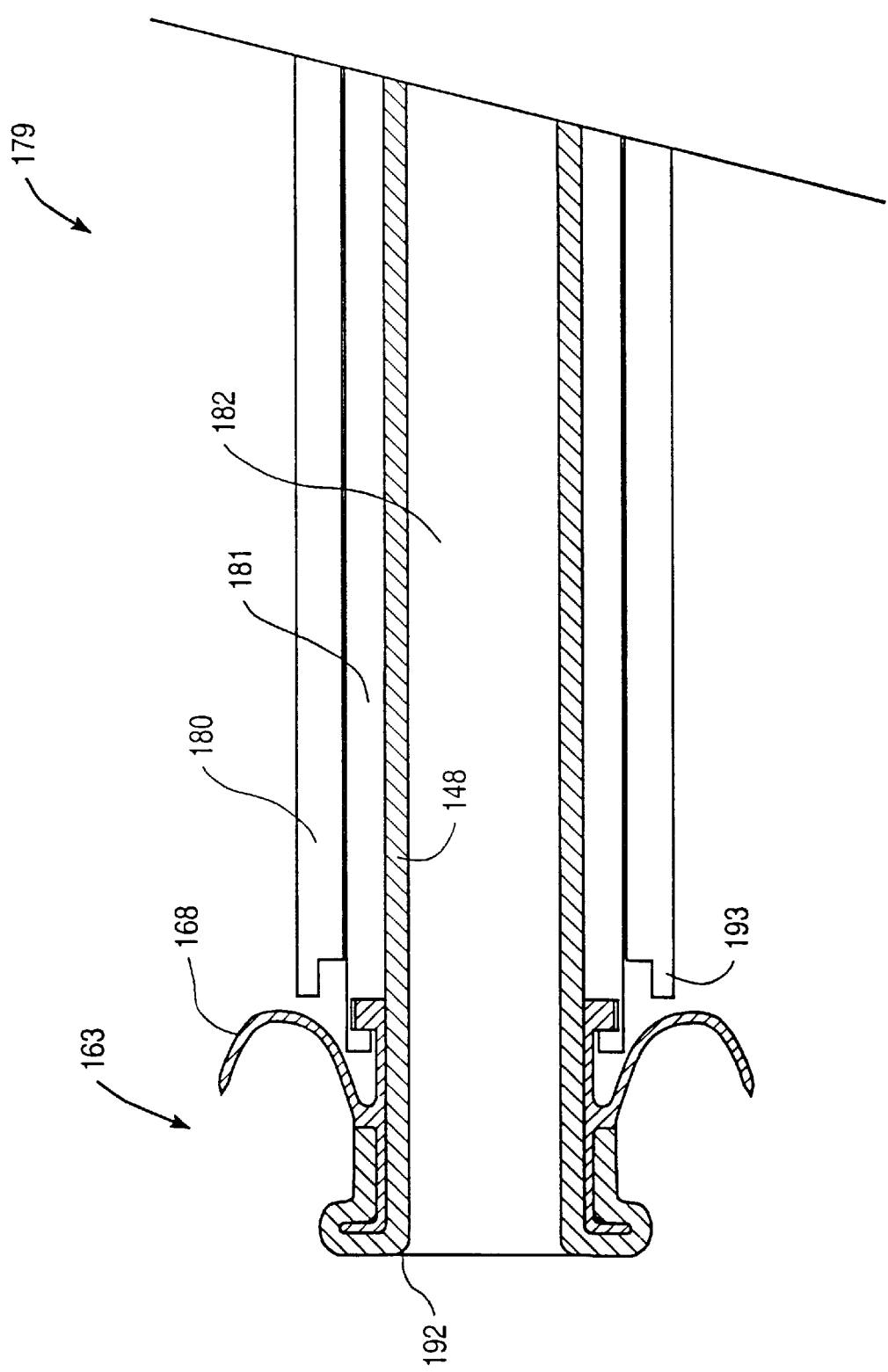
FIG. 14 is a cross sectional view of the distal end of the staple applying tool of FIG. 13 holding the one-piece anastomosis staple device of FIG. 9 with a graft vessel attached thereto.

A close-up view of the anastomosis staple 163 and the distal end of the staple applying tool 178 is shown in FIG. 14. The anastomosis staple 163 in this embodiment has a tubular body 164 which is permanently attached to a plurality of circumferentially distributed attachment legs 168. The tubular body 164 has a distal tubular extension 166 with a flange 167 for eversion and attachment of the graft vessel 148. There is also a proximal tubular extension 169 which has a pair of tabs 170 for grasping the staple with a staple retainer 188 on the distal end of the inner tube 181 of the staple applying tool 179. An end view of the tabs 170 is shown in FIG. 15A. The staple retainer 188 at the distal end of the inner tube 181 shown in detail in FIG. 15B, has a pair of longitudinal slots 189 corresponding to the two tabs 170 of the anastomosis staple. Connected to the longitudinal slots 189 is a circumferential groove 190 within the inner tube 188. The staple 163 is attached to the staple retainer 188 by aligning the tabs 170 with the longitudinal slots 189 and sliding the tabs into the slots 189. When the tabs 170 reach the bottom of the longitudinal slots 189, the staple 163 is rotated with respect to the inner tube 181 so that the tabs 170 enter the circumferential groove 190. A ridge 191 on the distal side of the groove 190 holds the tabs 170 within groove 190 to retain the staple 163 on the end of the inner tube 181.

It should be noted that a number of methods of attaching the tubular member 164 to the stapling mechanism 179 are possible besides the bayonet attachment illustrated. The end of the stapling mechanism 179 may be configured to grasp the tubular member 164 on the inner diameter or the outer diameter distal to the point of attachment 176 of the staple legs 168, allowing the proximal tubular extension 169 of the anastomosis staple 163 to be eliminated. This modification would allow a lower profile anastomosis attachment to be created.

To prepare the graft vessel 148 for anastomosis, an anastomosis staple 163 is attached to the distal end of the staple applying tool 179 as just described, then, using a suture or an elongated grasping tool, the graft vessel 148 is drawn into the inner lumen 182 of the tool until the end 192 of the graft vessel 148 to be anastomosed extends a short distance from the distal end of the tool. At this point, the end 192 of the graft vessel 148 to be anastomosed is everted over the distal tubular extension 166 and the flange 167 as shown in FIG. 14. A suture can be tied around the everted end 192 of the graft vessel 148 proximal to the flange 167 to retain the graft vessel 148 on the staple 163, if desired.

Thus prepared, the staple 163 is advanced toward an opening 152 that has been previously made in the target vessel wall 150 with an aortic punch or other appropriate tool. Preferably, the opening 152 is made with a diameter approximately equal to the outer diameter of the distal tubular extension 166 of the staple 163 just proximal to the flange 167. The flange 167 with the everted end 192 of the graft vessel 148 is passed through the opening 152 in the target vessel 150, as shown in FIG. 10. The target vessel wall 150 may need to be stretched slightly to allow the flange 167 to pass through the opening 152. The elastic recovery of the target vessel wall 150 creates a compressive force where the target vessel wall 150 surrounds the distal tubular extension 166 with the everted end 192 of the graft vessel 148 which contributes to the fluid-tight seal of the anastomosis.

Once the flange 167 has been passed through the opening 152 in the wall of the target vessel 150, the anastomosis staple 163 is pulled back slightly so that the flange 167, covered by the everted graft vessel wall 192, is against the inner surface of the target vessel wall 150. Then, the staple 167 is actuated by pulling on the lever 185, which moves the outer tube 180 distally until the staple driver 193 at the distal end of the outer tube 180 bears on the attachment legs 168. As the staple driver 193 advances, the attachment legs 168 bend at the fulcrum 176 where they attach to the tubular member 164. The arc-shaped third segments 175 of the attachment legs 168 penetrate and traverse the wall of the target vessel 150. Once the third segments 175 of the attachment legs 168 have traversed the wall, the staple 163 begins to compress the tissue of the target vessel wall 150 radially against the distal tubular extension 166 of the anastomosis staple 163 by any of the mechanisms previously discussed. After the attachment legs 168 of the anastomosis staple 163 have been fully actuated, the lever 185 is released and the staple applying tool 179 is rotated to disengage the staple retainer 188 from the tabs 170 on the proximal tubular extension 169 of the staple 163. The staple applying tool 179 is withdrawn and the anastomosis is complete.

Figure 16:
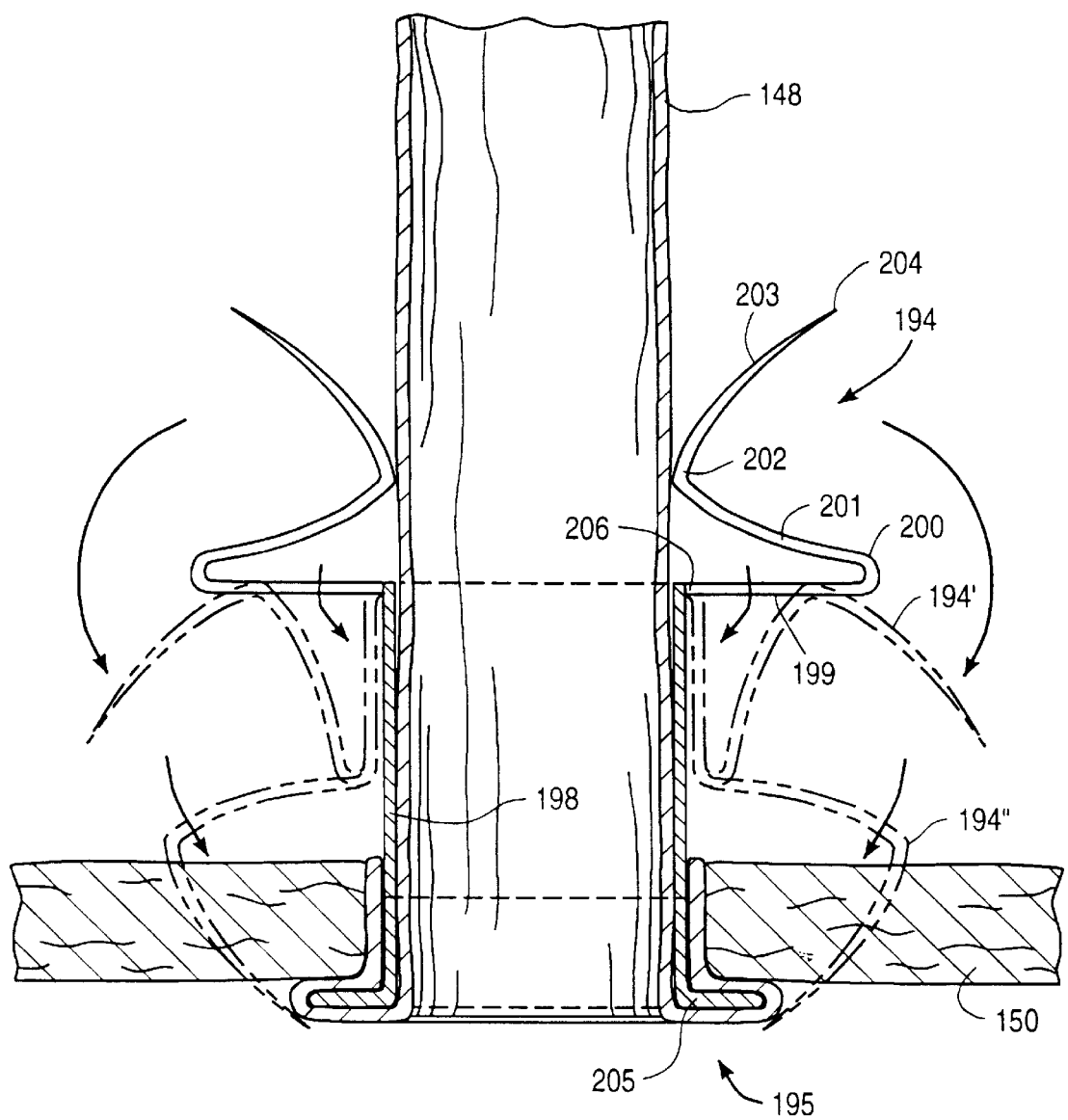
FIG. 16 is a cross sectional schematic of another alternate embodiment of the one-piece anastomosis staple device being actuated to form an end-to-side anastomosis.

FIG. 16 shows another potential configuration for the staple legs 194 of the one-piece anastomosis staple 195. In this embodiment, the staple legs 194 have a compound curved transition segment 197 which provides two different axes of rotation for the staple legs 194 as they are actuated. The staple legs 194 attach to the proximal end of the tubular body member 198. A first segment 199 of the staple leg 194 extends approximately radially from the point of attachment 206. There is a U-shaped bend 200 at the end of the first segment 199 that connects it to a second segment 201 which lies roughly parallel to the first segment 199. A third segment 202 attaches the second segment 201 to the fourth, and most distal, segment 203 of the staple leg. The fourth segment 203 has an arc-shaped curve whose center of rotation is approximately at the center of the U-shaped curve 200 between the first 199 and second 201 segments. The distal tip 204 of the fourth segment 203 is sharpened so that it easily penetrates the target vessel wall 150.

In the operation of this embodiment of the anastomosis staple, the staple legs 194 are initially in the position shown by solid lines 194 in FIG. 16. In this position the staple legs 194 are held well above the flange 205 on the distal end of the tubular body member, making it easier to insert the flange 205, with the everted graft vessel 192 attached, into the opening in the target vessel 150 and to seat the flange 205 against the inner surface of the target vessel 150. When the staple driver is advanced, the staple legs 194 initially rotate about attachment point 206 between the first segment and the tubular body member. After the staple leg 194 has rotated approximately 90 degrees, to the position shown by phantom lines 194', the first segment 199 comes into contact with the exterior of the tubular body member 198 and it stops rotating. Advancing the staple driver further causes the second 201, third 202 and fourth 203 segments of the staple leg 194 to rotate around the U-shaped curve 200 connecting the first 199 and second 201 segments. The U-shaped curve 200 opens up to about 90 degrees as the curved fourth segment 203 of the staple leg 194" penetrates the target vessel wall 150, attaching the graft vessel 148 to the target vessel 150 to complete the anastomosis.

Another embodiment of the two-piece anastomosis staple is shown in FIGS. 17A–17D. This embodiment differs somewhat in its construction from the embodiment of FIG. 1 although the operational principles are basically the same. The anastomosis staple 207 again includes an anchor member 208 and a coupling member 209 which interconnect. The anchor member 208 is made with a ring-shaped frame 210 which is pierced by two parallel rows of slots 211, 212. The metal 213 between the slots 211, 212 is deformed outward slightly to allow insertion of wire attachment legs 214. After the attachment legs 214 are inserted, the metal 213 is pressed inward to firmly attach the wire attachment legs 214 to the frame 210. Either before or after attachment to the ring-shaped frame 210, the wire attachment legs 214 can be formed with a desired curve, such as one of the curves described in FIGS. 8A–8G. The distal tips 215 of the wire attachment legs are sharpened so that they easily penetrate the target vessel wall 150. The use of round wire attachment legs 214 with conically sharpened points 215, as opposed to the flat attachment legs 105 with chisel-shaped points 212 of FIG. 1, has shown some advantage in preliminary testing, in that the round wire legs 214 cause less trauma to the tissue of the target vessel wall 150 as they penetrate it. This may be due to the tendency of the conically sharpened tips 215 of the attachment legs 214 to dilate the tissue as they pass through the target vessel wall 150 more than to cut it. The tissue of the target vessel wall 150 is thus left more intact and may be less prone to dissections or other structural failure.

A plurality of retaining clips 216 are integrally formed on the proximal edge of the ring-shaped frame 210. The retaining clips 216 perform the function of coupling the anchor member to the coupling member, similar to the interior surface features 117 of the anchor member 101 of FIG. 1. The coupling member 209, shown in FIG. 17B, has a tubular body 217 with a plurality of graft holding points 218 extending from its distal edge. If desired, the graft holding points 218 could be relocated, replaced with other gripping features, or eliminated entirely to avoid piercing the graft vessel 148 at the point of eversion. The graft holding points 218 perform one of the functions of the exterior surface features 116 of the coupling device 102 shown in FIG. 1 in that they attach the graft vessel 148 to the coupling member 209.

This embodiment of the two-piece anastomosis staple 207 can be applied with a slightly modified version of the anastomosis stapling tool 118 of FIGS. 2, 6 and 7, following the sequence of steps of FIGS. 5A–5G. The inner tube 124 of the stapling mechanism 119 grasps the anchor member 208 by either the ring-shaped frame 210 or the first segment of the attachment legs with the L-shaped legs of the staple retainer. After a small incision 151 has been made in the target vessel wall 150 at the desired anastomosis site, the stapling mechanism 119, with the vessel punch mechanism 120 inserted into the inner lumen 128, is positioned at the anastomosis site. The anvil 136 of the vessel punch 120 is inserted through the incision 151 and drawn back slightly to support the target vessel wall 150 so that the wire attachment legs 214 can be driven into the wall 150. The wire attachment legs 214 are then deformed by the stapling mechanism 119 to attach the anchor member 208 to the target vessel wall 150. The vessel punch 120 is then actuated to form a hole 152 through the target vessel wall 150 centered within the ring-shaped frame 210, as described in relation to FIG. 5D. The anchor member 208 is now attached to the target vessel wall 150 with the ring shaped frame 210 centered around the opening in the vessel wall 152, as shown in FIG. 17B. In this illustrative embodiment, the wire attachment legs 214 are configured so as to only partially penetrate the target vessel wall 150 so that they are embedded within the target vessel wall 150 in their final, deployed configuration. This variation of the method may be preferred for attachment to some types of body tissues as the target vessel 150. The wire attachment legs 214 may also be pierced through the entire target vessel wall 150 before they are deformed so that they reside against the interior of the target vessel wall 150, as shown in FIG. 5C.

Once the anchor member 208 is attached to the target vessel 150, the vessel punch mechanism 120 is withdrawn and the graft insertion tool 121 with the graft vessel 192 everted over the distal end of the coupling member 209 is inserted into the inner lumen 128 of the stapling mechanism 119. The graft insertion tool 121 is used to press the coupling member 209 into the ring-shaped frame 210 of the anchor member 208 until the everted end 192 of the graft vessel 148 is firmly sealed against the outer surface of the target vessel wall 150 and the retaining clips 216 have seated over the proximal end of the coupling member 209. The coupling member 209 is held in the ring-shaped frame 210 by the retaining clips 216. The graft holding points 218 may be made so that they penetrate through the graft vessel wall 192 and into the target vessel wall 150, as shown in FIG. 17C, to increase the security of the anastomosis attachment. It should be noted that other sequences of operations are also possible for this embodiment, such as punching the opening in the target vessel wall prior to attachment of the anchor member.

Another embodiment of the two-piece anastomosis staple device 219 is shown in FIGS. 18A–18F. This embodiment of the device lends itself to different manufacturing methods than the previously described embodiments. The anchor member 220 shown in perspective in FIG. 18A can be formed from a single piece of sheet metal by a combination of punching and drawing steps. The anchor member 220 has a plate 221 which is curved to fit the contours of the exterior surface of the target vessel wall 150, as seen in the end view FIG. 18B. For performing an aortic anastomosis, the radius of curvature of the plate 221 would typically be between 10 and 20 mm in an adult human. The plate 221 would be approximately 10 to 20 mm in width and 10 to 25 mm in length. The plate 221 is punched so as to form integral attachment legs 222. This illustrative embodiment is shown with four integrally formed attachment legs 222, as best seen in top view FIG. 18C. A tubular proximal extension 223 is formed on the curved plate 221 by drawing the sheet metal plate 221 to form a cylindrical extension 223, then piercing or drilling it to open the proximal end of the cylinder. A final forming or stamping operation forms a radiused flange 224 at the proximal end of the tubular extension 223 that serves as a strain relief to prevent sharp bends or kinking of the graft vessel 148 close to the anastomosis site.

This embodiment of the anchor member can be attached to the target vessel wall by a sequence of operations similar to that described in relation to FIGS. 5A–5G. Alternatively, the sequence of operations can be re-ordered so that the target vessel is punched before placement of the anchor member similar to that described for the one-piece embodiment of FIG. 9. Thus, either of the anastomosis stapling mechanisms 118, 179 previously described could easily be adapted to hold the anchor member 208 of FIG. 18 and to drive the attachment legs 222 into the target vessel wall 150.

The coupling member 225 in this embodiment is a toroidal ring 225 made of a resilient biocompatible material such as plastic, rubber or a springy metal having an outside diameter slightly smaller than the inside diameter of the cylindrical extension 223. The coupling member 225 is shown in FIG. 18D. The graft vessel 148 is prepared for anastomosis by passing the end of the vessel through the central opening of the toroidal ring 225 and everting it back 192 over the ring, as shown in the FIG. 18E. The ring 225, with the graft vessel 192 everted over it, is then collapsed or folded enough so that it can be inserted into the proximal tubular extension 223 of the anchor member 220. Once through the cylindrical extension 223, the toroidal ring 225 recoils to its expanded size, sealing the graft vessel wall 192 against the wall of the target vessel 150 and preventing the end of the graft vessel 192 from pulling out of the tubular extension 223. Alternatively, a cylindrical ring-shaped coupling member with locking features, similar to those shown in FIGS. 1 and 17B, can be used in conjunction with the anchor member of FIG. 18A.

Figure 19A:
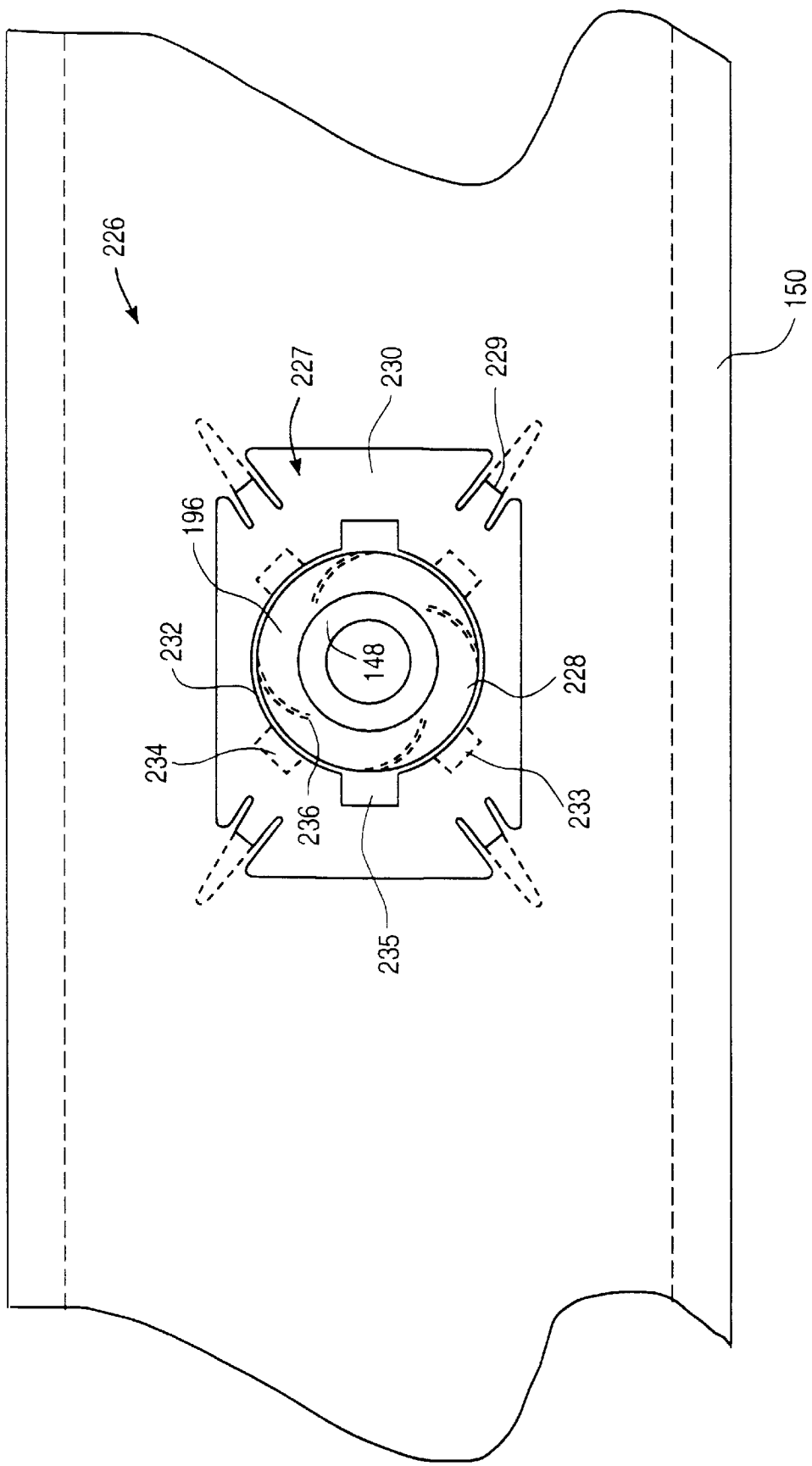
FIG. 19A–19B shows a third alternate construction of the two-piece anastomosis staple device of FIG. 1.
Figure 19B:
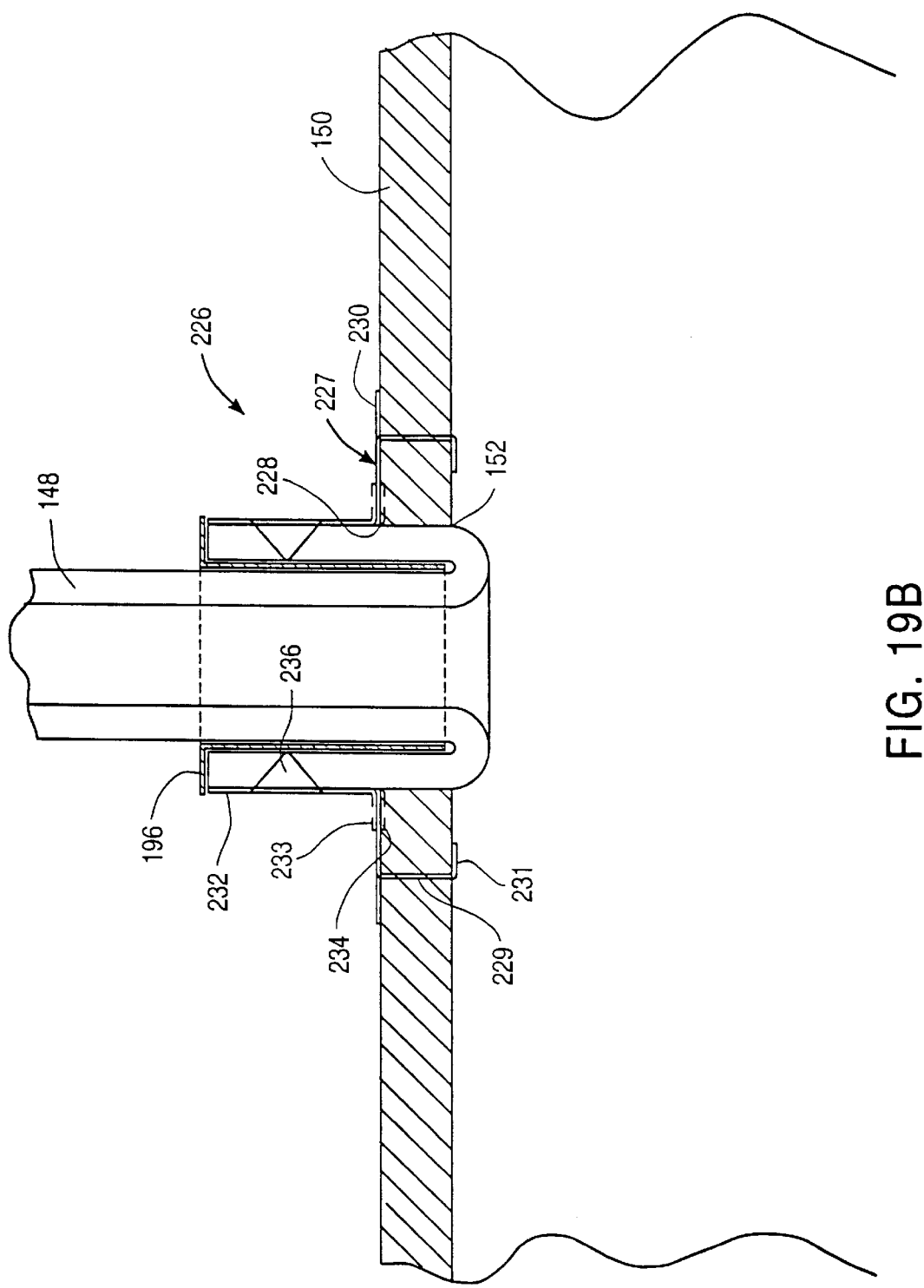

FIGS. 19A and 19B show an alternate construction 226 of the two-piece anastomosis staple 219 device of FIGS. 18A–18E. In this variation of the device, the anchor member 227 may be made from a flat piece of sheet metal that is punched to form a flange 238 with a central aperture 228 and integrally formed attachment legs 229. The anchor member 227 is attached to the target vessel 150 with the central aperture aligned 228 with a preformed hole 152 in the wall of the target vessel 150. Alternatively, the anchor member 227 can be placed before the hole 152 is punched. The attachment legs 229 are shaped with straight distal segments, as shown by the phantom lines 231', that penetrate the target vessel wall 150 in a linear fashion. A stapling device with a staple deforming anvil is passed through the hole 152 in the target vessel wall 150 to deform the attachment legs 229 so that they grip the target vessel wall 150, as shown by the solid lines 231. The attachment legs 229 can be deformed one at a time or some or all of the attachment legs 229 can be deformed at once depending on the design of the stapling device. Alternatively, the attachment legs 229 can be precurved and driven into the target vessel wall 150 from the outside.

The central aperture 228 in the flange 230 of the anchor member 227 has attachment features that interlock with matching attachment features on a first tubular coupling member 232. As an illustration of one possible configuration, the first coupling member is shown with two pairs of tabs 233, 234 extending radially from the distal edge of the first tubular coupling member 232. One pair of tabs 234 is slightly more distal than the other pair 233. The central aperture 228 of the anchor member 227 has a matching pair of slots 235 extending from the aperture 228. The first coupling member 232 is joined to the anchor member 227 by aligning the more distal pair of tabs 234 with the slots 235, pushing the tabs 234 through the slots 235, then turning the coupling member 232 until the tabs 234 are locked onto the edges of the aperture 228. The first tubular coupling member 232 may be made with integrally formed graft holding points 236 which are cut and bent inward from the wall of the first tubular coupling member 232 to hold the everted graft in place. The graft may be everted over a second tubular coupling member 196, which is inserted into the first tubular coupling member 232 and is attachable to the first tubular coupling member at the proximal ends of the tubular coupling members, as shown in FIG. 19B.

FIG. 20 shows a fourth alternate construction 237 of the two-piece embodiment of the anastomosis staple device 100 of FIG. 1. The anchor member 238 of the anastomosis staple device 237 may be formed from a piece of sheet metal, similarly to the other alternate embodiments previously described. The anchor member 238 has a distal plate 239 which may be flat or curved to match the exterior curvature of the target vessel 150. Multiple attachment legs 240 are cut from the plate material 239, sharpened at the ends 241, and bent with a first section 242 that angles upwardly from the plate 239 and a second section 243 that is angled downward to pierce the target artery wall, as shown in phantom lines 243' in FIG. 20. Preferably, the second section 243 is curved with a radius of curvature approximately equal to the length of the first section 242. A tubular proximal extension 244 with a slight hourglass shape extends from the distal plate 239 of the anchor member 238.

The coupling member 245 of the anastomosis staple device 237, shown in FIG. 20, is made in a tubular shape of a biocompatible resilient material such as plastic, rubber or a springy metal, such as a nickel-titanium alloy. The tubular coupling member 245 has a slight hourglass shape in axial cross section, matching the interior shape of the tubular proximal extension 244 of the anchor member 238. If desired, the tubular coupling member 245 can be made with slightly thickened proximal 246 and distal 247 extremities which act as O-rings molded integrally with the wall of the tube. The tubular coupling member 245 can be made with a continuous tubular wall or with a longitudinal slot in the wall of the tube to increase the resiliency of the coupling member. Alternatively, the tubular coupling member 245 can be made of a coiled spring with an hourglass shape in axial cross section.

As with the previously described embodiments, the anchor member 238 can be applied to the exterior of the target vessel 150 either before or after an opening 152 has been created with a vessel punch. To place the anchor member 238, the plate 239 of the anchor member 238 is pressed against the exterior surface of the target vessel 150 at the anastomosis site and the attachment legs 240 are pressed to drive the sharpened tips 241 through the target vessel wall 150. If an opening 152 has not yet been made in the target vessel wall 150, a vessel punch is inserted through the lumen 244 of the proximal tubular extension 244 to create an opening 152 in the wall 150 concentric with the tubular extension 244.

Meanwhile, the graft vessel 148 is prepared by placing it through the lumen of the tubular coupling member and everting the end 192 of the graft vessel 148 over the outside of the coupling member 245. To complete the anastomosis, the coupling member 245 with the end 192 of the graft vessel 148 attached is collapsed or folded and inserted into the proximal tubular extension 244 of the anchor member 238. The resilience of the coupling member 245, combined with the matching hourglass shapes of the two parts of the staple device, locks the parts together to form a leak-proof anastomosis.

The coupling member 245 can be dimensioned so that the distal end of the coupling member 245 extends through the opening 152 in the target vessel wall and the everted edge 192 of the graft vessel 148 seals within the opening 152, as illustrated, or against the interior surface of the target vessel 150 similarly to the one-piece embodiment of the anastomosis staple device illustrated in FIG. 9.

Alternatively, the coupling member 245 can be shaped so that it presses the everted edge 192 of the graft vessel 148 against the exterior surface of the target vessel 150 to create a leak-proof seal similar to the embodiment of FIG. 1.

Figure 21A:
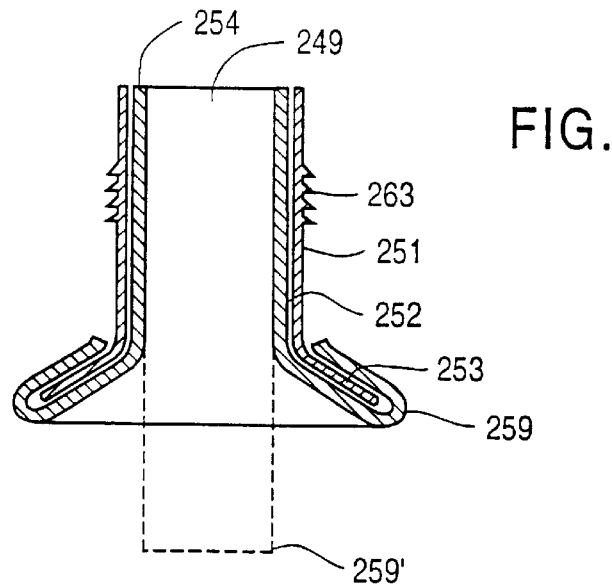
FIGS. 21A–21C are side partial cross section views of a first embodiment of an anastomotic fitting according to the invention.
Figure 21B:
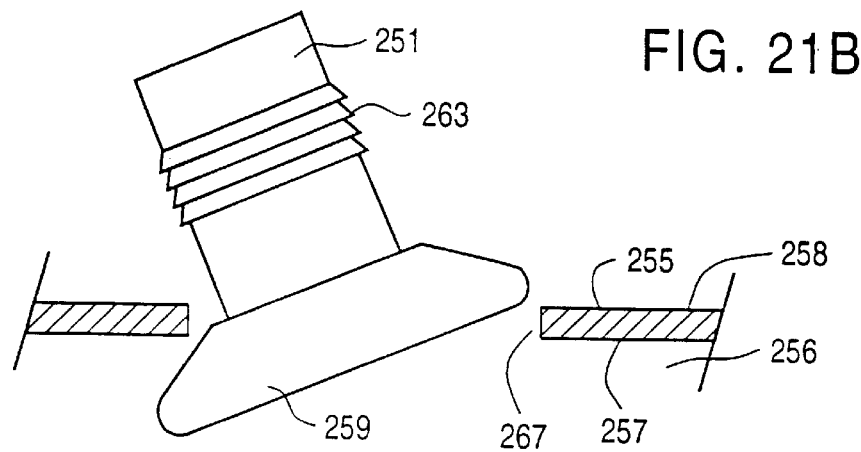
Figure 21C:
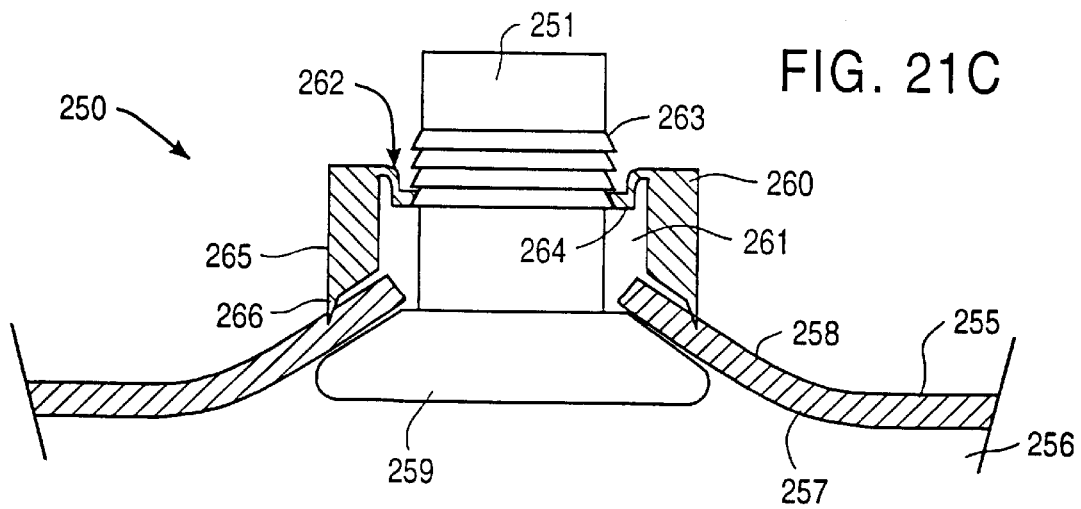

In a further aspect of the invention, an anastomosis fitting is provided for rapidly and reliably creating an end-to-side anastomosis between a graft vessel and a target vessel. A first representative embodiment of an anastomotic fitting 250 according to this second aspect of the present invention is shown in FIGS. 21A–21C. The anastomotic fitting 250 is made up of two coacting parts: a) a tubular inner sleeve 251 which has an internal lumen 252 of sufficient size to accommodate the external diameter of the graft vessel 254 and an inner flange 253 which is attached or formed at the distal end of the sleeve 251 so as to be positioned within the lumen 256 of the target vessel 255, and b) an outer flange 260 which has a central orifice 261 that is sized to fit over the exterior of the inner sleeve 251 to be positioned against the exterior surface 258 of the target vessel wall 255. The anastomotic fitting 250 is thus held in place by compressing the target vessel wall 255 between the inner 253 and outer 260 flanges. An adjustable locking mechanism 262 holds the outer flange 260 on the inner sleeve 251 at a selected position to create a tailored degree of tissue compression at the anastomotic site. The anastomosis fitting 250 can be made of various biocompatible materials, such as stainless steel, titanium alloys, plastic, pyrolytic carbon, etc. Additionally, biocompatible coatings could be applied to the inner and/or outer surfaces of the fitting 250 to increase its acceptance by the body tissues or to reduce thrombosis.

The inner sleeve 251 is a tubular member with an internal lumen252 large enough to accommodate the external diameter of the graft vessel 254, either a natural graft vessel or an artificial graft vessel. Natural saphenous vein autografts typically have an internal diameter between 3 mm and 10 mm and an external diameter between 4 mm and 11 mm. Pedicled arterial grafts, such as the internal mammary artery or the gastroepiploic artery typically have an internal diameter between 2 mm and 7 mm and an external diameter between 3 mm and 8 mm, with thicker, more muscular walls. Artificial prosthetic graft vessels, made of materials such as Dacron or Goretex, typically have a diameter of 3 mm to 30 mm. The tubular inner sleeve 251 should be made of a rigid biocompatible material, such as stainless steel, titanium alloys or a rigid biocompatible plastic. The wall thickness of the sleeve is preferably about 0.2 mm to 2.0 mm.

The distal end of the inner sleeve is flared at an angle of approximately 45 to 75 degrees to form a conical inner flange 253. The inner flange 253 has an outer diameter of approximately 1.3 to 2.5 times the inner diameter of the inner sleeve 251. The use of a conical or rounded inner flange 253 helps to improve the hemodynamic efficiency of the anastomosis connection by improving the orifice coefficient at the entrance to the graft vessel 254. It also assures that the finished anastomosis will not protrude into the lumen 246 of the target vessel 255 or upset the hemodynamic flow in that vessel. The exterior of the tubular inner sleeve 251 has a series of circumferential ridges 263 or threads which may be sawtooth in shape.

The outer flange 260 as a central orifice 261 which is sized to fit over the exterior of the tubular inner sleeve 251. The outer flange 260 has an outer diameter of approximately 1.3 to 3.0 times the inner diameter of the inner sleeve 251. A ratchet mechanism 264 within or adjacent to the central orifice 261 of the outer flange 260 engages the circumferential ridges 263 on the exterior of the tubular inner sleeve 251. The ratchet 264 can be strictly a one-way mechanism so that the outer flange 260 can only move in the direction of the inner flange 253 or a release mechanism can be incorporated so that the outer flange 260 can be moved away from the inner flange 253 in case of premature activation of the ratchet mechanism 264. Alternatively, the outer flange 260 could be threaded to the exterior of the tubular inner sleeve 251. The distal edge 265 of the outer flange 260 may incorporate a plurality of attachment spikes 266 that engage and hold the wall of the target vessel 255 and/or the everted wall 259 of the graft vessel 254 when the outer flange 260 is applied. In the preferred embodiment which is intended for creating an anastomosis between a coronary artery bypass graft and the ascending aorta, the outer flange 260 has 4 to 12 spikes of 1 to 3 mm length and 0.2 to 0.5 mm diameter. Variations of this configuration may be made where appropriate for different graft vessels and target vessels.

Figure 23D:
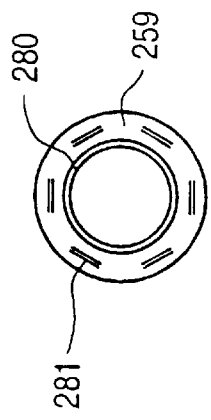
FIGS. 23A–23D are side cross section views of another variant of the embodiment of the anastomosis fitting of FIGS. 21A–21C and FIGS. 22A–22C.
Figure 23C:
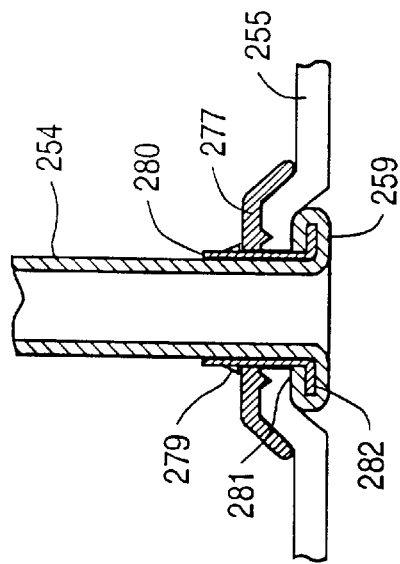
Figure 23B:
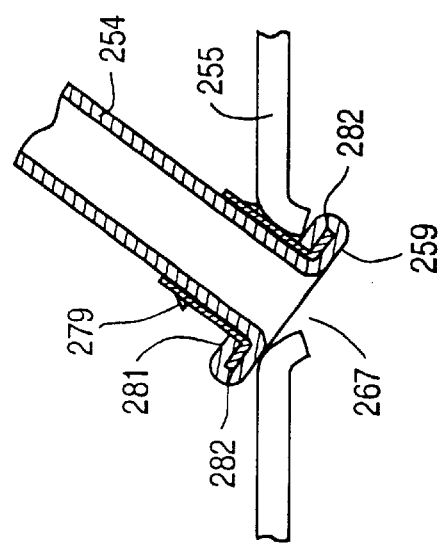
Figure 23A:
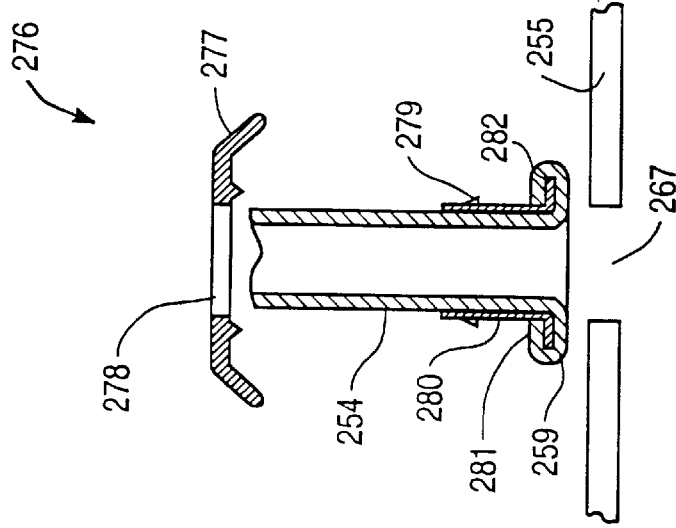

The anastomosis is performed by passing the end 259 of the graft vessel 254 through the inner lumen 252 of the tubular inner sleeve 252 until the end of the vessel extends a short distance from the distal end of the sleeve, as shown by phantom lines 259' in FIG. 21A. The end 259 of the graft vessel 254 is then everted over the conical inner flange 253 of the fitting 250 to form an atraumatic attachment, as shown in FIG. 23A. If desired, a loop of suture can be tied around the everted end 259 of the graft vessel 254 to hold it in place on the inner flange 253 and/or the tubular inner sleeve 251. The conical inner flange 253 and the everted end 259 of the graft vessel 254 are then passed through an opening 267 that has previously been made in the wall of the target vessel 255 with an instrument such as a vessel punch, as shown in FIG. 21B. The diameter of the opening 267 in the target vessel wall is preferably about the same as the external diameter of the tubular inner sleeve 251. The opening 267 may need to stretch slightly to allow the conical inner flange 253 to pass through. The elastic recovery of the target vessel wall 255 around the opening 267 helps to create an anastomotic seal by contracting around the inner sleeve 251 and the everted graft vessel wall 259. The outer flange 260 is then slid onto the proximal end of the inner sleeve 251. If the anastomosis being performed is the first anastomosis of a free graft, such as a saphenous vein graft, with the other end of the graft unattached, then the outer flange 260 can be slid over the graft vessel 254 from the free end. If the other end of the graft vessel 254 is not free, such as when performing a second anastomosis or a distal anastomosis on a pedicled graft like the IMA, then the outer flange 260 should be back loaded onto the graft vessel 254 or preloaded onto the proximal end of the inner sleeve 251 before the end 259 of the graft vessel 254 is attached to the inner flange 253 of the fitting 250. The outer flange 260 is slid down the inner sleeve 251 until it contacts the exterior wall 258 of the target vessel 255 and a desired degree of compression of the target vessel wall 255 is applied between the inner 253 and outer 260 flanges. The ratchet mechanism 264 of the outer flange 260 locks the flange 260 in place on the tubular inner sleeve 251 to complete the anastomosis, as shown in FIG. 21C.

FIGS. 22A–22D show an anastomosis fitting 268 which is a variation of the embodiment of FIGS. 21A–21C. In this variant the inner flange 269 has a flat annular configuration, rather than a conical shape as in the previously described embodiment. To insure that the completed anastomosis does not protrude into the blood flow lumen 256 of the target vessel 255, the outer flange 270 of the fitting is concave on its distal surface 271. The central orifice 272 of the outer flange 270 tapers proximally to a locking ring 273 within the central orifice 272 that slips over and locks with a collar 274 on the proximal end of the tubular inner sleeve 275. As shown in FIG. 22C, when the outer flange 270 is applied to the exterior surface 258 of the target vessel 255 and locked onto the collar 274 of the tubular inner sleeve 275, the inner flange 269 is drawn into the concave outer flange 270, so that the anastomosis is flush with or recessed into the inner wall 257 of the target vessel 255. This helps to assure a hemodynamically correct inflow at the entrance to the graft vessel 254. Two or more collars 274 may be provided on the tubular inner sleeve 275 to allow adjustable compression by the anastomotic fitting 268.

FIGS. 23A–23D show another variant 276 of the embodiment of the anastomosis fitting of FIGS. 21A–21C and FIGS. 22A–22D. In this variant the concave outer flange 277 has a simple central orifice 278 without a locking ring. The locking mechanism is provided by multiple downwardly oriented tangs 279 or tapered ridges, which have been formed in the sidewall of the tubular inner sleeve 280 by cutting, punching or molding. The outer flange 277 is slid over the proximal end of the inner sleeve 280 and over the tangs 279, which engage the proximal end of the outer flange 277 to lock the outer flange 277 into place on the inner sleeve 280, as illustrate in FIG. 23C. If desired, multiple parallel rows of tangs 279 can be provided at different axial locations on the inner sleeve 280 to accommodate different thicknesses of the target vessel wall 255 and to provide a tailored degree of tissue compression at the anastomosis site. Optionally, the underside of the outer flange 277 may have a plurality of attachment points which engage and hold the target vessel wall 255 near the opening 267 in it, adding security to the anastomosis attachment without piercing the target vessel wall 255.

FIGS. 23A–23D also illustrate a variation of the method for applying the anastomosis fitting. In this embodiment, the method includes applying a suture 281 to the everted end 259 of the graft vessel 254 to secure it to the inner flange 282. As best seen in the top view FIG. 23D, the everted end 259 of the graft vessel 254 has been secured to the inner flange 282 of the fitting by making a running stitch around the end of the graft vessel with a suture 281 on the back of the inner flange 282 and tying it to create a purse string that holds the end 259 of the graft vessel 254 in place.

A second representative embodiment of an anastomotic fitting 283 employing inner 284 and outer 285 flanges has an expanding inner flange 284 which facilitates the atraumatic attachment of the graft vessel 254 to the fitting 283 and makes it easier to pass the inner flange 284 and the everted graft vessel 259 through the opening 267 in the target vessel wall 255. Two variations of such an expanding inner flange are shown in FIGS. 24A–24D and FIGS. 25A–25H. The graft vessel 254 is passed through an internal lumen 287 of an inner sleeve 286 which has the expandable inner flange 284 attached at its distal end. The end 259 of the graft vessel 254 is everted over the unexpanded inner flange 284'. The inner flange 284' and the everted end 259 of the graft vessel 254 are passed through the opening 267 in the target vessel wall 255. Once the inner flange 284' of the fitting 283 is in the lumen 256 of the target vessel 255, it is expanded to a diameter 284 which is significantly larger than the opening 267 in the target vessel wall 255. Then an outer flange 285 is applied and locked into a selected position on the inner sleeve 286 as described above to complete the anastomosis.

Figure 24A:
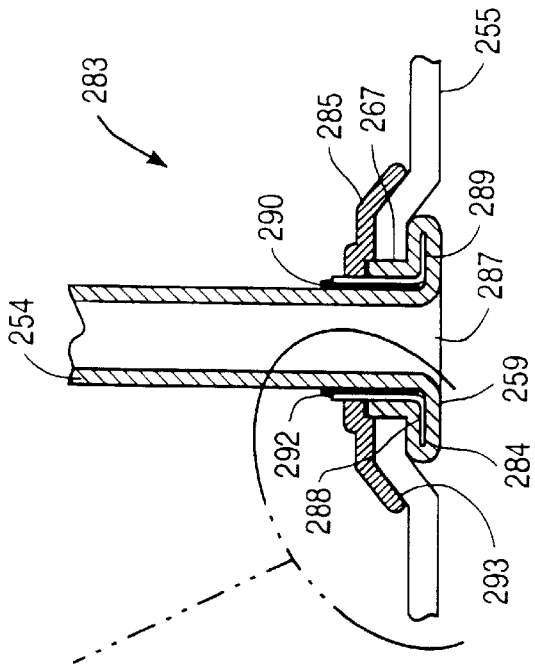
FIGS. 24A–24B are side cross section views of a second embodiment of the anastomotic fitting of the invention having an expanding inner flange.

In the first variant of the expanding inner flange 284, shown in FIGS. 24A–24D, the flange 284 and a portion of the inner sleeve 286 are slotted to create multiple fingers 288 which are initially collapsed inward toward the center of the inner sleeve 286. The ends of the fingers form sector-shaped sections 289 of the flange 284, as seen in the distal end view of FIG. 24D. When the flange 284 is collapsed inward 284', as in FIG. 24C, the sectors 289 fit together to form a smaller diameter flange 284' with a passage 287' through the center large enough for a collapsed graft vessel 254 to fit through. A tubular former 290 is slidably received within the slotted inner sleeve 286 and has an axial lumen 291 large enough to receive the graft vessel 254. The tubular former 290 initially resides in a proximal position, as shown in FIG. 24A. The tubular former 290 has a ridge 292 at its proximal end that positions the tubular former 290 in the correct location with respect to the inner sleeve 286 when the tubular former 290 is in its distal, deployed position. An outer flange 285, with a concave distal surface 293 may be permanently attached to the inner sleeve 286 proximal to the expanding inner flange 284. Alternatively, the outer flange 285 can be provided as a separate component which is attached to the inner sleeve 286 after the graft vessel 254 has been attached or at the end of the anastomosis procedure.

Figure 24B:
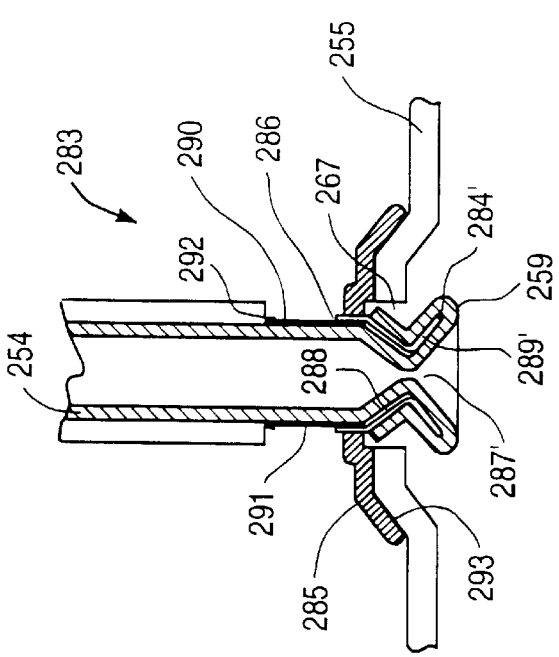
Figure 24C:
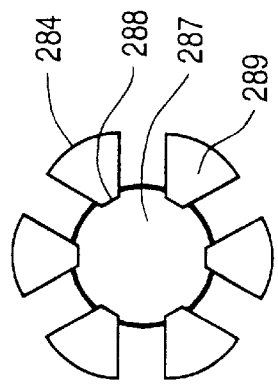
FIGS. 24C and 24D are distal end views of the expanding inner flange in the collapsed position and the expanded position, respectively.
Figure 24D:
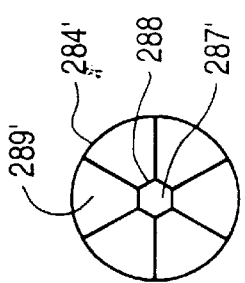

In operation, the graft vessel 254 is inserted through the axial lumen 291 of the tubular former 290 and through the internal lumen 287 of the slotted inner sleeve 286 and through the central opening 287' between the collapsed sectors 289' of the inner flange 284'. The end 259 of the graft vessel 254 is everted over the collapsed sectors 289' of the flange 284'. The collapsed flange 282' and the everted end 259 of the graft vessel 254 are inserted through the opening 267 in the target vessel 255. Then, the tubular former 290 is slid distally within the slotted inner sleeve 286. The tubular former 290 forces the fingers 288 outward, expanding the flange 284 within the target vessel 255. If the outer flange 285 is already attached to the inner sleeve 286 at this point, the distal surface 283 of the outer flange 285 is pressed against the exterior surface 258 of the target vessel 255 as the expandable inner flange 284 is being deployed to complete the anastomosis. If, on the other hand, the outer flange 285 has been supplied as a separate component, the outer flange 285 is slipped over the proximal end of the inner sleeve 286 after the expandable inner flange 284 has been deployed and a desired degree of tissue compression is applied between the inner 284 and outer 285 flanges of the fitting 283 to complete the anastomosis, as shown in FIG. 24B.

Figure 25F:
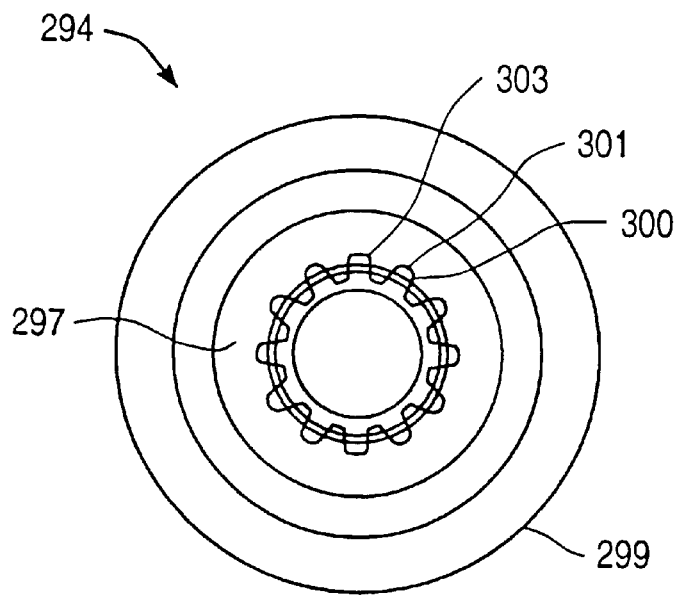
Figure 25G:
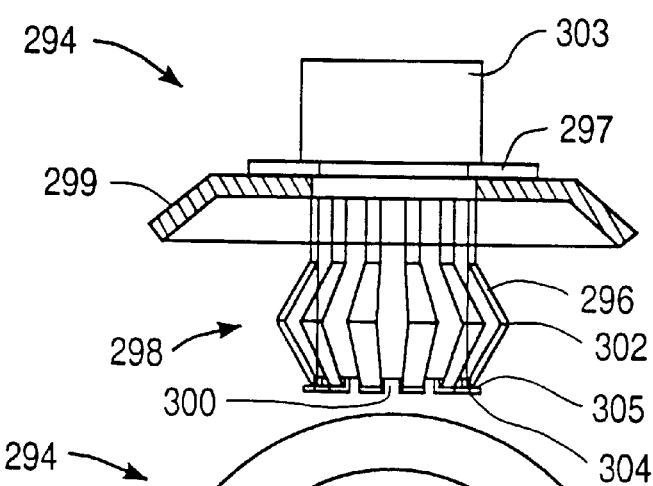
Figure 25H:
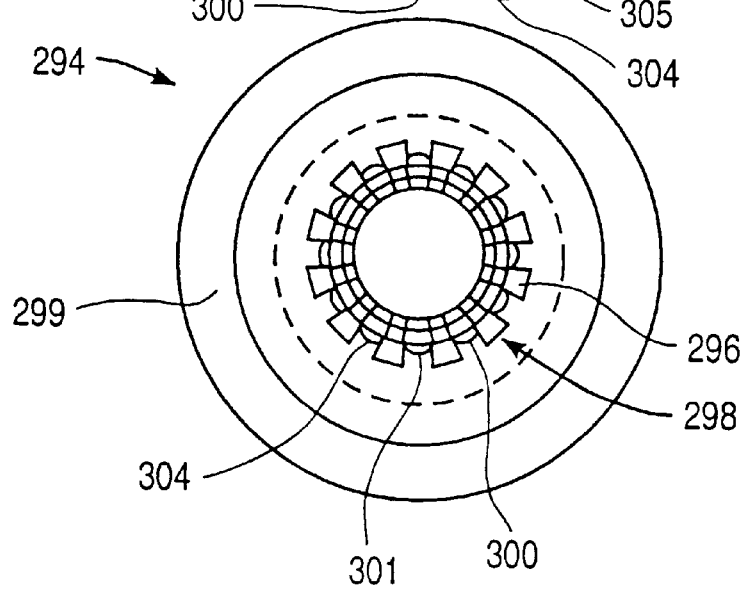

A second variant of the anastomotic fitting 294 with an expanding inner flange 298 is shown in FIGS. 25A–25H. The inner sleeve 295 of the fitting 294 is slotted along its entire length to form multiple fingers 296 that are oriented essentially longitudinally to the inner sleeve 295. A collar 297 on the proximal end of the slotted inner sleeve 295 joins the multiple fingers 296 together in a tubular configuration. A concave outer flange 299 is captured on the slotted inner sleeve 295 by the proximal collar 297. As seen in the end view in FIG. 25E, the inside diameter of the collar 297 has notches 301 which are extensions of the slots 300 between the fingers 296 of the inner sleeve 295. Each of the fingers 296 has a bend 302 in it to predispose it to bend outward at the middle when contracted longitudinally. A tubular forming tool 303 for expanding the inner flange 298 is slidably received within the slotted inner sleeve 295. The distal end of the tubular forming tool 303 is crenellated with multiple radially extending tabs 304. The multiple radially extending tabs 304, as seen in the end view in FIG. 25F, are configured to fit through the notches 301 in the collar 297 and into the slots 301 of the inner sleeve. The tubular forming tool 303 is inserted into the slotted inner sleeve 295 by aligning the radially extending tabs 304 with the notches 301 in the collar 297 and sliding it distally along the slots 300 until the tabs 304 pass the distal ends 305 of the fingers 296. Then, the tubular forming tool 303 is rotated slightly so that the radially extending tabs 304 engage the distal ends 305 of the fingers 296 of the slotted inner sleeve 295, as shown in FIG. 25A.

The anastomosis is performed by passing the graft vessel 254 through the internal lumen of the forming tool 303 within the slotted inner sleeve 295 and everting it 259 over the distal ends 305 of the fingers 296. A loop of suture 306 can be used to hold the everted vessel 259 in place. The fingers 296 of the fitting 294 and the everted end 259 of the graft vessel 254 are inserted through an opening 267 in the target vessel wall 255. When the tubular forming tool 303 is slid proximally with respect to the slotted inner sleeve 295, the radially extending tabs 304 of the tubular forming tool 303 bear against the distal ends 305 of the fingers 296 compressing them longitudinally. The fingers 296 bow outward, folding at the bend 302 to expand and create an inner flange 298 which engages the inner surface 257 of the target vessel wall 255. The tubular forming tool 303 is pulled further proximally until the newly formed inner flange is drawn into the concave outer flange 299, compressing the target vessel wall 255 and recessing the inner flange 298 and the anastomotic connection into the target vessel wall 255, as shown in FIG. 25D. The tubular forming tool 303 can now be removed by rotating it with respect to the slotted inner sleeve 295 so that the tabs align with the slots 300 and withdrawing it from the fitting 294. The mass of foreign material that is left as an implant at the anastomotic site is thus reduced.

Alternatively, the inner sleeves 295 and the tubular forming tool 303 can be formed integrally or welded together as one piece, in which case both the inner sleeve 295 and the tubular forming tool 303 would remain in the finished anastomosis. As a further alternative, the tubular forming tool 303 could be made to break away from the inner sleeve 295 when a certain force is applied.

In a further aspect of the invention, the anastomotic fitting has a single-piece construction with an inner sleeve that is integrally attached to a fixed inner flange and to a deformable outer flange. Three variants of the anastomotic fitting with a deformable outer flange and their forming tools are shown in FIGS. 26A–26I, 27A–27D and 28A–28I.

The first variant of the anastomotic fitting 306 with a deformable outer flange is shown in FIGS. 26A–26I. The anastomotic fitting 306 has a tubular main body 307 having an internal lumen 303 sized to accommodate the external diameter of the graft vessel 254. A fixed inner flange 309 is attached to the distal end of the tubular body 307. On the proximal end of the tubular body 307 are a plurality of hingedly attached outer flange segments 310. In this illustrative embodiment, there are four such flange segments 310 which are enlarged at their outer edges to form sector-shaped segments 310 of the outer flange 311. The hinge portion 312 of each flange segment 310 is a deformable strip of metal 312 connecting the flange segment 310 to the main tubular body 307. Preferably, the tubular body 307, the inner flange 309 and the flange segments 310 of the outer flange 311, including the deformable hinge portion 312, are integrally formed of a single piece of biocompatible metal, such as stainless steel, a titanium alloy or a cobalt alloy (e.g. Carpenter MP35).

Figure 26A:
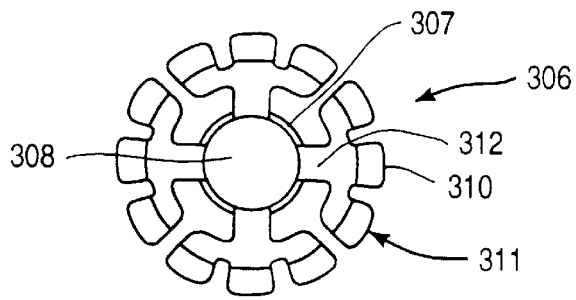
FIGS. 26A–26I show a third embodiment which is a one-piece anastomotic fitting with a deformable outer flange.
Figure 26B:
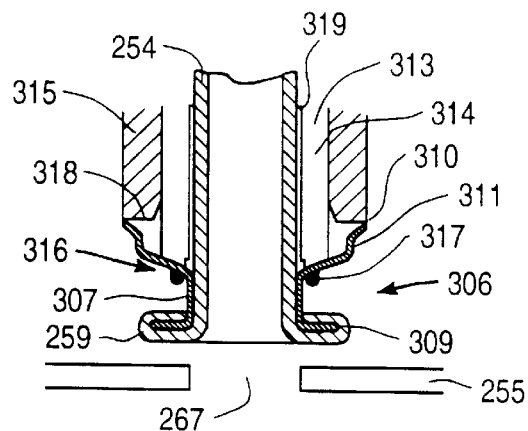
Figure 26C:
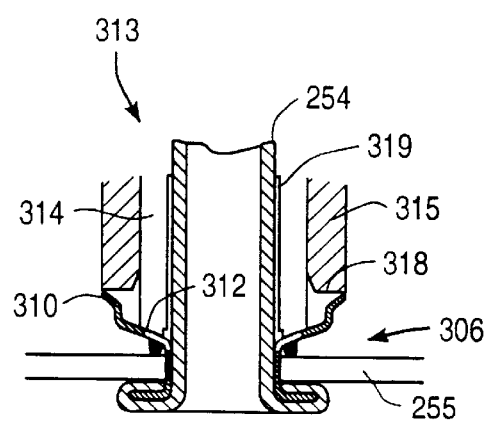
Figure 26D:
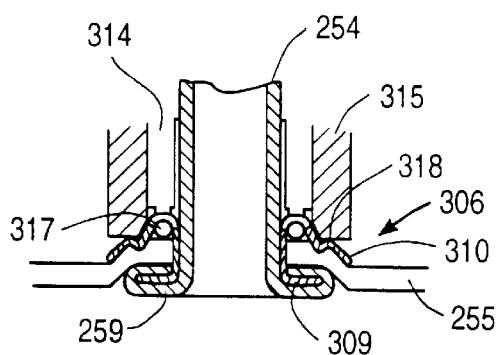
Figure 26E:
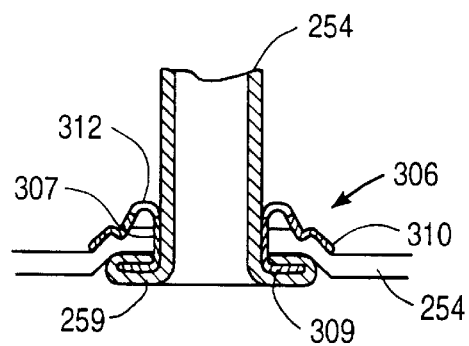
Figure 26F:
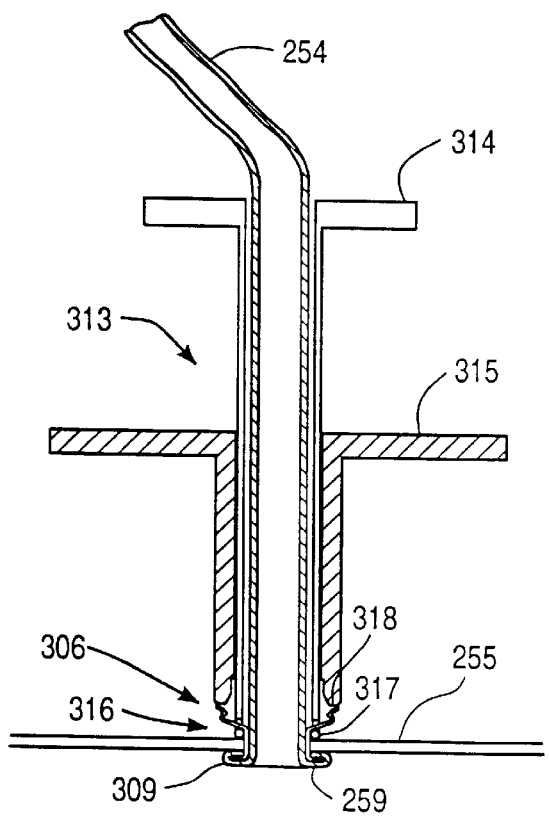
Figure 26G:
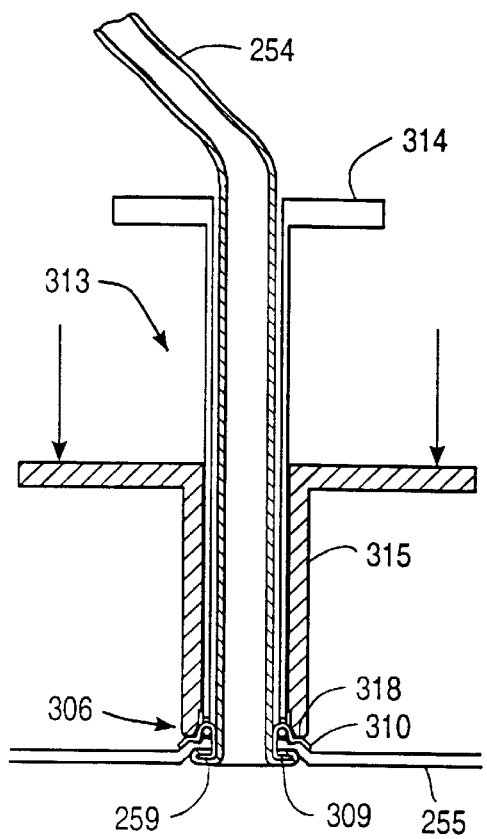
Figure 26H:
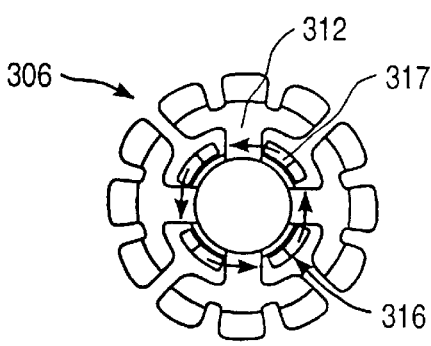
Figure 26I:
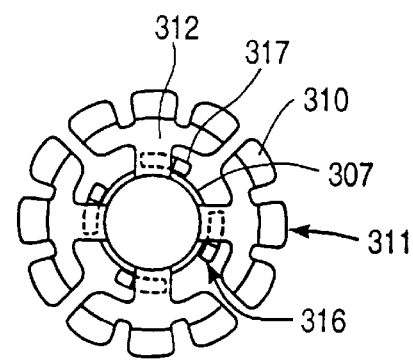
Figure 27A:
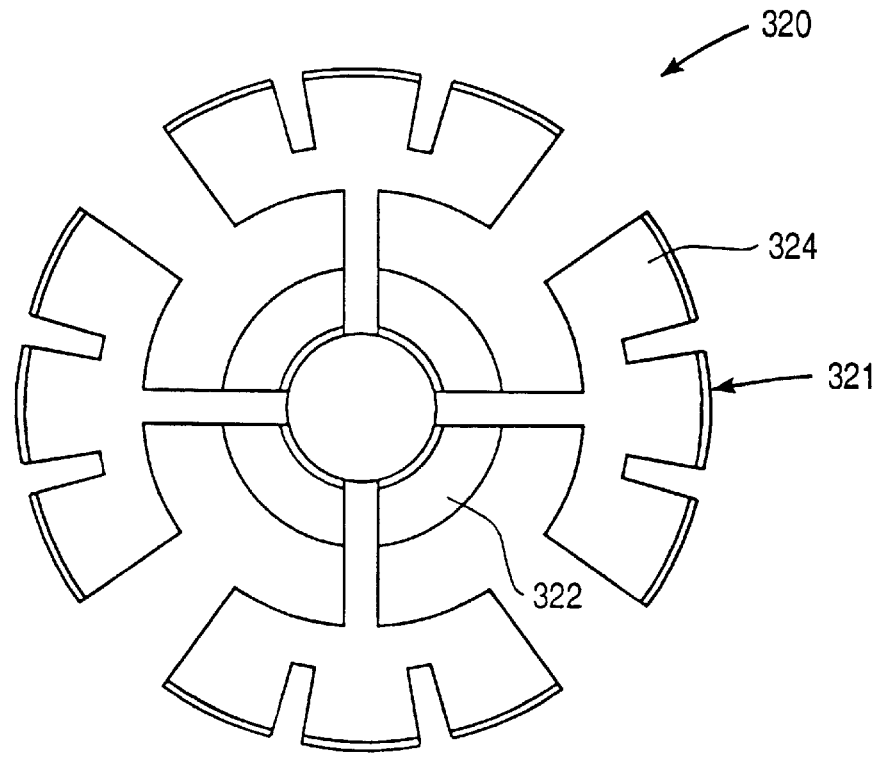
FIGS. 27A–27D show a second variant of the anastomotic fitting with a deformable outer flange.
Figure 27B:
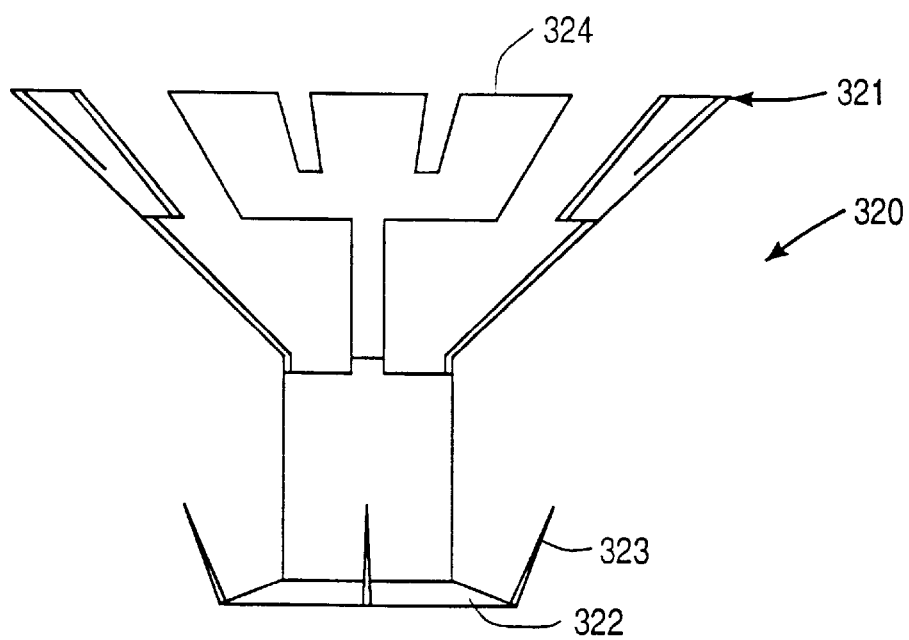
Figure 27C:
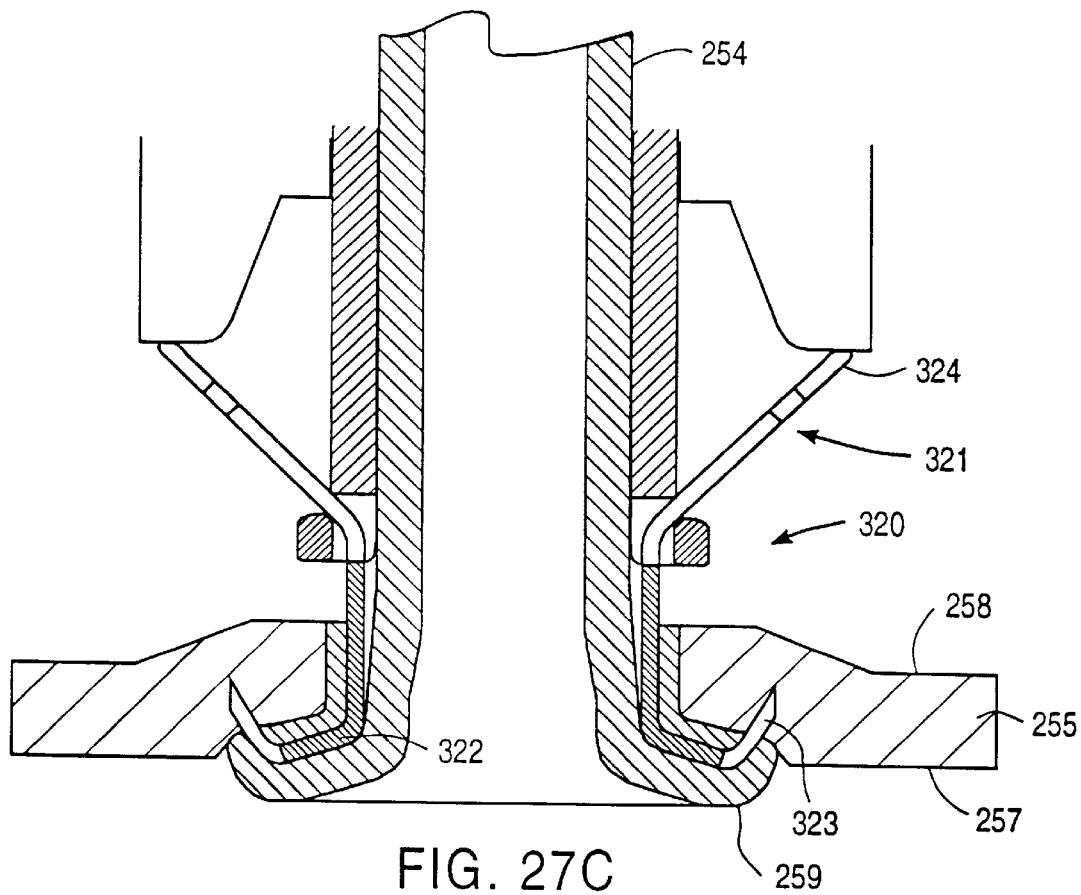
Figure 27D:
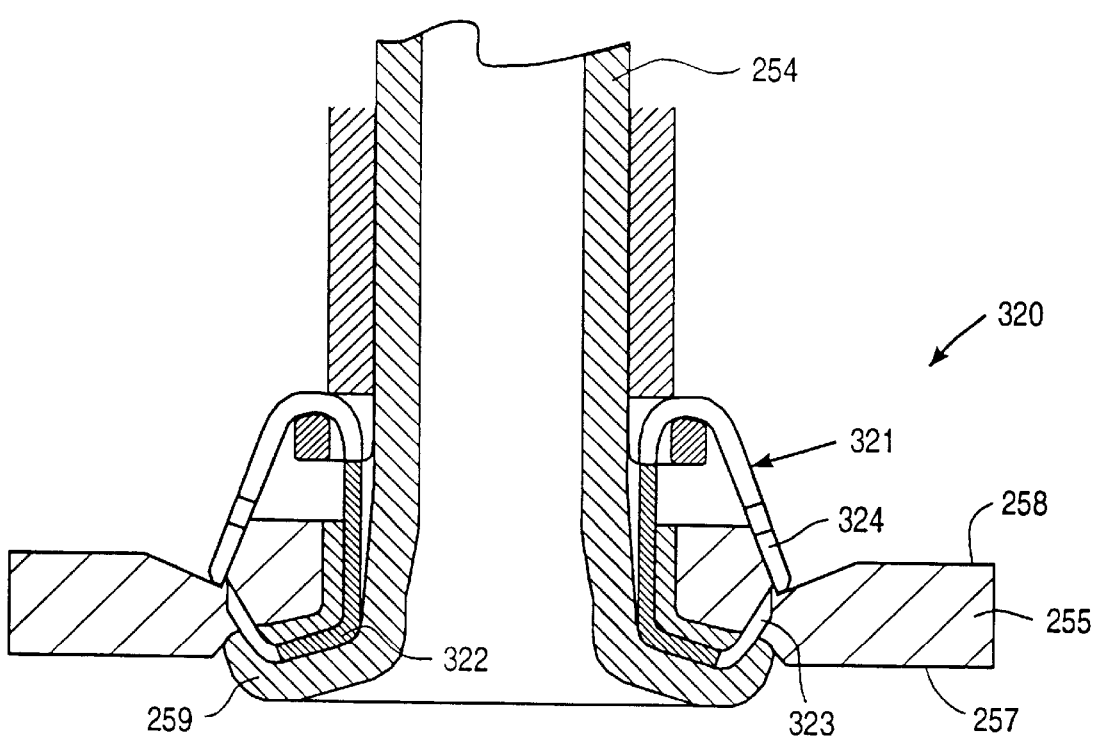

The distal end of a device 313 for applying the anastomosis fitting is shown in FIG. 26B. The device has an inner tubular member known as the anvil 314 and an outer tubular member called the driver 315. The distal end of the anvil 314 has a gripper 316 for holding onto the anastomosis fitting 306. The gripper 316 in the preferred embodiment has a bayonet-type fitting with four L-shaped gripping fingers 317 which hold the fitting 306 by hooking onto each of the flange segments 310 at the deformable hinge portion 312. The driver slides 315 telescopically over the outside of the anvil 314 and has an annular driving surface 318 on its distal end configured to engage the outer ends of each flange segment 310. The anvil 314 and the driver 315 can be made in a long version, approximately 15 to 30 cm in length, for performing port-access CABG surgery or a short version, approximately 10 to 20 cm in length, for performing standard open-chest CABG surgery.

The fitting 306 is prepared for performing the anastomosis by attaching the fitting 306 to the gripper 316 on the distal end of the anvil 314. Then, the graft vessel 254 is passed through the inner lumen 319 of the anvil 314 until the end 259 to be anastomosed extends a short distance from the distal end of the fitting 306. The end of the graft vessel 259 is everted over the inner flange 309 of the fitting to form an atraumatic attachment between the two. If the anastomosis being performed is part of a port-access CABG surgery procedure, the fitting on the end of the application tool is inserted into the patient's chest through an access port made through one of the intercostal spaces. The inner flange 309 and the everted end 259 of the graft vessel 254 are inserted through an opening 267 that has been made in the wall of the target vessel 255. The fitting 306 is pulled back slightly so that the inner flange 309 is flush against the interior surface 257 of the target vessel. Then, the driver 315 is pushed distally with respect to the anvil 314 until the driving surface 318 deforms the outer flange segments 310 against the exterior surface 258 of the target vessel wall 255 and the desired degree of compression of the vessel wall 255 is obtained. The anvil 314 is rotated slightly to release the gripper 316 from the flange segments 310 of the fitting 306 and the application device 313 is withdrawn from the patient's body.

The second variant of the anastomotic fitting 320 with a deformable outer flange 321 is shown in FIGS. 27A–27D.

This variant is largely the same as the first variant just described in connection with FIGS. 26A–26I with the exception of the inner flange 322 construction. In this embodiment, the inner flange 322 is slightly conical in order to provide a more hemodynamically efficient inlet to the graft vessel 254 at the anastomosis. In addition, a plurality of attachment spikes 323 preferably 6 to 8 spikes, have been provided along the periphery of the inner flange 322. In a preferred configuration, the anastomotic fitting 320 is fully deployed, the spikes 323 penetrate through the everted wall 259 of the graft vessel 254 and into the wall of the target vessel 255 to create a more secure attachment for the anastomosis. When the outer flange segments 324 are deformed against the exterior surface 258 of the target vessel 255 and compress the vessel wall 255 such that they engage the spikes 323 on the inner flange 322 for a very secure attachment.

The third variant of the anastomotic fitting 325 with a deformable outer flange 326 is shown in FIGS. 28A–28I. The anastomotic fitting 325 has a tubular main body 327 with an internal lumen 328 sized to accommodate the external diameter of the graft vessel 254. The walls of the tubular body 327 have a pair of L-shaped slots 329 that are open at the top of the tubular body 327 to form a bayonet fitting. An inner flange 330, which may be slightly conical in shape, is attached to the distal end of the tubular body 327. Attached to the proximal end of the tubular body 327 is a deformable outer flange 326, comprising a multiplicity of axially-oriented bars 331 separated by axial slots. 332 The axially-oriented bars 331 are attached at their distal ends to the tubular main body 327, and are joined at their proximal ends by a ring 333 forming the proximal end of the fitting 325 The bars 331 are bent outwardly near their centers 334 so that the bars 331 preferentially bend outwardly when compressed. The tubular body 327, the inner flange 330 and the deformable outer flange 326 are preferably machined of a single piece of biocompatible metal, such as stainless steel, a titanium alloy or a cobalt alloy. The geometry of this device could also be configured so that the bars 331 of the outer flange 326 start off almost straight, and are deformed further to reach their final geometry.

Figure 28A:
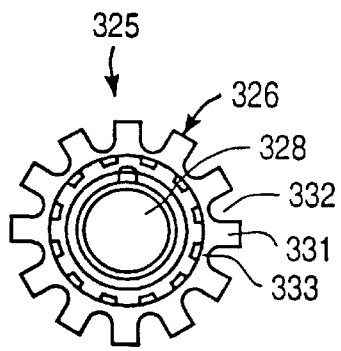
FIGS. 28A–28I show a third variant of the anastomotic fitting with a deformable outer flange.
Figure 28B:
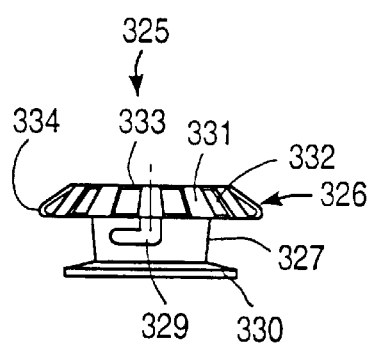
Figure 28C:
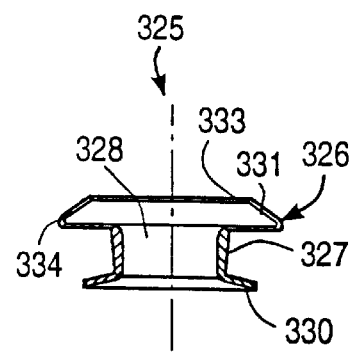
Figure 28D:
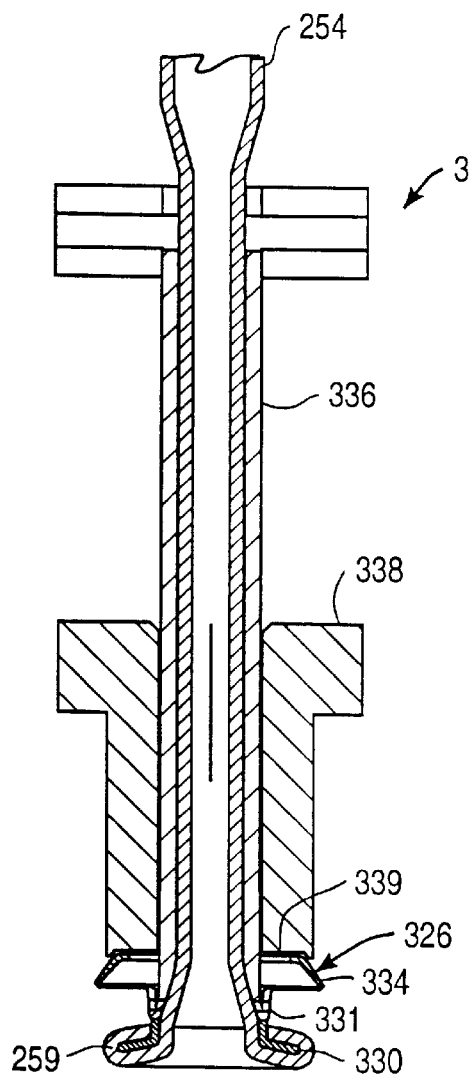
Figure 28E:
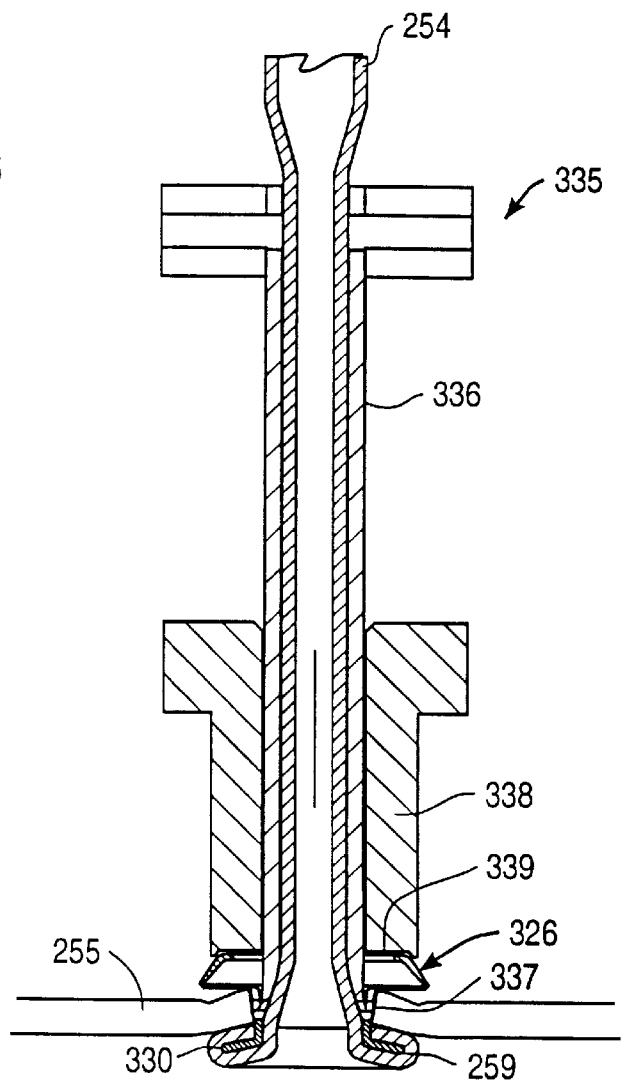
Figures 28H, 28I:
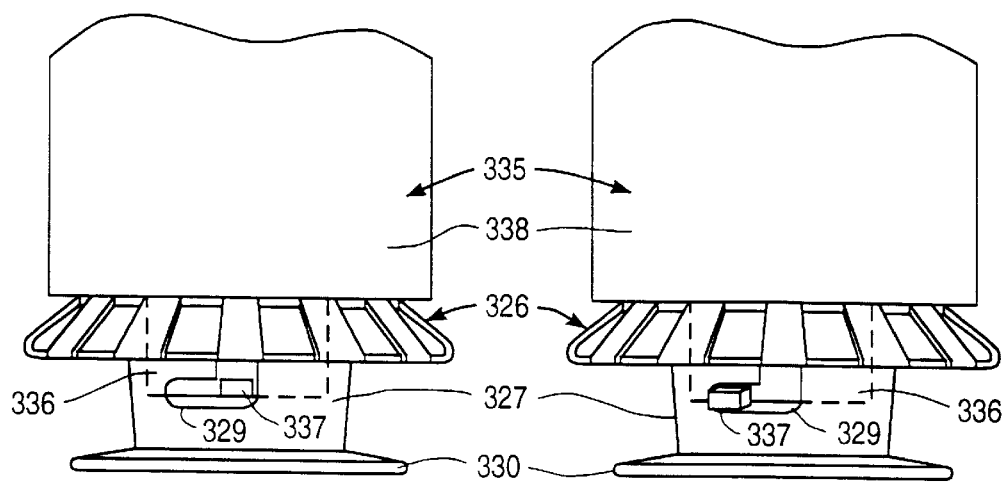
Figures 28F, 28G:
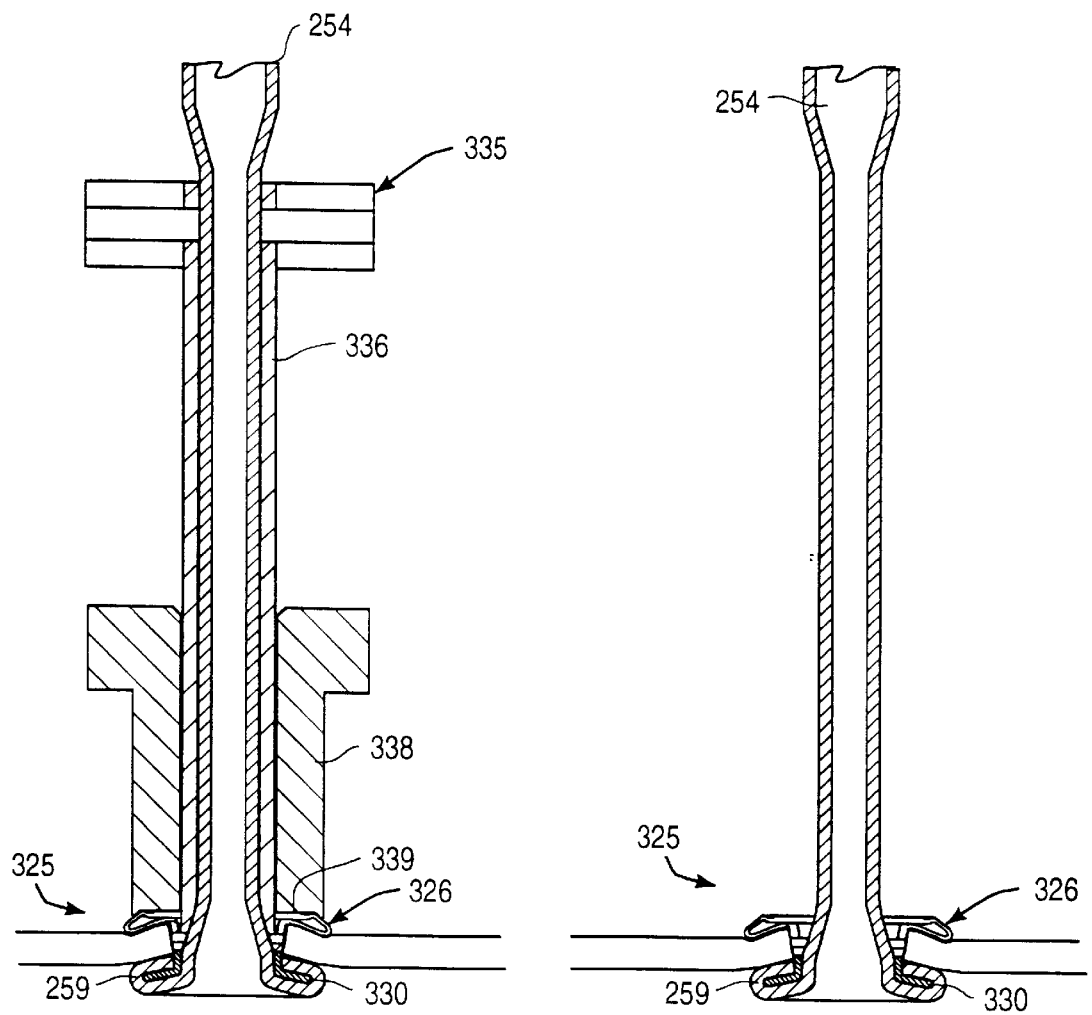

A device 335 or applying the anastomotic fitting is shown in FIG. 28D–F. The device 335 has an inner tubular member 336 which has a pair of radially extending tabs 337 on its distal end that interlock within the L-shaped slots 329 in the tubular body 327 of the fitting 325. An outer tubular member 338, the pusher 338, slides telescopically over the outside of the inner tubular member 336 and has an annular driving surface 339 on its distal end. This anastomosis fitting application device 335 can be made in a long version for port-access CABG surgery or a short version for standard open-chest CABG surgery.

The fitting 325 is prepared for performing the anastomosis by attaching the anastomotic fitting 325 to the inner tubular member 336. Then, the graft vessel 154 is passed through the inner lumen 340 of the inner tubular member 336 until the end 159 to be anastomosed extends a short distance from the distal end of the fitting 325. The end 159 of the graft vessel 154 is everted over the inner flange 330 of the fitting 325 to form an atraumatic attachment, as shown in FIG. 28D. If the anastomosis being performed is part of a port-access CABG surgery procedure, the fitting 325 on the end of the application tool 335 is inserted into the patient's chest through an access port made through one of the intercostal spaces. The inner flange 330 and the everted end 159 of the graft vessel 154 are inserted through an opening 267 that has been made in the wall of the target vessel 225, as shown in FIG. 28E. The fitting 325 is pulled back slightly so that the inner flange 330 is flush against the interior surface 257 of the target vessel 255. Then, the pusher 338 is moved distally with respect to the inner tubular member 336 until the driving surface 339 contacts the proximal surface of the deformable outer flange 326. The pusher 338 deforms the outer flange 326 by compressing the bars 331, which bend outwardly and fold into a flattened configuration, as shown in FIG. 28F, to form a radially spoked outer flange 326'. The pusher 338 further deforms the bars 331 to press the outer flange 326' against the exterior surface 258 of the target vessel wall 255 and obtain the desired degree of compression between the inner 330 and outer 326' flanges. The inner tubular member 336 is removed by rotating it with respect to the fitting 325 and withdrawing the tabs from the L-shaped slots 329.

Figure 29A:
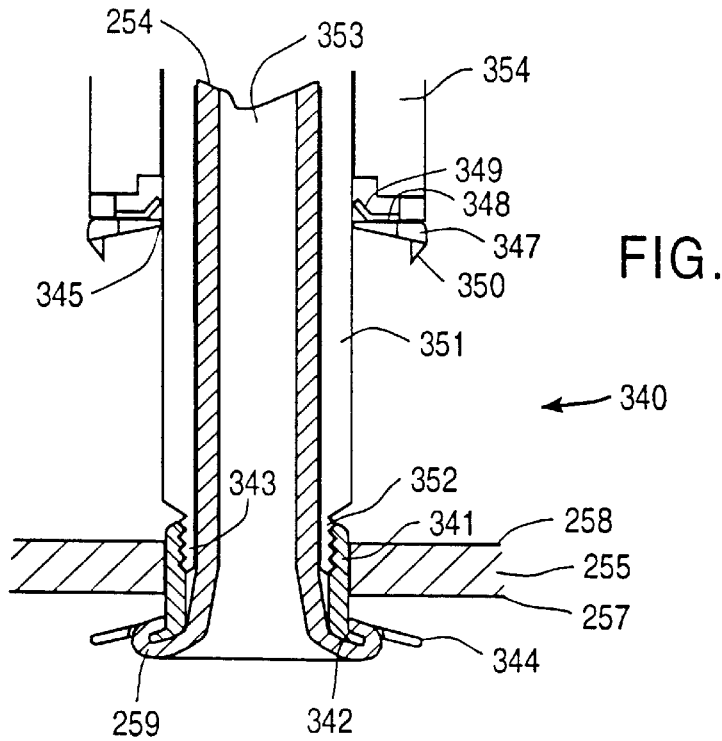
FIGS. 29A–29C show an embodiment of the anastomotic fitting having a secondary flange washer which attaches to the inner flange.
Figure 29B:
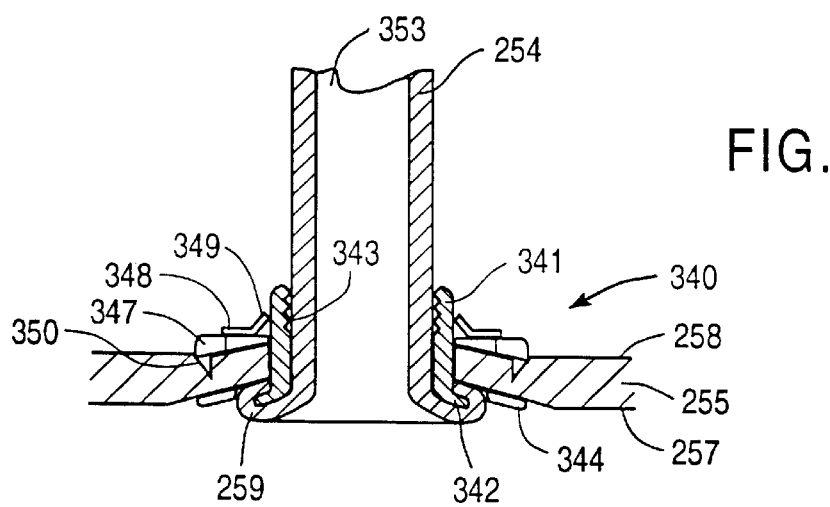
Figure 29C:
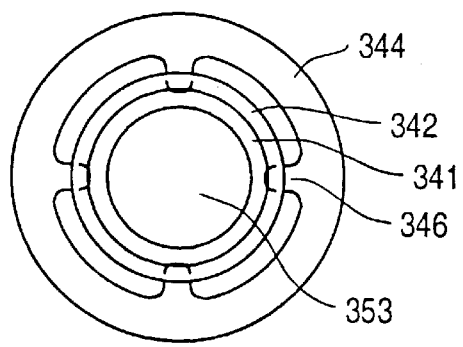

A further embodiment of an anastomosis fitting 340 according to the invention is illustrated in FIG. 29A–C. The anastomosis fitting of FIG. 29A–C may be particularly advantageous with older patients, diabetic patients and other patients whose veins are no longer as resilient as they once were, where it may be difficult to stretch the saphenous vein graft enough to evert it over a large inner flange. This is also true of many artificial graft materials that will not stretch at all to evert them over a large flange. The anastomosis fitting 340 of FIG. 29A–C has a tubular body member 341 with a small primary inner flange 342 attached to the distal end. Threads 343 or similar features on the inner surface the proximal end of the tubular body member 341 facilitate grasping the tubular body member 341 with an application instrument. A secondary inner flange washer 344 has a central orifice 345 with inwardly facing tabs 346 configured to engage the primary inner flange 342, as seen in distal end view 29C. An outer flange 347 is configured to slide over the proximal end of the tubular body 341 and is locked in place by a self-locking retaining washer 348 with upwardly inclined tabs 349 that frictionally engage the outer surface of the tubular body 341, allowing the outer flange 347 to slide in the distal direction with respect to the tubular outer body 341, but not in the proximal direction. The outer flange 341 may have a plurality of attachment spikes 350 on its distal surface to penetrate the outer wall 258 of the target vessel 255.

In operation, first the outer flange 347 with its retaining washer 348 and then the secondary inner flange washer 344 are back loaded onto the holder 352 of the application device 351. Next, the tubular body 341 is threaded onto the distal end of the holder 352. The graft vessel 254 is passed through the internal lumen 353 of the application instrument 351 and the distal end 259 of the graft vessel 254 is everted over the small primary inner flange 342 of the anastomosis fitting 340. The secondary inner flange washer 344 is then slid distally so that it bears against the proximal face of the inner flange 342, as shown in FIG. 29A. The primary inner flange 342, with the everted graft vessel 259 attached, and the secondary inner flange washer 344 are inserted through an opening 267 that has been made in the target vessel wall 255 as shown in FIG. 29A. A slight tension is exerted on the application instrument 351 to seat the primary inner flange 342 and the secondary inner flange washer 344 against the interior surface 257 of the target vessel wall 255 and the driver 354 is advanced distally to press the outer flange 347, with its self-locking retaining washer 348, onto the exterior of the tubular body member 341 until the desired degree of compression between the inner 242, 344 and outer flanges is obtained. The holder 352 is disengaged from the tubular body member 341 and the entire application instrument 351 is withdrawn from the body.

A distal end view of the completed anastomosis is shown in FIG. 29C. The larger diameter of the secondary inner flange washer 344 adds to the security of the anastomosis attachment, while it does not require the graft vessel 254 to be stretched to fit over a large inner flange. Only a very small amount of foreign material is exposed within the target vessel lumen and it is spaced a short distance from the actual anastomosis site which may reduce the likelihood of complications. Because the secondary inner flange 344 washer only contacts the primary inner flange 342 and the everted graft vessel wall 259 at four small points, it will not interfere with the intima-to-intima approximation of the graft vessel 259 and the target vessel 255 which is preferred in order to promote endothelialization of the anastomosis site.

Figure 30A:
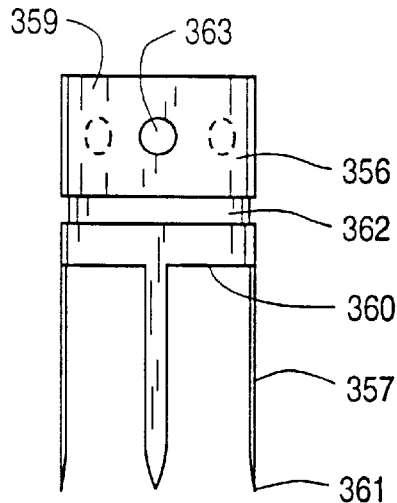

FIGS. 30A–30F illustrate an embodiment of the anastomosis fitting 355 of the present invention which combines an inner tubular member 356 having deformable attachment legs 357 at its distal end, with an outer flange 358. The deformable attachment legs 357 have an initial position 357 allowing the graft vessel 254 to be easily everted over and penetrated by the attachment legs 357. The attachment legs 357 are subsequently deformed to a deployed position 357' wherein the attachment legs 357' perform the function of the inner flange in many of the above-described embodiments by engaging the interior surface 257 of the target vessel 255 and compressing the tissue between the attachment legs 357' and the outer flange. 358 The inner tubular member 356 is shown in FIG. 30A. The tubular member 356 is preferably made from a biocompatible metal, such as an alloy of stainless steel, titanium or cobalt. The tubular member 356 has an internal lumen 359 of sufficient size to accommodate the external diameter of the graft vessel 254. The tubular member 356 is made with a plurality of attachment legs 357 extending axially from its distal end 360. This illustrative embodiment is shown with four attachment legs 357. Other exemplary embodiments may have from three to twelve attachment legs 357 depending on the sizes of the graft vessel 254 and target vessel 255 to be joined. The attachment legs 357 preferably have a width of approximately 0.5–2.0 mm, more preferably about 1.0 mm, and a thickness of approximately 0.1–0.5 mm, more preferably about 0.25 mm. The width and thickness of the attachment legs 357 is chosen so that the legs 357 will be relatively rigid when they are in their deployed position 357', yet they are still easily deformed using the special forming dies 369, 370, 371 provided with the anastomosis system. The distal ends 361 of the attachment legs 357 are sharpened to easily penetrate the walls of the graft vessel 254 and target vessel 255. The exterior surface of the tubular member 256 may be made with a groove or slot 362 around its circumference as a detent for the outer flange 358 spaced a calculated distance from the distal end 360 of the tubular member 356 to provide a desired degree of compression on the anastomosis when the outer flange 358 locks into the groove. 362 A plurality of holes 363 through the wall of the tubular member 356 (three holes 363 in this illustrative embodiment) are located near the proximal end of the tubular member 356 to facilitate grasping the device 355 with an application instrument 372.

Figure 30B:
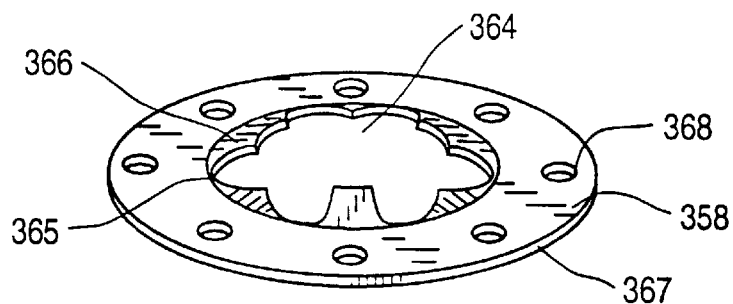

The outer flange 358, illustrated in FIG. 30B, has a central orifice 364 which is sized to fit over the exterior of the tubular member 356. The outer flange 358 has a locking mechanism, which includes a self-locking retaining washer 365 with upwardly inclined locking tabs 366 integrally formed with the outer flange, 358 to slidably position the outer flange 358 on the exterior surface of the tubular member 356. Alternatively, the self-locking retaining washer 365 can be manufactured separately and attached to the outer flange 358 The upwardly inclined locking tabs 366 allow the retaining washer 365 to slide in the distal direction over the exterior of the tubular member 356, but resist sliding in the proximal direction. When the upwardly inclined locking tabs 366 lock into the groove 362 in the exterior surface of the tubular body 356 it forms a more permanent attachment, strongly resisting movement in the proximal direction. Other locking mechanisms can also be used for positioning the outer flange 358 with respect to the tubular member 356, such as ratchet mechanisms, detents, or releasable locking devices. The distal surface 367 of the outer flange 358 is configured to contact the exterior surface 258 of the target vessel 255. Preferably, the distal surface 367 of the outer flange 358 is slightly concave, as illustrated. If desired, the outer flange 358 may be made with short spikes extending from its distal surface. The outer periphery of the outer flange 358 is perforated with a series of holes 368, which are positioned to be aligned with the distal ends 361' of the attachment legs 357' of the tubular member 356 when the fitting 355 is fully deployed. Making the holes 368 in a multiple of the number of attachment legs 357, as in the present example which has eight holes 368, corresponding with four attachment legs 357, facilitates aligning the holes 368 with the distal ends 361' of the attachment legs 357'. The outer flange 358 is preferably made from a biocompatible metal, such as an alloy of stainless steel, titanium or cobalt or a biocompatible polymer. Alternatively, a separate locking washer 365 made from a biocompatible metal can be joined to an outer flange 358 made of a polymer or other biocompatible material.

The anastomosis fitting 355 is part of a complete anastomosis system for forming and applying the anastomosis fitting 355 to create an end-to-side anastomosis. A set of three forming dies 369, 370, 371 are configured to deform the attachment legs 357 of the anastomosis fitting 355 from their initial position 357 to a deployed position 357', and a specialized grasping tool 372 is used to insert the deployed inner tubular member 356 through an opening 267 in the side wall of the target vessel 355. These tools, which will be described in more detail in the operational description below, facilitate the rapid and repeatable deployment of the anastomosis fitting 355 with a minimum of manual manipulation required.

Figure 30C:
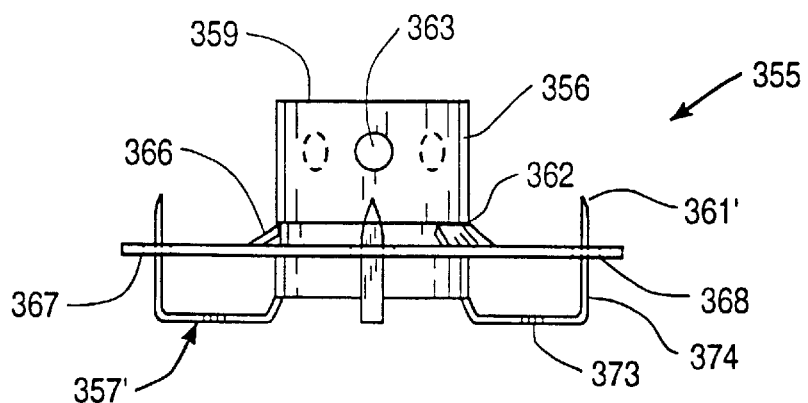
Figure 30D:
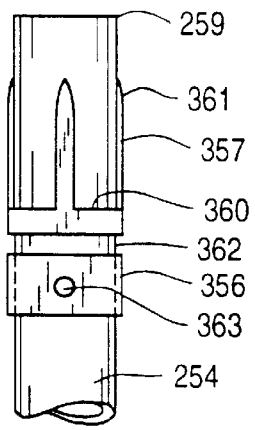

In operation, the end-to-side anastomosis procedure is performed using the anastomosis fitting 355 by first preparing the free end 259 of the graft vessel 254 for attachment. If the anastomosis being performed is a second anastomosis or is being performed on the free end of a pedicled graft, the outer flange 358 must first be backloaded onto the graft vessel 254 with the distal surface 367 facing the end 259 of the vessel to be attached. If the anastomosis is being performed as the first anastomosis on a free graft, the outer flange 358 can be backloaded onto the graft vessel 254 at this time or it can be passed over graft vessel 254 from the far end at a later point in the procedure, whichever is preferable. Next, the free end 259 of the graft vessel 254 is passed through the internal lumen 359 of the inner tubular member 356 so that it extends a short distance from the distal end 360 of the tubular member 356, as shown in FIG. 30C. The free end 259 of the graft vessel 254 is everted and the attachment legs 357 are pierced through the everted wall 259 of the graft vessel 254 to prepare the graft vessel 254 as shown in FIG. 30D. If desired, a loop of suture can be tied around the everted end 259 of the graft vessel 254 to help secure the graft vessel 254 in its everted position over the exterior surface of the tubular member 356.

Figure 30E:
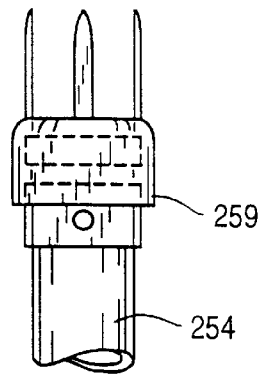

After piercing the graft vessel wall 259, the attachment legs 357 of the tubular member 356 are deformed from their axially extending position 357 by first bending them outward so that they extend radially from the distal end 360 of the tubular member 356, then bending the distal ends 361' of each of the attachment legs 357' so that they are directed proximally with respect to the tubular member 356, as shown in FIG. 30E. For a typical application of the anastomosis fitting 355 in making an end-to-side anastomosis between a saphenous vein graft and the ascending aorta, the radially extending portion 373 of each deployed attachment leg 357' is about 3–4 mm long, and the proximally directed distal portion 374 of each deployed attachment leg 357' is about 2–5 mm long. These dimensions will vary somewhat depending on the size and the wall thickness of the graft vessel and the target vessel to be joined.

Figures 30F, 30G:
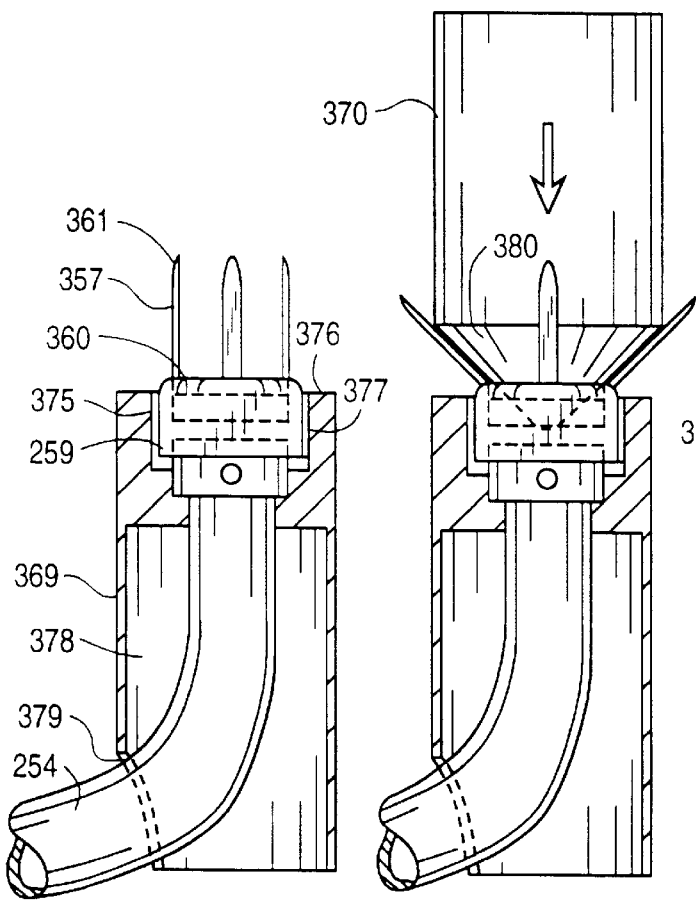
Figure 30H:
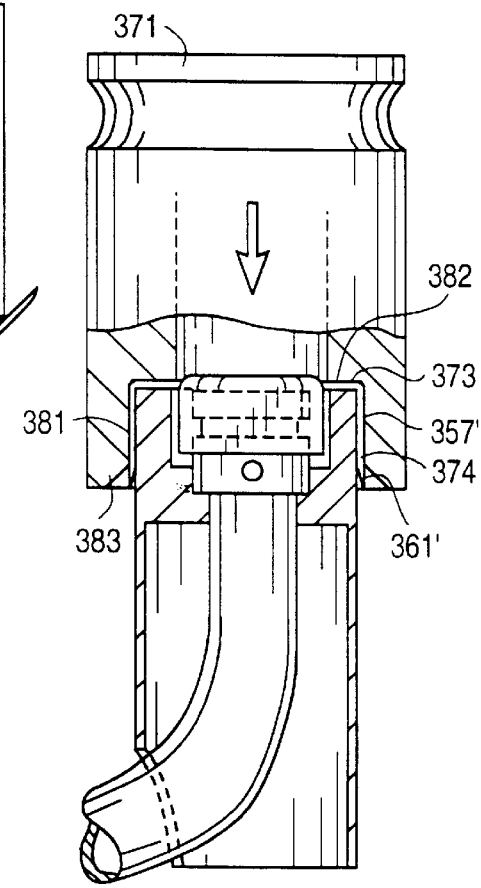

A set of three forming dies 369, 370, 371 are provided for rapidly and repeatably forming the anastomosis fitting 355 into the deployed position shown in FIG. 30E. The first die 369 is cylindrical in shape with a counterbored recess 375 on one end which is sized to hold the proximal end of the tubular member 356 of the anastomosis fitting. An annular forming surface 376 on the end of the die 369 surrounds the counterbored recess 375. An annular space 377 between the counterbored recess 375 and the annular forming surface 376 provides sufficient clearance for the everted end 259 of the graft vessel 254 when the inner tubular member 356 of the anastomosis fitting 355 is inserted into the counterbored recess 375. The proximal end of the graft vessel 354 extends through a central lumen 378 in the first die 369 and exits the die through a notch 379 in the far end of the die 369 which communicates with the lumen 378. The second die 370 has a conically tapered end 380 which is used to initiate the outward bend of the attachment legs 357 by pressing the tapered end 380 between the attachment legs 357, as shown in FIG. 30G. The third die 371 is cylindrical in shape with a counterbore 381 on one end that is sized to fit over the outside of the first die 369 with a radial clearance sufficient for the thickness of the attachment legs 357'. There is a forming shoulder 382 within the counterbore 381 of the third die 371, and there is a tapered edge 383 leading into the counterbore 381. The third die 3 71 is placed over the distal end of the inner tubular member 356 after the attachment legs 357 have been bent outward by the second die 370. As the counterbore 381 of the third die 371 slides over the exterior of the first die, 369 the radially extending portion 373 of the attachment legs 373 are formed between the forming shoulder 382 of the third die 371 and the annular forming surface 376 of the first die 369 and the proximally extending portion 374 of the attachment legs 357' is formed between the exterior of the first die 369 and the counterbore 381 of the third die 371, as shown in FIG. 30H.

The tubular member 356 of the anastomosis fitting 355, which has been formed to its deployed position, is withdrawn from the first die 369 and is grasped with the special grasping tool 372. The grasping tool 372 has expandable jaws 384, 385 which fit between the graft vessel 354 and the inner lumen 359 of the tubular member 356. The jaws 384, 385 are shaped like sectors of a cylinder with an exterior diameter approximately equal to the inner diameter of the tubular member 356. Each of the sectors is somewhat smaller than a semi-cylinder so that the jaws 384, 385 can be collapsed small enough to easily fit within the internal lumen 359 of tubular member 357. A thumbscrew, or other suitable mechanism, on the grasping tool 372 expands the jaws 384, 385 so that they bear against the interior surface of the tubular member 356. Lugs 386 corresponding to the three holes 363 in the proximal end of the tubular member 356 engage the three holes 363 to enhance the grasping tool's grip on the tubular member 356.

Using the grasping tool 382, the bent attachment legs 357' and the distal end 360 of the tubular member, with the everted end 259 of the graft vessel 254 attached, are inserted through an opening 267 in the target vessel wall 255 that has previously been made with an aortic punch or similar instrument, as shown in FIG. 30I. The opening 367 is preferably made so that it is approximately the size of the external diameter of the tubular member 356 to provide compression around the everted end 259 of the graft vessel 254 to help create an anastomotic seal. Since the opening 267 is slightly smaller than the diameter of the bent attachment legs 357', the opening 267 must be stretched slightly to allow the attachment legs 357' to pass through the opening 267. Insertion can be effectively accomplished by passing two of the attachment legs 357' through the opening 267 in the target vessel wall 255, then gently stretching the opening 267 with forceps to insert the remaining attachment legs 357'.

Once the attachment legs 357' have been passed through the opening 267 in the target vessel wall 255, the inner tubular member 356 is pulled back with enough force to cause the sharpened distal ends 361' of the attachment legs 357' to pierce the interior surface 257 of the target vessel wall 255. This action also serves to approximate the everted end 259 of the graft vessel 254 with the interior surface 257 of the target vessel 255 to effect the desired intimal surface-to-intimal surface approximation between the two vessels. The sharpened distal ends 361' of the attachment legs 357' can be assisted in piercing the target vessel wall 255 by pressing on the exterior 258 of the target vessel wall 255 with an elastomeric-tipped probe while maintaining some tension on the tubular body 356 of the fitting using the grasping tool 372. The anastomosis is completed by sliding the central orifice 364 of the outer flange 358 over the exterior surface of the tubular member 356 and moving the outer flange 358 distally while keeping some tension on the tubular member 356 to create tissue compression at the anastomosis site to assure an anastomotic seal. A probe 387 with a distal pushing surface 388 can be used to press the outer flange 358 onto the tubular member 356. The distal pushing surface 388 of the probe 387 is slotted and angled so that it can be used from the side of the grasping tool 372. The proximally directed distal ends 361' of the attachment legs 357' pass through the holes 363 around the periphery of the outer flange 358, as shown in FIG. 30J. If desired, the distal surface 367 of the outer flange 358 can be made somewhat concave to help create a hemodynamically efficient transition between the target vessel lumen 256 and the graft vessel lumen 249. The self-locking retaining washer 365 of the outer flange 358 locks into the circumferential groove 362 on the exterior of the tubular member 356 to permanently hold the outer flange 358 in a fixed position relative to the tubular member 356.

Figure 31A:
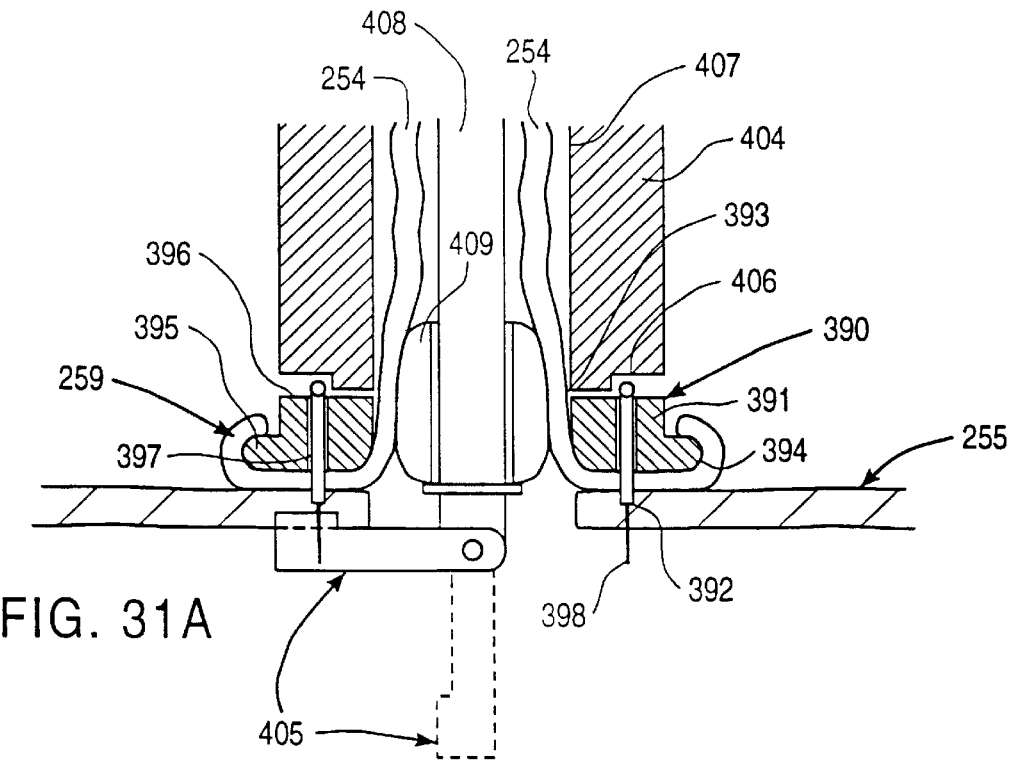
FIGS. 31A–31F show a first embodiment of an anastomotic device combining a fastening flange with a plurality of staple members.
Figures 31E, 31F:
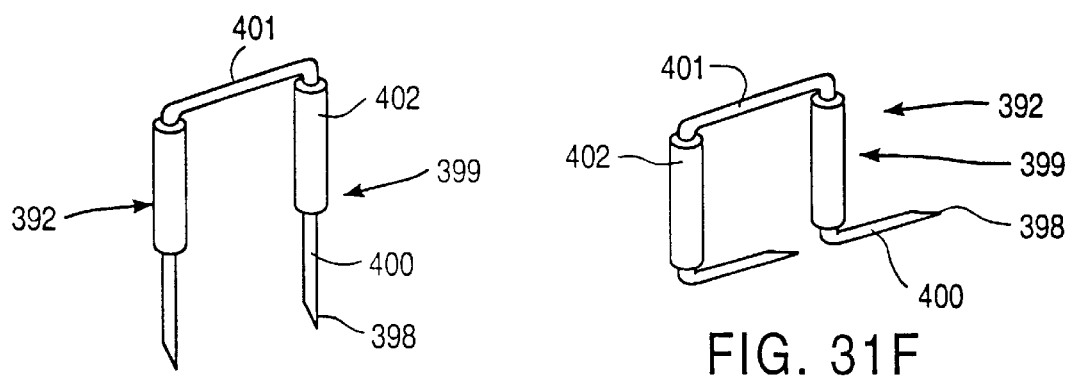
Figures 31B, 31C, 31D:
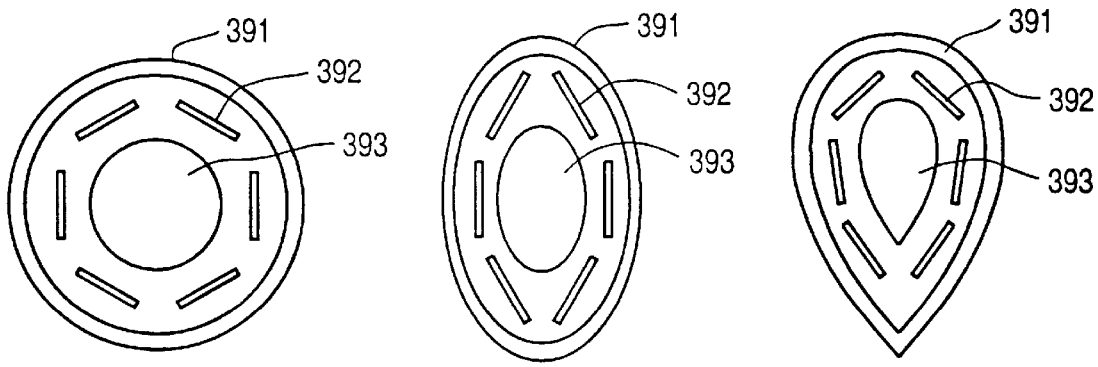

FIG. 31A shows a further embodiment of an anastomosis device 390 according to the invention that combines a fastening flange 391 with a plurality of staple members 392. The device 390 includes a fastening flange 391 which has a central orifice 393 of sufficient size to accommodate the external diameter of the graft vessel 254. The external diameter of a saphenous vein graft used in CABG surgery can range from 3 to 10 mm. The fastening flange 391 and the central orifice 393 can be made circular, as shown in FIG. 31B, for making a typical right angle anastomosis. Alternatively, the fastening flange 391 and/or the central orifice 393 can be made elliptical, oval, egg-shaped or tear drop shaped, as shown in FIGS. 31C and 31D, for making a more hemodynamically efficient angled Anastomosis.

Many of the anastomotic fittings and staples described herein lend themselves to noncircular configurations, such as elliptical or teardrop shapes. Each of the detailed descriptions of the various embodiments should be assumed to include noncircular flanges as an optional configuration. The fastening flange 391 is made with a distal surface 394 over which the free end 259 of the graft vessel 254 is everted, as shown in FIG. 31A. The fastening flange 391 can be made with an annular ridge 395 or with other features on its outer surface to help attach the everted end 259 of the graft vessel 254 to the flange 391. The distal surface 394 of the fastening flange 391 may be contoured to provide a close fit between the everted edge 259 of the graft vessel 254 and the exterior wall 258 of the target vessel 255. If the target vessel 254 diameter is very large compared to the diameter of the graft vessel 254, as in a coronary artery bypass graft to ascending aorta anastomosis, then a planar distal surface 394 on the fastening flange 391 may sufficiently approximate the exterior surface 258 of the target vessel 255. However, if the graft vessel 254 diameter is closer to the diameter of the target vessel 255, as in a bypass graft to coronary artery anastomosis, then the fastening flange 391 should be made with a cylindrical or saddle-shaped contour on the distal surface 394 that closely approximates the exterior contour of the target vessel 255. The fastening flange 391 should be made of a biocompatible material such as stainless steel, titanium alloys, or a biocompatible polymer. The fastening flange 391 acts as an external stent which holds the anastomosis site open and patent, so the flange material is preferably rigid or at least sufficiently resilient to hold its intended shape.

The fastening flange 391 with the everted end 259 of the graft vessel 254 attached to it is fastened to the exterior wall 258 of the target vessel 255 with the central orifice 393 aligned with an opening 267 in the target vessel wall 255 that has been previously made using a vessel punch or similar instrument. The fastening flange 391 is held in place by a plurality of fastening members 292, which in this embodiment take the form of metallic surgical staples 292 which are shown in FIG. 31E. The surgical staples 292, preferably 4–12 of them arranged around the periphery of the fastening flange 391, traverse from the proximal side 396 to the distal side 394 of the flange 391, then pierce the everted graft vessel wall 259 and the wall of the target vessel 255. It is preferable that the staples 292 pass through premade holes 397 in the fastening flange 391, however, if the fastening flange 391 is made of a resilient material, the staples 392 may pierce the flange 391 as they pass through it. The distal ends 398 of the staples 392 are deformed by a forming device or anvil against the interior surface 257 of the target vessel wall 255 to hold the device in place to complete the anastomosis.

The staples 392 can be specially constructed so that they will deform at the appropriate point on the attachment legs 399. One way to achieve this desired result is to make the core 400 of the staple 392, including the crossbar 401 and the two attachment legs 399, of a soft deformable metal such as annealed stainless steel. A proximal portion of each of the attachment legs 399 is surrounded by a stiffening sleeve 402 that is made of a more rigid material, such as hard stainless steel hypodermic tubing. The stiffening sleeves 402 prevent the proximal portion of the attachment legs 392 from deforming. The stiffening sleeves 402 should be sized so that their length corresponds to slightly less than the combined thickness of the flange 391, the graft vessel wall 259 and the target vessel wall 255 so that, when the attachment legs 399 are bent at the distal edge of the stiffening sleeves 402, a tailored amount of compression is applied at the anastomotic site to ensure a leak proof attachment without excessive crushing of the tissue which could lead to necrosis. Alternatively, the staples could be manufactured with attachment legs 399 having a thicker cross section proximal portion and a thinner cross section distal portion so that the attachment legs 399 will deform at the appropriate point.

The anastomosis device 390 is part of a complete anastomosis system that includes a specially adapted application device 403 for creating the anastomosis. The distal end of the application device 403 can be seen in FIG. 31A. A staple driver 404 pushes the staples 392 from the proximal end, while a specially constructed anvil 405 reaches into the lumen 256 of the target vessel 255 to deform the distal ends 398 of the attachment legs 399. The staple driver 404 has an annular distal surface 406 which presses against the crossbars 401 of the staples 392. In one embodiment, the staple driver 404 can be tubular with an internal lumen 407 large enough to accommodate the graft vessel 254, allowing the graft vessel 254 to be passed through the staple driver 404 from the proximal end to the distal end. Alternatively, the staple driver 404 can be made with a C-shaped cross section with a side opening that is large enough to pass the graft vessel through from the side. The anvil 405 is articulated on the distal end of an elongated shaft 408. The shaft 408 is long and narrow enough to pass through the lumen 249 of the graft vessel 254 from the free end of the graft. The anvil 405 is passed through the graft vessel lumen 249 in an orientation axially aligned with of the shaft 408 and, once it is in the lumen 256 of the target vessel 255, it is articulated at 90°, as shown in FIG. 31A. A cylindrical or olive-shaped centering element 409, such as an inflatable centering balloon on the shaft 408, can be used to center the shaft 408 of the anvil 405 within the lumen 249 of the graft vessel 254 and within the central orifice 393 of the flange 291. The anvil 305 can now be rotated about the shaft 308 to deform the distal ends 398 of the attachment legs 399.

The application device 403 can operate by two different mechanisms. It can operate in a manner similar to other surgical staplers by aligning the staple driver 404 and the anvil 405 on opposite ends of a staple 292, then moving them axially toward one another, by moving either the staple driver 404 distally, or the anvil 405 proximally, or a combination of the two motions. This relative movement compresses the staple leg 399 in between the anvil 405 and the staple driver 404 and deforms it to hold the anastomosis together. An alternative mechanism involves rotating the anvil 405 with respect to the staple driver 404 and the anastomosis device 390 like a wiper to sequentially bend over the distal ends 398 of the staples 392, as shown in FIG. 31F. The staple driver 404 may be equipped with a gripping means for holding the fastening flange 391 to prevent any resultant torque on the flange 391 from being transferred to the delicate vascular tissues. Alternatively, the olive-shaped centering element 409 or balloon could have sufficient bearing surface that the delicate vascular tissues do not suffer any significant damage. An alternative embodiment would have two or more wiper anvil elements 405 spaced symmetrically about the axis of the shaft 408, so that opposing staples 392 are bent simultaneously, reducing the net torque applied to the centering element 409 and the tissues.

FIG. 32A shows another variation of the anastomosis device of FIG. 31A. This variation of the anastomosis device 410 uses preformed spring-like fastening staples 411. As in the previously described device, the anastomosis device 410 includes a fastening flange 412 with a central orifice 413 of sufficient size to accommodate the exterior diameter of the graft vessel 254. A plurality of preformed fastening staples 411 are arranged around the periphery of the fastening flange 412. Preferably, the staples 411 are preloaded into premade axial holes 414 through the fastening flange 412. The staples 411 should be made of a highly resilient biocompatible spring material, such as spring-tempered stainless steel or titanium alloys. Superelastic materials, such as nickel-titanium alloys, can also be used for forming the spring-like staples. Information about the composition and treatment of superelastic metal alloys useful in the manufacture of the spring like staples can be found in U.S. Pat. No. 4,665,906, entitled Medical Devices Incorporating SIM Alloy Elements, the entire disclosure of which is hereby incorporated by reference. Two alternate forms for the spring-like staples 411, 420 are shown in FIGS. 32B and 32C. FIG. 32B shows a single staple 411 which has one attachment leg 415. The distal end 416 of the attachment leg 415 is sharpened to easily pierce the blood vessel walls. A distal portion 417 of the attachment leg 415 is bent at an acute angle with respect to a central portion 418 of the leg 415. Similarly, a proximal portion 419 of the leg 415 is bent at an acute angle with respect to the central portion 418. The proximal portion 419 and the distal portion 417 of the staple 411 can be angled in the same direction with respect to the central portion 418 to make a C-shaped staple, as shown in FIG. 32B, or the proximal 419 and distal 417 portions can be angled in opposite directions to create a Z-shaped staple. FIG. 32C shows a double staple 420 which has two parallel attachment legs 415. The distal end 415 of each attachment leg 415 is sharpened to easily pierce the blood vessel walls. The distal portions 417 of the attachment legs 415 are bent at an. acute angle with respect to the central portions 418 of the legs 415. The proximal portions 419 of the legs 415 are also bent at an acute angle with respect to the central portions 418. The proximal portions 419 of the attachment legs 415 are linked together by a crossbar 421. The double staple 420 has an advantage in that the crossbar 421 linking the two attachment legs 415 keeps the staple 420 aligned within the fastening flange 412. When using double staples 420 with the fastening flange 412, the axial holes 414 through the flange 412 should be made as pairs of holes 414 spaced apart by approximately the length of the crossbar 421 of the staple 420. Similar to the single staple 411 of FIG. 32B, the double staple 420 can be made with the proximal portions 419 and the distal portions 417 of the attachment legs 415 angled in the same direction with respect to the central portions 418 to make a C-shaped staple, when viewed from the side, or the proximal 419 and distal 417 portions can be angled in opposite directions to create a Z-shaped staple as shown in FIG. 32C.

The operation of either staple version can be understood from the sequence of drawings in FIGS. 32D, 32E, and 32F. The following operational description using the single staple 411 of FIG. 32B is, therefore equally applicable to the double staple 420 of FIG. 32C. The staples 411 are preferably preloaded into the fastening flange 412 so that the distal bend 427 of the staple legs 415 is captured within and straightened by the hole 414 through the flange 412. The resilience of the spring material prevents the staple legs 415 from taking a permanent set when they are straightened out to load them into the holes 414 in the flange 412.

If a superelastic nickel-titanium alloy is used for the spring-like staples 411, then the shape-memory property of the alloy can be used to facilitate loading the staples 411 into the flange 412. To do this, the staple 411 would first be annealed in the desired shape for the final staple. Then, the staple 411 would be plastically deformed below its transition temperature to straighten out the distal bend 427. The straightened staples 411 are easily inserted into the holes 414 in the flange 412. Finally, the staples 411 are heated above their shape-memory transition temperature to make them resume their annealed shape. Preferably, the transition temperature is below body temperature so that the alloy of the staple 411 is in its martensitic or superelastic phase when the staple 411 is deployed within the body. Since the distal bend 427 is captured within the hole 414 in the flange 412, it is held straight until the staple 411 is deployed in the following steps.

The free end 259 of the graft vessel 254 is everted over the distal surface 422 of the fastening flange 412, as shown in FIG. 32D, and the device 410 is aligned with an opening 267 that has been previously made in the target vessel wall 255. To help align the central orifice 413 of the flange 412 with the opening 267 in the target vessel 255, an alignment device 423 can be inserted through the lumen 249 of the graft vessel 254 from the opposite end of the graft. The alignment device 423 has a narrow, elongated shaft 424 which fits through the lumen 249 of the graft vessel 254 and an atraumatic centering element 425, such as an inflatable centering balloon on the distal end of the shaft 424. The centering element 425 serves to align the central orifice 413 of the flange 412 and the graft vessel lumen 249 with the opening 267 in the wall of the graft vessel 255. The alignment device 425 can also be used to apply a mild amount of traction on the target vessel wall 255 to better approximate the everted end 259 of the graft vessel 254 and the target vessel 255 when making the anastomosis. Alternatively, the centering element 425 could be replaced with a vessel punch introduced through the graft vessel lumen 249, as in the embodiments described in connection with FIGS. 2–5.

Once the everted end 259 of the graft vessel 254 and the target vessel 255 have been properly approximated, the staple driver 426 is advanced distally, as shown in FIG. 32E. The distal ends 416 of the staples 411 pierce the everted graft vessel wall 259 and the target vessel wall 255 and the distal portion 417 of the attachment legs 415 traverses the vessel walls in a linear path. As the distal bend 427 of the attachment legs 415 exit the hole 414 in the fastening flange 412, the distal portions 417 begin to resume their acute angle bend. By the time the staple driver 426 reaches its most distal position, the distal bend 427 of the attachment legs 415 is fully reconstituted within the lumen 256 of the target vessel 255. When the staple driver 426 is withdrawn, the spring action of the proximal bend 428 in the attachment legs 415 pulls the staple 411 back slightly to embed the distal portions 417 of the attachment legs 415 into the interior surface 257 of the target vessel wall 255, as shown in FIG. 32F. The spring action of the staples 411 also serves to exert compressive force between the fastening flange 412 and the target vessel wall 255 to assure a leak proof and secure attachment.

During the manufacture of the staples 411, the distal bends 427 on the staple attachment legs 415 can be made with almost any desired orientation. The distal bends 427 can be oriented to turn the distal portion 417 of the attachment legs 415 toward the opening 267 in the target vessel wall 255, as shown in FIG. 32F, or the distal portions 417 can be oriented pointing away from the opening 267. Alternatively, the distal portions 417 can be aligned so that they bend tangentially to the opening 267. The tangential distal portions can be oriented so that they cross one another. Perhaps more advantageously, the tangential distal portions 417 can be oriented so that they all bend in the same direction, as shown in FIG. 32G, so that a more complete gap-free seal is made all around the periphery of the anastomosis.

FIGS. 33A–33D and 34A–34D show two variations of an anastomosis device 430 having a fastening flange 431 and a plurality of S-shaped staple members 432 formed from a superelastic metal alloy such as a nickel-titanium alloy. The fastening flange 431 has a central orifice 433 which is sized to accommodate the exterior diameter of the graft vessel 254. The fastening flange 431 has an annular distal ridge 434 and an annular proximal ridge 435 around its outer surface. There are a plurality of holes 436 arranged in a circle around the periphery of the central orifice 433 of the flange 431 passing through the flange 431 from the proximal surface to the distal surface 438. Each of the holes 436 is sized to slidably receive one of the S-shaped staple members 432. There are a plurality of cylindrical lugs 439 extending from the proximal surface 437 of the flange 431. Preferably, the lugs 439 are arranged in a circle concentric with the central orifice 433 and there are an equal number of lugs 439 to the number of holes 436 in the flange 431 with the lugs 439 spaced equidistant from adjacent holes 436.

The S-shaped superelastic alloy staple members 432 are shown in perspective FIG. 33D. The staple member 432 is formed with a straight central segment 440 that is attached to a hook-shaped distal segment 441 and a proximal segment 442 which bends at an angle just under 90 degrees from the central segment 440 in a plane that is approximately at a right angle to the plane defined by the hook-shaped distal segment 441. The distal tip 443 of the hook-shaped distal segment 441 is sharpened to easily penetrate the graft vessel wall 254 and the target vessel wall 255. FIG. 34D shows a slight variation of the staple member 432 of FIG. 33D. This variation differs from the previous one in that the distal segment 444 is bent at an acute angle to the central segment rather than being a fully formed hook. The S-shaped staples 432 are annealed in the desired configuration so that they will retain the annealed shape. The extremely resilient nature of the superelastic alloy allows the staple members 432 to be completely straightened without causing plastic deformation of the staples so that they will return to their annealed shape.

The anastomosis device 430 is prepared for use by passing the graft vessel 254 through the central orifice 433 of the fastening flange 431 then everting the distal end 259 of the graft vessel 254 over the distal surface 437 of the flange 431. A suture 445 can be tied around the everted end 259 of the graft vessel 254 to secure it to the flange 431. The distal ridge 434 of the flange 431 prevents the tied graft vessel 259 from slipping off of the flange 431. Next, the staple members 432 are straightened and passed through the holes 436 in the flange 431 from the proximal surface 437 to the distal surface 438. The distal curve 441 of the staples 432 is restrained in the straightened position by the sliding fit with the holes 436 in the flange 431. When the staples 432 emerge from the distal surface 438 of the flange 431, they pierce the everted wall 259 of the graft vessel 254. At this point the fastening flange 431 with the everted end 259 of graft vessel 254 attached to it is approximated to the exterior surface 258 of the target vessel 255 with the central orifice 433 and the lumen 249 of the graft vessel 254 centered on an opening 267 that has been made in the wall of the target vessel 255. The distal ends 443 of the staple members 432 pass through the opening 267 in the target vessel wall 255.

Once the graft vessel 254 and the target vessel 255 are properly approximated, an annular staple driver 446 is used to push the staple members 432 distally through the holes 436 in the flange 431 so that they emerge into the lumen 256 of the target vessel 255. As the distal ends 443 of the staple members 431 emerge from the distal surface 438 of the flange 431 the distal segments 441 resume their annealed shape. The hook-shaped distal segments 441 of the staple members 431 in FIG. 33D curve back toward the interior surface 257 of the target vessel and penetrate the target vessel wall 255. The proximal segments 442 of the staple members 432 are positioned between the lugs 439 on the proximal surface 437 of the flange 431 to lock the staples 432 from rotating with respect to the flange 431. FIG. 33C shows a proximal view of the anastomosis device 430 with the staple members 432 deployed. This view is shown without the graft vessel or the target vessel present for the sake of clarity. As best seen in FIG. 33B, the acute angle of the proximal segment 442 acts like a spring to pull back on the staple member 432 to help the distal segment 441 to pierce the target vessel wall 255 and to help create compression between the flange 431 and the target vessel wall 255 to create a leak proof anastomotic seal between the graft vessel 254 and the target vessel 255.

The deployment of the anastomosis device in FIGS. 34A–34D is essentially the same as just described up until the point when the distal ends 444 of the staple members 432 begin to emerge into the target vessel lumen 256. As the distal ends 443 of the staple members 432 emerge from the distal surface 438 of the fastening flange 431, they resume their acute angle bend. Rather than penetrating the target vessel wall 255, the distal segments 444 of the staple member 432 align themselves flat against the interior surface 257 of the target vessel 255 and press against the vessel wall 255, compressively clamping the fastening flange 431 and the everted end 259 of the graft vessel 254 to the target vessel wall 255. The acute angle of the proximal segment 442 acts like a spring to pull back on the staple member 432 to keep the distal segment 444 snug against the interior surface 257 of the target vessel wall 255.

FIGS. 35A–35F show another variation of an anastomosis device 447 using a fastening flange 448 and attachment staple 449 combination. The fastening flange 448 is a cylindrical member with an internal lumen 450 large enough to accommodate the external diameter of the graft vessel 254. The flange 448 has a distal surface 451 over which the free end 254 of the graft vessel 259 may be everted. An annular ridge 452 around the outer surface of the flange 448 at the distal end helps to hold the everted graft vessel 259 in place and serves as part of a locking mechanism for the attachment staples 449, as will be described below. The attachment staples 449 are in the form of U-shaped hooks with barbed points 453 on their distal tips. Each staple 449 has a proximal portion 454 which is slidably received within an axial hole 456 through the cylindrical wall 457 of the fastening flange 448. The proximal end 455 of the proximal portion 454 is sharpened for easily piercing the tissue of the graft vessel wall 254. A U-shaped bend 458 connects the proximal portion 454 of the staple 449 to the barbed, pointed distal portion 453.

Figure 35C:
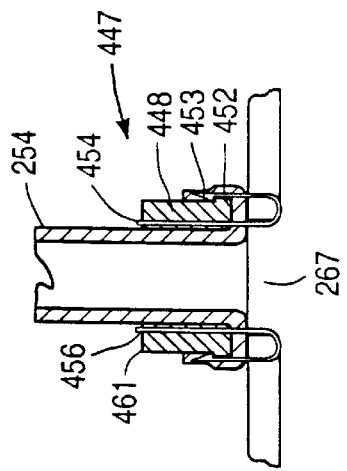
FIGS. 35A–35F show an anastomosis device using U-shaped staple members with barbed points.
Figure 35B:
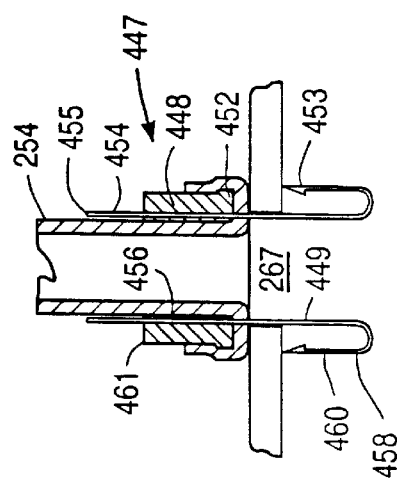

The anastomosis device 447 is applied by removing the U-shaped staples 449 from the flange 448. The end 259 of the graft vessel 254 is passed through the internal lumen 450 of the flange 448 until the graft vessel 254 extends a short distance from the distal end 459 of the flange 448. Then, the end 259 of the graft vessel 254 is everted back over the distal end 259 of the flange 448. Once the graft vessel 254 is everted over the flange 448, the staples 449 are reinserted into the holes 456 in the flange 458 by piercing the proximal end 445 through the everted wall 259 of the graft vessel 254. Marks or other visual indications can be provided on the side of the cylindrical flange 448 to aid in aligning the proximal ends 455 of the staples 449 with the holes 456. The proximal portions 454 of the staples 449 are partially advanced into the flange 448 as shown in FIG. 35B. The U-shaped ends 458 of the staples 449 are inserted through an opening 267 in the wall of the target vessel 255 which has previously been made using a vessel punch or similar instrument. Two alternate methods can be used for inserting the staples 449 through the opening 267 in the target vessel wall 255. In the first method, shown in FIG. 35C, the U-shaped ends 458 of the staples are extended from the cylindrical flange 448 far enough that they easily deflect inward toward the center of the opening 267 in the target vessel wall 255 when they contact the edge of the opening 267 so that they can be simultaneously inserted through the opening 267. In the second method, the U-shaped ends 458 of the staples 449 are rotated, as shown in FIG. 35D, so that the U-shaped ends 458 all fit within a circle that will pass through the opening 267 in the target vessel wall 255. Once the U-shaped ends 458 of the staples 449 are within the lumen 256 of the target vessel 255, the staples 449 can be rotated so that the U-shaped ends 458 extend radially outward from the fastening flange 448. The distal surface 459 of the cylindrical flange 448 with the everted graft vessel 259 attached to it is approximated to the exterior surface 258 of the target vessel 255, then the staples 449 are withdrawn in the proximal direction so that the barbed, pointed distal ends 453 pierce the target vessel wall 255. The distal portion 460 of the staple 449 passes through the target vessel 255 wall in a linear path, then pierces the everted edge 259 of the graft vessel wall 254 a second time. When the barbed end 453 of staples 449 pass the annular ridge 452 on the distal end 459 of the flange 448 the barbs 453 engage the proximal surface of the ridge 452, locking the staples 448 in position to permanently attach the anastomotic device 447 in place. The excess length on the proximal portion 454 of the U-shaped staples 449 may be cut off flush with the proximal end 461 of the cylindrical flange 448. Alternatively, the proximal portion 454 of the staple 449 can be bent over at the proximal end 461 of the cylindrical flange 448 for a second means of attachment, then the excess length cut off.

Figure 35A:
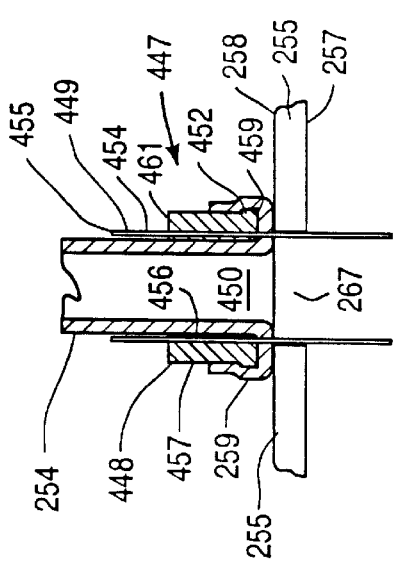
Figure 35F:
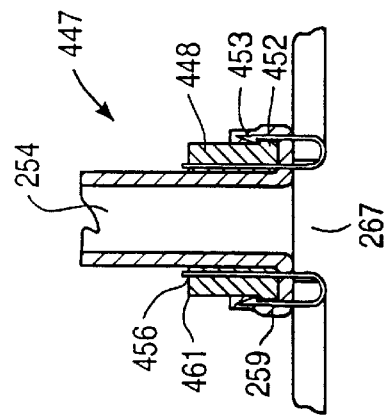
Figure 35E:
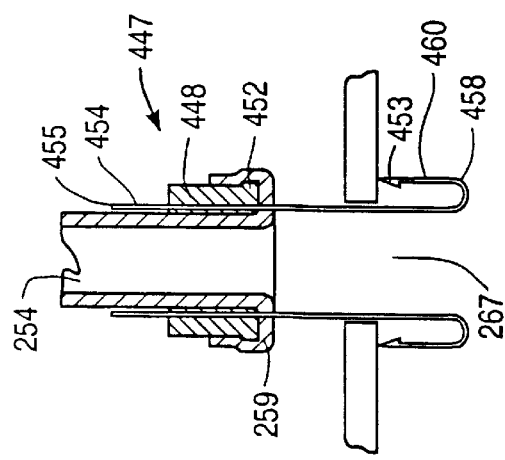
Figure 35D:
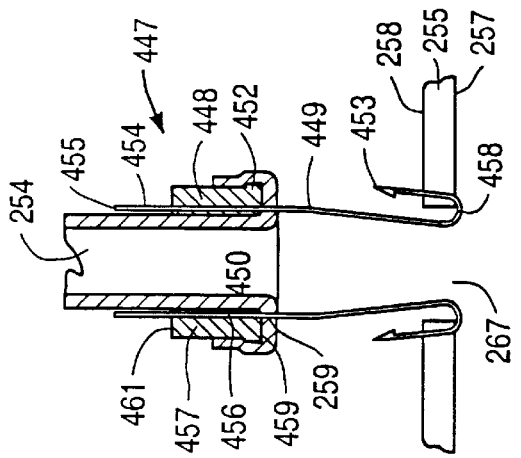

Two alternative versions of the anastomosis device of FIG. 35A, using different locking means for the U-shaped staples, are shown in FIGS. 36A–36C and 37A–37C. FIG. 36A shows an anastomosis device 462 with a fastening flange 463 and a plurality of non-barbed U-shaped staples 464 and a locking collar 465 for locking the U-shaped staples 464 onto the fastening flange 463. The flange 463 and the staples 464 are applied in much the same way as described above for the previous embodiment, by inserting the staples 464 through the opening 267 in the target vessel 255 and withdrawing them in the proximal direction so that the distal ends 466 of the staples 464 pierce the target vessel wall 255 and emerge alongside the outer surface of the fastening flange 463. A locking collar 465 is then pressed onto the proximal end 467 of the fastening flange 463, as shown in FIG. 36B, crimping the distal ends 466 of the staples 464 and locking them to the flange 463 in the process. The excess length of the proximal portion 468 of the staples 464 is cut off flush with the proximal end 467 of the fastening flange 463 to complete the anastomosis, as shown in FIG. 36C.

FIG. 37A shows a second anastomosis fitting 469 with non-barbed U-shaped staples 470 and a locking collar 471 for locking the U-shaped staples onto the fastening flange 472 of the fitting 469. The fastening flange 472 in this embodiment has a conical surface 473 on the outer surface of the flange 472 proximal to the distal rim 474 of the flange 472. The proximal end 475 of the fastening flange 472 has a series of parallel annular locking ridges 476 around its exterior surface. A locking collar 471 has an interior taper 477 which matches the conical taper 473 of the fastening flange 472 and a series of parallel locking ridges 478 on the proximal end. After the flange 472 and the staples 470 have been applied as described above, the locking collar 471 is pressed onto the flange 472, as in FIG. 37B. The distal portion 479 of the U-shaped staple 470 is wedged between the mating conical tapers 473, 477. The locking ridges 478 of the locking collar 471 engage the locking ridges 476 of the flange 472 to permanently lock the anastomosis device 469 in place and the anastomosis is completed by cutting off the proximal portions 480 of the staples 470 flush with the proximal end of the flange 475, as shown in FIG. 37C.

The anastomosis fittings of FIGS. 33–37 may also be manufactured using staple elements made of a highly elastic material, such as a superelastic nickel-titanium alloy, so that the staples may be preformed with U-shaped ends which can be straightened and loaded into the holes in the fastening flange. The staples would be deployed by pushing them out the distal end of the flange so that they pass through the wall of the graft vessel into the target vessel, after which, they resume their U shape within the lumen of the target vessel. The highly elastic staple elements could be locked onto the fastening flange using any of the methods described in connection with FIGS. 33–37.

FIGS. 38A–38C and 39A–39C show one-piece versions of an anastomosis device using a fastening flange and attachment staple combination. FIG. 38A shows an anastomosis device 481 that has a fastening flange 482 and integrally formed staple members 483. The fastening flange 482 is a flat annular ring which may be formed from a flat sheet of a biocompatible metal. The staple members 483, which may be formed from the same sheet of metal, attach to the inner diameter 484 of the ring 482 and are initially bent 90° from the flange 482 so that they extend in the distal direction, as shown in FIG. 38B. The inner diameter 484 of the flange fits over a tubular inner member 485 of an application tool 486. The graft vessel 254 is passed through an inner lumen 487 within the tubular member 485 and then the end 259 of the graft vessel 254 is everted over the distal end 488 of the tubular member 485. The application tool 486 is used to approximate the end 259 of the graft vessel 254 to an opening 267 that has previously been made in the wall of the target vessel 255. A tubular staple driver 489 slides telescopically over the exterior of the tubular inner member 485. The fastening flange 482 is moved distally by sliding the staple driver 489 axially with respect to the inner tubular member 485, which forces the sharpened distal ends 490 of the integral staple legs 483 through the everted wall 259 of the graft vessel 254 and the wall of the target vessel 255. Once the staple legs 483 have traversed the graft vessel 254 and target vessel walls 255, the distal ends 490 of the staple legs 483 are deformed to lock the anastomosis device 481 in place as shown in FIG. 38C.

Different methods can be used for deforming the distal ends 490 of the staple legs 483 to attach the anastomosis device 481. An articulating anvil, similar to the one described in FIG. 31A can be inserted through the lumen 249 of the graft vessel 254 to work cooperatively with the staple driver 489 to deform the distal ends 490 of the staple legs 483. Alternatively, the fastening flange 482 and the staple legs 483 can be made of a spring-like elastic or superelastic alloy and preformed into their final desired shape. The inner tubular member 485 of the staple application device 486 seen in FIG. 38B holds the preformed distal bend 491 in the staple legs 483 straight until the anastomosis device 481 is deployed by the staple driver 489. Another alternative is to make the anastomosis device 481 and the staple legs 483 from a shape-memory alloy, such as a nickel-titanium. The staple legs 483 are annealed in their final shape. Then, the staple legs 483 are plastically deformed below the material's transition temperature to straighten out the distal bends 491. The straightened staple legs 483 are driven through the walls of the graft vessel 254 and the target vessel 255 and the staple legs 483 are heated above their shape-memory transition temperature to make them resume their annealed shape. The material is preferably chosen so that the transition temperature is at or near body temperature so that heating the staple above the transition temperature does not cause damage to the delicate vascular tissues.

FIG. 39A shows an additional anastomosis device 492 that has a fastening flange 493 and integrally formed staple members 494. The fastening flange 493 in this case is a cylindrical ring formed from a tube of a biocompatible metal. The staple members 494 are attached to the distal edge of the cylindrical fastening flange 493. Optionally, there are also proximal fastening members attached to the proximal edge of the cylindrical fastening flange 493. This variation of the anastomosis device can be applied with any of the methods just described in connection with FIGS. 37A–37C. If the anastomosis device 492 has been made of an elastic or superelastic alloy, the optional proximal fastening members 495 can serve as spring members to compress the anastomotic attachment, similar to the proximal portions of the spring-like staples 411, 420 described in connection with FIGS. 32A–32F.

FIGS. 40A–40D show a two-piece version of an anastomosis device 496 having a fastening flange and integrally formed staple members. In this case, the fastening flange of the device is formed of two concentric cylindrical flange rings 497, 498. A plurality of interlocking staple members 499, 500 extend from the distal edges of both cylindrical flange rings 497, 498. Preferably, the staple members 499, 500 are integrally formed with the cylindrical flange rings 497, 498. The staple members 499 of the inner flange ring 497 are angled so that they spiral downward from the ring 497 in a clockwise direction. The staple members 500 of the outer flange ring 498 are oppositely angled so that they spiral downward from the ring 497 in a counterclockwise direction. Corresponding locking features 501, 502 on the inner surface of the outer flange ring 498 and on the outer surface of the inner flange ring 497 are capable of locking the two flange rings 498, 497 together in a fixed position. Indentations on one flange ring, with corresponding detents on the other flange ring are one of the many possibilities for the locking features 501, 502.

Figure 40C:
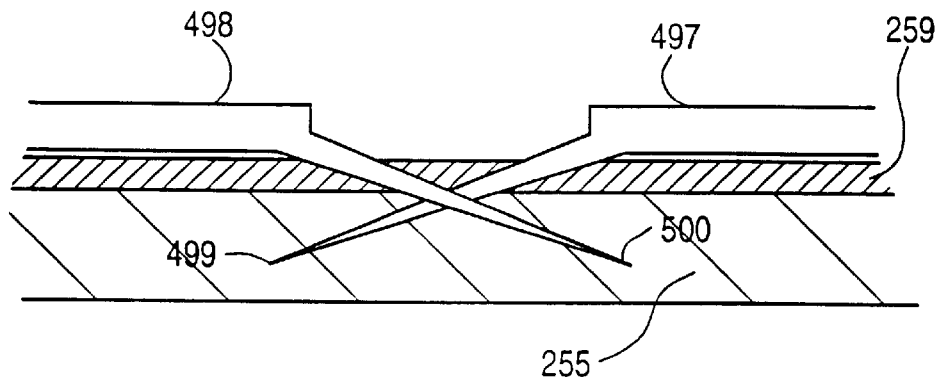
FIGS. 40A–40D show a two-piece anastomosis device having two concentric ring flanges with integral staple members.
Figure 40A:
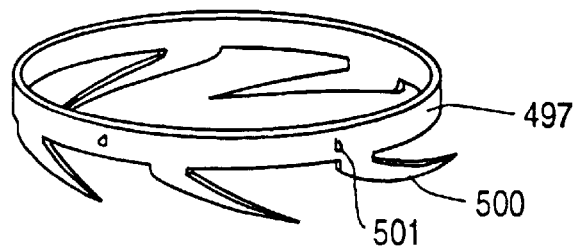
Figure 40B:
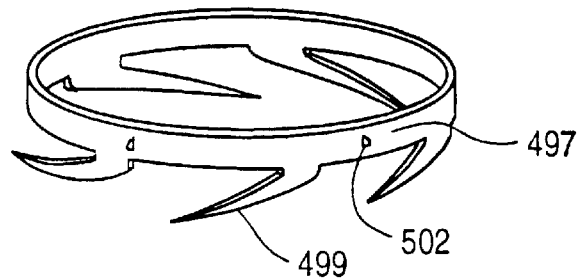
Figure 40D:
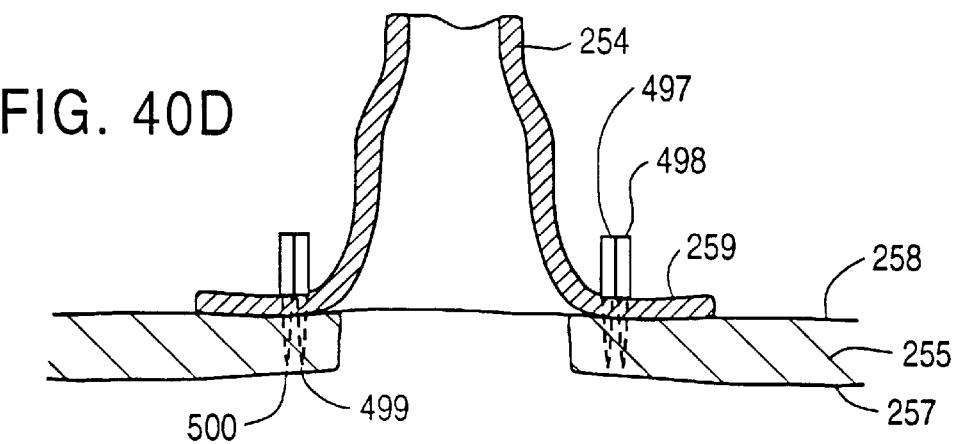

The anastomosis device 496 is applied by separately placing first the outer flange ring 498, then the inner flange ring 497 around the distal end 259 of the graft vessel 254. The end 259 of the graft vessel 254 is then everted and approximated to the exterior wall 258 of the target vessel 255 surrounding an opening 267 which has been previously made in the wall, as shown in FIG. 40C. The inner ring 497 is moved distally along the graft vessel 497 until the points of the staple members 499 contact the everted vessel wall 259. The inner ring 497 is pressed into the everted graft vessel wall 259 and simultaneously rotated in a clockwise direction, thereby driving the staple members 497 through the graft vessel wall 259 and the target vessel wall 255. Next, the outer ring 498 is moved distally along the graft vessel 254 until it is concentric with the inner ring 497. Then the outer ring 498 is pressed into the everted graft vessel wall 259 and simultaneously rotated in a counterclockwise direction, driving the staple members 500 through the graft vessel wall 259 and the target vessel wall 255. When the locking features 501 of the outer ring 498 coincide with the locking features 502 of the inner ring 497, the outer 498 and inner 497 rings become locked together. As the flange rings 497, 498 are rotated in opposite directions, the staple members 499, 500 of the inner 497 and outer rings 498 penetrate the vessel walls in opposite directions as shown in FIG. 40C, effectively locking the anastomosis device 496 to the exterior 258 of the target vessel 255.

Alternatively, the inner 497 and outer rings 498 of the flange can be applied simultaneously to the everted end 259 of the graft vessel 254 by arranging the rings 497, 498 concentrically, then pressing the staple members 499, 500 into the graft vessel wall 259 while counter-rotating the inner 497 and outer 498 rings. This could best be done with an instrument that holds and rotates the inner 497 and outer 498 rings mechanically.

FIGS. 41A–41E show another approach to making an anastomosis device 503 having a fastening flange 504 and a plurality of individual staple members 505. The method of deployment used in this embodiment allows the staple members 505 to be made of a normally elastic metal alloy, such as spring-tempered stainless steel. The fastening flange 504 in this embodiment is a tubular element with a central orifice 506 which is surrounded by an inner wall 507, a distal surface 508, and an outer wall 509 defining an annular space 510 between the inner 507 and outer walls 509. The annular distal surface interconnects the inner 507 and outer 509 walls. The annular space 510 is sized to fit the staple members 505 prior to deployment, as shown in FIG. 41A. A staple application tool 511 has an annular staple driver 512 which fits into the annular space 510 within the flange 504. The distal surface 508 and the inner wall 507 of the flange 504 is slotted with pairs of L-shaped slots 513 to allow penetration of the staple members 505 through the distal surface 508.

Alternatively, the flange 504 may have a solid body and the annular space 510 can be replaced by a series of individual staple slots formed in the body of the flange by a process like electrical discharge machining. The individual staple slots can each be sized to fit a single staple member 505. Each individual staple slot should communicate with a single slot or a pair of slots in the distal surface 508 of the fastening flange 504 for proper deployment of the staple members 505, depending on whether the staple members are single or double-leg staples. In this case, the annular staple driver 512 of the application tool 511 must be replaced with an array of individual staple drivers sized to fit into the individual staple slots.

The staple members 505 for this embodiment can be made as J-shaped, single-leg staples 505' or as U-shaped, double-leg staples 505. When viewed from the side, the single 505' and double-leg staples 505 are both roughly the shape of an inverted J, as seen in FIG. 41A. The double-leg staples 505 combine two such J-shaped staple legs 514 with a crossbar 515 that connects the proximal ends of the staple legs 514 to form staples 505 that are roughly U-shaped when viewed from the front or from the top, as in FIG. 41E. The staple legs 514 are formed with a central segment 516 that is attached at an acute angle to a proximal segment 517. A short intermediate segment 518 may be used to connect the proximal segment 517 to the central segment 516 of the staple member 505. The proximal end of each of the proximal segments 517 is joined to the crossbar 515 of the staple member 505. A distal segment 519 is attached to the central segment 516 at an obtuse angle so that it is approximately parallel to the proximal segment 517. The distal end 520 of the distal segment 519 is sharpened to easily penetrate the graft vessel wall 259.

The anastomosis device 503 is prepared by passing the graft vessel 254 through the central orifice 506 of the fastening flange 504 and everting it over the distal surface 508 of the flange 504. As an alternative to the loop of suture described in previous embodiments of the device, a vessel cap 521 may be used to secure the everted graft vessel 259 to the fastening flange 509. The vessel cap 521 is a toroidal ring with an L-shaped cross section that fits around the outer diameter of the distal surface 508 of the fastening flange 504 and holds the everted end 259 of the graft vessel 254 in place.

Next, the fastening flange 504 with the everted end 259 of the graft vessel 254 attached is approximated to the exterior 258 of the target vessel 255 with the central orifice 506 aligned with an opening 267 through the target vessel wall 255, as shown in FIG. 41A. The staple driver 512 is then advanced in the distal direction to press against the attachment legs 514 of the staple members 505 and force the distal ends 520 of the staple members 505 through the slots 513 in the distal end 508 of the fastening flange 504 to pierce the graft vessel wall 259 and enter the target vessel lumen 256 through the opening 267 in the target vessel wall 255, as shown in FIG. 41B. As the staple driver 512 is advanced further the crossbar 515 of the staple member 505 contacts the distal wall 508 of the fastening flange 504 and the staple member 505 begins to rotate about the point of contact, as shown in FIG. 41C. The distal segments 519 of the staple members 505 capture the target vessel wall 255 and pull it tight against the distal surface 508 of the fastening flange 504, as shown in FIG. 41D, to form a leak proof anastomotic seal between the everted graft vessel wall 259 and the target vessel 255.

FIGS. 42A–42D illustrate another one-piece embodiment of the anastomosis device 522 with a fastening flange 523 and attached staple members 524. Preferably, the anastomosis device 522 is made from a deformable biocompatible metal, such as a stainless steel alloy, a titanium alloy or a cobalt alloy. If desired a surface coating can be applied to the anastomosis device to improve the biocompatibility or other material characteristics.

In contrast to some of the previously described embodiments, in this version of the anastomosis device 522, the fastening flange 523 resides on the interior surface 258, of the target vessel wall 255 when the anastomosis is completed. To avoid any problems with hemolysis, thrombogenesis or foreign body reactions, the total mass of the fastening flange 523 has been reduced to an absolute minimum to reduce the amount of foreign material within the target vessel lumen 256.

The fastening flange 523 is in the form of a wire ring 523 with an internal diameter which when fully extended is just slightly larger than the diameter of the graft vessel 254 and of the opening 267 made in the target vessel wall 255. Initially, the wire ring 523 has a rippled wave-like shape to reduce the diameter of the ring 523 so that it will easily fit through the opening 267 in the target vessel wall 255. A plurality of staple members 524 extend from the wire ring 523 in the proximal direction. In the illustrative embodiment shown in FIG. 42A, there are nine staple members attached to the wire ring fastening flange 523. Other variations of the anastomosis device 522 might typically have from four to twelve staple members 524 depending on the size of the vessels to be joined and the security of attachment required in the particular application. The staple members 524 can be formed integrally with the wire ring fastening flange 523 or the staple members 524 could be attached to the ring 523 by welding or brazing methods. The proximal ends 525 of the staple members 524 are sharpened to easily pierce the target vessel wall 255 and the graft vessel wall 259. Preferably, the proximal ends 525 of the staple members 524 have barbs 526 to improve the security of the attachment when the device is deployed.

Figure 42A:
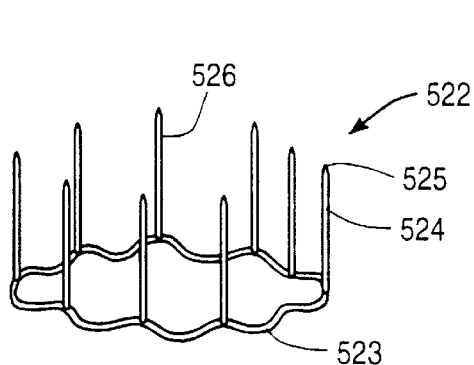
FIGS. 42A–42D illustrate a one-piece embodiment of the anastomosis device with a fastening flange and attached staple members.
Figure 42B:
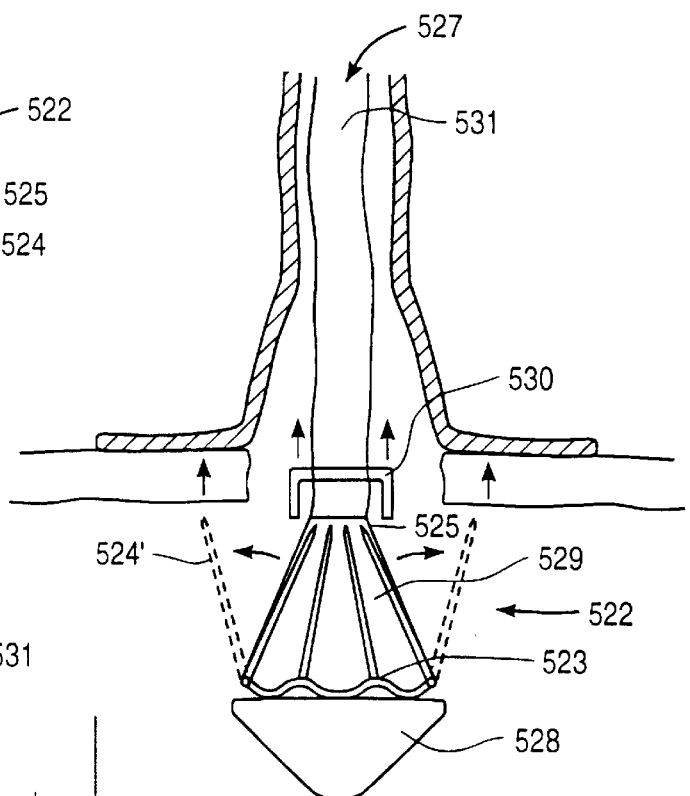

The anastomosis device 522 is prepared for use by mounting the device onto the distal end of a specially adapted application instrument 527, as shown in FIG. 42B. The fastening flange 523 is mounted onto an anvil 528 attached to the distal end of the elongated shaft 531 of the application instrument 527. The staple members 524 are compressed inward against a conical holder 529 attached to the instrument 527 just proximal to the anvil 528. The staple members 524 are held in this compressed position by a cap 530 which is slidably mounted on the elongated shaft 531. The cap 530 moves distally to cover the sharpened, barbed ends 525 of the staple members 524 and to hold them against the conical holder 529. The application instrument 527 is then inserted through the lumen 249 of the graft vessel 254. This can be done by inserting the instrument through the graft vessel lumen 249 from the proximal to the distal end of the graft vessel 254, or it can be done by backloading the elongated shaft 531 of the instrument into the graft vessel lumen 249 from the distal end to the proximal end, whichever is most convenient in the case. The anvil 528 and holder 529 on the distal end of the application instrument 527 with the anastomosis device 522 attached is extended through the opening 267 into the lumen 256 of the target vessel 255.

Next, the distal end 259 of the graft vessel wall 254 is everted against the exterior surface 258 of the target vessel wall 255 with the graft vessel lumen 249 centered on the opening 267 in the target vessel wall 255. The cap 530 is withdrawn from the proximal ends 525 of the staple members 524, allowing the staple members 524 to spring outward to their uncompressed position shown by the phantom lines 524' in FIG. 42B. The application instrument 527 is then drawn in the proximal direction so that the staple members 524' pierce the target vessel wall 255 surrounding the opening 267 and the everted end 259 of the graft vessel 254.

The application instrument 527 has an annular staple former 532 which surrounds the outside of the graft vessel 254. Some slight pressure on the everted graft vessel wall 259 from the annular staple former 532 during the piercing step assists in piercing the staple members 524' through the graft vessel walls 259. Care should be taken not to apply too much pressure with the staple former 532 at this point because the staple members 524' could be prematurely deformed before they have fully traversed the vessel walls. If desired, an annular surface made of a softer material, such as an elastomer, can be provided on the application instrument 527 to back up the vessel walls as the staple members 524' pierce through them.

Figure 42C:
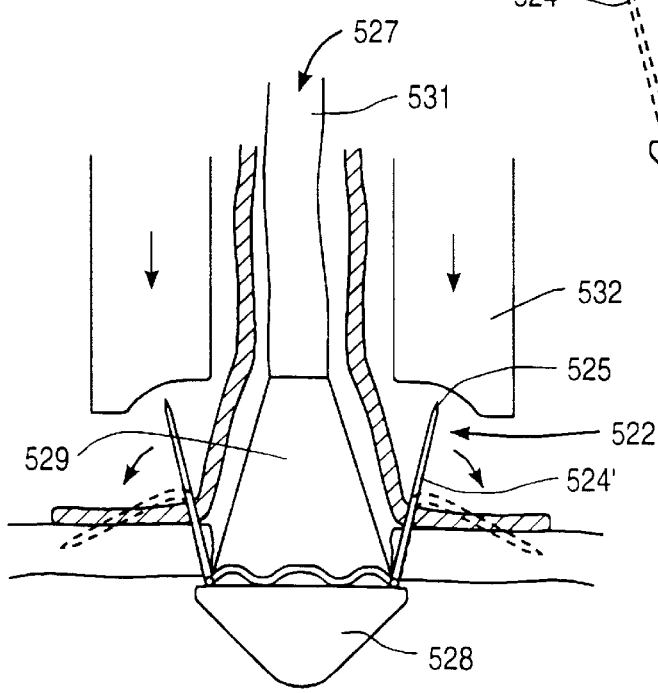
Figure 42D:
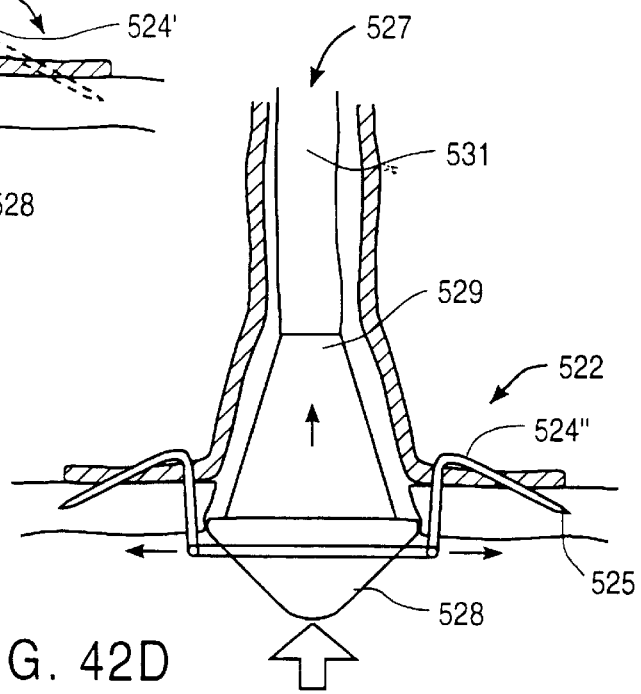

Once the staple members 524' have fully traversed the target vessel wall 255 and the graft vessel wall 259, as shown in FIG. 42C, the staple former 532 is brought down with greater force while supporting the fastening flange 523 with the anvil 528. The staple members 524' are deformed outward, as shown by the phantom lines 524", so that the sharpened, barbed ends 525 pierce back through the everted graft vessel wall 259 and into the target vessel wall 255 to form a permanent attachment. To complete the anastomosis, the anvil 528 is withdrawn through the graft vessel lumen 249. As the anvil 528 passes through the wire ring fastening flange 523, it straightens out the wave-like ripples so that the wire ring 523 assumes its full uncompressed diameter, as shown in FIG. 42D. Alternatively, the wire ring fastening flange 523 can be made of a resilient material so that the flange 523 can be compressed and held in a rippled or folded position until it is released within the target vessel lumen 256, whereupon it will resume its full, expanded diameter. Another alternative construction would be to make the anastomosis device of a shape-memory alloy so that the wire ring fastening flange 523 can be compressed and inserted through the opening in the target vessel 267, whereupon it would be returned to its full expanded diameter by heating the device 522 to a temperature above the shape-memory transition temperature.

Figure 43A:
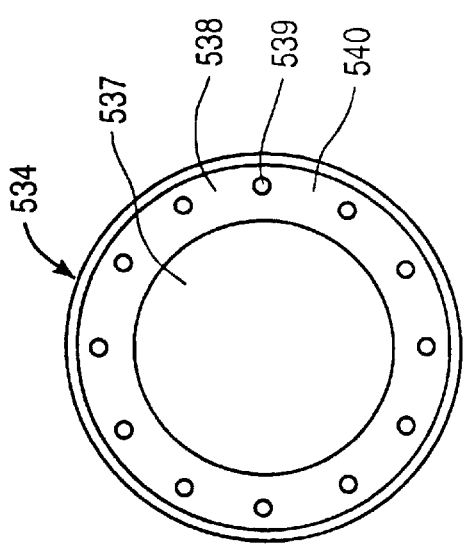
FIGS. 43A–43B show the fastening flange of an anastomosis device using preformed superelastic alloy staple members in a top view and a side view, respectively.
Figure 43B:
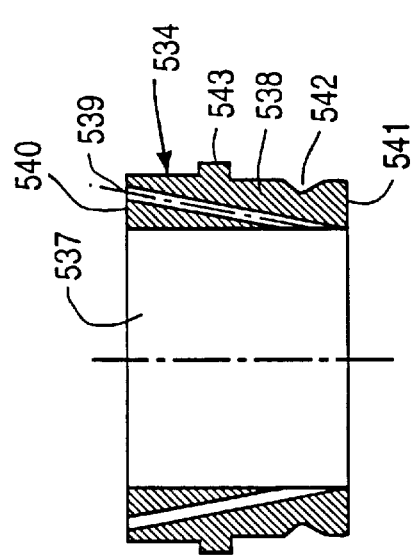

FIGS. 43A–43B, 44A–44B, and 45A–45E show a complete system for creating an end-to-side vascular anastomosis using an anastomosis device 533 with a fastening flange 534 and a plurality of staple members 535 made of a highly resilient or superelastic metal. The system includes a specially adapted application instrument 536 for applying the anastomosis device 533. FIG. 43A shows a top view of the fastening flange 534 of the anastomosis device 533. FIG. 43B shows the fastening flange 534 of FIG. 43A in cross section from the side. The fastening flange 534 is generally cylindrical in shape with a central orifice 537 of sufficient diameter to accommodate the external diameter of the graft vessel 254. The wall 538 of the fastening flange has a plurality of holes 539 extending from the proximal surface 540 of the flange to the distal surface 541 of the flange. Preferably there are an even number of holes 539, two for each of the staple members 535, which may number from four to twelve depending on the size of the vessels to be anastomosed. The illustrated embodiment has twelve holes 539 to accommodate six staple members 535. The holes 539 are preferably angled toward the central orifice 537 from the proximal end 540 to the distal end 541 so that they exit the wall 538 of the flange 534 at the juncture of the distal surface 541 of the flange and the internal surface of the central orifice 537. In the illustrative embodiment shown in FIGS. 43A and 43B the holes 539 are angled at approximately 10 degrees to the longitudinal axis of the flange 534. Other angles are also possible, from –10 to +20 degrees from the longitudinal axis of the flange 534 The fastening flange 534 has a circumferential notch 542 on the exterior of the flange 534 close to the distal end 541 of the flange to aid in attachment of the graft vessel wall 254. There is also a circumferential ridge 543 around the exterior of the fastening flange 534 proximal to the notch 542 to assist in gripping the flange 534 for the operation of the application tool 536.

Figure 44B:
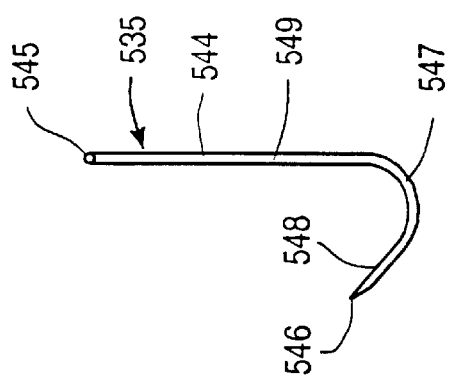
FIGS. 44A–44B show the superelastic alloy staple members of the anastomosis device in a front view and a side view, respectively.
Figure 44A:
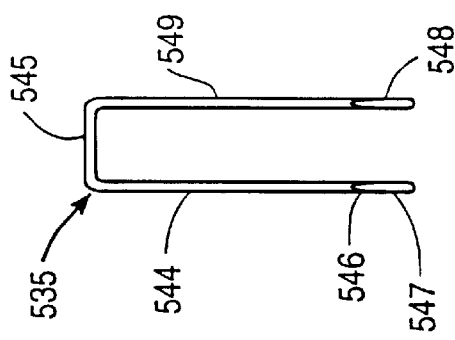

FIGS. 44A and 44B show the staple member 535 of the anastomosis device 533 in a front view and a side view. The staple members 535 are preferably formed from wire made of a highly resilient biocompatible metal such as a spring-tempered alloy of stainless steel, titanium, or cobalt, or more preferably of a superelastic metal alloy, such as a nickel-titanium alloy. The wire preferably has a diameter between 0.006 and 0.025 inches, depending on the stiffness of the metal alloy chosen. Nickel-titanium wire with a diameter of 0.010 to 0.012 inches has been found to be very suitable for this application. The staple members 535 are roughly an inverted U shape when viewed from the front with two attachment legs 544 joined together at their proximal ends by a crossbar 545, as shown in FIG. 44A. When viewed from the side as in FIG. 44B, the staple members 535 are roughly J-shaped with the distal ends 546 of the attachment legs 544 curving back toward the proximal end of the staple member 535. Each of the J-shaped hooks 547 ends in a short straight section 548 with a sharpened distal end 546 to easily penetrate the graft vessel 259 and target vessel 255 walls. The staple members 535 should be annealed or cold worked in the illustrated configuration, whichever treatment is most appropriate for the metal alloy chosen, so that the staple member has a permanent elastic memory which makes it return to the treated shape.

The holes 539 through the fastening flange 534 are sized so that there is a close sliding fit between the attachment legs 544 of the staple members 535 and the interior of the holes 539. The anastomosis device 533 is prepared for use by inserting the two attachment legs 544 of each staple member 535 into two adjacent holes 539 in the fastening flange 534, until the curved distal portion 547 of the attachment legs 544 are entirely within the holes 539. When inserting the staple members 535, they should be oriented so that the curve of the distal ends 547 of the attachment legs 544 will be biased outward from the central orifice 537 of the fastening flange 534 when extended distally from the holes 539 in the flange 534. Because of the close sliding fit, the interior walls of the holes 539 constrain the curved distal ends 547 of the attachment legs 544 in a straight position, as shown in FIG. 43B. The straight proximal portion 549 of the staple members 535 extend proximally from the proximal end 540 of the fastening flange 534 as shown.

The preparation of the anastomosis device 533 can also be accomplished using the shape-memory property of a nickel-titanium alloy. The staple members 535 would be formed as shown in FIGS. 44A and 44B and annealed to create a shape-memory. The attachment legs 544 of the staple members 535 are then straightened by cold working them below the transition temperature of the shape-memory alloy. In the straightened condition, the distal ends 547 of the attachment legs 544 are easily inserted into the holes 539 in the fastening flange 534. Care must be taken to orient the staple members 535 so that the curve of the distal ends 547 of the attachment legs 544 will be biased outward from the central orifice 537 of the fastening flange 534. Once all of the staple members 535 have been inserted into the holes 539 of the fastening flange 534, the entire anastomosis device 533 can be warmed above the transition temperature of the shape-memory alloy so that the distal ends 547 of the attachment legs 544 will try to return to their curved shape. Being constrained by the interior walls of the holes 539, the attachment legs 544 will remain straight, but they will have an elastic memory that will cause them to resume their curved shape when they are released from the confinement of the holes 539.

With the anastomosis device 533 thus prepared, it is ready to be inserted into the application instrument 536 which is shown in FIGS. 45A–45E. The application instrument 536 consists of two separate, but interacting, mechanisms, a stapling mechanism 550 and a punching mechanism 551. The punching mechanism 551 is sized to be slidingly received within an internal lumen 552 of the stapling mechanism 550. Most of the parts of the application instrument 536, unless otherwise specified, are preferably made of a high-strength, dimensionally stable polymer material, such as acetal, ABS, HDPE, PTFE, etc. Alternatively, the application instrument 536 could be made from stainless, steel, titanium or other metals, if desired.

The stapling mechanism 550 has a generally cylindrical holder 553 which has a proximal end 554 and a distal end 555. An internal lumen 556 extends from the proximal end 554 to the distal end 555. The distal end 555 of the holder 553 is adapted to hold the fastening flange 534 of the anastomosis device 533. A through hole 557 in the distal end of the holder 553 is sized to be a light press fit around the proximal end 540 of the fastening flange 534. A counterbore 558 on the distal end of the through hole 557 fits the circumferential ridge 543 of the fastening flange 534 to axially locate the fastening flange 534 with respect to the holder 553. A staple driver 559, which is generally tubular in shape, is slidably received within the internal lumen 556 in the holder 553. The staple driver 559 has a T-shaped handle 560 attached to its proximal end for operating the stapling mechanism 550. The proximal end of the staple driver 559 has a short tubular extension 561 with a circumferential groove 562 around the exterior of the tubular extension 561. The distal end has an annular staple driving surface 563.

To insert the anastomosis device 533 into the distal end of the stapling mechanism 550, the proximal ends 549 of the staple members 535 must be flexed slightly toward the central axis of the fastening flange 534 so that they will all fit through the through hole 557 on the distal end of the holder 553. Once the proximal ends 549 of the staple members 535 have been inserted, the proximal end of the fastening flange 540 is inserted into the through hole 557 with the circumferential ridge 543 seated into the counterbore 558.

The stapling mechanism 550 is now ready for attachment of the graft vessel 254 to the fastening flange 534. To begin, the graft vessel 254 is passed through the internal lumen 552 of the holder 553 and the staple driver 559. This can be done by tying a suture around one end of the graft vessel 254, passing the suture through the stapling mechanism 550 and drawing the graft vessel 254 through. Alternatively, an elongated hook or grasping instrument can be inserted through the lumen 552 of the stapling mechanism 550 to draw the graft vessel 254 through. The distal end 259 of the graft vessel 254 is then everted over the distal end 541 of the fastening flange 534. If desired, a loop of suture 564 can be tied around the everted end 259 of the graft vessel 254 at the location of the circumferential notch or groove 542 to secure the graft 259 to the fastening flange 534. The proximal end 565 of the graft vessel 254 can also be everted and temporarily attached with a loop of suture to the proximal extension 561 of the staple driver 559 to make the graft vessel 254 easier to handle.

At this point, the vessel punch mechanism 551 should be inserted into the stapling mechanism 550 through the lumen 249 of the graft vessel 254. The vessel punch mechanism 551 consists of a housing 566, a cutter 567, an anvil 568, a clamp 569, a clamp knob 570 and a punch knob 571. The housing 566 is generally cylindrical in shape. There are two inner chambers 572, 573 in the housing which are separated by an internal wall 574. The distal chamber 572 is sized to have a light press fit over the holder 553 of the stapling mechanism 550. A pair of set screws 575 in the side wall 576 of the distal chamber 572 are provided to secure the housing 566 to the holder 553. The side wall 576 of the distal chamber 572 has pair of opposing open-ended slots 577 that are sized to fit over the T-shaped handle 560 of the staple driver 559 and allow the handle 560 to move axially within the slots 577. The proximal chamber 573 has an internal thread 579 that matches an external thread 579 on the clamp knob 570. A counterbored hole 580 through the internal wall 574 connects the proximal 573 and distal 522 chambers.

The cutter 567 of the vessel punch mechanism 551 is a long slender tubular member which is preferably made of a hardenable alloy of stainless steel. The distal end 581 of the cutter 567 is slightly enlarged with respect to the shaft 582 of the cutter 567, and there is a counterbore 583 within the enlarged distal end 581. The distal edge of the cutter 567 has a sharp, beveled cutting edge 584. Preferably, at least the cutting edge 584 of the tubular cutter 567 is hardened. The proximal end of the cutter shaft 582 has a snug press fit into the counter hole 580 through the internal wall 574 of the housing 566. The punch mechanism 551 also includes a clamp 569. The clamp 569 has a long tubular shaft 585 which is sized to be slidably received within the internal lumen 586 of the cutter shaft 582. An enlarged head 587 on the distal end of the shaft 585 is sized to fit within the counterbore 583 in the distal end of the cutter 567. The distal end of the enlarged head 587 has an annular clamping surface 588. The proximal end of the clamp shaft 585 is inserted into the cutter 567 and glued or otherwise fastened to the clamp knob 570 which is threaded into the proximal chamber 573 of the housing 566. The anvil 568 of the punch mechanism 551 is preferably made of stainless steel. The anvil 568 has an elongated shaft 589 that has a sliding fit with the internal lumen 590 of the clamp 569. An enlarged head 591 on the distal end of the shaft 589 is sized to fit within the counterbored distal end 583 of the cutter with a very close clearance between the head of the anvil 591 and the cutter 567. The proximal end of the shaft 589 is threaded to attach it to the punch knob 571. The punch knob 571 has a distal extension 592 which is threaded to fit into a threaded hole 593 on the proximal end of the clamp knob 570.

When the clamp knob 570 is rotated with respect to the housing 566, the clamp 569 is advanced proximally or distally with respect to the cutter 567. In its farthest distal position, the clamping surface 588 of the clamp 569 is just distal to the cutting edge 584 of the tubular cutter 567. When the punch knob 571 is rotated with respect to the clamp knob 570, the anvil 568 is advanced proximally or distally with respect to the clamp 569. By moving the anvil 568 proximally with respect to the clamp 569 when the clamp is in its farthest distal position, the tissue of the target vessel wall can be clamped between the clamp and the anvil. When the clamp knob 255 and the punch knob 571 are rotated in unison, the anvil 568 and the clamp 569 can be withdrawn into the tubular cutter 567 to effect the cutting action of the punch mechanism 551. Preferably, the clamp 569, the anvil 568 and the tubular cutter 567 are keyed to one another or otherwise rotationally fixed so that they move axially with respect to one another without relative rotation.

The punch mechanism 551, as it has just been described, is inserted into the stapling mechanism 550 through the lumen 249 of the graft vessel 254. The clamp 569 of the punch mechanism 551 should be advanced to its farthest distal position before inserting the punch 551 through the graft vessel 254 to avoid damaging the interior wall of the graft vessel 254 with the cutter 567 as it passes through. The set screws 575 in the housing 566 of the punch mechanism 551 are screwed into corresponding holes 594 in the holder 553 of the stapling mechanism 550 to secure the two interacting mechanisms together. The graft vessel 254 occupies an annular space 595 between the punch mechanism 551 and the interior surface of the stapling mechanism 550. Thus assembled, the anastomosis system, which includes the anastomosis device 533 attached to the graft vessel 254 and the application instrument 536, is prepared to perform an end-to-side anastomosis between the graft vessel 254 and a target vessel 255.

Figure 45A:
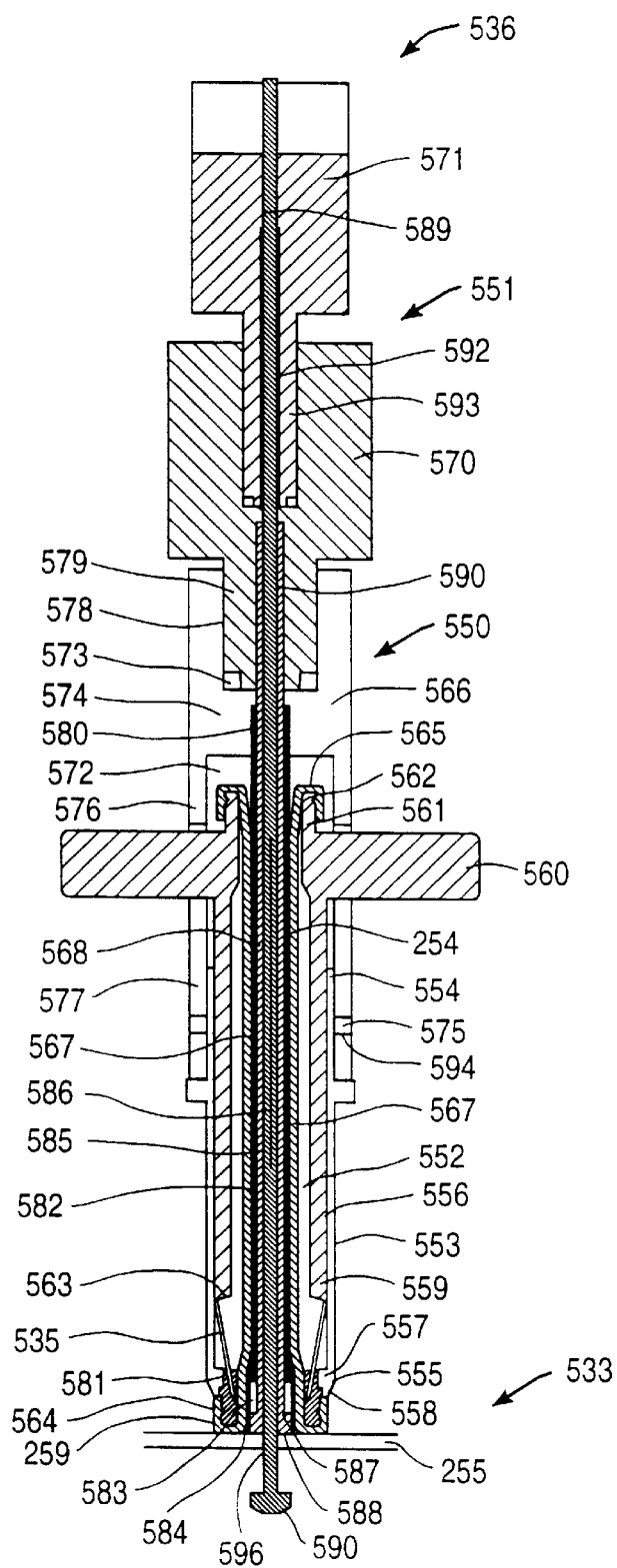
FIGS. 45A–45E show the sequence of operations of an application instrument for the anastomosis device of FIGS. 43A–43B and FIGS. 44A–44B.
Figure 45B:
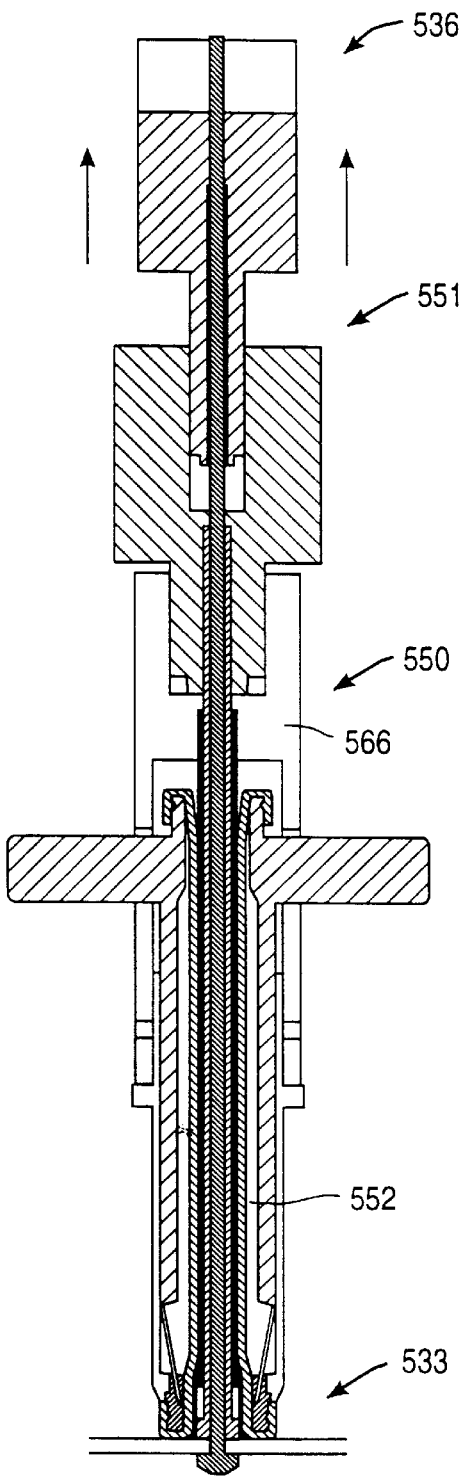

The operation of the application instrument 536 is illustrated in FIGS. 45A–45E. A slit 596 is made in the wall of the target vessel 255 with a scalpel or other sharp instrument. If it has not been done already, the clamp 569 of the punch mechanism 551 is advanced distally by turning the clamp knob 570 until the clamp surface 588 extends slightly beyond the cutting edge 584 of the cutter 567, and the anvil 568 of the punch mechanism 551 is advanced distally by turning the punch knob 571 until the anvil head 591 extends distally from the application instrument 536. The anvil head 591 of the punch mechanism 551 is inserted through the slit 596 into the lumen 256 of the target vessel 255, and the distal edge 541 of the fastening flange 534 with the everted end 259 of the graft vessel 254 attached is approximated to the exterior surface 258 of the target vessel 255, as shown in FIG. 45A. The target vessel wall 255 is then clamped by the punch mechanism 551 by turning the punch knob 571 to move the anvil head 591 proximally until the target vessel wall 255 is firmly gripped between the anvil head 591 and the clamp surface 588, as shown in FIG. 45B. The clamp feature of the punch mechanism 551 prevents the cutter 567 from prematurely cutting through the wall of the target vessel 255 and it provides a firm support to the target vessel wall 255 for the stapling step which follows.

If the anastomosis system is being used to create a proximal anastomosis between a graft vessel and the aorta during a CABG procedure, the clamping feature provides an additional benefit at this point in the procedure. In order to reduce the crossclamp time that the patient is subjected to, many cardiac surgeons prefer to perform the proximal anastomosis while the patient's heart is still beating. This requires isolating a portion of the aortic wall with a nonoccluding side-biting clamp to prevent excessive bleeding from the opening formed in the aorta. This has a number of disadvantages: 1) even a nonoccluding side-biting clamp presents additional resistance to aortic blood flow, possibly reducing cardiac output which may already be low, 2) the side-biting clamp tends to distort the aortic wall, making it harder to create a neat anastomosis, 3) conventional side-biting clamps are difficult to apply in a closed-chest or port-access thoracoscopic CABG procedure, and 4) side-biting clamps may break atherosclerotic tissue loose from the inner wall of the aorta, possibly causing strokes or other complications. The clamping feature reduces the need for the side-biting clamp by clamping directly to the aortic wall around the slit made by the scalpel for inserting the anvil. This creates a fluid-tight seal preventing bleeding through the aortotomy opening, so that the side-biting clamp can be released and removed from the site. It is also possible to avoid the need for the side-biting clamp entirely by quickly inserting the anvil head 591 of the punch mechanism 551 and tightening the clamp 569 immediately after creating the aortotomy slit before significant blood loss can occur. If the head of the anvil 591 were made with a blade or trocar extending from its distal surface, the device 536 could pierce and dilate an opening in the aorta wall in the same motion as inserting the anvil 591 through the opening, potentially saving time and blood loss.

Figure 45C:
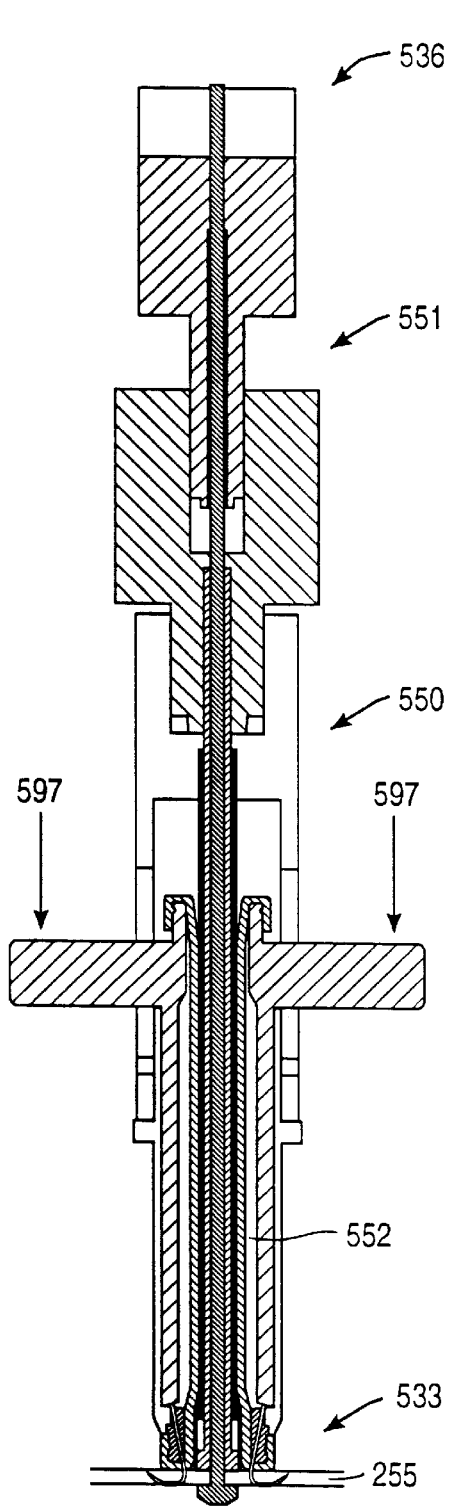

In the stapling step, the staple driver 559 is advanced distally by pressing on the T-shaped handle 560, as shown by arrows 597 in FIG. 45C. This causes the distal end 563 of the staple driver 559 to press against the crossbars 545 of the staple members 535 and forces the attachment legs 544 to exit through the holes 539 in the distal end 541 of the fastening flange 534. As the attachment legs 544 emerge from the holes 539, the sharpened distal ends 546 of the attachment legs 544 pierce the graft vessel wall 259 and the short straight section 548 traverses the graft vessel wall 259 in a linear path. Optionally, the staples 535 can be advanced through the graft vessel wall 259 before the graft vessel 259 is approximated to the target vessel 255 so that the surgeon can verify that all of the staple attachment legs 544 have properly pierced the everted graft vessel wall 259. The sharpened distal ends 546 of the attachment legs 544 then pierce the target vessel wall 255. The clamping feature 569 of the punch mechanism 551 supports the target vessel wall 255 and keeps it closely approximated to the everted end 259 of the graft vessel 254 as the staple members 535 penetrate it. As the attachment legs 544 penetrate the target vessel wall 255, the curved sections 547 of the attachment legs 544 emerge from the confinement of the holes 539 in the fastening flange 534 and the elastic memory of the unrestrained curve causes the attachment legs 544 to take a curved path outwardly from the central orifice 537 through the target vessel wall 255. The distal ends 547 of the attachment legs 544 resume their J shape, as shown in FIG. 45C, firmly attaching the fastening flange 534 and the everted graft vessel 259 to the exterior surface 258 of the target vessel 255.

Figure 45D:
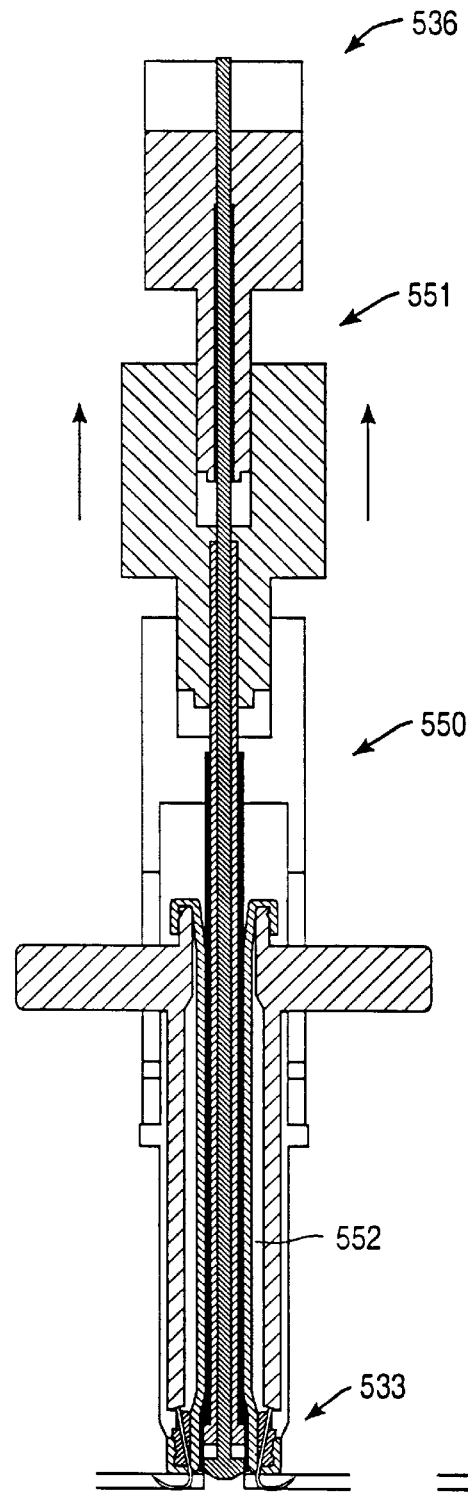
Figure 45E:
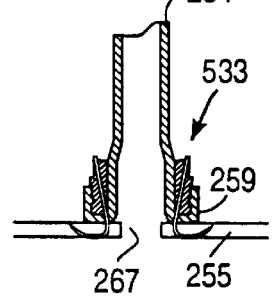

Once the fastening flange 534 and the graft vessel 254 are attached, an opening 267 is made in the target vessel wall 255 by turning the clamp knob 570 and punch knob 571 in unison to withdraw the anvil 568 and the clamp 569, with the target vessel wall 255 gripped between them, into the tubular cutter 567, as shown in FIG. 45D. This action shears off a small, circular portion of the target vessel wall 255 to form a fluid communication between the lumen 256 of the target vessel 255 and the lumen 249 of the graft vessel 254. To complete the anastomosis, the fastening flange 534 is released from the holder 553 and the punch mechanism 551 and the entire application instrument 536 are withdrawn, as shown in FIG. 45E.

FIGS. 46A–46D illustrate a second embodiment of the anastomosis system using an anastomosis device 600 with an inner fastening flange 601, an outer flange 602 and staple members 603 made of a superelastic nickel-titanium alloy. The system includes a stapling mechanism 604 for attaching the anastomosis device 600 to the wall of the target vessel 255 through a previously made opening 267. The anastomosis device 600 has a fastening flange 605, which is shown in top view in FIG. 46C and in side cross section views in FIGS. 46A and 46B. The fastening flange 605 includes a tubular body 606 which has an internal lumen 607 of sufficient diameter to accommodate the external diameter of the graft vessel 254. Attached to the distal end of the tubular body 606 is an inner flange 601 over which the free end 259 of the graft vessel 254 will be everted. On the proximal end 610 of the tubular body 606 are three radially extending lugs 608, which facilitate grasping the anastomosis device 600 while performing the anastomosis. The exterior of the tubular body 606 has an external step 609 so that it is slightly larger in diameter at its proximal end 610 than at its distal end 611. The interior of the tubular body 606 has an internal step 612 so that the internal diameter of the tubular body is slightly smaller at the distal end 610 than at the proximal end 611. A plurality of holes 613 pass through the fastening flange 605 from the internal step 612 to the distal surface 611 of the inner flange 601. The holes 613 are arranged in pairs, six pairs in this illustrative example, to accommodate a like number of staple members 603.

An outer flange 602 is concentrically located on the tubular body 606. The outer flange 602 is attached to the tubular body 606 by a self-locking ring washer 614 which has inclined lugs 615 which allow the ring washer 614 to slide distally with respect to the tubular body 606, but which prevent it from sliding proximally. The ring washer 614 can be made integrally with the outer flange 602 or a separate sheet metal ring washer 614 can be attached to the outer flange 602, as illustrated. The internal orifice 616 of the ring washer 614 and the outer flange 602 is made with three wide slots 617 between the inclined lugs 615 to allow them to be placed onto the tubular body 606 over the lugs 615 which extend from the proximal end 610 of the tubular body 606. The outer flange 602 has a distal surface 618 which is slightly concave. The peripheral edge 619 of the outer flange 602 has six notches 620 cut into it which coincide with the location of the distal ends 621 of the staple members 603 after they are deployed, as shown in FIG. 46C.

The staple members 603 are generally an inverted U shape when viewed from the front as in FIG. 46D. Two attachment legs 622 are joined together at their proximal ends by a crossbar 623. Viewed from the side as in FIG. 46B, the staple members are somewhat J-shaped with the sharpened distal ends 624 curving back in the proximal direction. The staple members 603 are preferably formed from wire made of a highly resilient biocompatible metal such as a spring-tempered alloy of stainless steel, titanium, or cobalt, or more preferably of a superelastic metal alloy, such as a nickel-titanium alloy.

For clarity only the distal end of the stapling mechanism 604 has been shown in FIG. 46A. Suitable handle means are provided at the proximal end for actuating the stapling mechanism 604. The stapling mechanism 604 has an outer sleeve 625, which is a tubular member having three L-shaped fingers 626 extending from its distal end that grasp the radially extending lugs 615 on the proximal end of the tubular body 606 like a bayonet connector. The clamp sleeve 627 is a tubular member which slides telescopically over the exterior of the outer sleeve 625. A staple guide 628 resides within the outer sleeve 625. The staple guide 628 is a tubular member having a plurality of slots 629, equal to the number of staple members 603 in the anastomosis device, extending through the wall from the proximal end to the distal end of the guide 628. The slots 629 in the guide 628 are sized to fit the staple members 603 therein and to constrain the J-shaped attachment legs 622 of the staple members 603 in a straight position prior to deployment, as shown in FIG. 46A. The staple guide 628 can be made by cutting a plurality of slots 629 through the wall of the tubular member with electrical discharge machining, or the staple guide 628 can be made from two closely fitting concentric tubes by cutting slots like splines in the external surface of the inner tube and sliding the outer tube over it to close the slots. The staple driver 630 is a tubular member which is slidably received within the outer sleeve 625. A plurality of fingers 631 extend from the distal end of the staple driver 630. The fingers 631 of the staple driver 630 are sized to be slidably received within the slots 629 of the staple guide 628.

The anastomosis device 600 is prepared by inserting the staple members 603 into the slots 629 in the staple guide 628 in the stapling mechanism 604. The staple guide 628 holds the staple members 603 in a straightened position within the stapling mechanism 604. The fastening flange 605 is inserted into the stapling mechanism 604 and the radially extending lugs 608 are grasped by the L-shaped fingers 626 of the outer sleeve 625. The staple holes 613 through the tubular body 606 are carefully aligned with the distal ends 621 of the staple members 603 and the staple driver 630 is advanced slightly to start the staple members 603 into the holes 613. The anastomosis device 600 is now prepared to perform an end-to-side anastomosis between a graft vessel 254 and the wall of a target vessel 255 as follows.

To begin, the graft vessel 254 is inserted through the central lumen 607 of the fastening flange 605 and the internal lumen 632 of the stapling mechanism 604 by drawing it through with a suture or an elongated grasping instrument. The distal end 259 of the graft vessel 254 is then everted over the inner flange 601 on the distal end 611 of the fastening flange 605. The inner flange 601 with the everted end 259 of the graft vessel 254 attached is inserted through an opening 267 in the target vessel wall 255 that has previously been made using an aortic punch or similar instrument. The staple driver 630 is advanced distally, causing the sharpened ends 621 of the staple members 603 to pierce the everted wall 259 of the graft vessel 254 and enter the lumen 256 of the target vessel 256. As the staple members 603 emerge from the distal end 611 of the fastening flange 605, the attachment legs 622 resume their J-shaped curve and penetrate the interior surface 257 of the target vessel wall 255, as shown in FIG. 46D. Once the staple members 603 are completely deployed, the clamp sleeve 627 is advanced distally with respect to the outer sleeve 625, which forces the outer flange 602 to move in the distal direction with respect to the tubular body 606. As the outer flange 602 moves distally, the inner flange 601 and the target vessel wall 255 are pulled into the concave distal surface 618 of the outer flange 602 to form a smooth, hemodynamically efficient connection between the lumen 256 of the target vessel 255 and the lumen 249 of the graft vessel 254. The stapling mechanism 604 is now removed by rotating the outer sleeve 625 to release its grasp on the tubular body 606 and withdrawing the entire stapling mechanism 604. It should be noted that the embodiment of FIG. 46, like the embodiment of FIG. 43, could optionally be manufactured without an inner flange 601, whereby the inner wall 257 of the target vessel 255 is supported by the staple members 603 themselves.

Figure 47A:
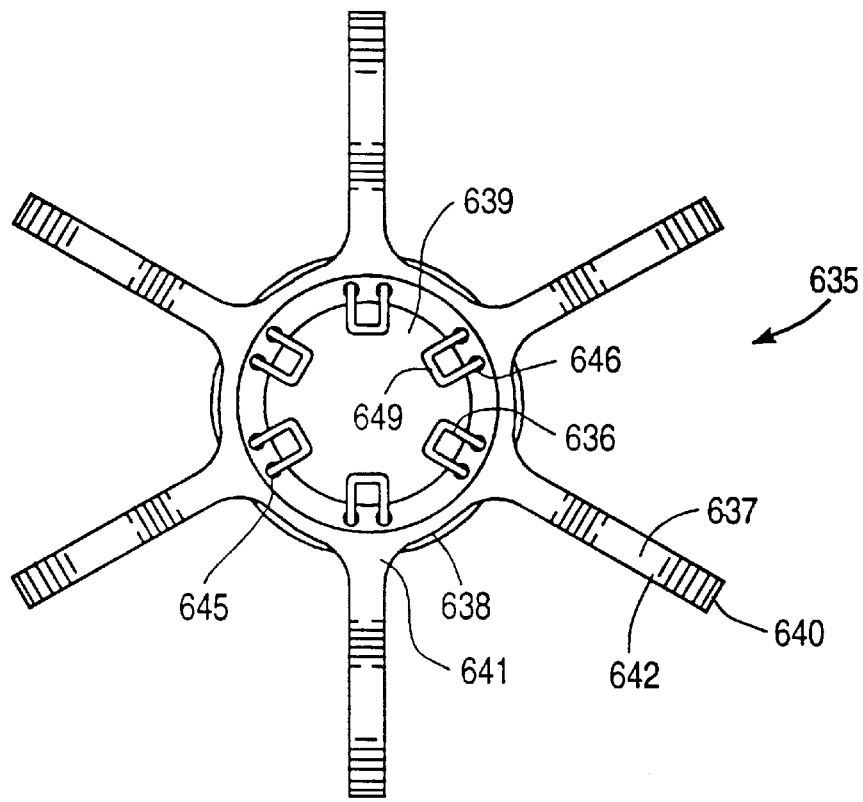
FIGS. 47A–47B show an anastomosis staple device combining a fastening flange with precurved inner staple members of a highly resilient material and deformable outer attachment legs in an undeployed state.
Figure 47B:
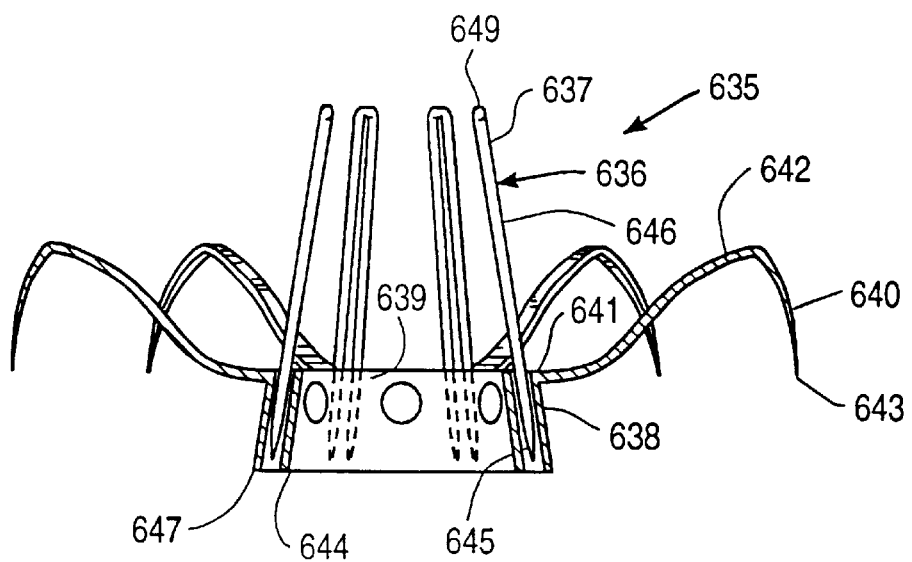
Figure 48A:
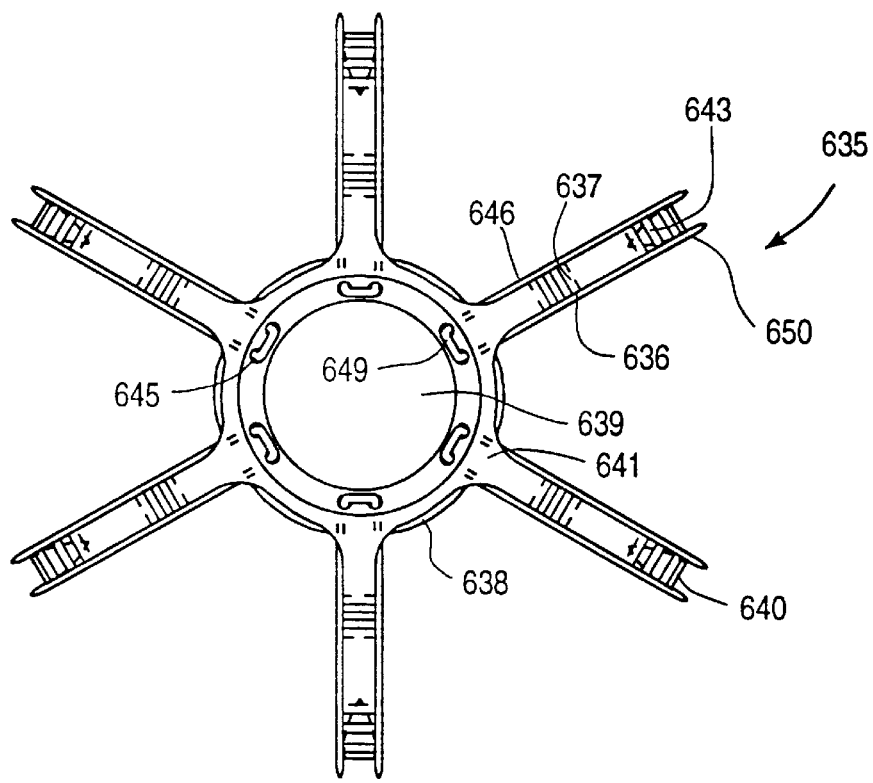
FIGS. 48A–48B show the anastomosis staple device of FIGS. 47A–47B in a deployed state.
Figure 48B:
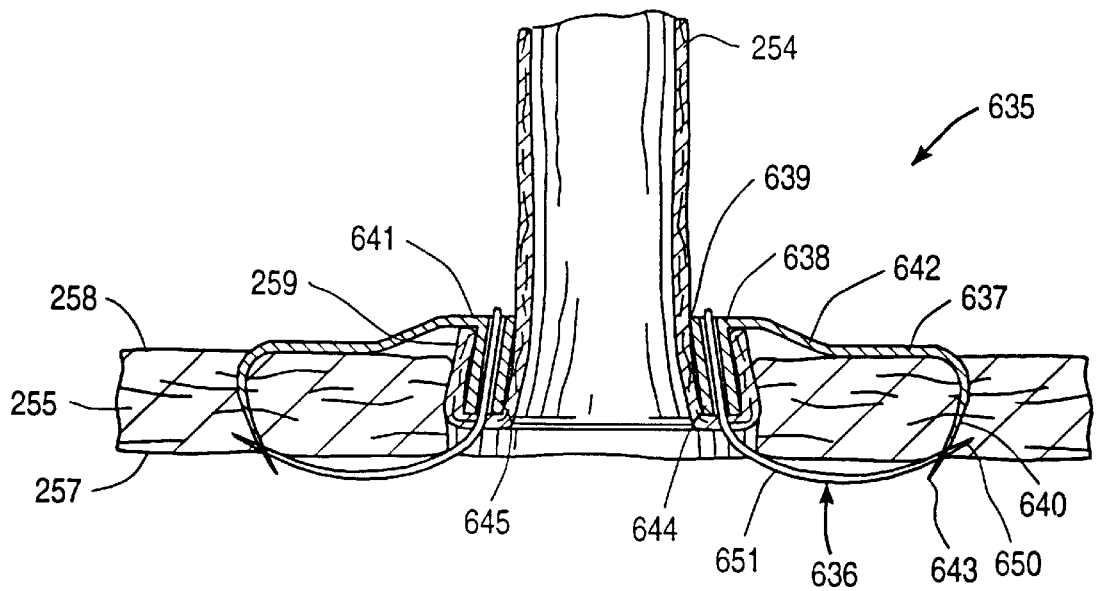

FIGS. 47A–47B, 48A–48B, and 49A–49C show an anastomosis staple device 635 which combines a plurality of precurved inner staple members 636 of a highly resilient material with a plurality of deformable outer attachment legs 637. FIGS. 47A–47B show a top view and a side cross section view of the anastomosis staple in an undeployed state. FIGS. 47A–47B show a top view and a side cross section view of the anastomosis staple in a deployed state. FIGS. 49A–49C show the sequence of operations for deploying the anastomosis staple device. As shown in FIGS. 47A–47C, the device 635 has a ring-shaped bushing 638 with an internal diameter 639 of sufficient size to accommodate the exterior diameter of the graft vessel 254. A plurality of deformable attachment legs 637, six in this exemplary embodiment, are attached to the proximal end of the ring-shaped bushing 638. The deformable attachment legs 637 are preferably made of a metal which can be plastically deformed and which will maintain its final deformed shape, such as stainless steel or a titanium alloy. The attachment legs 637 can be machined integrally with the ring-shaped bushing 638 as shown, or the attachment legs 637 can be made separately, for instance by stamping, electrical discharge machining or die cutting a ring of attachment legs 637 from sheet metal, and fastening the attachment legs 637 to the ring-shaped bushing 638. The attachment legs 637 are typically 0.012 inches thick, 0.040 inches wide and 0.230 inches long. The thickness and width of the attachment legs can vary somewhat depending on the stiffness of the material chosen for the attachment legs 637. It may be desirable to radius the edges of the attachment legs 637 or to make the attachment legs 637 round in cross section in order to reduce the potential for initiating cracks or tears in the target vessel wall 255. The length of the attachment legs 637 can be varied to accommodate different wall thicknesses of the graft vessels 254 and target vessels 255 to be attached.

The attachment legs 637 are typically formed flat, then bent or stamped into a curved configuration as shown in FIGS. 47B. The distal portion 640 of each attachment leg 637 is curved in a circular arc whose center coincides approximately with the point of attachment 641 between the attachment leg 637 and the ring-shaped bushing 638. The attachment point 641 serves as the bending fulcrum for the attachment legs 637 when they are deformed during the anastomosis procedure. The intermediate portion 642 of the attachment legs 637 can be left relatively straight, or an intermediate curve 642 can be formed in the attachment legs 637, as shown in FIG. 47B. The distal ends 643 of the attachment legs 637 are sharpened so that they will easily penetrate the target vessel walls 255.

The ring-shaped bushing 638 has a distal surface 644 over which the end 259 of the graft vessel 254 will be everted. The distal end 644 of the ring-shaped bushing 638 is flared out slightly to provide a more secure attachment of the everted end 259 of the graft vessel 254 to the bushing 638. There are a plurality of axial holes 645 in the wall of the ring-shaped bushing 638 which communicate with the distal surface 644 of the bushing 638. The holes 645 are sized to have a close sliding clearance with the legs 646 of the inner staple members 636. Preferably, the axial holes 645 are arranged in pairs to accommodate both legs of U-shaped inner staple members 636. As shown in FIG. 47A, the currently preferred embodiment has six pairs of axial holes 645 for six U-shaped inner staple members 636. The axial holes 645 are angled outward slightly, typically by about 10 degrees, from the central axis of the ring-shaped bushing 638. Angling the axial holes 645 outward tends to reduce the distance from the distal surface 644 of the bushing 638 to the bottom of the curve of the staple members 636 once the staple members 636 have been deployed. There are also a plurality of transverse holes 647 through the wall of the ring-shaped bushing 638 to facilitate gripping the bushing 638 with the staple application instrument 648.

The staple members 636 are generally an inverted U shape when viewed from the front as in FIG. 47A. Two staple legs 646 are joined together at their proximal ends by a crossbar 649. Viewed from the side as in FIG. 48B, the deployed staple members 636 are somewhat J-shaped with the sharpened distal ends 650 curving back approximately 180 degrees in the proximal direction. The staple members 636 are preferably formed from wire made of a highly resilient biocompatible metal such as a spring-tempered alloy of stainless steel, titanium, or cobalt, or more preferably of a superelastic metal alloy, such as a nickel-titanium alloy. The anastomosis staple device 635 is prepared for use by inserting the curved distal ends 651 of the J-shaped staples into the axial holes 645 in the ring-shaped bushing 638. The internal walls of the axial holes 645 hold the curved ends 651 of the staple members 636 in a straightened position within the ring-shaped bushing 638.

The anastomosis staple of FIGS. 47A–47B and 48A–48B is part of a complete anastomosis system which includes a specialized staple application instrument 648 for performing the anastomosis procedure. The staple application instrument 648 is shown in FIGS. 50A–50B. As seen in FIG. 50B, the instrument 648 has a gripper 652 which is adapted to hold the ring-shaped bushing 638 of the staple device. The gripper 652 is a generally tubular member that has a plurality of gripping fingers 653 extending axially from its distal end. Each of the gripping fingers 653 has an inwardly turned distal tip 654 which is sized to fit into one of the transverse holes 647 in the ring-shaped bushing 638. The gripping fingers 653 are spring-biased outward. A combination gripper actuator and outer attachment leg driver 655 is slidably received on the exterior of the gripper shaft 656. The actuator/driver 655 is generally tubular in shape, having a lumen 657 with a close sliding fit over the exterior of the gripper 652 and a radiused annular staple driving surface 658 on its distal end. When the actuator/driver 655 is slid distally over the exterior of the gripping fingers 653, the outwardly biased fingers 653 are pressed inward so that they grip the ring-shaped bushing 638 by engaging the transverse holes 647.

An inner staple driver 659 is slidably received within the inner lumen 661 of the tubular shaft 656 of the gripper 652. The inner staple driver 659 has an annular staple driving surface 660 on its distal end. The inner staple driver 659 has an internal lumen 662 that can accommodate the graft vessel 254 during the anastomosis procedure. The gripper 652, the actuator/driver 655 and the inner staple driver 659 are held together by a pair of alignment pins 663 which are threaded into the wall of the actuator/driver 655. The gripper shaft 656 has a pair of opposing axial slots 664 that allow it to slide axially with respect to the actuator/driver 655. The inner staple driver 659 has a pair of opposing L-shaped slots 665 oriented to allow the inner staple driver 659 to slide axially with respect to the gripper 652 and the actuator/driver 655. The inner staple driver 659 can be moved to a locked position to prevent premature activation of the inner staples 636 by withdrawing it distally and rotating it so that the alignment pins 663 enter the L-shaped portion 666 of the slots 665.

In preparation for the anastomosis procedure, the proximal end of the ring-shaped bushing 638, with the proximal ends of the inner staples 636 extending from it, is inserted into the gripper 652 with the transverse holes 647 aligned with the ends 654 of the gripping fingers 653. The inner staple driver 659 should be withdrawn to the locked position before the staple device 648 is inserted. The actuator/driver 655 is advanced distally, causing the ends 654 of the gripping fingers 653 to flex inward and engage the transverse holes 647 in the ring-shaped bushing 638. The actuator driver 655 can be advanced distally until it rests against, but does not deform, the attachment leg 637 of the staple device 635.

At this point the graft vessel 254 is passed through the internal lumen 662 of the staple applying instrument 648 until a short length of the graft 254 extends from the distal end of the instrument 635. The end 259 of the graft 254 is then everted over the distal surface 644 of the ring-shaped bushing 638. If desired, a loop of suture can be tied around the everted end 259 of the graft vessel 254 to secure it to the bushing 638. The staple instrument 635, with the everted end 259 of the graft vessel 254 attached, is approximated to the exterior surface 258 of the target vessel 255 where an opening 267 in the target vessel wall 255 has previously been made with a vessel punch or similar instrument. If the anastomosis is part of a port-access CABG procedure, the instrument 635 is inserted into the chest of the patient through an access port made in one of the intercostal spaces.

The ring-shaped bushing 638 is inserted into the opening 267 in the target vessel wall 255 to approximate the intimal surface on the everted end 259 of the graft vessel 254 with the intimal surface 257 of the target vessel 255, as shown in FIG. 49A. Preferably, the opening 267 in the wall of the target vessel 255 is made slightly smaller than the outer diameter of the ring-shaped bushing 638 so that there is some compression around the bushing 638 which helps to seal the anastomosis against leakage. The inner staple driver 659 is rotated to release it from the locked position and advanced distally to drive the inner staple members 636 through the everted wall 259 of the graft vessel 254. As the staple members 636 exit the axial holes 645 in the bushing 638, they resume their J-shaped curve 651 so that they curve back distally and penetrate the interior surface 257 of the target vessel wall 255, as shown in FIG. 49B. After the inner staple members 636 have been deployed, a light tension is exerted on the staple applying instrument 648 to make sure that the inner staple members 636 are well seated and the actuator/driver 655 is advanced distally to deform the outer attachment legs 637. The sharpened distal ends 643 of the attachment legs 637 penetrate the exterior 258 of the target vessel wall 255 in a circular arc, gathering the tissue and compressing it against the exterior of the ring-shaped bushing 638 and the everted edge 259 of the graft vessel 254 to form a leak-proof anastomotic seal, as shown in FIG. 49C. The actuator/driver 655 is withdrawn in the proximal direction, thereby releasing the ring-shaped bushing 638 from the gripper 652, and the entire staple applying instrument 648 is withdrawn from the anastomosis site.

Figure 51:
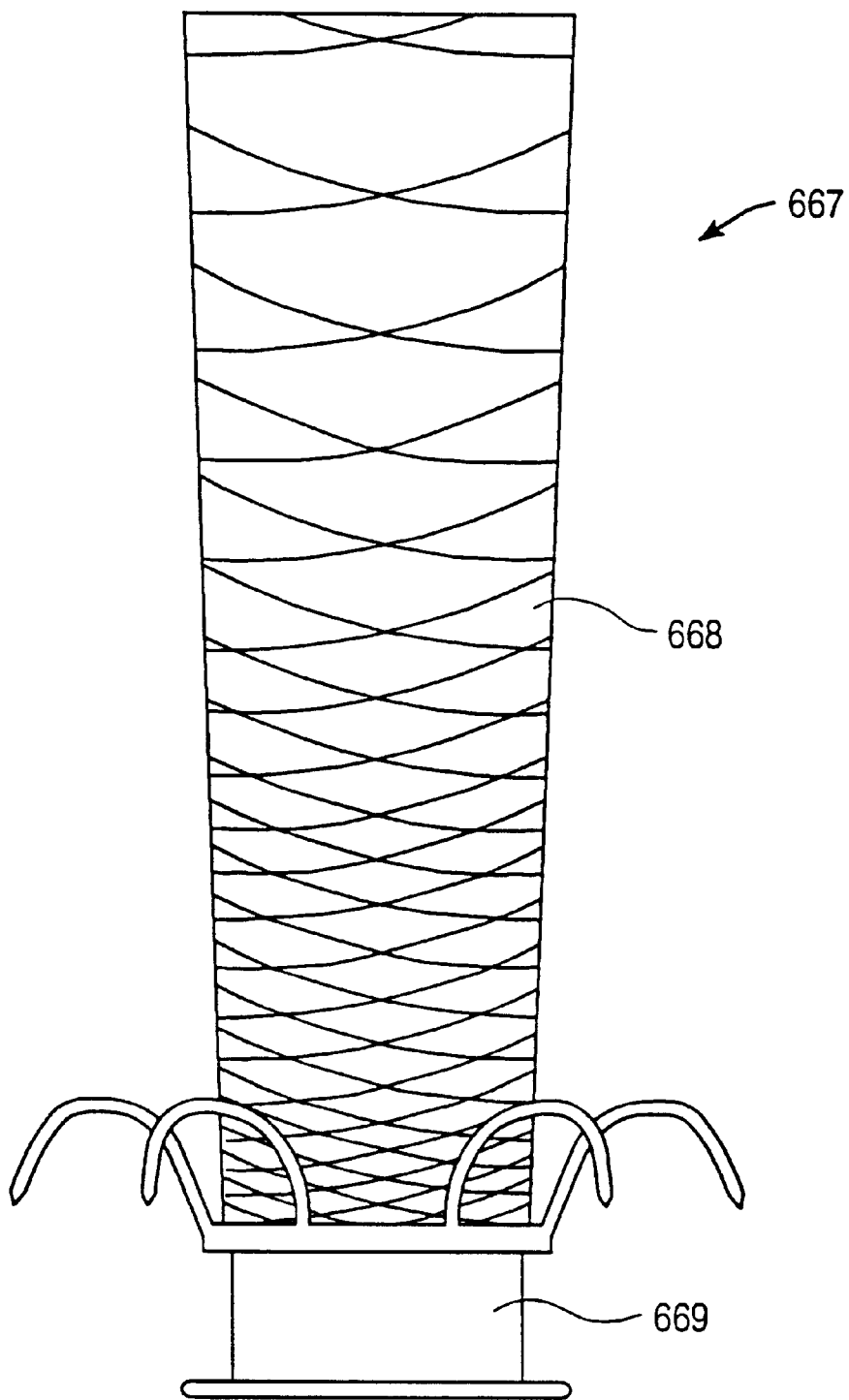
FIG. 51 shows a combination strain relief and compliance mismatch transition sleeve for use with any of the anastomosis devices of the present invention.

FIG. 51 shows an additional feature which can be used with any of the anastomosis devices described above. This feature is a combination strain relief and compliance mismatch transition sleeve 667. One of the current theories about long-term patency and the causes of restenosis in bypass grafts proposes that the mismatch in vessel compliance between the target vessels, which include the aorta and the coronary arteries, and the graft vessel, typically a saphenous vein, can contribute to the development of intimal hyperplasia, stenosis and occlusion in the graft vessel, especially at the anastomosis where the compliance mismatch is most apparent. Joining a highly compliant vessel, such as a saphenous vein, to a relatively noncompliant vessel, like the aortic wall, places extra strain on the vessels and on the anastomosis. Another cause for mismatched compliance at an anastomosis site is the joining of a compliant blood vessel with a highly noncompliant artificial graft vessel. Additionally, turbulence in the blood flow at the anastomosis site may exacerbate the problem, accelerating the stenosis process. It is preferable that all of the vessels be equally compliant or at least that there is a gradual transition in compliance from one vessel to another. As such, it would be desirable to provide the anastomosis devices with a means to create a gradual transition in compliance between the vessels at the anastomosis site.

Another concern in anastomosis procedures is to create a gradual curve in the graft vessel leading away from the anastomosis site. This is sometimes necessary because the most convenient angle for attaching the graft vessel to the target vessel does not match the desired path for the graft vessel away from the anastomosis. For instance, in CABG surgery the desired path for the graft vessel is often parallel to the ascending aorta, however the graft vessel must be joined to the ascending aorta at some angle in order to create the anastomosis. Creating a gradual curve leading away from the anastomosis site to avoid kinking or narrowing of the graft vessel lumen is sometimes problematic. This is especially true when the graft vessel is joined at right angles to the ascending aorta. It would be desirable therefore to provide the anastomosis devices with a reliable means to create a gradual curve in the graft vessel leading away from the anastomosis site.

The combination strain relief and compliance mismatch transition sleeve 667 is a flexible tubular member 668 which can be appended to the proximal end of the anastomosis device 669 to support the graft vessel 254 leading away from the anastomosis site. The flexible tubular member 668 may have any or all of gradually decreasing stiffness, increasing compliance and increasing diameter as it extends proximally from the anastomosis device 669. This will give the graft vessel 254 a gradual curve, a gradual change in its radial compliance, and a gradual change in diameter from the constrained diameter within the anastomosis device 669 to an unconstrained diameter some distance from the device 669.

The strain relief sleeve 667 can be made in any one of several possible constructions, including braided wire or monofilament, a wire or plastic coil, a solid polymer tube or a composite construction, such as a wire coil embedded in a polymer wall. The strain relief sleeve 667 may also be made of a soft, stretchy, biocompatible polymer, such as polyurethane, silicone, or Cortex (expanded PTFE).

Figure 52:
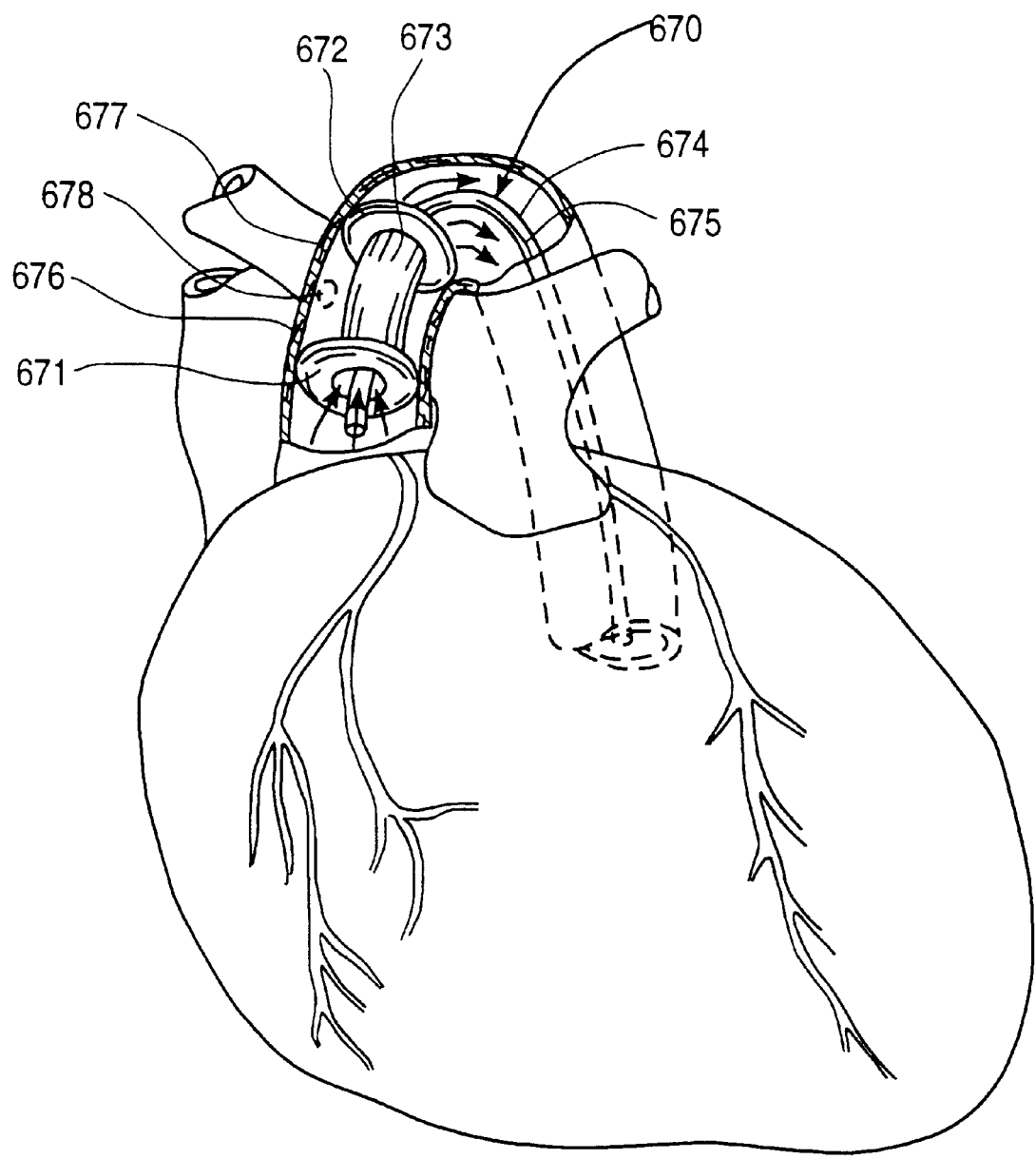
FIG. 52 shows a dual-balloon perfusion endoaortic clamp catheter for isolating a portion of the aortic wall while performing a proximal anastomosis in CABG surgery.

FIG. 52 shows a device 670 for isolating a portion of the target vessel lumen 256 to facilitate performing an anastomosis using any of the devices and techniques described herein. The isolation device 670 may be used as an alternative to the side-biting clamp described above for use in the proximal anastomosis procedure during CABG surgery. The side-biting clamp is used in CABG surgery to isolate a portion of the aortic wall so that the proximal anastomosis can be performed while the heart is still beating without excessive bleeding at the anastomosis site. Placing a side-biting clamp thoracoscopically during port-access CABG surgery may prove problematic. A perfusion endoaortic clamp catheter 670, as shown in FIG. 52, performs the same functions as the side-biting clamp with a percutaneously placed catheter. The catheter 670 has a first doughnut-shaped balloon 671 and a second doughnut-shaped balloon 672 which are interconnected by a large-bore perfusion tube 673. The balloons 671 672 and the perfusion tube 673 are mounted on the distal end of an elongated catheter shaft 674. The balloons 671, 672 and the perfusion tube 673 are preferably made of a semi-elastic polyurethane material so that it can be collapsed for percutaneous entry and so it will resume the appropriate shape when they are deployed. The catheter shaft 674 may have a single inflation lumen 675 which connects to both balloons 671, 672 or separate inflation lumens connected to each balloon. If desired, the catheter 670 may also be provided with a flushing lumen which connects to a flushing port located on the exterior of the perfusion tube 673 between the balloons 671, 672 for flushing the anastomosis site 678 with clear saline to improve visibility.

In operation, the balloons 671, 672 and the perfusion tube 673 are introduced percutaneously into a peripheral artery, such as the femoral artery and advance into the ascending aorta 676, preferably under fluoroscopic visualization. When the surgeon is prepared to make the aortotomy incision to start the proximal anastomosis procedure, the first and second balloons 671, 672 are inflated, isolating the portions of the aortic wall 677 between the two balloons 671, 672 from the blood flow in the aorta. Blood continues to flow through the large-bore perfusion tube 673, supplying the rest of the body with blood. With the aortic wall 677 isolated, the aortotomy incision can be made at the anastomosis site 678 and the anastomosis completed by any of the methods described in the specification. After the anastomosis is complete, the balloons 671, 672 are deflated and the catheter is withdrawn from the aorta 676.

This catheter approach has certain advantages over the use of a side-biting clamp. First, it isolates a larger portion of the aortic wall so that the surgeon has more choice in the placement of the anastomotic sites. Second, because it isolates a larger portion of the aortic wall it also allows multiple anastomoses to be made to the aorta without having to move the clamp. Third, it does not distort the wall of the aorta as the side-biting clamp does. This may allow more accurate placement of the anastomotic sites and more effective attachment of the anastomosis devices and therefore reduced leakage of the anastomoses.

A second, smaller scale version of a similar catheter device 679 is shown in FIG. 53 for isolating a section of a coronary artery 682 while performing a distal anastomosis. This device would allow the section of the coronary artery 682 close to the anastomosis to be isolated from the blood flow without blocking blood flow to vital myocardium downstream of the anastomosis site. The availability of rapid and reliable anastomosis devices, such as those described herein, could open the door to performing CABG surgery on patients whose hearts are still beating, with no need at all for cardioplegic arrest. The rapidity of the anastomosis procedure using these devices will minimize the interference from the wall motion of the beating heart that makes hand sutured anastomoses problematic. However, two other obstacles remain:

1) excessive bleeding at the anastomotic site when the coronary artery is incised, and 2) temporary ischemia of the myocardial tissue downstream of the anastomosis site. The catheter 679 in FIG. 53 solves both of these potential problems.

The distal end of the catheter has a distal balloon 680 and a proximal balloon 681 separated by a few centimeters distance along the catheter shaft 683. The balloons 680, 681 may be elastic balloons made of latex, polyurethane or silicone, or they may be inelastic balloons made of polyethylene, polyester or polyamide. The catheter shaft 683 may have a single inflation lumen 648 which connects to both balloons 680, 681 or separate inflation lumens connected to each balloon. If desired, the catheter 679 may also be provided with a flushing lumen which connects to a flushing port located on the catheter shaft 683 between the balloons 680, 681 for flushing the anastomosis site 690 with clear saline to improve visibility. In addition, the catheter shaft 683 has a perfusion lumen 685 for blood flow through the catheter 679. The perfusion lumen 685 has one or more inflow ports 686 on the catheter shaft 683 proximal to both of the balloons 680, 681 and at least one outflow port 687 at the end of the catheter 679, distal to both of the balloons 680, 681.

In operation, the catheter 679 is introduced into the coronary artery 682 through a coronary guiding catheter 688 which is preferably introduced percutaneously from the femoral or brachial artery. The distal balloon 680 is advanced past the stenosis 689 in the artery 682, preferably under fluoroscopic visualization, and placed distal to the desired anastomosis site 690. The proximal balloon 681 is placed proximal to the desired anastomosis site 690 at a point which may be proximal or distal to the stenosis 689. The inflow ports 686 of the perfusion lumen 685, however, should be located proximal to the stenosis 689. The proximal 681 and distal 680 balloons are inflated to isolate the area between them from the blood flow through the coronary artery 682. Blood continues to flow into the artery distal to the catheter 679 through the perfusion lumen 685. The distal anastomosis procedure can now be performed on the isolated section of the coronary artery. When the anastomosis is complete, the balloons 680, 681 are deflated and the catheter 679 is withdrawn.

A third catheter device 691 is shown in FIG. 54. This catheter device 691 is configured to be delivered to the anastomosis site through the lumen 249 of the graft vessel 254 which has a number of potential advantages. First, the device 691 can be used without the need for a femoral or brachial artery puncture or a coronary guiding catheter to deliver the catheter 691 into the coronary arteries 682. Second, the catheter 691 can be deployed under direct or endoscopic visualization by the surgeon without the need for fluoroscopic imaging. Third, the T-shaped configuration of the catheter 691 can help to facilitate approximation of the graft vessel 254 and the target vessel 255 during the anastomosis procedure.

The catheter 691 has a proximal catheter body 692 connected to a T-shaped distal portion 693. The T-shaped distal portion 693 has two distal ends 694, 695, each having an inflatable balloon 696, 697 at its distal extremity. The balloons 696, 697 are each connected to one or more inflation lumens 698 that terminate in a luer fitting at the proximal extremity of the proximal catheter body 692. A perfusion lumen 699 connects a separate luer fitting at the proximal extremity of the proximal catheter body 692 to the extremities of both distal ends 694, 695 of the catheter 691, distal to the inflatable balloons 696, 697.

In operation, the T-shaped distal end 693 of the catheter is passed through the lumen 249 of the graft vessel 254 with the balloons 696, 697 deflated. An incision 700 is made in the wall of the coronary artery 682 or other vessel at the desired anastomosis site and both distal ends 694, 695 of catheter 691 are introduced into the coronary artery 682 through the incision 700. One distal end 695 of the catheter 691 is directed upstream of the anastomosis site and the other distal end 694 is directed downstream of the anastomosis site. Both of the balloons 696, 697 are inflated to isolate the portion of the coronary artery 682 between the balloons 696, 697 from the blood flow in the artery. Two modes of perfusion are possible with the catheter 691. If the upstream end 695 of the distal portion 693 of the catheter 691 receives enough blood flow, the blood will pass through the perfusion lumen 699 from the upstream side 695 to the downstream side 694 to perfuse the coronary artery 682 distal to the anastomosis site 700. If the blood flow is insufficient because of a severe stenosis or total occlusion upstream of the anastomosis site 700, blood and/or cardioplegic fluid can be injected into the catheter 691 through the luer fitting connected to the perfusion lumen 699 at the proximal end of the catheter 691.

With the anastomosis site 700 isolated from the blood flow, the graft vessel 254 can be approximated to the target vessel with the T-shaped catheter body 693 providing a guide for the approximation. The anastomosis can be performed in a blood-free environment using any one of the devices and methods described above. When the anastomosis is complete, the balloons 696, 697 can be deflated and the catheter withdrawn through the lumen 249 of the graft vessel 254.

The catheter devices described above are not limited in their use to CABG surgery. Either of the catheter devices could easily be modified to be the appropriate size for use during other bypass operations such as aorto-femoral bypass or femoral-femoral bypass.

Figure 59:
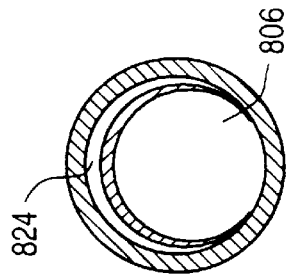
FIG. 59 is a cross-sectional view of the first coronary shunt of FIG. 58 along line A—A.
Figure 61:
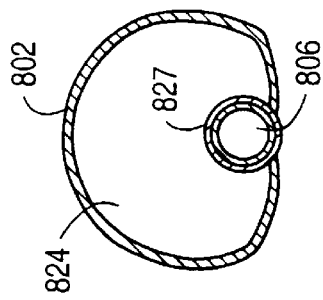
FIG. 61 is a cross-sectional view of the first coronary shunt of FIG. 60 along line B—B.
Figure 58:
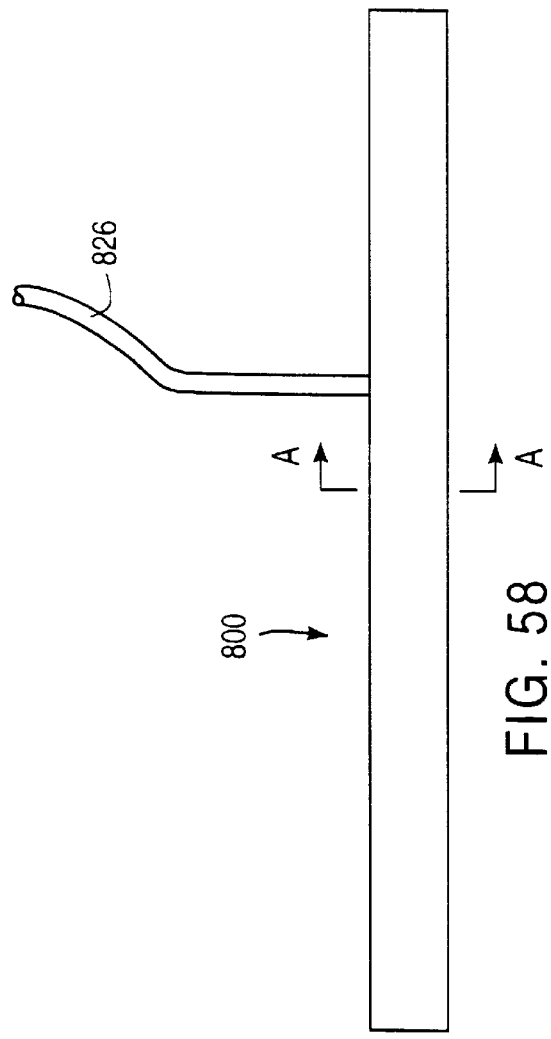
FIG. 58 shows a first coronary shunt.
Figure 60:
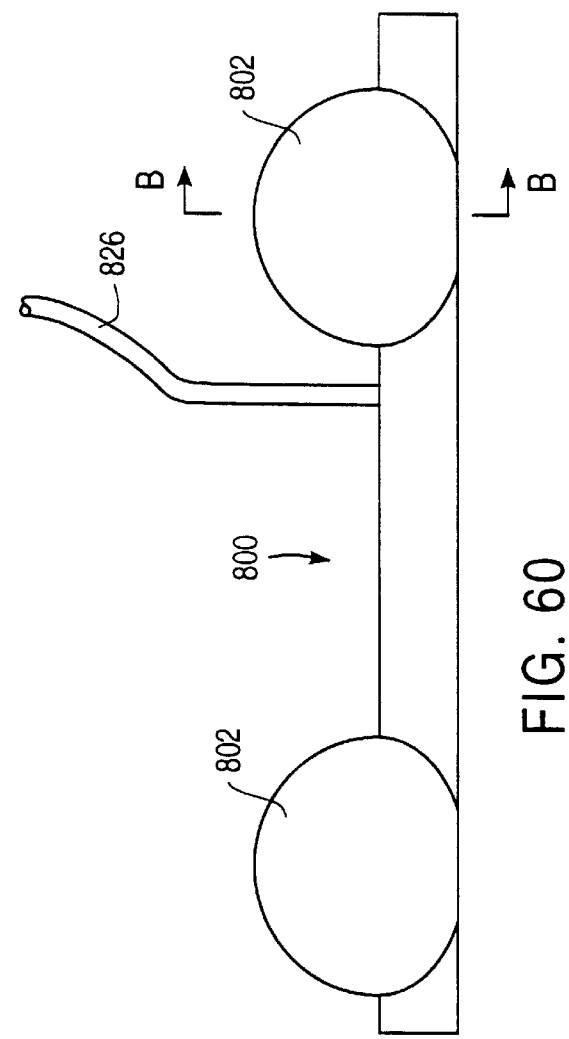
FIG. 60 shows the first coronary shunt of FIG. 59 with the occluding members inflated.

Referring to FIGS. 58–61, a first coronary shunt 800 is shown. The coronary shunt 800 includes inflatable occluding members 802. FIGS. 58 and 59 illustrate the occluding members 802 deflated and FIGS. 60 and 61 illustrate the occluding members 802 inflated. An advantage of the coronary shunt 800 is that the occluding members 802 may be deflated when inserting and removing the coronary shunt 800. A further advantage of the coronary shunt 800 is that it is preferably made of a flexible material which collapses to a small profile when removing the coronary shunt 800 from the coronary artery. The occluding members 802 are preferably sized and configured to occlude the coronary artery when inflated and preferably have a circular cross-sectional shape in a plane perpendicular to the longitudinal axis with the largest diameter being at least 1 mm and more preferably at least 6 mm. The lumen 806. preferably has a minimum cross-sectional flow area between 0.785 mm$^2$ and 12.5 mm$^2$ and more preferably between 0.785 mm$^2$ and 4.9 mm$^2$ with the preferred cross-sectional shape of the lumen being circular.

An inflation lumen 824 is fluidly coupled to the occluding members 802. The inflation lumen 824 preferably has a crescent-shaped cross-section. Referring to FIG. 59, lumen 806 is preferably at least 70%, and more preferably at least 80%, of the total cross-sectional area of the coronary shunt 800. An inflation fluid is injected into the occluding members 802 through an inflation tube 826 which is coupled to the inflation lumen 824D. The inflation tube 826 may be coupled to any suitable inflation device (not shown) such as a compressor or hand bulb. The inflation tube 826 may also be used like a tether which is pulled to remove the coronary shunt 800. The coronary shunt 800 is eccentrically positioned relative to the occluding members 802 so that the lumen 806 is positioned away from the opening in the coronary artery to reduce the likelihood that the coronary shunt is pierced by the anastomosis device.

The coronary shunt 800 is preferably made of cross-linked surlyn although any suitable material may be used. The wall thickness is preferably between 0.001 and 0.006 inch and more preferably between 0.002 inch and 0.004 inch. An advantage of using surlyn is that the coronary shunt 800 may be removed by simply pulling on the inflation tube 826 since the coronary shunt 800 is flexible. A short stiffening tube 827 may be positioned in the lumen 806 below the occluding members 802 or along the entire length of the coronary shunt 800 to prevent the occluding members 802 from constricting the lumen 806 when inflated. The coronary shunt 800 preferably has an overall length of between 0.5 and 1.5 cm, and more preferably between 0.75 cm and 1.25 cm, so that adequate space is provided between the occluding members 802 to perform the anastomosis without contacting the occluding members.

The method of using the coronary shunt 800 is now described. The method is preferably performed with the coronary shunts described herein, however, any other suitable device may be used without departing from the method of the present invention. The coronary shunt 800, and all of the other coronary shunts described herein, may be used during both beating heart procedures, in which the patient's heart remains beating, or for stopped heart procedures, in which the patient's heart is stopped and the patient is supported by a cardiopulmonary bypass system.

The coronary shunt 800 is preferably positioned in the coronary artery by inserting the coronary shunt 800 through an incision in the coronary artery. Alternatively, the coronary shunt 800 may be inserted percutaneously or endovascularly. The coronary shunt 800 is positioned so that the occluding members 802 are positioned on opposite sides of the opening in the coronary artery to provide a clear surgical site. The lumen 806 permits blood flow across the anastomosis site so that oxygenated blood may flow to the downstream side of the coronary artery. If necessary, a suture is applied around the coronary artery and the coronary shunt 800 to improve occlusion of the coronary artery.

The graft is then attached to the opening in the coronary artery. The graft is preferably cut at an angle to form an oval-shaped opening having a heel and a toe. The heel is attached to the coronary artery and sutures are placed from the heel to the toe on one side of the graft. Sutures are then placed on the other side of the graft.

After positioning the coronary shunt 800D in the coronary artery, a fluid or gas, such as saline or carbon dioxide, is injected into the occluding members 802 through the inflation tube 826 to inflate the occluding members 802 and occlude the coronary artery. The surgeon then begins the anastomosis in the manner described above. Before completing the anastomosis, the occluding members 802 are deflated and the coronary shunt 800 is removed. The opening is then closed thereby completing the anastomosis.

Referring to FIG. 62, a removal device 828 is shown which may be used with any of the coronary shunts described herein. The removal device 828 is particularly suited for removing the coronary shunt 800 when it is made of a flexible material. The removal device 828 has an elongate tubular portion 830 and a flared end 832. The removal device 828 prevents tearing or pulling of the sutures, graft and coronary artery when the coronary shunt is removed. The removal device 828 is particularly useful when the inflation tube 826 is attached to the coronary shunt between the occluding members. Although it is preferred to use the flared end 832, the end of the removal device 828 may have any shape, such as a T-shape, which prevents the coronary shunt from contacting the sutures, graft or coronary artery when removed.

Referring to FIG. 63, use of the removal device 828 is shown. The inflation tube 826 is passed through the tubular portion 830 and the flared end 832 is inserted into the opening between the heel H and toe T of the anastomosis. The inflation tube 826 is then pulled so that the coronary shunt 800 is collapsed by the flared end 832. The removal device 828 advantageously prevents the coronary shunt from exerting tearing forces on the sutures, graft or coronary artery. After the coronary shunt has been removed, the removal device 828 is withdrawn and the anastomosis is completed.

Referring to FIG. 64, a second coronary shunt 800A is shown. The coronary shunt 800A includes occluding members 802A having depressions 834 to receive a flexible filament (not shown), such as a suture, silastic or the like, which forms a tourniquet around the coronary artery. The filament ensures occlusion of the coronary artery and prevents migration of the shunt. The occluding members 802A are mounted to a tube 836 having a lumen 838 therethrough. The tube 836 may also include a reinforcing metal coil. The tube 836 and occluding members 802A may be made from any of the materials described herein and the overall dimensions of the coronary shunt 800A, lumen 828 and occluding members 802A are preferably the same as the coronary shunt 800 described above.

Referring to FIG. 65, an advantage of the coronary shunt 800A is that it can be separated into first and second parts 840, 842 which are easier to remove than the entire coronary shunt 800A. Separation of the coronary shunt 800A into first and second parts 840, 842 is particularly useful when the coronary shunt 800A is relatively stiff. After the coronary shunt 800A has been separated into first and second parts 840, 842, each of the first and second parts 840, 842 has a tether 808 attached thereto. The tether 808 may be a urethane coated suture which is solvent bonded to the coronary shunt 800A or dipped over when forming the coronary shunt 800A with a dipping process. Alternatively, the tether 808 may simply be a suture applied to the coronary shunt 800A by the surgeon before insertion into the coronary artery. Referring again to FIG. 64, a filament, such as a suture, silastic or the like, extends through the coronary shunt 800A with both ends of the flexible filament extending from the coronary shunt 800A to form the tethers 808. Although it is preferred to embed only one filament in the coronary shunt 800A, two separate filaments may be used and, furthermore, the filaments may be coupled to any portion of the coronary shunt 800A.

The coronary shunt 800A preferably includes a separable portion 844 made of a soft material, such as a polyurethane, which may be easily severed or cut. Cutting may be performed with conventional cutters, however, a specialized device which is guided by the tethers 808 may also be used. Alternatively, the filament itself may be wrapped around the coronary shunt and tensioned to "guillotine" the separable portion. Although it is preferred to cut the coronary shunt 800A to separate the first and second parts, the separation of the coronary shunt 800A may be accomplished in any other manner without departing from the scope of the invention. For example, the first and second parts 840, 842 may be coupled by a mechanical or frangible connection.

Use of the coronary shunt 800A is substantially the same as the coronary shunt 800 described above with the following exceptions. The coronary shunt 800A is inserted into the coronary artery with the occluding members 802A occluding the coronary artery. If necessary, a suture, silastic or the like is applied around the coronary artery and in the depressions 834 to occlude the coronary artery around the shunt 800A. The surgeon then begins attaching the graft to the coronary artery. When the anastomosis is nearly complete, the coronary shunt 800A is separated into the first and second parts 840, 842 which are then removed with the tethers 808. An advantage of the coronary shunt 800A is that the anastomosis may be substantially completed before removing the coronary shunt 800A since the first and second parts 840, 842 are easier to remove than the entire coronary shunt 800A.

Figure 66:
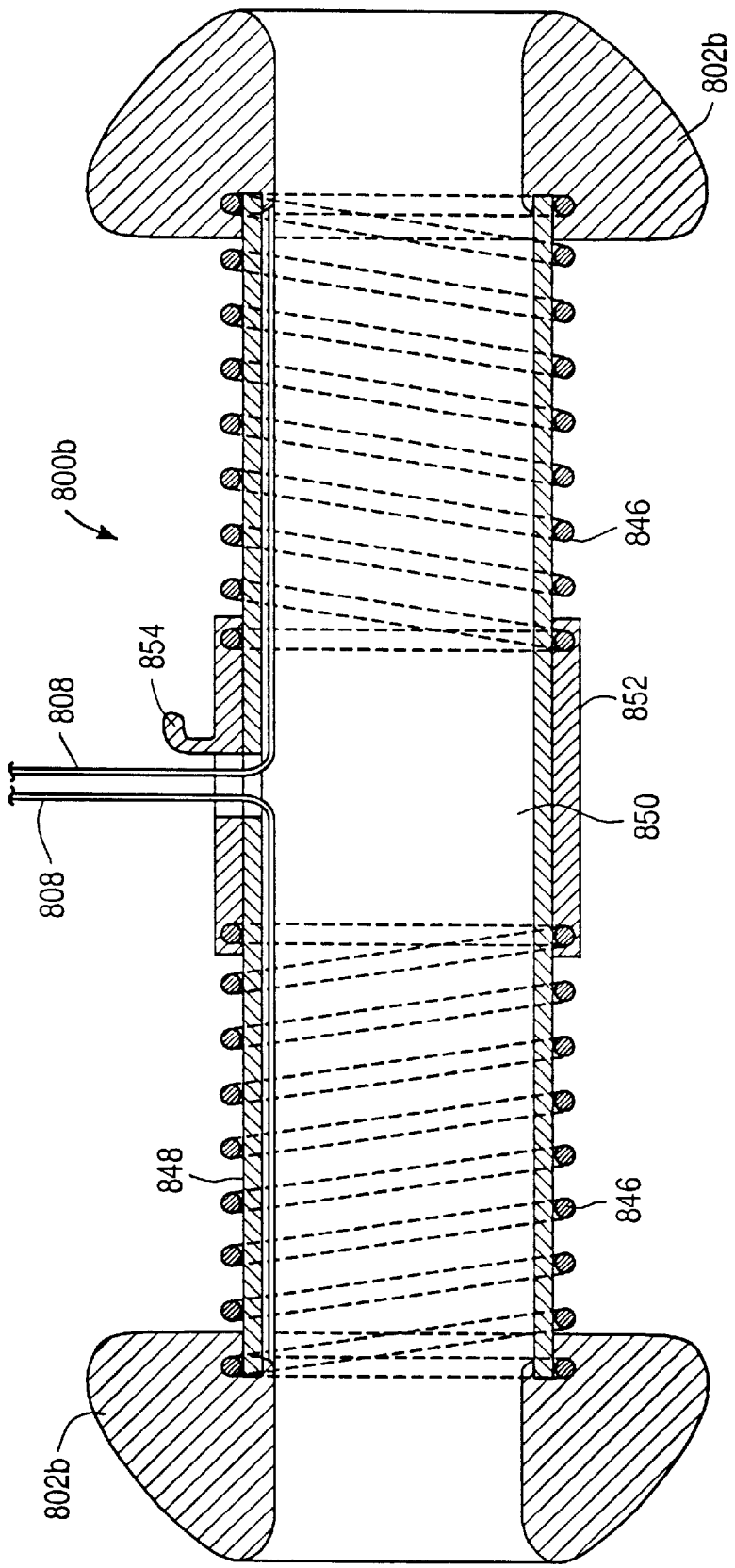
FIG. 66 is a cross-sectional view of a third coronary shunt in an expanded position.
Figure 67:
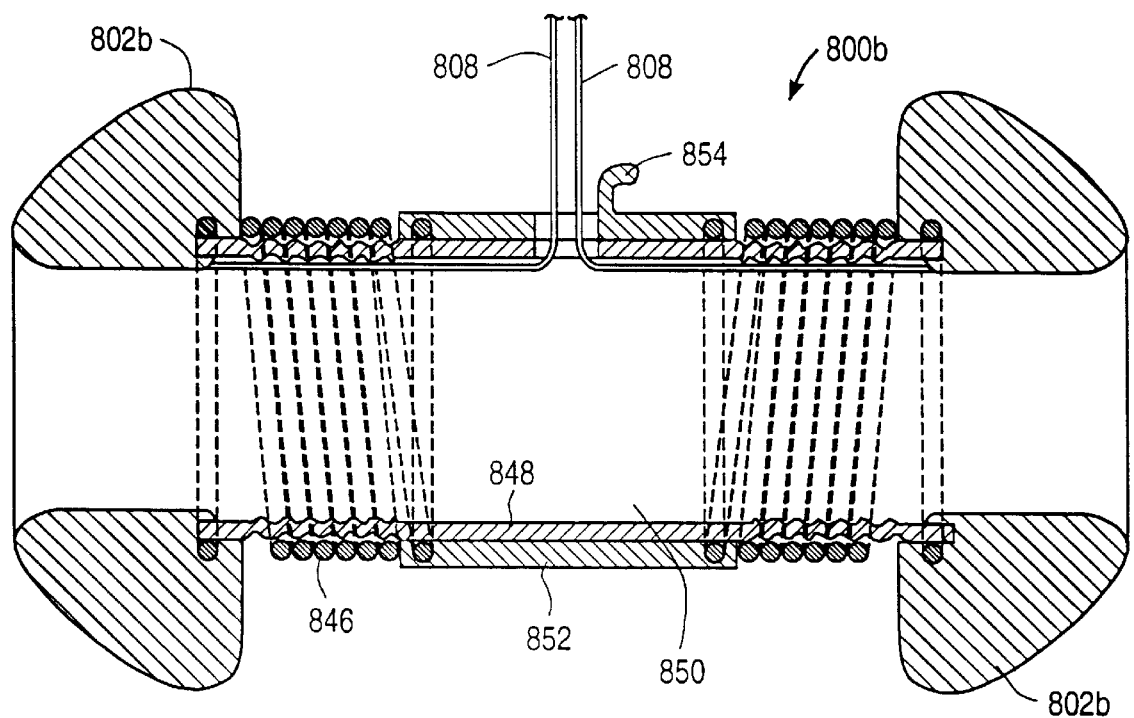
FIG. 67 is a cross-sectional view of the third coronary shunt in a collapsed position.

Referring to FIG. 66, a third coronary shunt 800B is shown. The coronary shunt 800B has occluding members 802B mounted to springs 846. The springs 846 advantageously permit compression of the coronary shunt 800B when inserting and removing the coronary shunt 800B. FIG. 66 illustrates the coronary shunt 800B in an expanded shape and FIG. 67 illustrates the coronary shunt 800B in a collapsed shape. The ends of the springs 846 are preferably embedded in the occluding members 802B. Although it is preferred to use springs 846, the compressibility of the coronary shunt 800B may also be provided with any other mechanism such as a resilient tube or a telescoping mechanism. Furthermore, although it is preferred to provide both sides of the coronary shunt with springs, only one side of the coronary shunt may include the spring 846.

A flexible sheath 848 extends through the spring 846 so that a fluid impermeable lumen 850 is provided. The flexible sheath 848 may be made of any suitable material and is preferably made of a polyurethane The sheath 848 is attached to a tube 852 which is preferably made of a relatively rigid material so that it cannot be pierced during the anastomosis. An extension 854, which is preferably in the shape of a hook, extends from the tube 852.

A tether 808 is embedded in each of the occluding members 802B. Referring to FIG. 67, the tether 808 is pulled to compress the spring 846 to the collapsed shape thereby reducing the length of the coronary shunt 800B. The extension 854 is grasped when pulling the tethers 808. The tether 808 may be any of the filaments described above.

Figure 68:
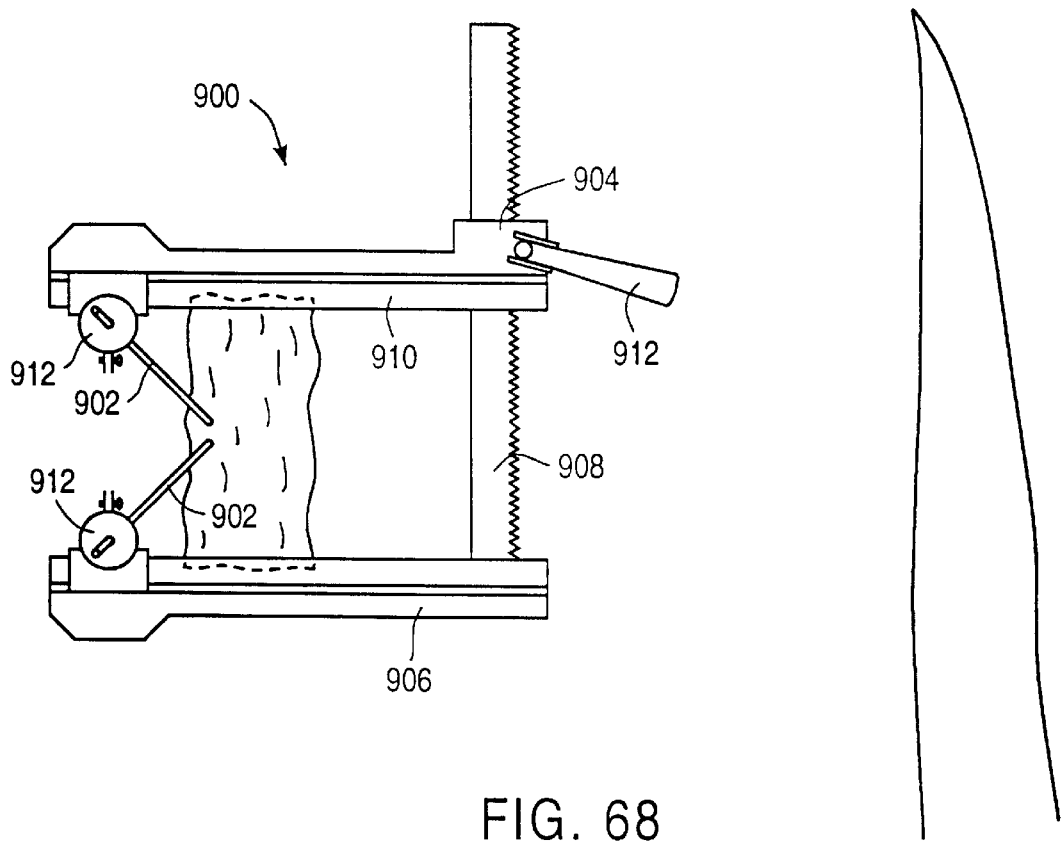
FIG. 68 is a plan view of a device for minimizing local displacements of the patient's heart during a beating heart procedure.

Referring to FIG. 68, a device 900 for minimizing displacements of an anastomosis site is shown. The device 900 is useful for beating heart coronary artery bypass procedures in which the patient's heart continues to beat during the anastomosis. The device 900 dampens displacements of a small portion of the heart around the anastomosis without affecting a large area of the heart so that normal heart functions continue.

The device 900 includes heart engaging members 902 which contact the patient's heart. The heart engaging members 902 are preferably mounted to a retractor 904 which may be any type of device which facilitates introduction of other surgical devices into a patient such as a trocar, tissue retractor, rib retractor or the like. Alternatively, the heart engaging members 902 may be supported by the operating table or an independent support structure. The retractor 904 includes a stationary blade 906, which is rigidly coupled to a rack 908, and a movable blade 910, which slides along the rack 908 when handle 912 is rotated. The retractor 904 may be used to retract the patient's ribs or may simply be used to retract tissue.

The heart engaging members 902 are mounted to displacing mechanisms 912. The displacing mechanisms 912 permit displacement of a distal end of the heart engaging members 902 for engaging the patient's heart as will be described below. In the preferred embodiment, the displacing mechanism 912 permits rotation and sliding of the heart engaging member 902. The two displacing mechanisms 912 and two heart engaging members 902 are the same and only one of the displacing mechanisms 912 and heart engaging members 902 is described below.

Figure 69:
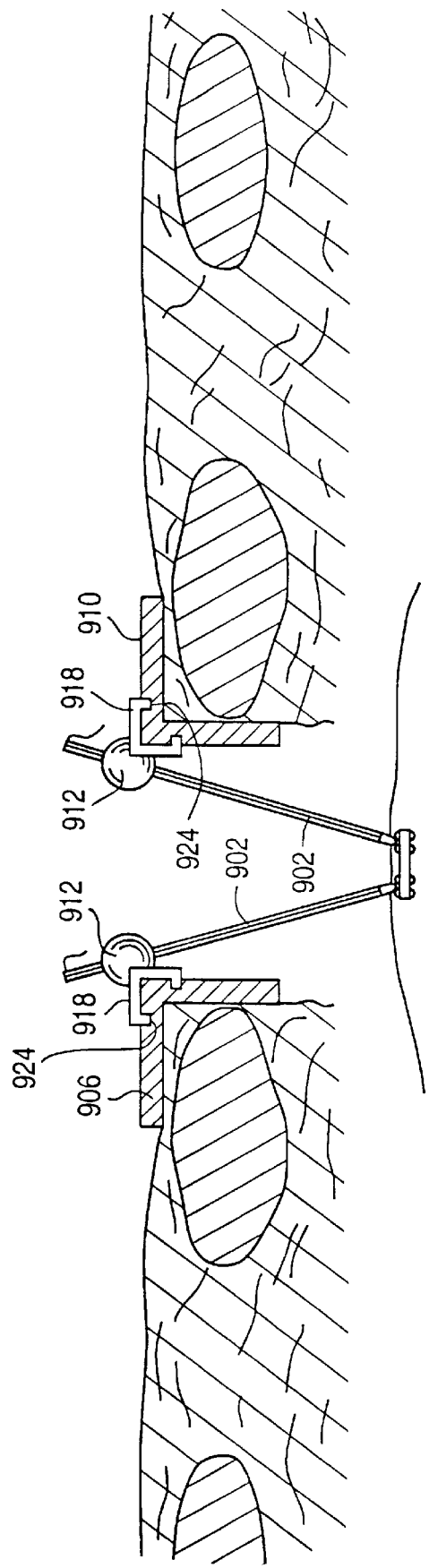
FIG. 69 is a cross-sectional view of FIG. 68.
Figure 70:
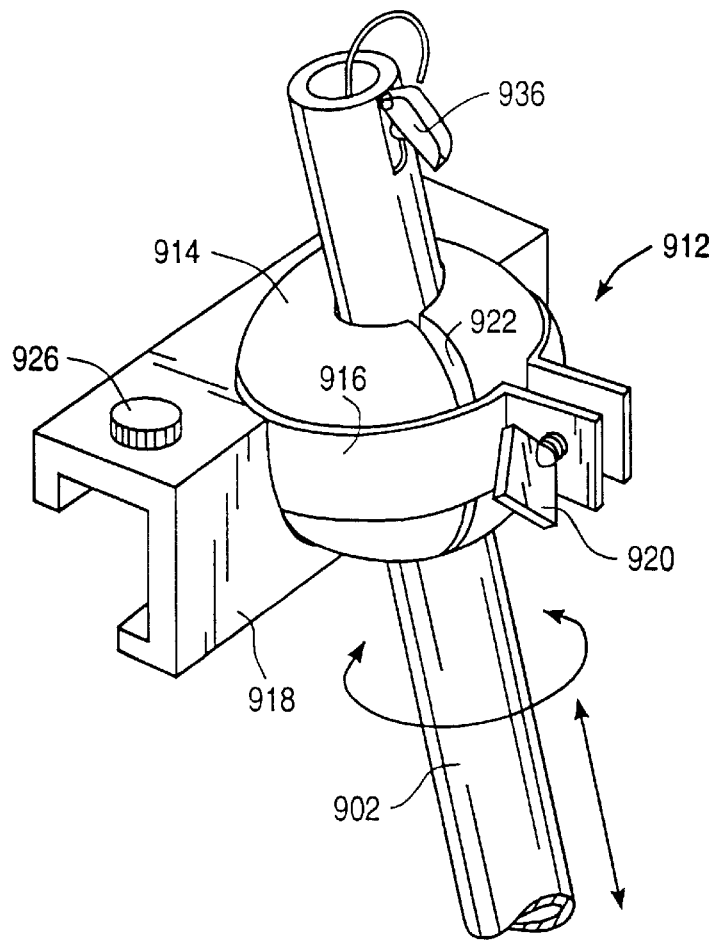
FIG. 70 illustrates a displacing mechanism.
Figure 71:
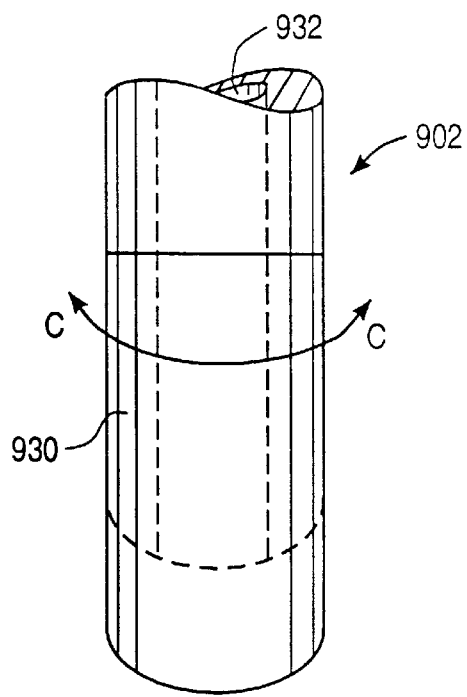
FIG. 71 is a side view of a distal end of a heart engaging member.
Figure 72:
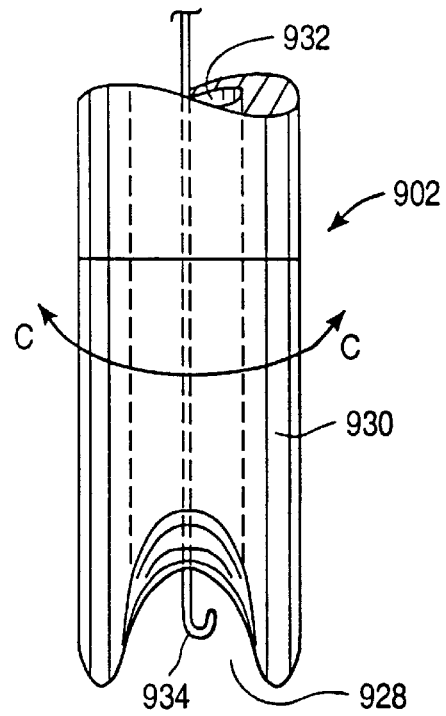
FIG. 72 illustrates another side view of the heart engaging member of FIG. 71.

Referring to FIG. 69 and 70, the displacing mechanism 912 includes a ball 914 which permits rotation of the heart engaging member 902. The ball 914 has a throughhole which slidably receives the heart engaging member 902. A locking strap 916 extends around the ball 914 and is mounted to a slide 918. A thumb screw 920 passes through the ends of the locking strap 916 for locking the orientation of the ball 914 and heart engaging member 902. The ball 914 has a slot 922 which permits radial expansion of the ball 914 when the thumb screw 920 is loosened so that the heart engaging member 902 and ball 914 may be freely displaced. When the desired orientation of the ball 914 and heart engaging member 902 are obtained, the thumb screw 920 is tightened to lock the ball 914 and heart engaging member 902 in the desired orientation. Although it is preferred to slidably couple the heart engaging member 902 to the ball 914, the heart engaging member 902 may include a telescoping element rather than the sliding connection.

The slide 918 is received in a slot 924 in the blades 906, 910 for sliding the displacing mechanism 912 on the retractor 904 or 906. A set screw 926 having a knob extends through the slide 918 and engages the retractor 904 or 906 for locking the slide 918 to the retractor 904. The displacing mechanism 912 and slide/slot configuration permits a wide variety of positions and orientations of the heart engaging member 902. Although it is preferred to use the displacing mechanism 912 and slide/slot configuration, any other mechanism may be used which permits multidimensional displacement of the heart engaging members 902. Furthermore, the heart engaging members 902 themselves may simply be made of a malleable material so that they may be deflected to the desired orientation. Although the heart engaging members 902 are preferably relatively straight rods, the heart engaging members 902 may also have an articulating distal portion without departing from the scope of the invention.

Figure 76:
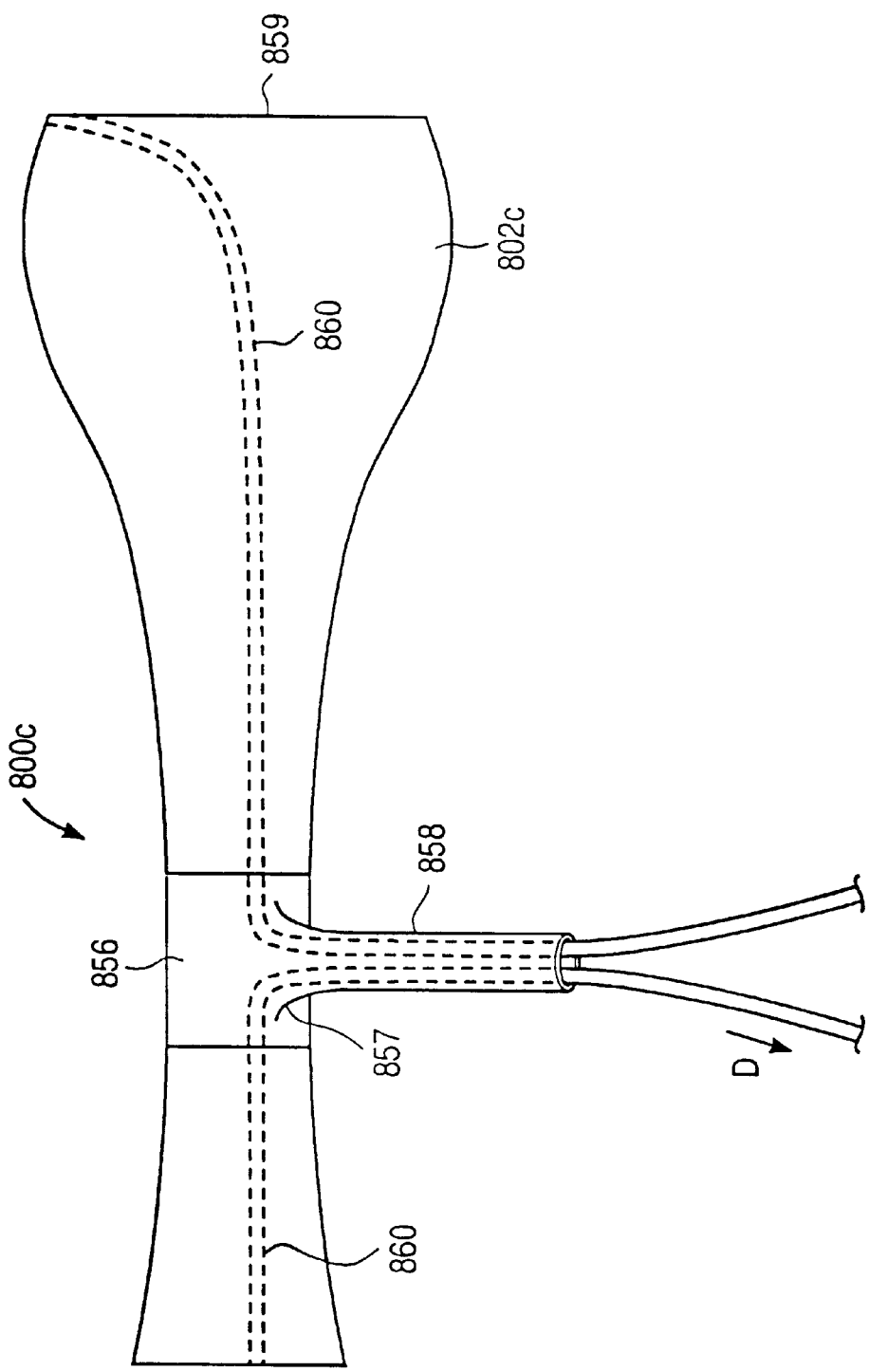
FIG. 76 shows the fourth coronary shunt partially unwrapped.

Referring to FIGS. 76 and 77, a distal end of the heart engaging member 902 is shown. The distal end of the heart engaging member 902 is preferably configured to fit around the coronary artery at a position in which the coronary shunt is positioned. As such, the distal end of the heart engaging members 902 has a recess 928 which is configured to receive the coronary shunt. The recess 928 is preferably saddle-shaped so that the distal end engages the coronary artery in a variety of angular orientations.

The distal end has a rotatable portion 930 so that the distal end can be rotated as necessary in the direction of arrow C—C to engage the heart and/or coronary shunt. The rotatable portion 930 preferably has a modest frictional resistance with respect to the remainder of the heart engaging member 902 to prevent rotation once the heart engaging member 902 engages the patient's heart. Alternatively, a locking mechanism may be provided for locking the position of the rotatable portion 930.

The heart engaging member 902 has a central passage 932 for receiving a flexible filament, such as a suture, silastic or the like. A hook 934 may be used to capture and pull the flexible filament through the central passage 932. Although it is preferred to provide the central passage 932, the heart engaging member 902 may include any other structure for retaining the filament including simple hooks or a circumferential flange around which the filament is tied. Referring to FIG. 70, the heart engaging members 902 preferably include a clamp 936 which holds the filament. Alternatively, the heart engaging member 902 may include a slit which holds the filament.

Figure 73:
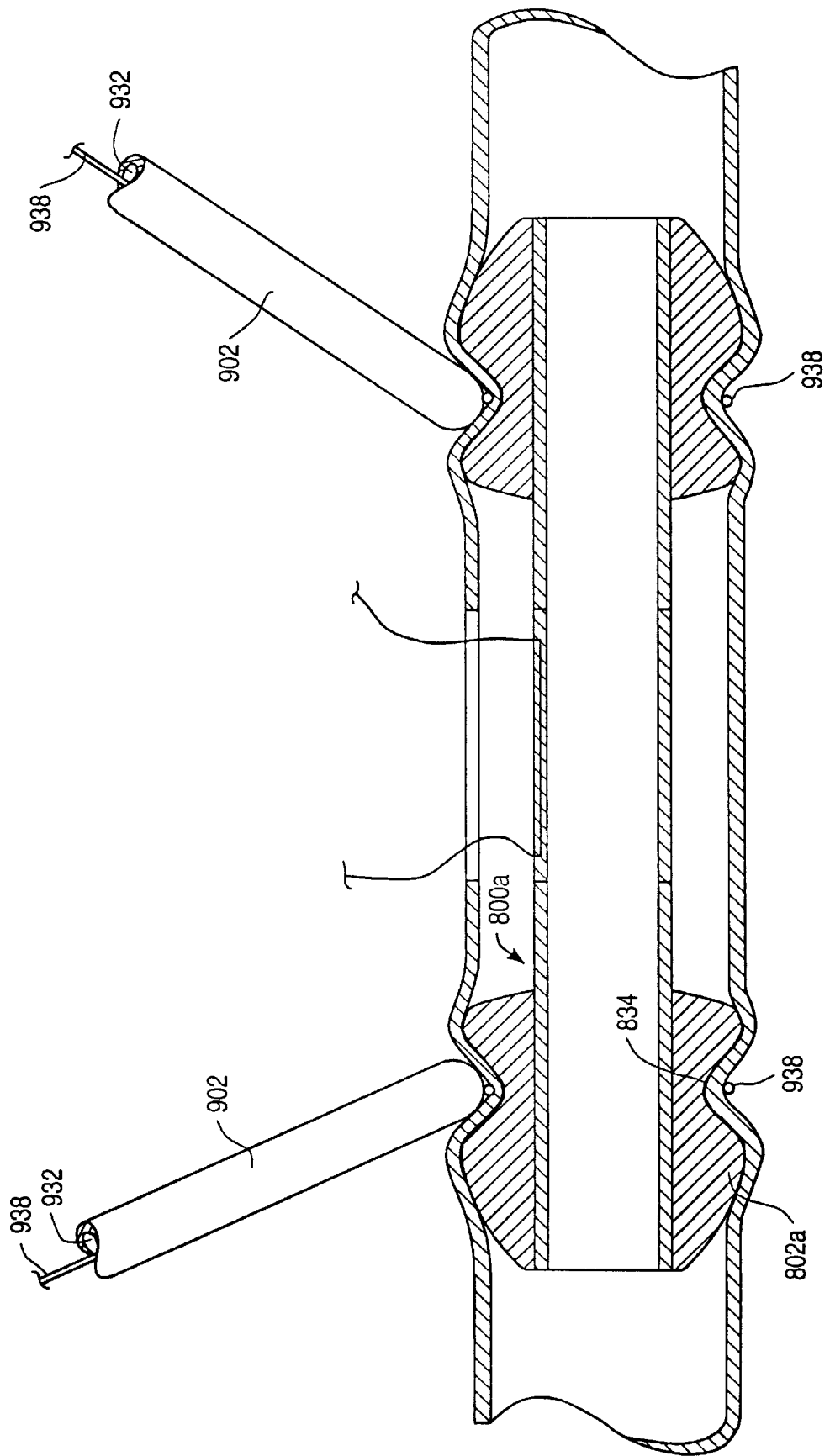
FIG. 73 illustrates the distal end of the heart engaging members contacting a patient's heart around a coronary artery in which the second coronary shunt is positioned.

Referring to FIGS. 73 and 78, the method of using the device is shown. The surgeon cuts an incision in the patient's chest, preferably between adjacent ribs, and the blades 906, 910 of the retractor 904 are used to retract tissue, and ribs if necessary, and create an opening in the patient's chest. Although it is preferred to undertake the coronary artery bypass grafting without cutting or significantly deflecting the ribs, it is within the scope of the invention to remove intercostal cartilage and retract the ribs as necessary.

A coronary shunt, such as the coronary shunt 800A, is then preferably positioned in the coronary artery. When using the coronary shunt 800A, a flexible filament 938 is placed around the coronary artery and in the depression 834 of the occluding members 802A. The filaments 938 ensure full occlusion of the coronary artery and anchor the heart to the heart engaging member 902. After the filaments 938 are placed, the filaments 938 are pulled through the central passage 932 in the heart engaging members 902.

The surgeon then decides on the angle of approach which will be used when performing the anastomosis. The heart engaging members 902 are then positioned on the blades 906, 910 of the retractor 904 so that the heart engaging members 902 extend toward the heart in a manner that will not interfere with the anastomosis instruments. Once the position of the heart engaging members 902 is selected, the set screws 926 are tightened to lock the slides 918 to the retractor 904 and the thumb screw 920 is tightened to lock the heart engaging member 902 to the ball 914. Although FIG. 68 shows the heart engaging members 902 on different blades 906, 910, both heart engaging members 902 may be mounted to the same blade 906, 910 depending upon the position and orientation of the coronary artery and the intended angle of approach when performing the anastomosis. The filaments 938 are then tensioned and secured at the clamps 936. The heart engaging members 902, together with the filaments 938, reduce displacements of the heart around the anastomosis. Although it is preferred to configure the distal end of the heart engaging members 902 with the recess 928 to engage the coronary shunt 800A, the distal end may take any other shape depending upon the particular method of securing the heart to the heart engaging member 902. For example, the distal end may include hooks, suction cups coupled to a vacuum pump, teeth or any other feature to secure the distal end to the heart. Furthermore, although it is preferred to use the device with the coronary shunt 800A, the device may also be used with a simple hollow tube or with no structure whatsoever in the coronary artery and only the flexible filaments 938. Finally, although it is preferred to secure the heart engaging members 902 at the coronary artery, the heart engaging members 902 may be secured to any other part of the heart.

Referring to FIG. 69 a fourth coronary shunt 800C is shown. The coronary shunt 800C includes occluding members 802C and a hub 856 having a tube 858 extending therefrom. The hub 856 is preferably made of a rigid material such as stainless steel or a rigid polymer. The tube 858 preferably has a rounded internal edge 857 similar to the removal device 828 described above.

Figures 74, 75:
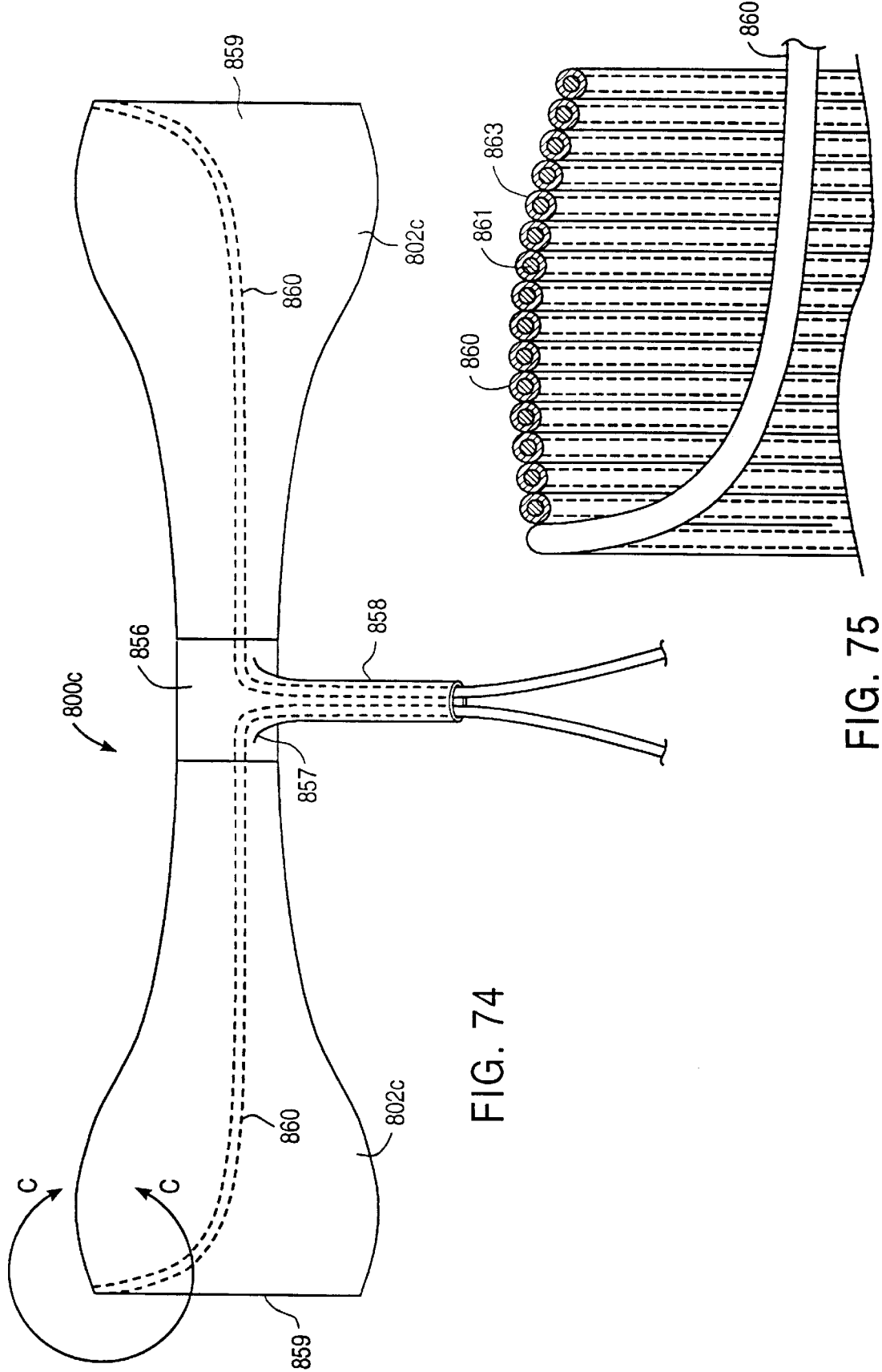
FIG. 74 shows a fourth coronary shunt.
FIG. 75 is cross-sectional view of the fourth coronary shunt around line C—C.

Two elongate filaments 860 have ends (not shown) attached to opposite sides of the hub. The filaments 860 are wound from the hub toward ends 859 of the coronary shunt 800C. Referring to FIG. 75, the filaments 860 then extend back through lumen 806C, hub 856 and tube 858. The filaments 860 are preferably a wire 861 coated with a polymer 863. The wire 861 is preferably a 0.004 inch diameter stainless steel wire or ribbon coated with polyurethane to a thickness of between 0.002 and 0.004 inch. The filaments 860 preferably have a circular cross-sectional shape, however, any other shape may also be used.

The filament 860 is wrapped around a mandrel and heated to fuse together adjacent portions of the polymer 863. The filaments 860 are preferably heated for a short time so that adjacent portions of the polymer 863 bond together at a small portion which may be easily broken. Although it is preferred to coat the wire 861 with the polymer 863 to form the filament 860, the filament 860 may simply be an uncoated polymer or steel wire which is tightly wound to form the lumen 806C. As will be described in further detail below, the filament 860 is pulled to unwind the coronary shunt 800C to facilitate removal of the coronary shunt 800C from the coronary artery.

Use of the coronary shunt 800C is now described with reference to FIGS. 74 and 76. The coronary shunt 800C is inserted into the coronary artery with the tube 858 extending through the opening in the coronary artery and two filaments 860 extending through the tube 858. The surgeon then begins attaching the graft to the coronary artery until the anastomosis is nearly complete. The surgeon then grasps one, or both, of the filaments 860 and pulls the filament 860 in the direction of arrow D while holding the tube 858 so that the filament 860 begins to unwind from the end 859 toward the hub 856. FIG. 76 shows one of the filaments 860 partially unwound by pulling the filament 860 in the direction of arrow D. The surgeon continues to pull the filament 860 until the filament 860 is completely unwound to the hub 856. The surgeon then grasps the other filament 860 and pulls it until the other filament 860 is also unwound. The surgeon then pulls tube 858 to remove the hub 856. An advantage of the coronary shunt 800C is that it may easily be removed from the coronary artery. Although the fourth coronary shunt has been described in connection with a coronary artery bypass grafting, the coronary shunt may be used in any other hollow structure in the body without departing from the scope of the invention.

Port-Access CABG Procedure

A vascular anastomosis procedure using the devices and methods of the present invention will now be described in relation to performing a proximal anastomosis on a free graft during a closed-chest or port-access coronary artery bypass graft surgical procedure. Closed-chest or port-access coronary artery bypass graft (CABG) surgery is a newly developed procedure designed to reduce the morbidity of CABG surgery as compared to the standard open-chest CABG procedure. The morbidity is reduced in the port-access CABG procedure by gaining access to the heart and the coronary arteries through one or more access ports which are made in the intercostal spaces of the patient's chest, thereby eliminating the need for a median sternotomy or other gross thoracotomy as is required in open-chest CABG surgery. A port-access coronary artery bypass graft surgical procedure using sutured anastomosis techniques is more fully described in co-pending patent applications, Ser. Nos. 08/023,778 and 08/281,891, which have been incorporated herein by reference.

To prepare the patient for the port-access CABG procedure, the patient is placed under general anesthesia and cardiopulmonary bypass (CPB) is established to support the patient's circulatory system during the surgical procedure. Preferably, a femoral-to-femoral CPB system is used to reduce the invasive nature of the procedure. One or more access ports 702 are made through the intercostal spaces 703 of the patient's chest by making an incision between the ribs 705 and placing a trocar with a cannula 704 through the wall of the chest. The trocar is then withdrawn, leaving the cannula 704 as an access port into the chest cavity. Typically, an endoscope, preferably a thoracoscopic surgical microscope, is placed through one of the access ports to allow direct visualization of the heart, the ascending aorta and the coronary arteries.

Meanwhile a graft vessel is prepared for creating the bypass graft which will redirect blood flow from the ascending aorta to one or more of the coronary arteries downstream of any blockage caused by atherosclerotic disease. Vessels which can be used as free grafts in CABG surgery include veins, such as the saphenous vein, arteries, such as one of the internal mammary arteries or the gastro-epiploic artery, and artificial grafts, such as Dacron or Goretex (expanded PTFE) grafts. If an autologous graft, such as a vein or an artery, is to be used, the vessel is generally harvested from the patient at this time.

Depending on the preference of the surgeon, the proximal anastomosis, which joins the graft vessel to the aorta, can be performed before or after the distal anastomosis, which joins the graft vessel to one or more of the coronary arteries. The distal anastomosis is generally performed while the patient's heart is stopped, whereas the proximal anastomosis may be performed with the heart stopped or while the heart is still beating, according to the preferences of the surgeon. To stop the heart, a special endo-aortic clamping catheter, which is described in the aforementioned patent applications, is inserted into the ascending aorta via a percutaneous entry or a surgical cutdown into the femoral artery. An endo-aortic clamping balloon on the distal end of the catheter is inflated in the patient's ascending aorta to block blood flow in the patient's aorta downstream of the coronary arteries. Cardioplegic solution is immediately infused into the patient's coronary arteries through a lumen in the catheter to temporarily stop the patient's heart from beating. Alternatively, the proximal anastomosis can be performed while the heart is still beating by using a side-biting clamp or other device to isolate a portion of the aortic wall from the aortic blood circulation. With a portion of the aortic wall isolated from the systemic circulation by either of these methods, the proximal anastomosis can be performed using any of the devices and methods previously described herein.

The rapidity and reliability of performing the anastomoses using the devices and methods of the present invention may, in some instances, allow the entire coronary artery bypass procedure, including the proximal and distal anastomoses to be performed without the need for cardiopulmonary bypass support or cardioplegic arrest of the heart. This would be of even greater benefit to the patient by further decreasing the morbity from the procedure and reducing the likelihood of side effects associated with CPB and cardioplegia. It would also be beneficial to the surgeon and the hospital by reducing the cost and complexity of the CABG procedure.

By way of example, the proximal anastomosis procedure will now be described using the two-part anastomosis staple device 100 of FIG. 1. A small incision 151 is made in the ascending aorta 707 at the anastomosis site 706 under endoscopic visualization. Then, the vessel punch mechanism 120 and the stapling mechanism 119 with the anchor member 101 of the anastomosis staple, which have previously been prepared as shown in FIG. 2, are introduced through one of the intercostal access ports 702 and positioned at the anastomosis site, as in FIG. 55. The anchor member 101 is attached to the ascending aorta 707 at the anastomosis site 706 according to the procedure in FIGS. 5A–5D, as follows. The anvil 136 of the vessel punch 120 is inserted though the incision 151 in the aortic wall 707, and the anchor member 101 is advanced distally so that the attachment legs 105 penetrate the aortic wall 707. Then, staple driver 127 is advanced to deform the attachment legs 105 and fasten the anchor member 101 to the exterior wall of the aorta 707. An opening 152 is then punched in the aortic wall 707 with the vessel punch 120 and the punch 120 is removed along with the tissue 153 excised by the punch. The graft insertion tool 121 and the graft vessel 148, which has previously been prepared with the coupling member 102 as shown in FIG. 6 by everting the distal end of the graft vessel 148 over the coupling member 102, are then inserted though the access port 702, as shown in FIG. 56, and the graft vessel 148 is attached to the ascending aorta 707 at the anastomosis site 706 by inserting the coupling member 102 into the anchor member 101 as shown in FIGS. 5F–5G.

Figure 57:
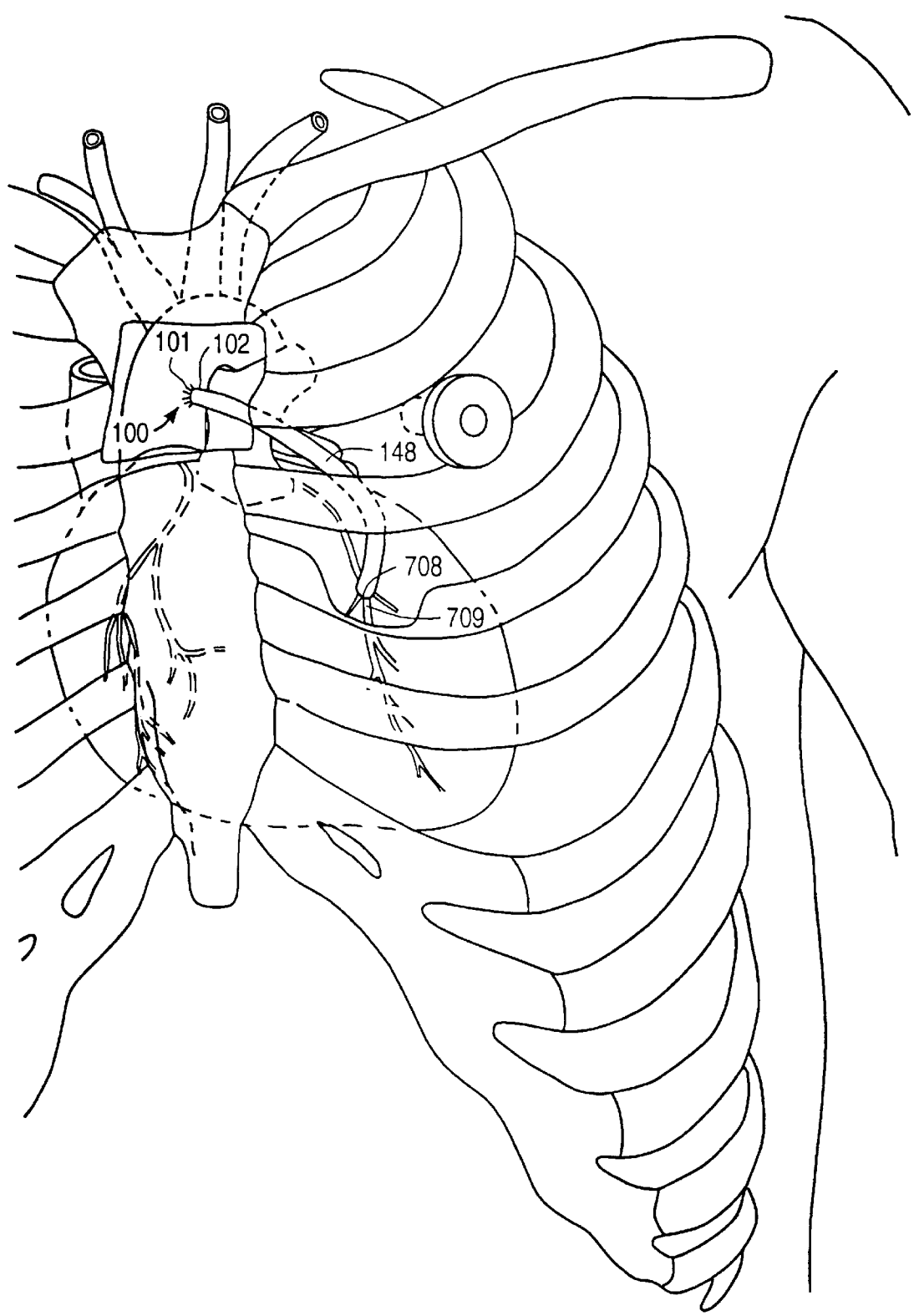

The bypass operation is then completed by anastomosing the distal end 708 of the graft vessel to the coronary artery 709 below the stenosis or occlusion, as shown in FIG. 57. The distal anastomosis can be performed using suturing techniques or the graft vessel 148 can be joined to the coronary artery 709 using a second anastomosis staple by following the steps shown in FIGS. 5A–5C and FIG. 7C, using the embodiment of the graft insertion tool 122 illustrated in FIGS. 7A–7C.

Alternatively, the proximal and distal anastomoses can be performed in the reverse order, as is preferred by some cardiac surgeons. In this case the distal anastomosis would be performed first, using the graft insertion tool 121 of FIGS. 6A–6C, followed by the proximal anastomosis performed using the graft insertion tool 122 of FIGS. 7A–7C. When performing the proximal anastomosis as the second anastomosis on a free graft, both ends of the graft vessel can be prepared for anastomosis by attaching a coupling member 102 to the proximal and the distal end of the graft vessel 148 and inserting the graft vessel 148 into the chest cavity of the patient through one of the access ports 702 after attaching anchor members 101 to both the aorta 707 and the coronary artery 709. Each of the coupling members 102 can then be inserted into its respective anchor member 101 using the appropriate insertion tool 121, 122. An alternate technique is to first attach the distal end of the graft vessel 148 to a coronary artery 709 using an anastomosis staple or sutures, according to the preference of the surgeon, then, after verifying the correct length of the graft vessel, drawing the proximal end 710 of the graft vessel 148 out of the chest cavity through one of the access ports 702. The free proximal end 710 of the graft vessel 148 can be prepared under direct vision by the surgeon by passing the free end of the graft vessel through the lumen of the coupling member 102 and everting it over the distal end 115 of the coupling member 102. The coupling member 102 with the proximal end 710 of the graft vessel attached can be reinserted into the chest cavity through the access port 702 and inserted into an anchor member 101 attached to the aortic wall 707 using the graft insertion tool 122 of FIGS. 7A–7C. This same technique can be used with the two-piece anastomosis staple for performing a distal anastomosis on a pedicled graft vessel or for performing a distal anastomosis on a free graft after the proximal anastomosis has already been made.

Figure 55:
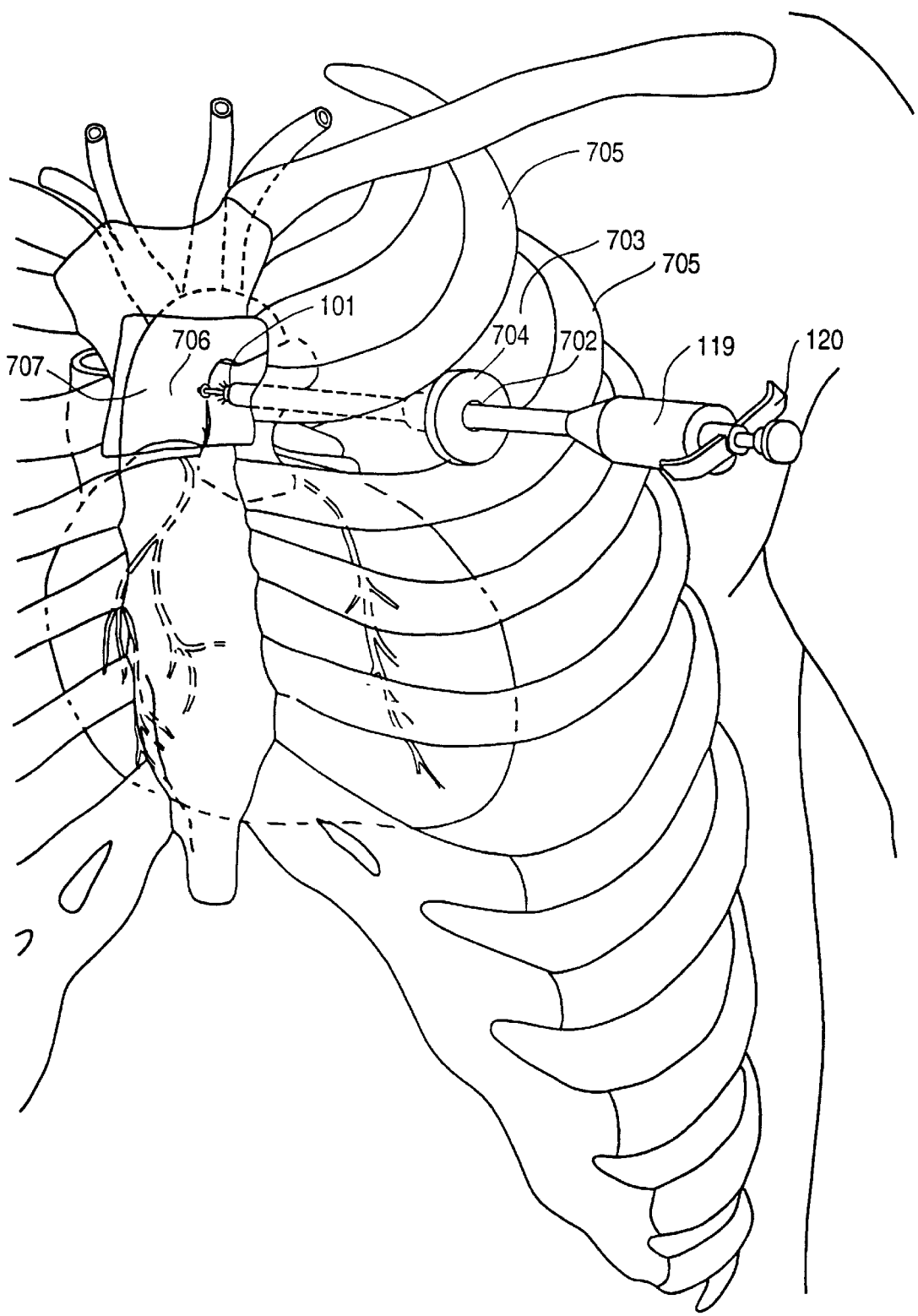
FIGS. 55, 56, 57 show the sequence of operations for creating an end-to-side anastomosis during port-access CABG surgery using the anastomosis stapling system of the present invention.
Figure 56:
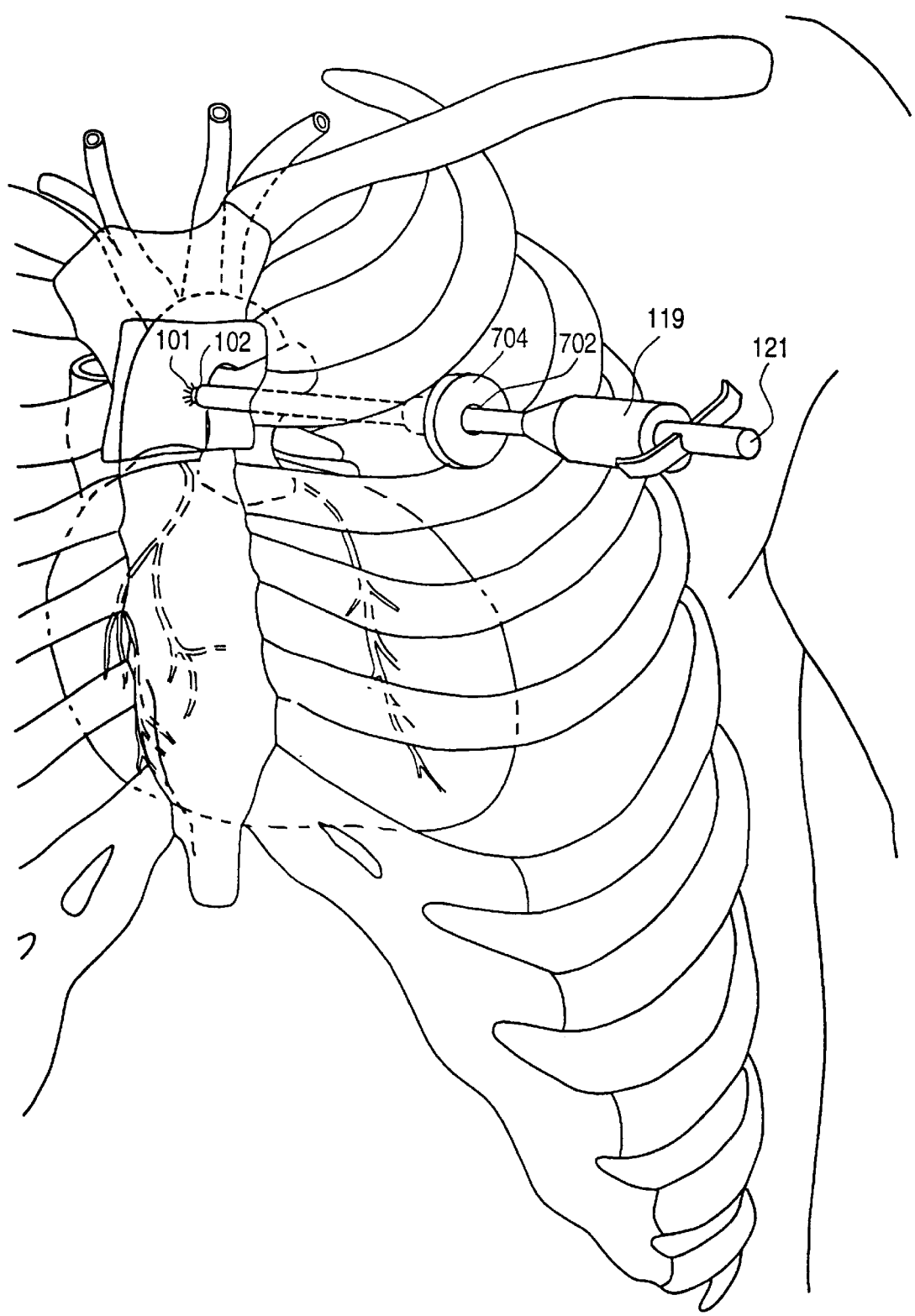

The operation of the one-piece anastomosis staples of FIGS. 9, 10, 11 or 12 can also be understood in relation to FIGS. 55–57. The graft vessel 148 and the one-piece anastomosis staple 163 are prepared as described above in relation to FIGS. 13 and 14. A small incision 151 is made in the ascending aorta 707 with a sharp blade at the intended anastomosis site 706, which has been isolated from the circulation with a side-biting clamp or other isolation device. An elongated punch, which may be similar to the vessel punch 120 described in relation to FIGS. 2 and 5D above, is inserted through one of the access ports 702 in the patient's chest. An opening 152 is made in the wall of the ascending aorta 707 by inserting the anvil of the punch through the incision, then pressing the actuating plunger to advance the tubular cutter over the anvil. The staple applying tool of FIG. 13 with the graft vessel 148 everted over the distal tubular extension 166 of the anastomosis staple 163, as shown in FIG. 14, is introduced through an access port 702 and positioned near the punched hole 152 in the ascending aorta 707 as illustrated in FIG. 55. The flanged end 167 of the distal tubular extension 166 is passed through the hole 152 so that it is in the position shown in FIG. 10. The wall of the ascending aorta 707 stretches slightly to allow the flange 167 to pass through the hole 152. The staple applying tool 179 is pulled back slightly to make sure the flange 167 of the staple 163 engages the interior wall of the aorta 707, then the lever 185 of the staple applying tool 179 is pulled to deform the attachment legs 168 of the staple 163 and drive them through the aortic wall 707, as shown in FIG. 10. The lever 185 is released and the staple applying tool 179 is rotated to disengage the staple retainer 188 from the tabs 170 on the proximal tubular extension 169 of the staple 163. The staple applying tool 179 is withdrawn and the anastomosis is complete.

As with the two-piece embodiment of the anastomosis staple, the one-piece anastomosis staple of FIG. 9 can also be used for creating the proximal and/or distal anastomoses on a graft vessel in either order, according to the preference of the surgeon. When performing the second anastomosis on a free graft or the distal anastomosis on a pedicled graft, the free end of the graft vessel can be drawn out of the chest cavity through one of the access ports to prepare the end of the graft vessel under direct vision by the surgeon. The graft vessel is prepared by passing the free end of the graft vessel through the lumen of the anastomosis staple and everting it over the distal flange. The anastomosis staple with the free end of the graft vessel attached can be reinserted into the chest cavity through the access port and attached to the wall of the target vessel, which may be the ascending aorta or one of the coronary arteries.

Although the foregoing description focuses on the use of the anastomosis system in closed-chest CABG surgery, the system is equally applicable to other situations that require vessel anastomosis, including, but not limited to renal artery bypass grafting, aorto-femoral bypass, femoral-femoral bypass and arterio-venous shunting, such as is commonly used for dialysis. Surgical anastomoses are also performed for various reasons on many different tubular organs of the body other than blood vessels, including the bowel, intestines, stomach and esophagus. While the devices and methods of the present invention are intended primarily for vascular anastomoses, some or all of the embodiments could also be modified for performing end-to-side anastomoses on other tubular organs. Any one of the one or two-piece embodiments of the anastomosis staple device can be supplied preattached to a prosthetic graft vessel. For instance, the two-piece anastomosis staple device could be supplied in a kit, including a natural or artificial graft that is prepared with a coupling member attached to one or both ends and one or two anchor members for attachment to the target vessel(s). Likewise, the one-piece anastomosis staple device can be supplied in a procedural kit preattached to a prosthetic graft vessel. This is equally applicable to artificial graft materials, such PTFE or Dacron grafts, or to natural biological graft materials, including allografts of human graft vessels, or xenografts such as bovine or porcine graft vessels, either freshly harvested, glutaraldehyde treated or cryogenically preserved. An anastomotic device application instrument, such as those described above, could also be supplied in the procedural kit with one of the anastomotic devices already attached to the distal end of the instrument.

While the above is a complete description of the preferred embodiments of the invention, various alternatives, modifications and equivalents may be used. Therefore, the above description should not be taken as limiting the scope of the invention, which is defined by the appended claims.

We claim:

1. A device for reducing displacements of a portion of a patient's heart during a beating heart anastomosis, comprising:

a support structure:

a first heart engaging member mounted to the support structure, the heart engaging member having a distal end configured to engage a patient's heart;

a first flexible filament coupled to the first heart engaging member;

a second heart engaging member mounted to the support structure, the heart engaging member also having a distal end configured to engage the patient's heart; and a second flexible filament coupled to the second heart engaging member.

2. The device of claim 1, wherein:

the support structure is a retractor.

3. The device of claim 2, wherein:

the first and second heart engaging members are slidably coupled to the retractor.

4. The device of claim 1, further comprising:

means for securing the first flexible filament to the first heart engaging member.

5. A device for reducing displacements of a portion of a patient's heart during a beating heart anastomosis, comprising:

a support structure;

a first heart engaging member mounted to the support structure, the heart engaging member having a distal end configured to contact an outer surface of a patient's heart, the first heart engaging member having means for securing the distal end to the outer surface of the patient's heart; and a second heart engaging member mounted to the support structure, the heart engaging member also having a distal end configured to contact the outer surface of the patient's heart, the second heart engaging member also having means for securing the distal end to the outer surface of the patient's heart.

6. The device of claim 5, wherein:

the support structure is a retractor.

7. The device of claim 5, wherein:

the first and second heart engaging members are slidably coupled to the support structure.

8. The device of claim 5, wherein:

the first and second heart engaging members are pivotably coupled to the support structure.

9. A device for reducing displacements of a portion of a patient's heart during a beating heart anastomosis, comprising:

a support structure;

a first heart engaging member mounted to the support structure, the heart engaging member having a distal end configured to contact a patient's heart, the first heart engaging member having means for securing the distal end to the patient's heart; and a second heart engaging member mounted to the support structure, the heart engaging member also having a distal end configured to contact the patient's heart, the second heart engaging member having means for securing the distal end to the patient's heart;

wherein the securing means for the first and second heart engaging members includes a filament.

10. A method for reducing displacements of a portion of a patient's heart, comprising:

passing a first flexible filament through a portion of a patient's heart;

coupling the first flexible filament to a first heart engaging member;

positioning the first heart engaging member in contact with the patient's heart;

anchoring the heart engaging member relative to the patient's beating heart; and tensioning the first flexible filament so that displacements of the portion of the patient's heart are reduced.

11. The method of claim 10, further comprising the steps of:

passing a second flexible filament through another portion of the patient's heart;

coupling the second flexible filament to a second heart engaging member;

positioning the second heart engaging member in contact with the patient's heart;

anchoring the heart engaging member relative to the patient's beating heart; and tensioning the second flexible element so that displacements of the portion of the patient's heart are reduced.

12. The method of claim 11, further comprising the steps of:

positioning a coronary shunt in a coronary artery of the patient, the coronary shunt having a blood flow lumen therethrough;

the passing steps being carried out so that the first and second filaments extend around the coronary artery and the coronary shunt.

13. The method of claim 12, further comprising the step of:

separating a first part of the coronary shunt from a second part of the coronary shunt;

removing the first part by pulling on a first flexible tether attached to the first part; and removing the second part by pulling on a second flexible tether attached to the second part.

14. The method of claim 10, further comprising the step of:

positioning a retractor in the patient's chest, the first heart engaging member being mounted to the retractor.

15. The method of claim 14, wherein:

the heart engaging member is slidably coupled to the retractor.

16. The method of claim 10, wherein:

the coupling step is carried out by passing the flexible filament through a passageway in the heart engaging member.

17. A method for reducing displacements of a portion of a patient's heart during a coronary artery bypass procedure in which the patient's heart remains beating, comprising:

providing a support structure having a first heart engaging member;

positioning a distal end of the first heart engaging member in contact with an outer surface of the patient's heart near an anastomosis site;

securing the distal end of the first heart engaging member to the outer surface of the patient's heart so that displacements of the outer surface of the patient's beating heart near the anastomosis site are reduced;

anchoring the first heart engaging member relative to the patient's beating heart so that displacements of the outer surface of the patient's heart around the distal end of the first heart engaging member are reduced; and performing a coronary artery bypass while the patient's heart is beating, the first heart engaging member reducing displacements of the anastomosis site.

18. The method of claim 17, further comprising the steps of:

positioning a distal end of a second heart engaging member in contact with the patient's heart, the second heart engaging member being mounted to the support structure;

securing the distal end of the second heart engaging member to the patient's heart; and anchoring the second heart engaging member relative to the patient's heart so that displacements of the patient's heart around the distal end of the second heart engaging member are reduced.

19. The method of claim 18, wherein:

the providing step is carried out with the first and second heart engaging members being slidably coupled to the support structure.

20. The method of claim 19, wherein:

the providing step is carried out with the support structure being a retractor.

21. A method for reducing displacements of a portion of a patient's heart, comprising:

providing a support structure having a first heart engaging member;

positioning a distal end of the first heart engaging member in contact with the patient's heart;

securing the distal end of the first heart engaging member to the patient's heart; and anchoring the first heart engaging member relative to the patient's beating heart so that displacements of the patient's heart around the distal end of the first heart engaging member are reduced;

the securing step being carried out with the distal end of the first heart engaging member being secured to the patient's heart with a filament.

\* \* \* \* \*